United States Patent
Bolli et al.

(10) Patent No.: US 12,319,672 B2
(45) Date of Patent: Jun. 3, 2025

(54) ALPHA-D-GALACTOPYRANOSIDE DERIVATIVES

(71) Applicant: Idorsia Pharmaceuticals Ltd, Allschwil (CH)

(72) Inventors: Martin Bolli, Allschwil (CH); John Gatfield, Allschwil (CH); Corinna Grisostomi, Allschwil (CH); Lubos Remen, Allschwil (CH); Christoph Sager, Allschwil (CH); Cornelia Zumbrunn, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 520 days.

(21) Appl. No.: 17/638,799

(22) PCT Filed: Aug. 28, 2020

(86) PCT No.: PCT/EP2020/074121
§ 371 (c)(1),
(2) Date: Feb. 25, 2022

(87) PCT Pub. No.: WO2021/038068
PCT Pub. Date: Mar. 4, 2021

(65) Prior Publication Data
US 2022/0281855 A1    Sep. 8, 2022

(30) Foreign Application Priority Data
Aug. 29, 2019   (WO) ................ PCT/EP2019/073063

(51) Int. Cl.
| C07H 19/12 | (2006.01) |
| C07D 405/14 | (2006.01) |
| C07D 413/14 | (2006.01) |
| C07D 417/14 | (2006.01) |

(52) U.S. Cl.
CPC ......... *C07D 405/14* (2013.01); *C07D 413/14* (2013.01); *C07D 417/14* (2013.01); *C07H 19/12* (2013.01)

(58) Field of Classification Search
None
See application file for complete search history.

(56) References Cited

U.S. PATENT DOCUMENTS

| 2014/0099319 A1 | 4/2014 | Traber |
| 2023/0295182 A1 | 9/2023 | Bolli et al. |
| 2023/0348442 A1 | 11/2023 | Bolli et al. |
| 2024/0109930 A1 | 4/2024 | Bolli et al. |
| 2024/0124427 A1 | 4/2024 | Bolli et al. |

FOREIGN PATENT DOCUMENTS

| WO | WO 02/057284 A1 | 7/2002 |
| WO | WO 2005/113568 A1 | 12/2005 |
| WO | WO 2005/113569 A1 | 12/2005 |
| WO | WO 2014/067986 A1 | 5/2014 |
| WO | WO 2014/078655 A1 | 5/2014 |
| WO | WO-2016120403 A1 * | 8/2016 | ......... A61K 31/7056 |
| WO | WO 2017/007689 A1 | 1/2017 |
| WO | WO 2018/011094 A1 | 1/2018 |
| WO | WO 2018/209255 A1 | 11/2018 |
| WO | WO 2018/209276 A1 | 11/2018 |
| WO | WO 2019/067702 A1 | 4/2019 |
| WO | WO 2019/067702 A9 | 4/2019 |
| WO | WO 2019/075045 A1 | 4/2019 |
| WO | WO 2019/089080 A1 | 5/2019 |
| WO | WO 2020/078807 A1 | 4/2020 |
| WO | WO 2020/078808 A1 | 4/2020 |
| WO | WO 2020/104335 A1 | 5/2020 |

(Continued)

OTHER PUBLICATIONS

U.S. Appl. No. 18/248,007, filed Apr. 5, 2023 (371(c) Date), Bolli et al.
U.S. Appl. No. 18/251,273, filed May 1, 2023 (371(c) Date), Bolli et al.
U.S. Appl. No. 18/264,751, filed Aug. 8, 2023 (371(c) Date), Bolli et al.
U.S. Appl. No. 18/548,833, filed Sep. 1, 2023 (371(c) Date), Bolli et al.
U.S. Appl. No. 17/633,895, filed Feb. 8, 2022 (371(c) Date), Bolli et al.
U.S. Appl. No. 17/633,941, filed Feb. 8, 2022 (371(c) Date), Bolli et al.
U.S. Appl. No. 17/634,512, filed Feb. 10, 2022 (371(c) Date), Bolli et al.
Arciniegas, E. et al., "Galectin-1 and Galectin-3 and Their Potential Binding Partners in the Dermal Thickening of Keloid Tissues," The American Journal of Dermatopathology, 2019, 41 (3), 193-204.

(Continued)

*Primary Examiner* — Traviss C McIntosh, III
(74) *Attorney, Agent, or Firm* — Hoxie & Associates LLC

(57) ABSTRACT

The present invention relates to compounds of Formula (I) wherein $Ar^1$, $R^1$ and $R^2$ are as described in the description, and A is 4,5-dihydroisoxazole-3,5-diyl, imidazolidin-4-one-1,3-diyl, oxazol-2-one-3,5-diyl and oxazolidine-2-one-3,5-diyl, 1,2,3-triazole-1,4-diyl, isoxazole-3,5-diyl, imidazole-1,4-diyl, and isothiazole-3,5-diyl; and their preparation, to pharmaceutically acceptable salts thereof, and to their use as pharmaceuticals, to pharmaceutical compositions containing one or more compounds of Formula (I), and especially to their use as Galectin-3 inhibitors.

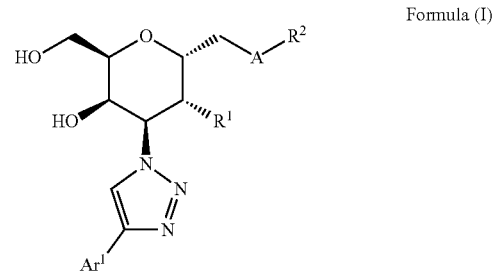

Formula (I)

23 Claims, No Drawings

(56) References Cited

FOREIGN PATENT DOCUMENTS

| WO | WO 2020/210308 A1 | 10/2020 |
|---|---|---|
| WO | WO 2021/001528 A1 | 1/2021 |
| WO | WO 2021/004940 A1 | 1/2021 |
| WO | WO 2021/028323 A1 | 2/2021 |
| WO | WO 2021/028336 A1 | 2/2021 |
| WO | WO 2021/028570 A1 | 2/2021 |
| WO | WO 2022/073969 A1 | 4/2022 |
| WO | WO 2022/090544 A1 | 5/2022 |
| WO | WO 2022/171594 A1 | 8/2022 |
| WO | WO 2022/184755 A1 | 9/2022 |

OTHER PUBLICATIONS

Barondes, S. et al., "Galectins: A Family of Animal βGalactoside-Binding Lectins," Cell, 1994, 76, 597-598.

Burguillos, M. et al., "Macroglia-Secreted Galectin-3 Acts as a Toll-like Receptor 4 Ligand and Contributes to Microglial Activation," Cell Reports, 2015, 10, 1626-1638.

Caniglia, J. et al., "A potential role for Galectin-3 inhibitors in the treatment of COVID-19," PeerJ, 2020, 8:e9392, 10 pages, doi:10.7717/peerj.9392.

Chen, W-S. et al., "Galectin-3 Inhibition by a Small-Molecule Inhibitor Reduces Both Pathological Corneal Neovascularization and Fibrosis," Investigative Ophthalmology & Visual Science, 2017, 58 (1), 9-20.

Chen, Y-J. et al., "Galectin-3 Enhances Avian H5N1 Influenza A Virus-Induced Pulmonary Inflammation by Promoting NLRP3 Inflammasome Activation," The American Journal of Pathology, 2018, 188 (4), 1031-1042.

Chiariotti, L. et al., "Galectin genes: Regulation of expression," Glycoconjugate Journal, 2004, 19, 441-449.

Dang, Z. et al., "Tubular Atrophy and Interstitial Fibrosis After Renal Transplantation Is Dependent on Galectin-3," Transplantation, 2012, 93 (5), 477-484.

Deroo, E. et al., "The role of galectin-3 and galectin-3-binding protein in venous thrombosis," Blood, 2015, 125 (11), 1813-1821.

Falcone, C. et al., "Galectin-3 Plasma Levels and Coronary Artery Disease: A New Possible Biomarker of Acute Coronary Syndrome," International Journal of Immunopathology and Pharmacology, 2011, 24 (4), 905-913.

Farhad, M. et al., "The role of Galectin-3 in modulating tumor growth and immunosuppression within the tumor microenvironment," OncoImmunology, 2018, 7 (6), e 1434467, 8 pages, https://doi.org/10.1080/2162402X.2018.1434467.

Galectin Therapeutics, "Combination Immunotherapy with Galectin-3 Inhibitor GR-MD-02 Enhances Effects in Pre-clinical Models and Early Results of Phase 1 Clinical Trials," Press Release, dated 2017, 3 pages.

Galectin Therapeutics, "Galectin Therapeutics Announces Results from Phase 2b NASH-CX Trial," Bloomberg, Press Release, dated 2017, 5 pages.

Galecto Biotech, "Galecto Biotech's Lead Molecule TD139 is Safe, Well Tolerated, with Direct Target Engagement and Biomarker Effects in a Clinical Phase Ib/IIa trial in IPF Patients," Press Release, dated 2017, 4 pages.

Gao, P. et al., "Galectin-3: its role in asthma and potential as an anti-inflammatory target," Respiratory Research, 2013, 14:136, 9 pages, doi: 10.1186/1465-9921-14-136.

Gehlken, C. et al., "Galectin-3 in Heart Failure: An Update of the Last 3 Years," Heart Failure Clinics, 2018, 14, 75-92.

Greene, T. et al., Eds., Protective Groups in Organic Synthesis, Wiley-Interscience, 1999.

Guha, P. et al., "Cod glycopeptide with picomolar affinity to galectin-3 suppresses T-cell apoptosis and prostate cancer metastasis," Proceedings of the National Academy of Sciences, 2013, 110 (13), 5052-5057.

Henderson, N. et al., "Galectin-3 regulates myofibroblast activation and hepatic fibrosis," Proceedings of the National Academy of Sciences, 2006, 103 (13), 5060-5065.

Henderson, N. et al., "Galectin-3 Expression and Secretion Links Macrophages to the Promotion of Renal Fibrosis," The American Journal of Pathology, 2008, 172 (2), 288-298.

Henderson, N. et al., "The regulation of inflammation by galectin-3," Immunological Reviews, 2009, 230, 160-171.

Hsu, D. et al., "Galectin-3 Expression is Induced in Cirrhotic Liver and Hepatocellular Carcinoma," International Journal of Cancer, 1999, 81, 519-526.

Jin, Q-h. et al., "Serum galectin-3: a risk factor for vascular complications in type 2 diabetes mellitus," Chinese Medical Journal, 2013, 126 (11), 2109-2115.

Johannes, L. et al., "Galectins at a glance," Journal of Cell Science, 2018, 131, jcs208884, 9 pages, doi:10.1242/jcs.208884.

Kikuchi, Y. et al., "Galectin-3-positive call infiltration in human diabetic nephropathy," Nephrology Dialysis Transplantation, 2004, 19 (3), 602-607.

Lacina, L. et al., "Glycophenotype of Psoriatic Skin," Folia Biologica (Praha), 2006, 52, 10-15.

Leffler, H. et al., "Introduction to galectins," Glycoconjugate Journal, 2004, 19, 433-440.

Li, P. et al., "Hematopoietic-derived Galectin-3 Causes Cellular and Systemic Insulin Resistance," HHS Public Access, Author manuscript, available in PMC 2017, 22 pages, face of article states: Published in final edited form as: Cell, 2016, 167(4), 973-984, doi: 10.1016/j.cell.2016.10.025.

Liu, F-T. et al., "Galectins in acute and chronic inflammation," Annals of the New York Academy of Sciences, 2012, 1253, 80-91.

Lowary, T. et al., "Recognition of synthetic O-methyl, epimeric, and amino analogues of the acceptor α-L-Fuc p-(1 → 2)-ß-D-Gal p-OR by the blood-group A and B gene-specified glycosyltransferases," Carbohydrate Research, 1994, 251, 33-67.

MacKinnon, A et al., "Regulation of Transforming Growth Factor-ß1-driven Lung Fibrosis by Galectin-3," American Journal of Respiratory and Critical Care Medicine, 2012, 185 (5), 537-546.

Mooring, S. et al., "Design and Synthesis of Novel Small-Molecule Inhibitors of the Hypoxia Inducible Factor Pathway," Journal of Medicinal Chemistry, 2011, 54, 8471-8489.

Mukaiyama, T. et al., "The Reactions of Primary Nitroparaffins with Isocyanates," Journal of the American Chemical Society, 1960, 82, 5339-5342.

Nachtigal, M. et al., "Galectin-3 Expression in Human Atherosclerotic Lesions," American Journal of Pathology, 1998, 152 (5), 1199-1208.

Nishi, Y. et al., "Role of Galectin-3 in Human Pulmonary Fibrosis," Allergology International, 2007, 56 (1), 57-65.

Noël, J-C. et al., "Galectin-3 is Overexpressed in Various Forms of Endometriosis," Applied Immunohistochemistry & Molecular Morphology, 2011, 19 (3), 253-257.

Rao, S. et al., "Regulation of Eosinophil Recruitment and Activation by Galectins in Allergic Asthma," Frontiers in Medicine, 2017, 4:68, 12 pages, doi:10.3389/fmed.2017.00068.

Rebholz, C. et al., "Plasma galectin-3 levels are associated with the risk of incident chronic kidney disease," Kidney International, 2018, 93, 252-259.

Remington, The Science and Practice of Pharmacy, 21st Edition, 2005, Part 5, "Pharmaceutical Manufacturing," published by Lippincott Williams & Wilkins.

Ruvolo, P., "Galectin 3 as a guardian of the tumor microenvironment," Biochimica et Biophysica Acta, 2016, 1863, 427-437.

Saegusa J. et al., "Galectin-3 Is Critical for the Development of the Allergic Inflammatory Response in a Mouse Model of Atopic Dermatitis," The American Journal of Pathology, 2009, 174 (3), 922-931.

Sano, H. et al., "Human Galectin-3 Is a Novel Chemoattractant for Monocytes and Macrophages," The Journal of Immunology, 2000, 165 (4), 2156-2164.

Sciacchitano, S. et al., "Galectin-3: One Molecule for an Alphabet of Diseases, from A to Z," International Journal of Molecular Sciences, 2018, 19, 379, 59 pages, doi:10.3390/ijms19020379.

(56) References Cited

OTHER PUBLICATIONS

Sharma, U. et al., "Novel anti-inflammatory mechanisms of N-Acetyl-Ser-Asp-Lys-Pro in hypertension-induced target organ damage," HHS Public Access, Author manuscript, available in PMC 2019, 17 pages, face of article states: Published in final edited form as: *Am J Physiol Heart Circ Physiol.,* 2008, 294(3):H1226-H1232, doi: 10.1152/ajpheart.00305.2007.

Stahl, P. et al., Eds., Handbook of Pharmaceutical Salts, Properties, Selection, and Use, Wiley-VCH, 2008.

Sundblad, V. et al., "Regulated expression of galectin-3, a multifunctional glycan-binding protein, in haematopoietic and non-haematopoietic tissues," Histology and Histopathology, 2011, 26, 247-265.

Taniguchi, T. et al., "Serum Levels of Galectin-3: Possible Association with Fibrosis, Aberrant Angiogenesis, and Immune Activation in Patients with Systemic Sclerosis," Journal of Rheumatology, 2012, 39 (3), 539-544.

Thandavarayan, R. et al., "14-3-3 protein regulates Ask1 signaling and protects against diabetic cardiomyopathy," Biochemical Pharmacology, 2008, 75, 1797-1806.

Vuong, L. et al., "An Orally Active Galectin-3 Antagonist Inhibits Lung Adenocarcinoma Growth and Augments Response to PD-L1 Blockade," Cancer Research, 2019, 79 (7), 1480-1492.

Witczak, Z. et al., Eds., Click Chemistry in Glycoscience: New Developments and Strategies, 2013, John Wiley & Sons, Inc., Hoboken, New Jersey.

Wouters, J. et al., Eds., Pharmaceutical Salts and Co-crystals, RSC Publishing, 2012.

Zhong, X. et al., "The role of galectin-3 in heart failure and cardiovascular disease," Clinical and Experimental Pharmacology and Physiology, 2019, 46, 197-203.

* cited by examiner

ALPHA-D-GALACTOPYRANOSIDE DERIVATIVES

CROSS REFERENCE TO RELATED APPLICATIONS

This application is the National Stage Entry under 35 U.S.C. § 371 of International Application No. PCT/EP2020/074121 filed Aug. 28, 2020, which claims priority to International Application No. PCT/EP2019/073063 filed Aug. 29, 2019, the contents of each of which are hereby incorporated by reference in their entireties.

The present invention relates to compounds of formula (I) which are galectin-3 inhibitors and their use in the prevention/prophylaxis or treatment of diseases and disorders that are related to galectin-3 binding to natural ligands. The invention also concerns related aspects including processes for the preparation of the compounds, pharmaceutical compositions containing one or more compounds of formula (I), and their medical use as Galectin-3 inhibitors. The compounds of formula (I)) may especially be used as single agents or in combination with one or more therapeutic agents.

Galectins are defined as a protein family based on conserved β-galactoside-binding sites found within their characteristic ~130 amino acid (aa) carbohydrate recognition domains (CRDs) (Barondes S H et al., Cell 1994; 76, 597-598). Human, mouse and rat genome sequences reveal the existence of at least 16 conserved galectins and galectin-like proteins in one mammalian genome (Leffler H. et al., Glycoconj. J. 2002, 19, 433-440). So far, three galectin subclasses were identified, the prototypical galectins containing one carbohydrate-recognition domain (CRD); the chimaera galectin consisting of unusual tandem repeats of proline- and glycine-rich short stretches fused onto the CRD; and the tandem-repeat-type galectins, containing two distinct CRDs in tandem connected by a linker (Zhong X., Clin Exp Pharmacol Physiol. 2019; 46:197-203). As galectins can bind either bivalently or multivalently, they can e.g. cross-link cell surface glycoconjugates to trigger cellular signaling events. Through this mechanism, galectins modulate a wide variety of biological processes (Sundblad V. et al., Histol Histopathol 2011; 26: 247-265).

Galectin-3 (Gal-3), the only chimaera type in the galectin family, has a molecular weight of 32-35 kDa and consists of 250 amino acid residues in humans, a highly conserved CRD and an atypical N-terminal domain (ND). Galectin-3 is monomeric up to high concentrations (100 µM), but can aggregate with ligands at much lower concentrations, which is promoted by its N-terminal non-CRD region via an oligomerisation mechanism that is not yet completely understood (Johannes, L. et al., Journal of Cell Science 2018; 131, jcs208884).

Gal-3 is widely distributed in the body, but the expression level varies among different organs. Depending on its extracellular or intracellular localization, it can display a broad diversity of biological functions, including immunomodulation, host-pathogen interactions, angiogenesis, cell migration, wound healing and apoptosis (Sundblad V. et al., Histol Histopathol 2011; 26: 247-265). Gal-3 is highly expressed in many human tumours and cell types, such as myeloid cells, inflammatory cells (macrophages, mast cells, neutrophils, T cells, eosinophils, etc.), fibroblasts and cardiomyocytes (Zhong X. et al., Clin Exp Pharmacol Physiol. 2019; 46:197-203), indicating that Gal-3 is involved in the regulation of inflammatory and fibrotic processes (Henderson N C. Et al., Immunological Reviews 2009; 230: 160-171; Sano H. et al., J Immunol. 2000; 165(4):2156-64). Furthermore, Gal-3 protein expression levels are up-regulated under certain pathological conditions, such as neoplasms and inflammation (Chiariotti L. et al., Glycoconjugate Journal 2004 19, 441-449; Farhad M. et al., Oncolmmunology 2018, 7:6, e1434467).

There are multiple lines of evidence supporting functional involvement of Gal-3 in the development of inflammatory/autoimmune diseases, such as asthma (Gao P. et al. Respir Res. 2013, 14:136; Rao S P et al. Front Med (Lausanne) 2017; 4:68), rheumatoid arthritis, multiple sclerosis, diabetes, plaque psoriasis (Lacina L. et al. Folia Biol (Praha) 2006; 52(1-2):10-5) atopic dermatitis (Saegusa J. et al. Am J Pathol. 2009, 174(3):922-31), endometriosis (Noel J C et al. Appl Immunohistochem Mol Morphol. 2011 19(3):253-7), or viral encephalitis (Liu F T et al., Ann N Y Acad Sci. 2012; 1253:80-91; Henderson N C, et al., Immunol Rev. 2009; 230(1):160-71; Li P et al., Cell 2016; 167:973-984). Recently Gal-3 has emerged as a key player of chronic inflammation and organ fibrogenesis development e.g. liver (Henderson N C et al., PNAS 2006; 103: 5060-5065; Hsu D K et al. Int J Cancer. 1999, 81(4):519-26), kidney (Henderson N C et al., Am. J. Pathol. 2008; 172:288-298; Dang Z. et al. Transplantation. 2012, 93(5):477-84), lung (Mackinnon A C et al., Am. J. Respir. Crit. Care Med 2012, 185: 537-546; Nishi Y. et al. Allergol Int. 2007, 56(1):57-65), heart (Thandavarayan R A et al. Biochem Pharmacol. 2008, 75(9):1797-806; Sharma U. et al. Am J Physiol Heart Circ Physiol. 2008; 294(3):H1226-32), as well as the nervous system (Burguillos M A et al. Cell Rep. 2015, 10(9):1626-1638), and in corneal neovascularization (Chen W S. Et al., Investigative Ophthalmology & Visual Science 2017, Vol. 58, 9-20). Additionally, Gal-3 was found to be associated with dermal thickening of keloid tissues (Arciniegas E. et al., The American Journal of dermatopathology 2019; 41(3): 193-204) and systemic sclerosis (SSc) especially with skin fibrosis and proliferative vasculopathy observed in such condition (Taniguchi T. et al. J Rheumatol. 2012, 39(3):539-44). Gal-3 was found to be up-regulated in patient suffering chronic kidney disease (CKD) associated-kidney failure, and especially in those affected by diabetes. Interestingly, data obtained from this patient population showed correlation between Gal-3 upregulation in glomeruli and the observed urinary protein excretion (Kikuchi Y. et al. Nephrol Dial Transplant. 2004, 19(3):602-7). Additionally, a recent prospective study from 2018 demonstrated that higher Gal-3 plasma levels are associated with an elevated risk of developing incident CKD, particularly among hypertension-suffering population (Rebholz C M. et al. Kidney Int. 2018 January; 93(1): 252-259). Gal-3 is highly elevated in cardiovascular diseases (Zhong X. et al. Clin Exp Pharmacol Physiol. 2019, 46(3):197-203), such as atherosclerosis (Nachtigal M. et al. Am J Pathol. 1998; 152(5):1199-208), coronary artery disease (Falcone C. et al. Int J Immunopathol Pharmacol 2011, 24(4):905-13), heart failure and thrombosis (Nachtigal M. et al., Am J Pathol. 1998; 152(5): 1199-208; Gehlken C. et al., Heart Fail Clin. 2018, 14(1): 75-92; DeRoo E P. et al., Blood. 2015, 125(11):1813-21). Gal-3 blood concentration is elevated in obese and diabetic patients and is associated with a higher risk for micro- and macro-vascular complication (such as heart failure, nephropathy/retinopathy, peripheral arterial disease, cerebrovascular event, or myocardial infarction) (Qi-hui-Jin et al. Chin Med J (Engl). 2013,126(11):2109-15). Gal-3 influences oncogenesis, cancer progression, and metastasis (Vuong L. et al., Cancer Res 2019 (79) (7) 1480-1492), and was shown to exert a role as a pro-tumor factor by acting within the micro tumor environment to suppress immune surveillance (Ruvolo P P. et al. Biochim Biophys Acta. 2016 March, 1863(3):427-437; Farhad M. et al. Oncoimmunology 2018 Feb. 20; 7(6):e1434467). Among the cancers that express high level of Gal-3 are found those affecting the thyroid gland, the central nervous system, the tongue, the breast, the gastric cancer, the head and neck squamous cell, the pancreas, the bladder, the kidney, the liver, the parathyroid, the salivary glands, but also lymphoma, carcinoma, non-small cell lung cancer, melanoma and neuroblastoma (Sciacchitano S. et al. Int J Mol Sci 2018 Jan. 26, 19(2):379).

Also, Gal-3 inhibition has been proposed to be beneficial in the treatment of COVID-19 (Caniglia J L et al. PeerJ 2020, 8:e9392) and influenza H5N1 (Chen Y J et al. Am. J. Pathol. 2018, 188(4), 1031-1042) possibly due to anti-inflammatory effects.

Recently, Gal-3 inhibitors have shown to have positive effects when used in combination immunotherapy (Galectin Therapeutics. Press Release, Feb. 7, 2017) and idiopathic pulmonary fibrosis (Galecto Biotech. Press Release, Mar. 10, 2017) and in NASH cirrhosis (Dec. 5, 2017). WO20180209276, WO2018209255 and WO2019089080 disclose compounds having binding affinity with galectin proteins for the treatment of systemic insulin resistance disorders. Thus, Gal-3 inhibitors, alone or in combination with other therapies, may be useful for the prevention or treatment of diseases or disorders such as fibrosis of organs, cardiovascular diseases and disorders, acute kidney injury and chronic kidney disease, liver diseases and disorders, interstitial lung diseases and disorders, ocular diseases and disorders, cell proliferative diseases and cancers, inflammatory and autoimmune diseases and disorders, gastrointestinal tract diseases and disorders, pancreatic diseases and disorders, abnormal angiogenesis-associated diseases and disorders, brain-associated diseases and disorders, neuropathic pain and peripheral neuropathy, and/or transplant rejection.

Several publications and patent applications describe synthetic inhibitors of Gal-3 that are being explored as antifibrotic agents (see for example WO2005113568, WO2005113569, WO2014067986, WO2016120403, US20140099319, WO2019067702, WO2019075045, WO2014078655, WO2020078807 and WO2020078808). WO2002057284, WO2005113569, and WO2014078655 disclose a broad generic scope of beta-configured galectin inhibitors. WO2016120403 and WO2020104335 disclose a broad generic scope of alpha-D-galactoside inhibitors of galectins.

The present invention provides novel compounds of Formula (I) which are alpha-configured galectin-3 inhibitors. The present compounds may, thus, be useful for the prevention/prophylaxis or treatment of diseases and disorders where modulation of Gal-3 binding to its natural carbohydrate ligands is indicated.

1) In a first embodiment, the invention relates to a compound of the Formula (I),

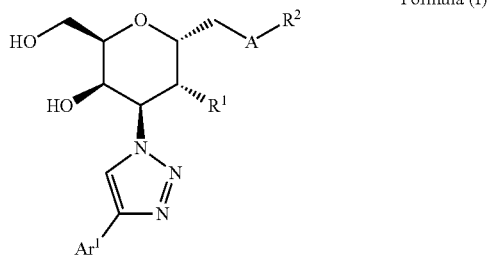

Formula (I)

wherein $Ar^1$ represents aryl (especially phenyl) which is unsubstituted, or mono-, di-, tri-, tetra-, or penta-substituted (especially mono-, di-, or tri-substituted), wherein the substituents are independently selected from halogen, methyl, cyano, methoxy, trifluoromethyl, trifluoromethoxy, and ethynyl;

[wherein said aryl is phenyl which is mono-, di-, or tri-substituted wherein at least one of said substituents is attached in a meta- or in para-position of said phenyl; wherein in particular, if present, such substituent in para-position is selected from halogen, methyl, cyano, methoxy, trifluoromethyl, trifluoromethoxy, and ethynyl (especially selected from halogen, methyl, cyano, and methoxy); and, if present, such substituent in meta-position is halogen];

5- or 6-membered heteroaryl (especially thiazolyl, pyridinyl), wherein said 5- or 6-membered heteroaryl independently is unsubstituted, mono- or di-substituted, wherein the substituents are independently selected from halogen, methyl, cyano, and methoxy; or 9- or 10-membered heteroaryl (especially benzothiazolyl), wherein said 9- or 10-membered heteroaryl independently is unsubstituted, or mono-substituted with methyl;

$R^1$ represents hydroxy;

$C_{1-4}$-alkoxy (especially methoxy);

—O—CO—$C_{1-3}$-alkyl;

O—CO—NH—$R^{N11}$ wherein $R^{N11}$ represents hydrogen or $C_{1-3}$-alkyl;

—O—CH$_2$—$C_1$-fluoroalkyl;

—O—CH$_2$-HET$^1$ wherein HET$^1$ represents a 5-membered heteroaryl (especially oxazolyl, thiazolyl, or imidazolyl) wherein said 5-membered heteroaryl independently is unsubstituted or mono-substituted with methyl; or —O—CH$_2$—CO—$R^{1X}$ wherein $R^{1X}$ represents hydroxy;

$C_{1-3}$-alkoxy (especially methoxy);

morpholin-4-yl; or

—NR$^{N21}$R$^{N22}$ wherein $R^{N21}$ and $R^{N22}$ both independently represent hydrogen or methyl; or $R^{N21}$ and $R^{N22}$ together with the nitrogen atom to which they are attached form a 4- to 6-membered heterocycloalkyl selected from azetidine-1-yl, pyrrolidine-1-yl, and piperidine-1-yl, wherein said 4- to 6-membered heterocycloalkyl is mono-substituted with hydroxy;

A represents 5-membered heterocycloalkylene or 5-membered heteroarylene; wherein said 5-membered heterocycloalkylene is selected from 4,5-dihydroisoxazole-3,5-diyl, imidazolidin-4-one-1,3-diyl, oxazol-2-one-3,5-diyl and oxazolidine-2-one-3,5-diyl; and said 5-membered heteroarylene is selected from 1,2,3-triazole-1,4-diyl, isoxazole-3,5-diyl, imidazole-1,4-diyl, and isothiazole-3,5-diyl; and $R^2$ represents $C_{1-6}$-alkyl (especially tert-butyl);

$C_{1-6}$-alkyl wherein said $C_{1-6}$-alkyl is mono-substituted with $C_{1-3}$-alkoxy (especially methoxy, ethoxy), —CO—$C_{1-4}$-alkoxy, —NH$_2$ or —NH—CO—$C_{1-4}$-alkoxy;

$C_{1-4}$-fluoroalkyl;

$C_{3-6}$-cycloalkyl wherein said $C_{3-6}$-cycloalkyl independently is unsubstituted, mono- or di-substituted wherein the substituents independently are selected from oxo, fluoro, —NH—CO—$C_{1-4}$-alkoxy, $C_{1-3}$-alkyl (especially methyl), $C_{1-3}$-alkoxy (especially methoxy), $C_1$-fluoroalkyl, cyano, —CH$_2$—CN, and —NH—CO—$C_{1-4}$-alkyl wherein said $C_{1-4}$-alkyl is mono-substituted with —NH$_2$ or —NH—CO—$C_{1-4}$-alkoxy; or said $C_{3-6}$-cycloalkyl together with 1,3-dioxolan-2,2-diyl forms a spiro-bicyclic moiety;

4- to 6-membered heterocycloalkyl wherein said heterocycloalkyl contains one ring oxygen atom and wherein said 4- to 6-membered heterocycloalkyl independently is unsubstituted or mono-substituted with $C_{1-4}$-alkyl (especially methyl or ethyl);

4- to 6-membered heterocycloalkyl wherein said heterocycloalkyl contains one ring sulfur atom (especially tetrahydro-2H-thiopyranyl) wherein said sulfur atom is unsubstituted or mono-substituted with oxo (=O); or said sulfur atom is disubstituted wherein one substituent is oxo (=O) and the other substituent is selected from oxo (=O), imido (=NH), $C_{1-3}$-alkylimido (=N—$C_{1-3}$-alkyl), 4,4-difluorocyclohexylimido and benzylimido (=N-benzyl) (thus forming a sulfinyl, sulfonyl, sulfonimidoyl, N-alkylsulfonimidoyl N-(4,4-difluorocyclohexyl)-sulfonimidoyl or N-benzylsulfonimidoyl group);

4- to 7-membered heterocycloalkyl wherein said heterocycloalkyl contains one ring nitrogen atom, wherein said nitrogen atom is unsubstituted or mono-substituted with $C_{1-6}$-alkyl;
—CO—$C_{1-6}$-alkyl; —CO—$C_{4-6}$-cycloalkyl;
—CO—$C_{1-3}$-fluoroalkyl; —CO—$C_{1-4}$-alkoxy;
—CO—NH—$C_{1-4}$-alkyl;
—SO$_2$—$C_{1-4}$-alkyl; —SO$_2$—NH—$C_{1-4}$-alkyl;
—CH$_2$—$C_{3-6}$-cycloalkyl;
—CO—$C_{1-6}$-alkyl wherein the $C_{1-6}$-alkyl is mono-substituted with amino;
—CH$_2$-oxetanyl;
thiazol-2-yl; oxazol-2-yl; benzo[d]thiazol-2-yl;
—CO-benzyloxy;
—CO—NH$_2$; —CO—NH—$C_{3-6}$-cycloalkyl;
—CO—NR$^{N31}$R$^{N32}$ wherein R$^{N31}$ and R$^{N32}$ both independently represent $C_{1-3}$-alkyl (especially methyl or ethyl);
—CO—NR$^{N41}$R$^{N42}$ wherein R$^{N41}$ and R$^{N42}$ together with the nitrogen atom to which they are attached form a 5- or 6-membered heterocycloalkyl (especially a pyrrolidinyl, piperidinyl, or piperazinyl ring) wherein said 5- or 6-membered heterocycloalkyl independently is unsubstituted or mono-substituted with $C_{1-3}$-alkyl (especially methyl);
—SO—$C_{1-6}$-alkyl;
—SO$_2$—$C_{1-3}$-fluoroalkyl; —SO$_2$—NH$_2$;
—SO$_2$—NR$^{N51}$R$^{N52}$ wherein R$^{N51}$ and R$^{N52}$ both independently represent $C_{1-3}$-alkyl (especially methyl);
—SO$_2$—NR$^{N61}$R$^{N62}$ wherein R$^{N61}$ and R$^{N62}$ together with the nitrogen atom to which they are attached form a 5- or 6-membered heterocycloalkyl (especially a pyrrolidinyl or piperidinyl, or morpholinyl ring), wherein said 5- or 6-membered heterocycloalkyl independently is unsubstituted or di-substituted with fluoro;
—SO$_2$-phenyl wherein said phenyl is unsubstituted or mono-substituted with methyl;
—SO(NH)—$C_{1-6}$-alkyl; or —SO(N—$C_{1-3}$-alkyl)-$C_{1-6}$-alkyl;

and wherein said 4- to 7-membered heterocycloalkyl carries no further substituent in addition to said substituent on the ring nitrogen atom, or carries one further substituent which is $C_{1-4}$-alkyl (especially methyl) (wherein it is understood that such $C_{1-4}$-alkyl is attached to a ring carbon atom);

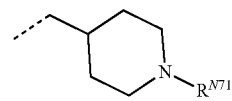

wherein R$^{N71}$ represents hydrogen or —CO—$C_{1-4}$-alkoxy (especially —CO-tert-butoxy);
cyclopentenyl;
L-OH, wherein L represents
$C_{1-6}$-alkylene;
chloro-$C_{2-6}$-alkylene;
1-phenyl-ethan-1,1-diyl or 1-(2-fluorophenyl)-ethan-1,1-diyl;
(cyclopropyl)-(pyridin-2-yl)-methylene;
$C_{4-6}$-cycloalkylene wherein said $C_{4-6}$-cycloalkylene independently is unsubstituted, mono- or di-substituted wherein the substituents independently are methyl, fluoro, or —CO—R$^{O2}$ wherein R$^{O2}$ represents hydroxy or $C_{1-4}$-alkoxy;
cyclopropylene-(CH$_2$)$_n$—* wherein n represents the integer 0 or 1, and wherein the asterisk indicates the bond which is connected to the —OH group;
4- to 7-membered heterocycloalkylene wherein said heterocycloalkylene contains one ring oxygen atom; or
4- to 7-membered heterocycloalkylene wherein said heterocycloalkylene contains one ring nitrogen atom, wherein said nitrogen atom is unsubstituted or mono-substituted with —CO—$C_{1-4}$-alkyl, or —CO—$C_{1-4}$-alkoxy;

5- or 6-membered heteroaryl (especially pyrazolyl, thiazolyl, pyridinyl, pyrimidinyl), wherein said 5- or 6-membered heteroaryl independently is unsubstituted or mono-substituted, wherein the substituents independently are $C_{1-4}$-alkyl (especially methyl), $C_{1-3}$-fluoroalkyl, halogen (especially bromo), $C_{1-4}$-alkoxy (especially methoxy), or $C_{1-4}$-fluoroalkoxy;
2-oxo-1,2-dihydropyridin-4-yl, 6-oxo-1,6-dihydropyridin-3-yl, or 1-methyl-2-oxo-1,2-dihydropyridin-4-yl;

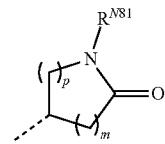

wherein m and p independently represent the integer 1 or 2; and R$^{N81}$ represents hydrogen or $C_{1-4}$-alkyl (especially methyl);
$C_{0-3}$-alkylene-phenyl (especially phenyl, —CH$_2$-phenyl or —CH(CH$_3$)-phenyl); wherein the phenyl independently is unsubstituted, mono-, di-, or tri-substituted, wherein the substituents independently are $C_{1-4}$-alkyl, $C_{1-3}$-fluoroalkyl, halogen (especially fluoro or chloro), hydroxy, $C_{1-4}$-alkoxy (especially methoxy), or $C_{1-4}$-fluoroalkoxy (especially difluoromethoxy);

9-membered heteroaryl (especially indazolyl and 1H-benzo[d]imidazolyl);

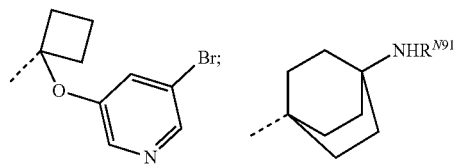

wherein $R^{N91}$ represents hydrogen or —CO—$C_{1-4}$-alkoxy (especially —CO-tert-butoxy);

or $R^2$ represents a group of the structure ($R^{2-B}$):

wherein ring (B) represents a non-aromatic 5-membered ring fused to the phenyl group, wherein ring (B) comprises two heteroatoms independently selected from nitrogen and oxygen; wherein said ring (B) independently is mono- or di-substituted, wherein one of said substituents is oxo, and the other substituent, if present, is $C_{1-3}$-alkyl (especially methyl) [notably such group ($R^{2-B}$) is 1-methyl-2-oxo-2,3-dihydro-1H-benzo[d]imidazol-5-yl, or 2-oxo-2,3-dihydrobenzo[d]oxazol-6-yl].

The compounds of Formula (I) contain five stereogenic or asymmetric centers, which are situated on the tetrahydropyran moiety and which are in the absolute configuration as drawn for Formula (I). In addition, the compounds of Formula (I) may contain contain one, and possibly more, further stereogenic or asymmetric centers, such as one or more additional asymmetric carbon atoms. The compounds of Formula (I) may thus be present as mixtures of stereoisomers or preferably as pure stereoisomers. Mixtures of stereoisomers may be separated in a manner known to a person skilled in the art.

In case linker A represents 4,5-dihydroisoxazole-3,5-diyl, the carbon atom at position 5 of said ring is preferably in absolute (S)-configuration:

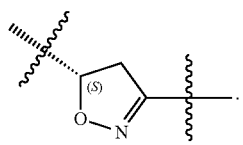

In case linker A represents oxazolidine-2-one-3,5-diyl, the carbon atom at position 5 of said ring is preferably in absolute (R)-configuration:

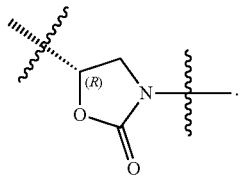

In case a particular compound (or generic structure) is designated as being in a certain absolute configuration, e.g. as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In case for a certain compound any stereogenic or asymmetric center in a given chemical name is designated as being in (RS)-configuration, this means that such stereogenic or asymmetric center in such compound may be present in (R)-configuration, in (S)-configuration, or in any mixture of epimers with regard to such center. In case two such stereogenic or asymmetric centers in (RS)-configuration are present in one molecule, it is understood that the order of absolute configuration does not indicate any defined relative configuration with regard to the two centers. For example, the compound (2R,3R,4S,5R,6R)-4-(4-(2,3-difluoro-4-methylphenyl)-1H-1,2,3-triazol-1-yl)-5-hydroxy-2-((5-((1RS,2RS)-2-hydroxycyclopentyl)isoxazol-3-yl)methyl)-6-(hydroxymethyl)tetrahydro-2H-pyran-3-yl acetate encompasses enantiomerically enriched (2R,3R,4S,5R,6R)-4-(4-(2,3-difluoro-4-methylphenyl)-1H-1,2,3-triazol-1-yl)-5-hydroxy-2-((5-((1R,2R)-2-hydroxycyclopentyl)isoxazol-3-yl)methyl)-6-(hydroxymethyl)tetrahydro-2H-pyran-3-yl acetate, (2R,3R,4S,5R,6R)-4-(4-(2,3-difluoro-4-methylphenyl)-1H-1,2,3-triazol-1-yl)-5-hydroxy-2-((5-((1R,2S)-2-hydroxycyclopentyl)isoxazol-3-yl)methyl)-6-(hydroxymethyl)tetrahydro-2H-pyran-3-yl acetate, (2R,3R,4S,5R,6R)-4-(4-(2,3-difluoro-4-methylphenyl)-1H-1,2,3-triazol-1-yl)-5-hydroxy-2-((5-((1S,2R)-2-hydroxycyclopentyl)isoxazol-3-yl)methyl)-6-(hydroxymethyl)tetrahydro-2H-pyran-3-yl acetate, and (2R,3R,4S,5R,6R)-4-(4-(2,3-difluoro-4-methylphenyl)-1H-1,2,3-triazol-1-yl)-5-hydroxy-2-((5-((1S,2S)-2-hydroxycyclopentyl)isoxazol-3-yl)methyl)-6-(hydroxymethyl)tetrahydro-2H-pyran-3-yl acetate, or any mixture of epimers with regard to the ((1RS,2RS)-2-hydroxycyclopentyl)isoxazol-3-yl) moiety of said compound.

In this patent application, a bond drawn as a dotted line, or interrupted by a wavy line, shows the point of attachment of the radical drawn. For example, the radicals drawn below

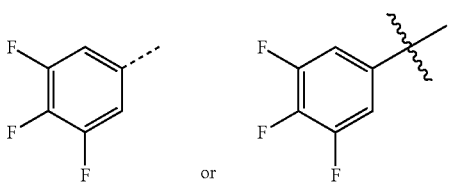

describe a 3,4,5-trifluorophenyl group.

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The present invention also includes isotopically labelled, especially $^2$H (deuterium) labelled compounds of Formula (I) according to embodiments 1) to 23), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of formulae (I), (II) and (III) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Where the plural form is used for compounds, salts, pharmaceutical compositions, diseases and the like, this is intended to mean also a single compound, salt, or the like.

Any reference to compounds of Formula (I) according to embodiments 1) to 23) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of Formula (I), as defined in any one of embodiments 1) to 21), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

In this patent application, the compounds are named using IUPAC nomenclature, but can also be named using carbohydrate nomenclature. Thus, the moiety:

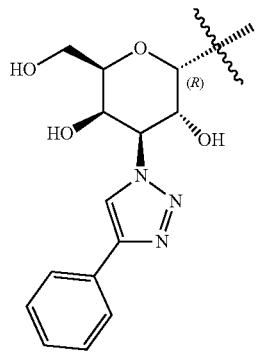

can be named (2R,3R,4R,5R,6R)-3,5-dihydroxy-6-(hydroxymethyl)-4-(4-phenyl-1H-1,2,3-triazol-1-yl)tetrahydro-2H- pyran-2-yl or, alternatively, 1,3-di-deoxy-3-[4-phenyl-1H-1,2,3-triazol-1-yl]-α-D-galactopyranoside-1-yl, wherein the absolute configuration of carbon atom carrying the point of attachment to the rest of the molecule is (2R)—, respectively, alpha. For example, compound 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)-N-ethylpiperidine-1-carboxamide is to be understood as also referring to: 1-(1,3-di-deoxy-3-[4-(3,4,5-trifluorophenyl)-1H-1,2,3-triazol-1-yl]-α-D-galactopyranose)-1-(5-((1-ethylamino-carbonyl)piperidin-4-yl)-1H-isoxazol-3-yl)-methane.

Whenever a substituent is denoted as optional, it is understood that such substituent may be absent (i.e. the respective residue is unsubstituted with regard to such optional substituent), in which case all positions having a free valency (to which such optional substituent could have been attached to; such as for example in an aromatic ring the ring carbon atoms and/or the ring nitrogen atoms having a free valency) are substituted with hydrogen where appropriate. Likewise, in case the term "optionally" is used in the context of (ring) heteroatom(s), the term means that either the respective optional heteroatom(s), or the like, are absent (i.e. a certain moiety does not contain heteroatom(s)/is a carbocycle/or the like), or the respective optional heteroatom(s), or the like, are present as explicitly defined. If not explicitly defined otherwise in the respective embodiment or claim, groups defined herein are unsubstituted.

In some instances, the compounds of Formula (I) may contain tautomeric forms. Such tautomeric forms are encompassed in the scope of the present invention. In case tautomeric forms exist of a certain residue, and only one form of such residue is disclosed or defined, the other tautomeric form(s) are understood to be encompassed in such disclosed residue. For example, the group 2-oxo-2,3-dihydro-1H-benzo[d]imidazol-5-yl is to be understood as also encompassing its tautomeric form 2-hydroxy-1H-benzo[d]imidazol-5-yl. Likewise, the group 2-oxo-2,3-dihydrobenzo[d]oxazol-6-yl is to be understood as also encompassing its tautomeric form 2-hydroxybenzo[d]oxazol-6-yl; and the group 2-oxo-1,2-dihydropyridin-4-yl (or alternatively named: pyridin-2(1H)-one-4-yl) is to be understood as also encompassing its tautomeric form 2-hydroxypyridin-4-yl.

The term "halogen" means fluorine, chlorine, or bromine, preferably fluorine.

The term "alkyl", used alone or in combination, refers to a saturated straight or branched chain hydrocarbon group containing one to six carbon atoms. The term "$C_{x-y}$-alkyl" (x and y each being an integer), refers to an alkyl group as defined before, containing x to y carbon atoms. For example, a $C_{1-6}$-alkyl group contains from one to six carbon atoms. Representative examples of alkyl groups are methyl, ethyl, propyl, isopropyl, butyl, isobutyl, tert.-butyl, pentyl, 3-methyl-butyl, 2,2-dimethyl-propyl and 3,3-dimethyl-butyl. For avoidance of any doubt, in case a group is referred to as e.g. propyl or butyl, it is meant to be n-propyl, respectively n-butyl. In case $R^2$ represents "$C_{1-6}$-alkyl" the term especially refers to methyl, ethyl, isopropyl, or tert-butyl; in particular to tert-butyl. In a sub-embodiment for $R^2$ representing "$C_{1-6}$-alkyl" the term refers to $C_{1-3}$-alkyl. In another sub-embodiment for $R^2$ representing "$C_{1-6}$-alkyl" the term refers to $C_{4-6}$-alkyl, in particular to tert-butyl.

The term "—$C_{x-y}$-alkylene-", used alone or in combination, refers to bivalently bound alkyl group as defined before containing x to y carbon atoms. The term "—$C_{0-y}$-alkylene-" refers to a direct bond, or to a —($C_{1-y}$)alkylene- as defined before. Preferably, the points of attachment of a —$C_{1-y}$-alkylene group are in 1,1-diyl, or in 1,2-diyl, or in 1,3-diyl arrangement. In case a $C_{0-y}$-alkylene group is used in combination with another substituent, the term means that either said substituent is linked through a $C_{1-y}$-alkylene group to the rest of the molecule, or it is directly attached to the rest of the molecule (i.e. a Co-alkylene group represents a direct bond linking said substituent to the rest of the molecule).

The alkylene group —$C_2H_4$— refers to —$CH_2$—$CH_2$— if not explicitly indicated otherwise. Examples of L representing "$C_{1-6}$-alkylene" are methylene, ethylene, propan-2,2-diyl, and 2-methyl-propan-1,2-diyl; and, in addition, 2-methyl-propan-2,3-diyl, and pentan-3,3-diyl.

The term "chloro-$C_{2-6}$-alkylene" refers to a $C_{2-6}$-alkylene group as defined before in which one hydrogen atom has been replaced with chloro. In case $R^2$ represents L-OH, wherein L represents "chloro-$C_{2-6}$-alkylene", the term especially refers to 1-chloro-3-hydroxy-2-methyl-propan-2-yl.

The term "alkenyl", used alone or in combination, refers to a straight or branched hydrocarbon chain containing two to five carbon atoms and one carbon-carbon double bond. The term "$C_{x-y}$-alkenyl" (x and y each being an integer), refers to an alkenyl group as defined before containing x to y carbon atoms. For example, a $C_{2-5}$-alkenyl group contains from two to five carbon atoms. An example of alkenyl group is notably prop-1-en-2-yl.

The term "fluoroalkyl", used alone or in combination, refers to an alkyl group as defined before containing one to four carbon atoms in which one or more (and possibly all) hydrogen atoms have been replaced with fluorine. The term "$C_{x-y}$-fluoroalkyl" (x and y each being an integer) refers to a fluoroalkyl group as defined before containing x to y carbon atoms. For example, a $C_{1-3}$-fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl, 2,2,2-trifluoroethyl and 1,1-difluoro-2-methyl-propan-2-yl, in particular trifluoromethyl. In case $R^2$ represents "$C_{1-4}$-fluoroalkyl", the term especially refers to 1,1-difluoro-2-methyl-propan-2-yl. The term "$C_1$-fluoroalkyl" especially refers to difluoromethyl.

The term "fluoroalkoxy", used alone or in combination, refers to an alkoxy group as defined before containing one to three carbon atoms in which one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example, a $C_{1-3}$-fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $C_1$-fluoroalkoxy groups such as trifluoromethoxy and difluoromethoxy, as well as 2,2,2-trifluoroethoxy.

The term "cycloalkyl", used alone or in combination, refers especially to a saturated monocyclic hydrocarbon ring containing three to seven carbon atoms. The term "$C_{x-y}$-cycloalkyl" (x and y each being an integer), refers to a cycloalkyl group as defined before containing x to y carbon atoms. For example, a $C_{3-6}$-cycloalkyl group contains from three to six carbon atoms. Representative examples of cycloalkyl groups are cyclopropyl, cyclobutyl, cyclopentyl, cyclohexyl, and cycloheptyl. Preferred are cyclopropyl, cyclobutyl, cyclopentyl and cyclohexyl. Said cycloalkyl groups are unsubstituted or substituted as explicitly defined. In case $R^2$ represents "$C_{3-6}$-cycloalkyl which together with 1,3-dioxolan-2,2-diyl forms a spiro-bicyclic moiety", the term especially refers to 1,4-dioxaspiro[4.5]decan-8-yl.

The term "—$C_{x-y}$-cycloalkylene-", used alone or in combination, refers to bivalently bound cycloalkyl group as defined before containing x to y carbon atoms. Preferably, the points of attachment of any bivalently bound cycloalkyl group are in 1,1-diyl, or in 1,4-diyl arrangement; or, in addition, in 1,2-diyl arrangement. Examples of $C_{4-6}$-cycloalkylene groups are cyclopentane-1,1-diyl, cyclohexane-1,1-diyl, and cyclohexane-1,4-diyl; and, in addition, cyclopropane-1,1-diyl, cyclopropane-1,2-diyl, cyclobutane-1,1-diyl, cyclobutane-1,2-diyl, and cyclopentane-1,2-diyl.

In case $R^2$ represents L-OH, wherein L represents "cyclopropylene-$(CH_2)_n$—*", the term especially refers to 2-hydroxy-cyclopropan-1-yl, 1-hydroxy-cyclopropan-1-yl, or 1-hydroxymethyl-cyclopropan-1-yl.

The term "alkoxy", used alone or in combination, refers to an alkyl-O— group wherein the alkyl group is as defined before. The term "$C_{x-y}$-alkoxy" (x and y each being an integer) refers to an alkoxy group as defined before containing x to y carbon atoms. Preferred are ethoxy and especially methoxy. Examples of $R^1$ representing "$C_{1-4}$-alkoxy" are methoxy, ethoxy, n-propoxy, and n-butoxy (especially methoxy); and, in addition, isopropoxy; most preferred is methoxy.

The term "heterocycloalkyl", used alone or in combination, and if not explicitly defined in a broader or more narrow way, refers to a saturated or unsaturated non-aromatic monocyclic hydrocarbon ring containing one or two ring heteroatoms independently selected from nitrogen, sulfur, and oxygen (especially one oxygen atom, one sulfur atom, one nitrogen atom, two nitrogen atoms, two oxygen atoms, or one nitrogen atom and one oxygen atom). The term "x- to y-membered heterocycloalkyl" refers to such a heterocycle containing a total of x to y ring atoms. For avoidance of doubt, in case a certain 4- to 7- or 4- to 6-membered heterocycloalkyl is defined as containing one ring heteroatom (such as one ring sulfur atom, one ring oxygen atom, or one ring nitrogen atom) it is understood that such 4- to 7-membered heterocycloalkyl contains exactly said one ring heteroatom and no further ring heteroatoms. Heterocycloalkyl groups are unsubstituted or substituted as explicitly defined. Examples of 4- to 6-membered heterocycloalkyl groups wherein said heterocycloalkyl contains one ring oxygen atom are oxetan-3-yl, and tetrahydro-2H-pyran-4-yl. Examples of 4- to 7-membered heterocycloalkyl groups wherein said heterocycloalkyl contains one ring nitrogen atom are azetidin-3-yl, pyrrolidin-3-yl and piperidin-4-yl. An example of 4- to 7-membered heterocycloalkyl groups wherein said heterocycloalkyl contains two nitrogen atoms is piperazin-1-yl, wherein preferably any substituent of such piperazin-1-yl is attached to a nitrogen atom of said piperazin-1-yl. Examples of 4- to 7-membered heterocycloalkyl groups wherein said heterocycloalkyl contains two oxygen atoms are 1,3-dioxolyl or 1,4-dioxinyl. An example of 4- to 7-membered heterocycloalkyl groups wherein said heterocycloalkyl contains one nitrogen atom and one oxygen atom is morpholin-4-yl wherein preferably such morpholin-4-yl group is unsubstituted.

In case $R^2$ represents "4- to 6-membered heterocycloalkyl containing one ring oxygen atom wherein said 4- to 6-membered heterocycloalkyl independently is mono-substituted with $C_{1-4}$-alkyl", the term especially refers to 3-methyloxetan-3-yl, 3-ethyloxetan-3-yl or 4-methyltetrahydro-2H-pyran-4-yl; in particular to 3-methyloxetan-3-yl.

In case $R^2$ represents "4- to 6-membered heterocycloalkyl wherein said heterocycloalkyl contains one ring sulfur atom and wherein said sulfur atom is unsubstituted or mono-substituted with oxo; or said sulfur atom is disubstituted wherein one substituent is oxo (=O) and the other substituent is selected from oxo, imido, $C_{1-3}$-alkylimido, 4,4-difluorocyclohexylimido and benzylimido", the term especially refers to the following groups:

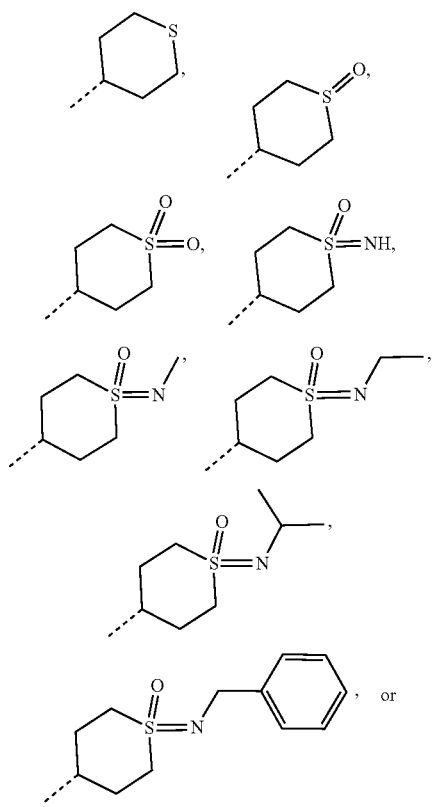

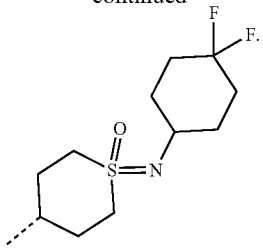

In case $R^2$ represents "4- to 7-membered heterocycloalkyl wherein said heterocycloalkyl contains one ring nitrogen atom, and wherein said nitrogen atom is mono-substituted with —SO(NH)—$C_{1-6}$-alkyl or —SO(N—$C_{1-3}$-alkyl)-$C_{1-6}$-alkyl", the term especially refers to the following groups:

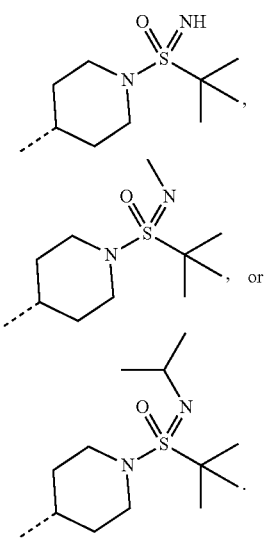

The term "heterocycloalkylene" used alone or in combination, refers to bivalently bound heterocycloalkyl group as defined before. Preferably, the point of attachment of linker A representing a 5-membered heterocycloalkylene is in a 1,3-diyl arrangement (wherein it is understood that said 1,3-diyl arrangement refers to a "meta" arrangement encompassing the respective 1,4- or 3,5-diyl arrangement in case numbering is to be adapted to the nomenclature of a certain heterocycloalkylene ring). An example of A representing "5-membered heterocycloalkylene" is 4,5-dihydroisoxazole-3,5-diyl; and, in addition, imidazolidin-4-one-1,3-diyl, oxazol-2-one-3,5-diyl and oxazolidine-2-one-3,5-diyl; in particular 4,5-dihydroisoxazole-3,5-diyl. The term "x- to y-membered heterocycloalkylene", used alone or in combination, refers to bivalently bound heterocycloalkyl group as defined before containing a total of x to y ring atoms. Examples of 4- to 7-membered heterocycloalkylene groups wherein said heterocycloalkylene contains one ring oxygen atom are oxetane-3,3-diyl and tetrahydro-2H-pyran-4,4-diyl. Examples of 4- to 7-membered heterocycloalkylene groups wherein said heterocycloalkylene contains one ring nitrogen atom are piperidin-4,4-diyl and azepan-4,4-diyl. Said heterocycloalkylene groups are unsubstituted or substituted as explicitly defined.

The term "aryl", used alone or in combination, means phenyl or naphthyl, preferably phenyl, wherein said aryl group is unsubstituted or substituted as explicitly defined.

The term "heteroaryl", used alone or in combination, and if not explicitly defined in a broader or more narrow way, means a 5- to 10-membered monocyclic or bicyclic aromatic ring containing one to a maximum of four heteroatoms, each independently selected from oxygen, nitrogen and sulfur. Representative examples of such heteroaryl groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; 6-membered heteroaryl groups such as pyridinyl, pyrimidinyl, pyridazinyl, pyrazinyl; and 8- to 10-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, thienopyridinyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined. The above-mentioned heteroaryl groups are unsubstituted or substituted as explicitly defined. For the substituent $R^2$ representing "5- or 6-membered heteroaryl", the term especially means pyrazolyl, thiazolyl, pyridinyl, or pyrimidinyl; in particular 1H-pyrazol-4-yl, thiazol-5-yl, pyridin-3-yl, pyridin-4-yl, pyrimidin-5-yl; or, in addition, thiazol-2-yl. For the substituent $R^2$ representing "9-membered heteroaryl", the term especially means indazolyl and 1H-benzo[d]imidazolyl; in particular 1H-indazol-5-yl, 1H-indazol-6-yl, and 1H-benzo[d]imidazol-5-yl.

The term "heteroarylene" used alone or in combination, refers to bivalently bound heteroaryl group as defined before. Preferably, the point of attachment of linker A representing a 5-membered heteroarylene is in a 1,3-diyl arrangement (wherein it is understood that said 1,3-diyl arrangement refers to a "meta" arrangement encompassing the respective 1,4- or 3,5-diyl arrangement in case numbering is to be adapted to the nomenclature of a certain heteroarylene ring). Examples of A representing 5-membered heteroarylene are 1,2,3-triazole-1,4-diyl and isoxazole-3,5-diyl; and, in addition, imidazole-1,4-diyl, and isothiazole-3,5-diyl; in particular isoxazole-3,5-diyl, and 1,2,3-triazole-1,4-diyl.

For avoidance of any doubt, in case linker A represents a bivalently bound heteroaryl or heterocycloalkyl group, it is understood that the point of attachment of the substituent $R^2$ may be at both possible positions of said heteroarylene or heterocycloalkylene biradical. For example, in case A represents isoxazole-3,5-diyl, the substituent $R^2$ may be attached at position 3 or at position 5 of said isoxazole; thus, referring to the following possible structures:

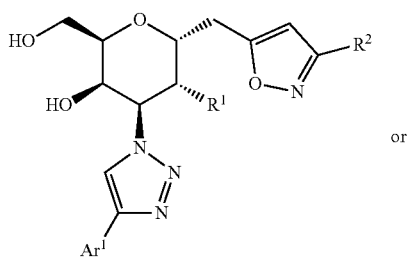

or

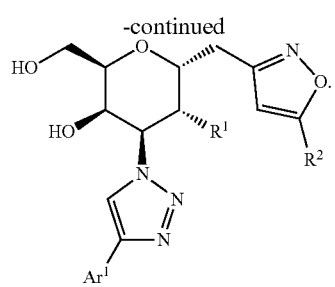

In case $R^2$ represents the structure

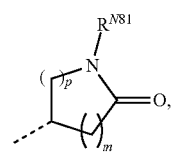

it especially refers to the following structures:

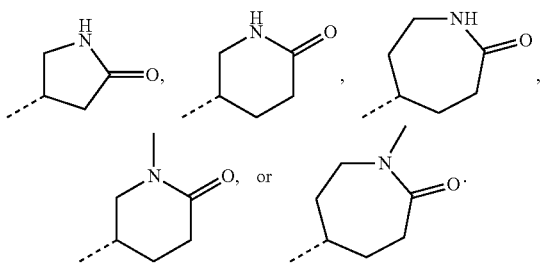

Examples of a "group of the structure ($R^{2-B}$):

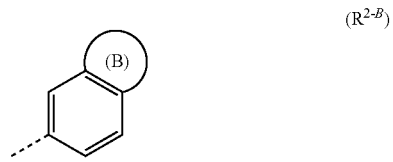

wherein ring (B) represents a non-aromatic 5-membered ring fused to the phenyl group, wherein ring (B) comprises two heteroatoms independently selected from nitrogen and oxygen; wherein said ring (B) independently is mono- or di-substituted, wherein one of said substituents is oxo, and the other substituent, if present, is $C_3$-alkyl" are especially the groups 2,3-dihydro-1H-benzo[d]imidazol-5-yl, 2,3-dihydro-1H-benzo[d]imidazol-6-yl, 2,3-dihydrobenzo[d]oxazol-5-yl, and 2,3-dihydrobenzo[d]oxazol-6-yl wherein said groups are independently mono- or di-substituted at the fragment corresponding to ring (B) as defined before. Particular examples are 1-methyl-2-oxo-2,3-dihydro-1H-benzo[d]imidazol-5-yl, or 2-oxo-2,3-dihydrobenzo[d]oxazol-6-yl].

The term "cyano" refers to a group —CN.

The term "oxo" refers to a group =O which is preferably attached to a chain or ring carbon or sulfur atom as for example in a carbonyl group —(CO)— (or a sulfonyl group —(SO$_2$)—).

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

Further embodiments of the invention are presented hereinafter:

2) A second embodiment relates to compounds according to embodiment 1), wherein $Ar^1$ represents phenyl which is mono-, di- or tri-substituted, wherein the substituents are independently selected from halogen, methyl, cyano, methoxy, trifluoromethyl, and ethynyl (especially from halogen, methyl, cyano, and methoxy); wherein at least one of said substituents is attached in a meta- and/or in para-position of said phenyl,
  wherein, if present, the substituent in para-position is preferably selected from halogen, methyl, cyano, methoxy, trifluoromethyl, and ethynyl (most preferably from halogen, methyl, cyano, and methoxy); and
  wherein, if present, the substituent in meta-position is preferably halogen.

3) Another embodiment relates to compounds according to embodiment 1), wherein $Ar^1$ represents phenyl which is mono-, di- or tri-substituted, wherein
  one of said substituents is attached in meta-position of said phenyl, wherein said substituent is halogen; and the remaining substituent(s), if present, is/are halogen (especially fluoro); or
  one of said substituents is attached in para-position of said phenyl, wherein said substituent is independently selected from methyl, cyano, and methoxy; and the remaining substituent(s), if present, is/are halogen (especially fluoro).

4) Another embodiment relates to compounds according to embodiment 1), wherein $Ar^1$ represents a phenyl group of the structure

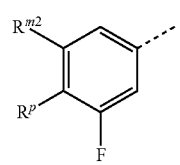

(Ar-I)

wherein
  $R^{m2}$ represents hydrogen or fluoro; and
  $R^p$ represents independently halogen (especially fluoro or chloro), methyl, cyano, or methoxy (notably $R^p$ represents fluoro, chloro, or methyl); or
  $R^{m2}$ represents hydrogen or fluoro; and
  $R^p$ represents hydrogen.

5) Another embodiment relates to compounds according to embodiment 1), wherein $Ar^1$ represents a phenyl group of the structure

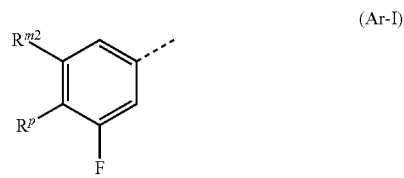

wherein
  $R^{m2}$ represents halogen (especially fluoro); and
  $R^p$ represents hydrogen, halogen (especially fluoro or chloro), methyl, cyano, or methoxy (notably $R^p$ represents fluoro, chloro, or methyl).

6) Another embodiment relates to compounds according to embodiment 1), wherein $Ar^1$ represents

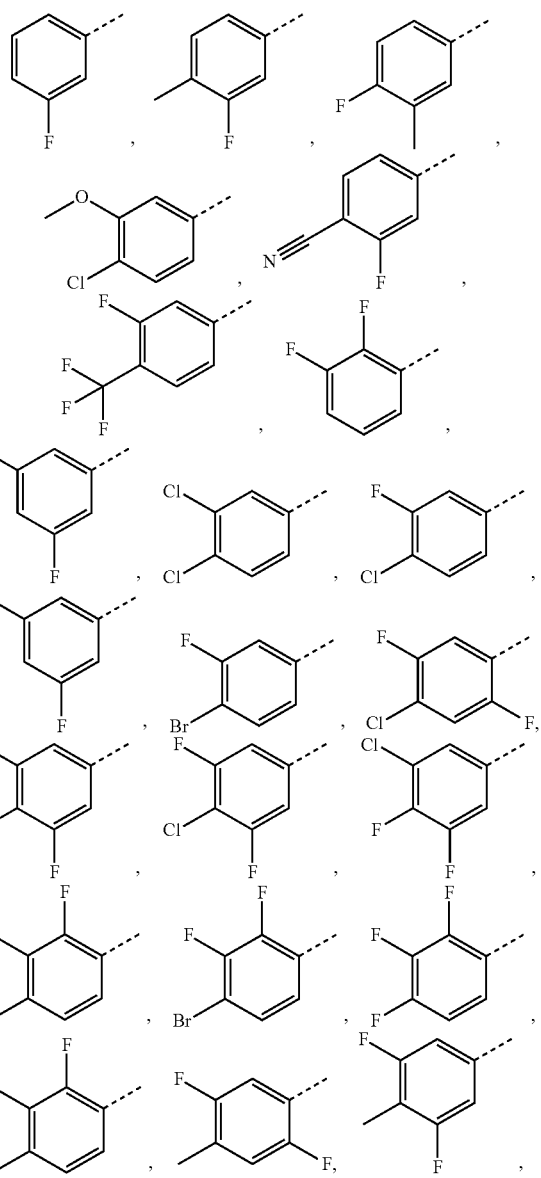

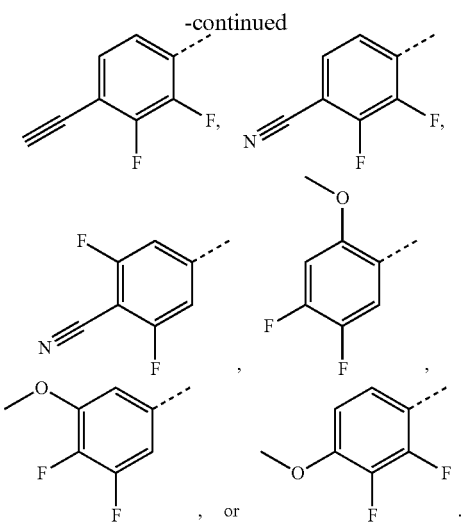

In a sub-embodiment of embodiment 6), $Ar^1$ represents 3,4,5-trifluorophenyl.

7) Another embodiment relates to compounds according to any one of embodiments 1) to 6), wherein $R^1$ represents
hydroxy;
methoxy;
—O—CO—$C_{1-3}$-alkyl (especially —O—CO-methyl);
—O—CH$_2$-HET$^1$ wherein HET$^1$ represents a 5-membered heteroaryl (especially oxazolyl, thiazolyl, or imidazolyl) wherein said 5-membered heteroaryl independently is unsubstituted or mono-substituted with methyl; or
—O—CH$_2$—CO—$R^{1X}$ wherein $R^{1X}$ represents
-hydroxy;
methoxy;
morpholin-4-yl; or 8) Another embodiment relates to compounds according to any one of embodiments 1) to 6), wherein $R^1$ represents hydroxy.

9) Another embodiment relates to compounds according to any one of embodiments 1) to 6), wherein $R^1$ represents methoxy.

10) Another embodiment relates to compounds according to any one of embodiments 1) to 9), wherein A represents 1,2,3-triazole-1,4-diyl or isoxazole-3,5-diyl (especially isoxazole-3,5-diyl, in particular isoxazole-3,5-diyl wherein $R^2$ is attached at position 3, or isoxazole-3,5-diyl wherein $R^2$ is attached at position 5).

11) Another embodiment relates to compounds according to any one of embodiments 1) to 9), wherein A represents isoxazole-3,5-diyl (in particular isoxazole-3,5-diyl wherein $R^2$ is attached at position 3, or isoxazole-3,5-diyl wherein $R^2$ is attached at position 5).

12) Another embodiment relates to compounds according to any one of embodiments 1) to 9), wherein A represents 4,5-dihydroisoxazole-3,5-diyl.

13) Another embodiment relates to compounds according to any one of embodiments 1) to 12), wherein $R^2$ represents
$C_{1-6}$-alkyl (especially tert-butyl);
$C_{1-6}$-alkyl wherein said $C_{1-6}$-alkyl is mono-substituted with $C_{1-3}$-alkoxy (especially methoxy, ethoxy), —CO—$C_{1-4}$-alkoxy, —NH$_2$ or —NH—CO—$C_{1-4}$-alkoxy;
$C_{1-4}$-fluoroalkyl;
$C_{3-6}$-cycloalkyl wherein said $C_{3-6}$-cycloalkyl independently is unsubstituted, mono- or di-substituted wherein the substituents independently are selected from oxo, fluoro, —NH—CO—$C_{1-4}$-alkoxy, $C_{1-3}$-alkyl (especially methyl), $C_{1-3}$-alkoxy (especially methoxy), $C_1$-fluoroalkyl, cyano, —CH$_2$—CN, and —NH—CO—$C_{1-4}$-alkyl wherein said $C_{1-4}$-alkyl is mono-substituted with —NH$_2$ or —NH—CO—$C_{1-4}$-alkoxy;
4- to 6-membered heterocycloalkyl wherein said heterocycloalkyl contains one ring oxygen atom and wherein said 4- to 6-membered heterocycloalkyl independently is unsubstituted or mono-substituted with $C_{1-4}$-alkyl (especially methyl or ethyl);
4- to 6-membered heterocycloalkyl wherein said heterocycloalkyl contains one ring sulfur atom (especially tetrahydro-2H-thiopyranyl) wherein said sulfur atom is unsubstituted or mono-substituted with oxo (=O); or said sulfur atom is disubstituted wherein one substituent is oxo (=O) and the other substituent is selected from oxo (=O), imido (=NH), $C_{1-3}$-alkylimido (=N—$C_{1-3}$-alkyl), 4,4-difluorocyclohexylimido and benzylimido (=N-benzyl) (thus forming a sulfinyl, sulfonyl, sulfonimidoyl, N-alkylsulfonimidoyl N-(4,4-difluorocyclohexyl)-sulfonimidoyl or N-benzylsulfonimidoyl group);
4- to 6-membered heterocycloalkyl wherein said heterocycloalkyl contains one ring nitrogen atom, wherein said nitrogen atom is unsubstituted or mono-substituted with
$C_{1-6}$-alkyl;
—CO—$C_{1-6}$-alkyl; —CO—$C_{4-6}$-cycloalkyl; —CO—$C_{1-3}$-fluoroalkyl; —CO—$C_{1-4}$-alkoxy; —CO—NH—$C_{1-4}$-alkyl;
—SO$_2$—$C_{1-4}$-alkyl;
—CH$_2$—$C_{3-6}$-cycloalkyl;
—CO—$C_{1-6}$-alkyl wherein the $C_{1-6}$-alkyl is mono-substituted with amino;
—CH$_2$-oxetanyl;
thiazol-2-yl; oxazol-2-yl; benzo[d]thiazol-2-yl;
—CO-benzyloxy;
—CO—NH—$C_{3-6}$-cycloalkyl;
—CO—$NR^{N31}R^{N32}$ wherein $R^{N31}$ and $R^{N32}$ both independently represent $C_{1-3}$-alkyl (especially methyl or ethyl);
—CO—$NR^{N41}R^{N42}$ wherein $R^{N41}$ and $R^{N42}$ together with the nitrogen atom to which they are attached form a 5- or 6-membered heterocycloalkyl (especially a pyrrolidinyl, piperidinyl, or piperazinyl ring) wherein said 5- or 6-membered heterocycloalkyl independently is unsubstituted or mono-substituted with $C_{1-3}$-alkyl (especially methyl);
—SO—$C_{1-6}$-alkyl;
—SO$_2$—$C_{1-3}$-fluoroalkyl;
—SO$_2$—$NR^{N51}R^{N52}$ wherein $R^{N51}$ and $R^{N52}$ both independently represent $C_{1-3}$-alkyl (especially methyl),
—SO$_2$—$NR^{N61}R^{N62}$ wherein $R^{N61}$ and $R^{N62}$ together with the nitrogen atom to which they are attached form a 5- or 6-membered heterocycloalkyl (especially a pyrrolidinyl or piperidinyl, or morpholinyl ring), wherein said 5- or 6-membered heterocycloalkyl independently is unsubstituted or di-substituted with fluoro;

—SO$_2$-phenyl wherein said phenyl is mono-substituted with methyl;

—SO(NH)—C$_{1-6}$-alkyl; or —SO(N—C$_{1-3}$-alkyl)-C$_{1-6}$-alkyl;

and wherein said 4- to 7-membered heterocycloalkyl carries no further substituent in addition to said substituent on the ring nitrogen atom, or carries one further substituent which is C$_{1-4}$-alkyl (especially methyl) (wherein it is understood that such C$_{1-4}$-alkyl is attached to a ring carbon atom);

L-OH, wherein L represents

C$_{1-6}$-alkylene;

chloro-C$_{2-6}$-alkylene;

1-phenyl-ethan-1,1-diyl or 1-(2-fluorophenyl)-ethan-1,1-diyl;

(cyclopropyl)-(pyridin-2-yl)-methylene;

C$_{4-6}$-cycloalkylene wherein said C$_{4-6}$-cycloalkylene independently is unsubstituted, or di-substituted wherein the substituents independently are methyl, or fluoro;

cyclopropylene-(CH$_2$)$_n$—* wherein n represents the integer 0 or 1, and wherein the asterisk indicates the bond which is connected to the —OH group;

4- to 6-membered heterocycloalkylene wherein said heterocycloalkylene contains one ring oxygen atom; or 4- to 6-membered heterocycloalkylene wherein said heterocycloalkylene contains one ring nitrogen atom, wherein said nitrogen atom is unsubstituted or mono-substituted with —CO—C$_{1-4}$-alkyl, or —CO—C$_{1-4}$-alkoxy;

5- or 6-membered heteroaryl (especially pyrazolyl, thiazolyl, pyridinyl, pyrimidinyl), wherein said 5- or 6-membered heteroaryl independently is unsubstituted or mono-substituted, wherein the substituents independently are C$_{1-4}$-alkyl (especially methyl), C$_{1-3}$-fluoroalkyl, halogen (especially bromo), or C$_{1-4}$-alkoxy (especially methoxy);

2-oxo-1,2-dihydropyridin-4-yl, 6-oxo-1,6-dihydropyridin-3-yl, or 1-methyl-2-oxo-1,2-dihydropyridin-4-yl;

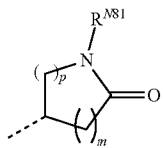

wherein m and p independently represent the integer 1 or 2; and R$^{N81}$ represents hydrogen or C$_{1-4}$-alkyl (especially methyl);

C$_{0-3}$-alkylene-phenyl (especially phenyl, or —CH(CH$_3$)-phenyl); wherein the phenyl independently is unsubstituted, mono-, di-, or tri-substituted, wherein the substituents independently are C$_{1-4}$-alkyl, C$_{1-3}$-fluoroalkyl, halogen (especially fluoro or chloro), hydroxy, C$_{1-4}$-alkoxy (especially methoxy), or C$_{1-4}$-fluoroalkoxy (especially difluoromethoxy);

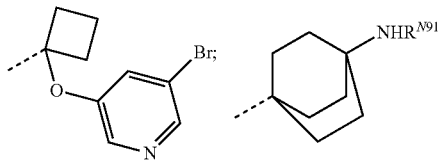

wherein R$^{N91}$ represents hydrogen or —CO—C$_{1-4}$-alkoxy (especially —CO-tert-butoxy);

or R$^2$ represents a group of the structure (R$^{2-B}$):

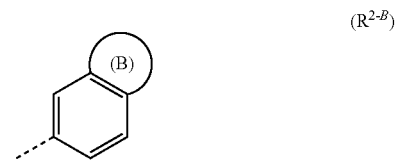

wherein ring (B) represents a non-aromatic 5-membered ring fused to the phenyl group, wherein ring (B) comprises two heteroatoms independently selected from nitrogen and oxygen; wherein said ring (B) independently is mono- or di-substituted, wherein one of said substituents is oxo, and the other substituent, if present, is C$_{1-3}$-alkyl (especially methyl) [notably such group (R$^{2-B}$) is 1-methyl-2-oxo-2,3-dihydro-1H-benzo[d]imidazol-5-yl, or 2-oxo-2,3-dihydrobenzo[d]oxazol-6-yl].

14) Another embodiment relates to compounds according to any one of embodiments 1) to 12), wherein R$^2$ represents C$_{1-6}$-alkyl (especially tert-butyl);

C$_{1-6}$-alkyl wherein said C$_{1-6}$-alkyl is mono-substituted with C$_{1-3}$-alkoxy (especially methoxy, ethoxy), —CO—C$_{1-4}$-alkoxy, —NH$_2$ or —NH—CO—C$_{1-4}$-alkoxy;

C$_{1-4}$-fluoroalkyl;

C$_{3-6}$-cycloalkyl wherein said C$_{3-6}$-cycloalkyl independently is unsubstituted, mono- or di-substituted wherein the substituents independently are selected from oxo, fluoro, —NH—CO—C$_{1-4}$-alkoxy, C$_{1-3}$-alkyl (especially methyl), C$_{1-3}$-alkoxy (especially methoxy), C$_1$-fluoroalkyl, cyano, —CH$_2$—CN, and —NH—CO—C$_{1-4}$-alkyl wherein said C$_{1-4}$-alkyl is mono-substituted with —NH$_2$ or —NH—CO—C$_{1-4}$-alkoxy;

4- to 6-membered heterocycloalkyl wherein said heterocycloalkyl contains one ring oxygen atom and wherein said 4- to 6-membered heterocycloalkyl independently is unsubstituted or mono-substituted with C$_{1-4}$-alkyl (especially methyl or ethyl);

4- to 6-membered heterocycloalkyl wherein said heterocycloalkyl contains one ring sulfur atom (especially tetrahydro-2H-thiopyranyl) wherein said sulfur atom is unsubstituted or mono-substituted with oxo (═O); or said sulfur atom is disubstituted wherein one substituent is oxo (═O) and the other substituent is selected from oxo (═O), imido (═NH), C$_{1-3}$-alkylimido (═N—C$_{1-3}$-alkyl), 4,4-difluorocyclohexylimido and benzylimido (═N-benzyl) (thus forming a sulfinyl, sulfonyl, sulfonimidoyl, N-alkylsulfonimidoyl N-(4,4-difluorocyclohexyl)-sulfonimidoyl or N-benzylsulfonimidoyl group);

4- to 6-membered heterocycloalkyl wherein said heterocycloalkyl contains one ring nitrogen atom, wherein said nitrogen atom is unsubstituted or mono-substituted with $C_{1-6}$-alkyl;

—CO—$C_{1-6}$-alkyl; —CO—$C_{4-6}$-cycloalkyl; —CO—$C_{1-3}$-fluoroalkyl; —CO—$C_{1-4}$-alkoxy; —CO—NH—$C_{1-4}$-alkyl;

—SO$_2$—$C_{1-4}$-alkyl;

—CH$_2$—$C_{3-6}$-cycloalkyl;

thiazol-2-yl; oxazol-2-yl; benzo[d]thiazol-2-yl;

—CO-benzyloxy;

—CO—NH—$C_{3-6}$-cycloalkyl;

—CO—NR$^{N31}$R$^{N32}$ wherein R$^{N31}$ and R$^{N32}$ both independently represent $C_{1-3}$-alkyl (especially methyl or ethyl);

—CO—NR$^{N41}$R$^{N42}$ wherein R$^{N41}$ and R$^{N42}$ together with the nitrogen atom to which they are attached form a 5- or 6-membered heterocycloalkyl (especially a pyrrolidinyl, piperidinyl, or piperazinyl ring) wherein said 5- or 6-membered heterocycloalkyl independently is unsubstituted or mono-substituted with $C_{1-3}$-alkyl (especially methyl);

—SO—$C_{1-6}$-alkyl;

—SO$_2$—$C_{1-3}$-fluoroalkyl;

—SO$_2$—NR$^{N51}$R$^{N52}$ wherein R$^{N51}$ and R$^{N52}$ both independently represent $C_{1-3}$-alkyl (especially methyl), —SO$_2$—NR$^{N61}$R$^{N62}$ wherein R$^{N61}$ and R$^{N62}$ together with the nitrogen atom to which they are attached form a 5- or 6-membered heterocycloalkyl (especially a pyrrolidinyl or piperidinyl, or morpholinyl ring), wherein said 5- or 6-membered heterocycloalkyl independently is unsubstituted or di-substituted with fluoro;

—SO$_2$-phenyl wherein said phenyl is mono-substituted with methyl;

—SO(NH)—$C_{1-6}$-alkyl; or —SO(N—$C_{1-3}$-alkyl)-$C_{1-6}$-alkyl;

and wherein said 4- to 7-membered heterocycloalkyl carries no further substituent in addition to said substituent on the ring nitrogen atom, or carries one further substituent which is $C_{1-4}$-alkyl (especially methyl) (wherein it is understood that such $C_{1-4}$-alkyl is attached to a ring carbon atom);

L-OH, wherein L represents
$C_{1-6}$-alkylene;
chloro-$C_{2-6}$-alkylene;
1-phenyl-ethan-1,1-diyl or 1-(2-fluorophenyl)-ethan-1,1-diyl;
$C_{4-6}$-cycloalkylene wherein said $C_{4-6}$-cycloalkylene independently is unsubstituted, or di-substituted wherein the substituents independently are methyl, or fluoro;
cyclopropylene-(CH$_2$)$_n$—* wherein n represents the integer 0 or 1, and wherein the asterisk indicates the bond which is connected to the —OH group;
4- to 6-membered heterocycloalkylene wherein said heterocycloalkylene contains one ring oxygen atom; or
4- to 6-membered heterocycloalkylene wherein said heterocycloalkylene contains one ring nitrogen atom, wherein said nitrogen atom is unsubstituted or mono-substituted with —CO—$C_{1-4}$-alkyl, or —CO—$C_{1-4}$-alkoxy;

2-oxo-1,2-dihydropyridin-4-yl, 6-oxo-1,6-dihydropyridin-3-yl, or 1-methyl-2-oxo-1,2-dihydropyridin-4-yl;

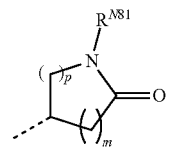

wherein m and p independently represent the integer 1 or 2; and R$^{N81}$ represents hydrogen or $C_{1-4}$-alkyl (especially methyl);

—CH(CH$_3$)-phenyl);

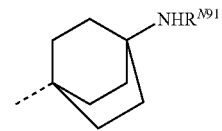

wherein R$^{N91}$ represents hydrogen or —CO—$C_{1-4}$-alkoxy (especially —CO-tert-butoxy);

or R$^2$ represents a group of the structure (R$^{2-B}$):

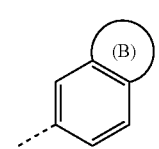

(R$^{2-B}$)

wherein ring (B) represents a non-aromatic 5-membered ring fused to the phenyl group, wherein ring (B) comprises two heteroatoms independently selected from nitrogen and oxygen; wherein said ring (B) independently is mono- or di-substituted, wherein one of said substituents is oxo, and the other substituent, if present, is $C_{1-3}$-alkyl (especially methyl) [notably such group (R$^{2-B}$) is 1-methyl-2-oxo-2,3-dihydro-1H-benzo[d]imidazol-5-yl, or 2-oxo-2,3-dihydrobenzo[d]oxazol-6-yl].

15) Another embodiment relates to compounds according to any one of embodiments 1) to 12), wherein R$^2$ represents
$C_{1-6}$-alkyl (especially tert-butyl);
$C_{1-6}$-alkyl wherein said $C_{1-6}$-alkyl is mono-substituted with $C_{1-3}$-alkoxy (especially methoxy, ethoxy), —CO—$C_{1-4}$-alkoxy, —NH$_2$ or —NH—CO—$C_{1-4}$-alkoxy;
$C_{1-4}$-fluoroalkyl;
$C_{3-6}$-cycloalkyl wherein said $C_{3-6}$-cycloalkyl independently is unsubstituted, mono- or di-substituted wherein the substituents independently are selected from oxo, fluoro, —NH—CO—$C_{1-4}$-alkoxy, $C_{1-3}$-alkyl (especially methyl), $C_{1-3}$-alkoxy (especially methoxy), $C_1$-fluoroalkyl, cyano, and —CH$_2$—CN;
4- to 6-membered heterocycloalkyl wherein said heterocycloalkyl contains one ring oxygen atom and wherein said 4- to 6-membered heterocycloalkyl independently is unsubstituted or mono-substituted with $C_{1-4}$-alkyl (especially methyl or ethyl);
L-OH, wherein L represents
$C_{1-6}$-alkylene;
$C_{4-6}$-cycloalkylene wherein said $C_{4-6}$-cycloalkylene independently is unsubstituted, or di-substituted wherein the substituents independently are methyl, or fluoro; or cyclopropylene-(CH$_2$)$_n$—* wherein n represents the integer 0 or 1, and wherein the asterisk indicates the bond which is connected to the —OH group; or
—CH(CH$_3$)-phenyl).

16) Another embodiment relates to compounds according to any one of embodiments 1) to 12), wherein R$^2$ represents
C$_{1-6}$-alkyl (especially tert-butyl);
C$_{1-6}$-alkyl wherein said C$_{1-6}$-alkyl is mono-substituted with C$_{1-3}$-alkoxy (especially methoxy, ethoxy);
C$_{1-4}$-fluoroalkyl; or
L-OH, wherein L represents
C$_{1-6}$-alkylene;
C$_{4-6}$-cycloalkylene wherein said C$_{4-6}$-cycloalkylene independently is unsubstituted; or
cyclopropylene-(CH$_2$)$_n$—* wherein n represents the integer 0 or 1, and wherein the asterisk indicates the bond which is connected to the —OH group.

17) Another embodiment relates to compounds according to any one of embodiments 1) to 12), wherein R$^2$ represents
C$_{1-6}$-alkyl (especially tert-butyl);
cyclobutyl, or cyclopentyl;
cyclohexyl which is mono- or di-substituted wherein the substituents independently are oxo, fluoro, or —NH—CO—C$_{1-4}$-alkoxy;
4- to 6-membered heterocycloalkyl wherein said heterocycloalkyl contains one ring oxygen atom;
4- to 7-membered heterocycloalkyl wherein said heterocycloalkyl contains one ring nitrogen atom, wherein said nitrogen atom is unsubstituted or mono-substituted with C$_{1-6}$-alkyl, —CO—C$_{1-6}$-alkyl, —CO—C$_{4-6}$-cycloalkyl, —CO—C$_{1-3}$-fluoroalkyl, —CO—C$_{1-4}$-alkoxy, —CO—NH—C$_{1-4}$-alkyl, —SO$_2$—C$_{1-4}$-alkyl, —SO$_2$—NH—C$_{1-4}$-alkyl, —CH$_2$—C$_{3-6}$-cycloalkyl, —CO—C$_{1-6}$-alkyl wherein the C$_{1-6}$-alkyl is mono-substituted with amino, —CH$_2$-oxetanyl, thiazol-2-yl, oxazol-2-yl, or benzo[d]thiazol-2-yl;
L-OH, wherein L represents
C$_{4-6}$-cycloalkylene wherein said C$_{4-6}$-cycloalkylene independently is unsubstituted or mono- or di-substituted wherein the substituents independently are methyl, or fluoro;
4- to 7-membered heterocycloalkylene wherein said heterocycloalkylene contains one ring oxygen atom; or
4- to 7-membered heterocycloalkylene wherein said heterocycloalkylene contains one ring nitrogen atom, wherein said nitrogen atom is unsubstituted or mono-substituted with —CO—C$_{1-4}$-alkyl, or —CO—C$_{1-4}$-alkoxy;
or R$^2$ represents a group of the structure (R$^{2-B}$):

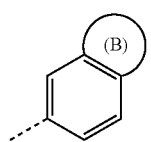

(R$^{2-B}$)

wherein ring (B) represents a non-aromatic 5-membered ring fused to the phenyl group, wherein ring (B) comprises two heteroatoms independently selected from nitrogen and oxygen; wherein said ring (B) independently is mono- or di-substituted, wherein one of said substituents is oxo, and the other substituent, if present, is C$_{1-3}$-alkyl (especially methyl) [notably such group (R$^{2-B}$) is 1-methyl-2-oxo-2,3-dihydro-1H-benzo[d]imidazol-5-yl, or 2-oxo-2,3-dihydrobenzo[d]oxazol-6-yl].

18) Another embodiment relates to compounds according to any one of embodiments 1) to 12), wherein R$^2$ represents
tert-butyl;
cyclobutyl, or cyclopentyl;
cyclohexyl which is mono- or di-substituted wherein the substituents independently are oxo, fluoro, or —NH—CO—C$_{1-4}$-alkoxy;
4- to 6-membered heterocycloalkyl wherein said heterocycloalkyl contains one ring oxygen atom;
4- to 7-membered heterocycloalkyl wherein said heterocycloalkyl contains one ring nitrogen atom, wherein said nitrogen atom is unsubstituted or mono-substituted with C$_{1-6}$-alkyl, —CO—C$_{1-6}$-alkyl, —CO—C$_{4-6}$-cycloalkyl, —CO—C$_{1-3}$-fluoroalkyl, —CO—C$_{1-4}$-alkoxy, —CO—NH—C$_{1-4}$-alkyl, —SO$_2$—C$_{1-4}$-alkyl, —CH$_2$—C$_{3-6}$-cycloalkyl, thiazol-2-yl, oxazol-2-yl, or benzo[d]thiazol-2-yl;
L-OH, wherein L represents
C$_{4-6}$-cycloalkylene wherein said C$_{4-6}$-cycloalkylene independently is unsubstituted; or
4- to 7-membered heterocycloalkylene wherein said heterocycloalkylene contains one ring nitrogen atom, wherein said nitrogen atom is unsubstituted or mono-substituted with —CO—C$_{1-4}$-alkoxy; or
2-oxo-1,2-dihydropyridin-4-yl.

19) Another embodiment relates to compounds according to any one of embodiments 1) to 12), wherein R$^2$ represents C$_{1-6}$-alkyl (especially tert-butyl).

20) The invention, thus, relates to compounds of the Formula (I) as defined in embodiment 1), or to such compounds further limited by the characteristics of any one of embodiments 2) to 19), under consideration of their respective dependencies; to pharmaceutically acceptable salts thereof; and to the use of such compounds as further described herein below. For avoidance of any doubt, especially the following embodiments relating to the compounds of Formula (I) are thus possible and intended and herewith specifically disclosed in individualized form: 1, 2+1, 3+1, 4+1, 5+1, 6+1, 7+1, 7+2+1, 7+3+1, 7+4+1, 7+5+1, 7+6+1, 8+1, 8+2+1, 8+3+1, 8+4+1, 8+5+1, 8+6+1, 9+1, 9+2+1, 9+3+1, 9+4+1, 9+5+1, 9+6+1, 10+1, 10+2+1, 10+3+1, 10+4+1, 10+5+1, 10+6+1, 10+7+1, 10+7+2+1, 10+7+3+1, 10+7+4+1, 10+7+5+1, 10+7+6+1, 10+8+1, 10+8+2+1, 10+8+3+1, 10+8+4+1, 10+8+5+1, 10+8+6+1, 10+9+1, 10+9+2+1, 10+9+3+1, 10+9+4+1, 10+9+5+1, 10+9+6+1, 11+1, 11+2+1, 11+3+1, 11+4+1, 11+5+1, 11+6+1, 11+7+1, 11+7+2+1, 11+7+3+1, 11+7+4+1, 11+7+5+1, 11+7+6+1, 11+8+1, 11+8+2+1, 11+8+3+1, 11+8+4+1, 11+8+5+1, 11+8+6+1, 11+9+1, 11+9+2+1, 11+9+3+1, 11+9+4+1, 11+9+5+1, 11+9+6+1, 12+1, 12+2+1, 12+3+1, 12+4+1, 12+5+1, 12+6+1, 12+7+1, 12+7+2+1, 12+7+3+1, 12+7+4+1, 12+7+5+1, 12+7+6+1, 12+8+1, 12+8+2+1, 12+8+3+1, 12+8+4+1, 12+8+5+1, 12+8+6+1, 12+9+1, 12+9+2+1, 12+9+3+1, 12+9+4+1, 12+9+5+1, 12+9+6+1, 13+1, 13+2+1, 13+3+1, 13+4+1, 13+5+1, 13+6+1, 13+7+1, 13+7+2+1, 13+7+3+1, 13+7+4+1, 13+7+5+1, 13+7+6+1, 13+8+1, 13+8+2+1, 13+8+3+1, 13+8+4+1, 13+8+5+1, 13+8+6+1, 13+9+1, 13+9+2+1, 13+9+3+1, 13+9+4+1, 13+9+5+1, 13+9+6+1, 13+10+1, 13+10+2+1, 13+10+3+1, 13+10+4+1, 13+10+5+1, 13+10+6+1, 13+10+7+1, 13+10+7+2+1, 13+10+7+3+1, 13+10+7+4+1, 13+10+7+5+1, 13+10+7+6+1, 13+10+8+1, 13+10+8+2+1, 13+10+8+3+1, 13+10+8+4+1, 13+10+8+5+1, 13+10+8+6+1, 13+10+9+1, 13+10+9+2+1, 13+10+9+3+1, 13+10+9+4+1, 13+10+9+5+1, 13+10+9+

6+1, 13+11+1, 13+11+2+1, 13+11+3+1, 13+11+4+1, 13+11+5+1, 13+11+6+1, 13+11+7+1, 13+11+7+2+1, 13+11+7+3+1, 13+11+7+4+1, 13+11+7+5+1, 13+11+7+6+1, 13+11+8+1, 13+11+8+2+1, 13+11+8+3+1, 13+11+8+4+1, 13+11+8+5+1, 13+11+8+6+1, 13+11+9+1, 13+11+9+2+1, 13+11+9+3+1, 13+11+9+4+1, 13+11+9+5+1, 13+11+9+6+1, 13+12+1, 13+12+2+1, 13+12+3+1, 13+12+4+1, 13+12+5+1, 13+12+6+1, 13+12+7+1, 13+12+7+2+1, 13+12+7+3+1, 13+12+7+4+1, 13+12+7+5+1, 13+12+7+6+1, 13+12+8+1, 13+12+8+2+1, 13+12+8+3+1, 13+12+8+4+1, 13+12+8+5+1, 13+12+8+6+1, 13+12+9+1, 13+12+9+2+1, 13+12+9+3+1, 13+12+9+4+1, 13+12+9+5+1, 13+12+9+6+1, 14+1, 14+2+1, 14+3+1, 14+4+1, 14+5+1, 14+6+1, 14+7+1, 14+7+2+1, 14+7+3+1, 14+7+4+1, 14+7+5+1, 14+7+6+1, 14+8+1, 14+8+2+1, 14+8+3+1, 14+8+4+1, 14+8+5+1, 14+8+6+1, 14+9+1, 14+9+2+1, 14+9+3+1, 14+9+4+1, 14+9+5+1, 14+9+6+1, 14+10+1, 14+10+2+1, 14+10+3+1, 14+10+4+1, 14+10+5+1, 14+10+6+1, 14+10+7+1, 14+10+7+2+1, 14+10+7+3+1, 14+10+7+4+1, 14+10+7+5+1, 14+10+7+6+1, 14+10+8+1, 14+10+8+2+1, 14+10+8+3+1, 14+10+8+4+1, 14+10+8+5+1, 14+10+8+6+1, 14+10+9+1, 14+10+9+2+1, 14+10+9+3+1, 14+10+9+4+1, 14+10+9+5+1, 14+10+9+6+1, 14+11+1, 14+11+2+1, 14+11+3+1, 14+11+4+1, 14+11+5+1, 14+11+6+1, 14+11+7+1, 14+11+7+2+1, 14+11+7+3+1, 14+11+7+4+1, 14+11+7+5+1, 14+11+7+6+1, 14+11+8+1, 14+11+8+2+1, 14+11+8+3+1, 14+11+8+4+1, 14+11+8+5+1, 14+11+8+6+1, 14+11+9+1, 14+11+9+2+1, 14+11+9+3+1, 14+11+9+4+1, 14+11+9+5+1, 14+11+9+6+1, 14+12+1, 14+12+2+1, 14+12+3+1, 14+12+4+1, 14+12+5+1, 14+12+6+1, 14+12+7+1, 14+12+7+2+1, 14+12+7+3+1, 14+12+7+4+1, 14+12+7+5+1, 14+12+7+6+1, 14+12+8+1, 14+12+8+2+1, 14+12+8+3+1, 14+12+8+4+1, 14+12+8+5+1, 14+12+8+6+1, 14+12+9+1, 14+12+9+2+1, 14+12+9+3+1, 14+12+9+4+1, 14+12+9+5+1, 14+12+9+6+1, 15+1, 15+2+1, 15+3+1, 15+4+1, 15+5+1, 15+6+1, 15+7+1, 15+7+2+1, 15+7+3+1, 15+7+4+1, 15+7+5+1, 15+7+6+1, 15+8+1, 15+8+2+1, 15+8+3+1, 15+8+4+1, 15+8+5+1, 15+8+6+1, 15+9+1, 15+9+2+1, 15+9+3+1, 15+9+4+1, 15+9+5+1, 15+9+6+1, 15+10+1, 15+10+2+1, 15+10+3+1, 15+10+4+1, 15+10+5+1, 15+10+6+1, 15+10+7+1, 15+10+7+2+1, 15+10+7+3+1, 15+10+7+4+1, 15+10+7+5+1, 15+10+7+6+1, 15+10+8+1, 15+10+8+2+1, 15+10+8+3+1, 15+10+8+4+1, 15+10+8+5+1, 15+10+8+6+1, 15+10+9+1, 15+10+9+2+1, 15+10+9+3+1, 15+10+9+4+1, 15+10+9+5+1, 15+10+9+6+1, 15+11+1, 15+11+2+1, 15+11+3+1, 15+11+4+1, 15+11+5+1, 15+11+6+1, 15+11+7+1, 15+11+7+2+1, 15+11+7+3+1, 15+11+7+4+1, 15+11+7+5+1, 15+11+7+6+1, 15+11+8+1, 15+11+8+2+1, 15+11+8+3+1, 15+11+8+4+1, 15+11+8+5+1, 15+11+8+6+1, 15+11+9+1, 15+11+9+2+1, 15+11+9+3+1, 15+11+9+4+1, 15+11+9+5+1, 15+11+9+6+1, 15+12+1, 15+12+2+1, 15+12+3+1, 15+12+4+1, 15+12+5+1, 15+12+6+1, 15+12+7+1, 15+12+7+2+1, 15+12+7+3+1, 15+12+7+4+1, 15+12+7+5+1, 15+12+7+6+1, 15+12+8+1, 15+12+8+2+1, 15+12+8+3+1, 15+12+8+4+1, 15+12+8+5+1, 15+12+8+6+1, 15+12+9+1, 15+12+9+2+1, 15+12+9+3+1, 15+12+9+4+1, 15+12+9+5+1, 15+12+9+6+1, 16+1, 16+2+1, 16+3+1, 16+4+1, 16+5+1, 16+6+1, 16+7+1, 16+7+2+1, 16+7+3+1, 16+7+4+1, 16+7+5+1, 16+7+6+1, 16+8+1, 16+8+2+1, 16+8+3+1, 16+8+4+1, 16+8+5+1, 16+8+6+1, 16+9+1, 16+9+2+1, 16+9+3+1, 16+9+4+1, 16+9+5+1, 16+9+6+1, 16+10+1, 16+10+2+1, 16+10+3+1, 16+10+4+1, 16+10+5+1, 16+10+6+1, 16+10+7+1, 16+10+7+2+1, 16+10+7+3+1, 16+10+7+4+1, 16+10+7+5+1, 16+10+7+6+1, 16+10+8+1, 16+10+8+2+1, 16+10+8+3+1, 16+10+8+4+1, 16+10+8+5+1, 16+10+8+6+1, 16+10+9+1, 16+10+9+2+1, 16+10+9+3+1, 16+10+9+4+1, 16+10+9+5+1, 16+10+9+6+1, 16+11+1, 16+11+2+1, 16+11+3+1, 16+11+4+1, 16+11+5+1, 16+11+6+1, 16+11+7+1, 16+11+7+2+1, 16+11+7+3+1, 16+11+7+4+1, 16+11+7+5+1, 16+11+7+6+1, 16+11+8+1, 16+11+8+2+1, 16+11+8+3+1, 16+11+8+4+1, 16+11+8+5+1, 16+11+8+6+1, 16+11+9+1, 16+11+9+2+1, 16+11+9+3+1, 16+11+9+4+1, 16+11+9+5+1, 16+11+9+6+1, 16+12+1, 16+12+2+1, 16+12+3+1, 16+12+4+1, 16+12+5+1, 16+12+6+1, 16+12+7+1, 16+12+7+2+1, 16+12+7+3+1, 16+12+7+4+1, 16+12+7+5+1, 16+12+7+6+1, 16+12+8+1, 16+12+8+2+1, 16+12+8+3+1, 16+12+8+4+1, 16+12+8+5+1, 16+12+8+6+1, 16+12+9+1, 16+12+9+2+1, 16+12+9+3+1, 16+12+9+4+1, 16+12+9+5+1, 16+12+9+6+1, 17+1, 17+2+1, 17+3+1, 17+4+1, 17+5+1, 17+6+1, 17+7+1, 17+7+2+1, 17+7+3+1, 17+7+4+1, 17+7+5+1, 17+7+6+1, 17+8+1, 17+8+2+1, 17+8+3+1, 17+8+4+1, 17+8+5+1, 17+8+6+1, 17+9+1, 17+9+2+1, 17+9+3+1, 17+9+4+1, 17+9+5+1, 17+9+6+1, 17+10+1, 17+10+2+1, 17+10+3+1, 17+10+4+1, 17+10+5+1, 17+10+6+1, 17+10+7+1, 17+10+7+2+1, 17+10+7+3+1, 17+10+7+4+1, 17+10+7+5+1, 17+10+7+6+1, 17+10+8+1, 17+10+8+2+1, 17+10+8+3+1, 17+10+8+4+1, 17+10+8+5+1, 17+10+8+6+1, 17+10+9+1, 17+10+9+2+1, 17+10+9+3+1, 17+10+9+4+1, 17+10+9+5+1, 17+10+9+6+1, 17+11+1, 17+11+2+1, 17+11+3+1, 17+11+4+1, 17+11+5+1, 17+11+6+1, 17+11+7+1, 17+11+7+2+1, 17+11+7+3+1, 17+11+7+4+1, 17+11+7+5+1, 17+11+7+6+1, 17+11+8+1, 17+11+8+2+1, 17+11+8+3+1, 17+11+8+4+1, 17+11+8+5+1, 17+11+8+6+1, 17+11+9+1, 17+11+9+2+1, 17+11+9+3+1, 17+11+9+4+1, 17+11+9+5+1, 17+11+9+6+1, 17+12+1, 17+12+2+1, 17+12+3+1, 17+12+4+1, 17+12+5+1, 17+12+6+1, 17+12+7+1, 17+12+7+2+1, 17+12+7+3+1, 17+12+7+4+1, 17+12+7+5+1, 17+12+7+6+1, 17+12+8+1, 17+12+8+2+1, 17+12+8+3+1, 17+12+8+4+1, 17+12+8+5+1, 17+12+8+6+1, 17+12+9+1, 17+12+9+2+1, 17+12+9+3+1, 17+12+9+4+1, 17+12+9+5+1, 17+12+9+6+1, 18+1, 18+2+1, 18+3+1, 18+4+1, 18+5+1, 18+6+1, 18+7+1, 18+7+2+1, 18+7+3+1, 18+7+4+1, 18+7+5+1, 18+7+6+1, 18+8+1, 18+8+2+1, 18+8+3+1, 18+8+4+1, 18+8+5+1, 18+8+6+1, 18+9+1, 18+9+2+1, 18+9+3+1, 18+9+4+1, 18+9+5+1, 18+9+6+1, 18+10+1, 18+10+2+1, 18+10+3+1, 18+10+4+1, 18+10+5+1, 18+10+6+1, 18+10+7+1, 18+10+7+2+1, 18+10+7+3+1, 18+10+7+4+1, 18+10+7+5+1, 18+10+7+6+1, 18+10+8+1, 18+10+8+2+1, 18+10+8+3+1, 18+10+8+4+1, 18+10+8+5+1, 18+10+8+6+1, 18+10+9+1, 18+10+9+2+1, 18+10+9+3+1, 18+10+9+4+1, 18+10+9+5+1, 18+10+9+6+1, 18+11+1, 18+11+2+1, 18+11+3+1, 18+11+4+1, 18+11+5+1, 18+11+6+1, 18+11+7+1, 18+11+7+2+1, 18+11+7+3+1, 18+11+7+4+1, 18+11+7+5+1, 18+11+7+6+1, 18+11+8+1, 18+11+8+2+1, 18+11+8+3+1, 18+11+8+4+1, 18+11+8+5+1, 18+11+8+6+1, 18+11+9+1, 18+11+9+2+1, 18+11+9+3+1, 18+11+9+4+1, 18+11+9+5+1, 18+11+9+6+1 18+12+1, 18+12+2+1, 18+12+3+1, 18+12+4+1, 18+12+5+1, 18+12+6+1, 18+12+7+1, 18+12+7+2+1, 18+12+7+3+1, 18+12+7+4+1, 18+12+7+5+1, 18+12+7+6+1, 18+12+8+1, 18+12+8+2+1, 18+12+8+3+1, 18+12+8+4+1, 18+12+8+5+1, 18+12+8+6+1, 18+12+9+1, 18+12+9+2+1, 18+12+9+3+1, 18+12+9+4+1, 18+12+9+5+1, 18+12+9+6+1, 19+1, 19+2+1, 19+3+1, 19+4+1, 19+5+1, 19+6+1, 19+7+1, 19+7+2+1, 19+7+3+1, 19+7+4+1, 19+7+5+1, 19+7+6+1, 19+8+1, 19+8+2+1, 19+8+3+1, 19+8+4+1, 19+8+5+1, 19+8+6+1, 19+9+1, 19+9+2+1, 19+9+3+1, 19+9+4+1, 19+9+5+1, 19+9+6+1, 19+10+1, 19+10+2+1, 19+10+3+1, 19+10+4+1, 19+10+5+1, 19+10+6+1, 19+10+7+1, 19+10+7+2+1, 19+10+7+3+1, 19+10+7+4+1, 19+10+7+5+1, 19+10+7+6+1, 19+10+8+1, 19+10+8+2+1, 19+10+8+3+1, 19+10+8+4+1, 19+10+8+5+1, 19+10+8+6+1, 19+10+9+1, 19+10+9+2+1, 19+10+9+3+1, 19+10+9+4+1, 19+10+9+5+1, 19+10+9+6+1, 19+11+1, 19+11+2+1, 19+11+3+1, 19+11+4+1, 19+11+5+1, 19+11+

6+1, 19+11+7+1, 19+11+7+2+1, 19+11+7+3+1, 19+11+7+4+1, 19+11+7+5+1, 19+11+7+6+1, 19+11+8+1, 19+11+8+2+1, 19+11+8+3+1, 19+11+8+4+1, 19+11+8+5+1, 19+11+8+6+1, 19+11+9+1, 19+11+9+2+1, 19+11+9+3+1, 19+11+9+4+1, 19+11+9+5+1, 19+11+9+6+1, 19+12+1, 19+12+2+1, 19+12+3+1, 19+12+4+1, 19+12+5+1, 19+12+6+1, 19+12+7+1, 19+12+7+2+1, 19+12+7+3+1, 19+12+7+4+1, 19+12+7+5+1, 19+12+7+6+1, 19+12+8+1, 19+12+8+2+1, 19+12+8+3+1, 19+12+8+4+1, 19+12+8+5+1, 19+12+8+6+1, 19+12+9+1, 19+12+9+2+1, 19+12+9+3+1, 19+12+9+4+1, 19+12+9+5+1, 19+12+9+6+1.

In the list above the numbers refer to the embodiments according to their numbering provided hereinabove whereas "+" indicates the dependency from another embodiment. The different individualized embodiments are separated by commas. In other words, "14+10+6+1" for example refers to embodiment 14) depending on embodiment 10), depending on embodiment 6), depending on embodiment 1), i.e. embodiment "14+10+6+1" corresponds to the compounds of formula (I) according to embodiment 1) further limited by all the features of the embodiments 6), 10), and 14).

21) Another aspect of the invention relates to compounds of the Formula (I) according to embodiment 1) which are also compounds of the Formula ($I_P$)

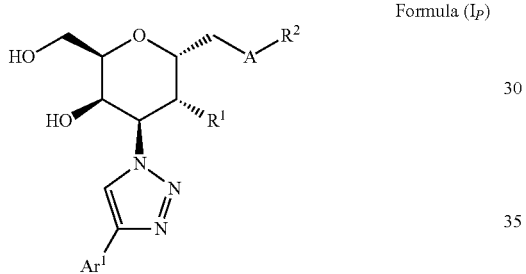

Formula ($I_P$)

wherein
$Ar^1$ represents aryl which is mono-, di-, tri-, or tetra-substituted, wherein the substituents are independently selected from halogen, methyl, cyano, and methoxy; [wherein in particular at least one of said substituents is attached in a meta- or in para-position of said phenyl; wherein, if present, such substituent in para-position is preferably selected from halogen, methyl, cyano, and methoxy; and, if present, such substituent in meta-position is preferably halogen];
$R^1$ represents hydroxy, $C_{1-4}$-alkoxy, —O—CO—$C_{1-3}$-alkyl, or —O—$CH_2$—COOH;
A represents a 5-membered heterocycloalkylene or a 5-membered heteroarylene, wherein said heterocycloalkylene or heteroarylene is 1H-1,2,3-triazole-1,4-diyl, isoxazole-3,5-diyl, or 4,5-dihydroisoxazole-3,5-diyl; and
$R^2$ represents
$C_{1-6}$-alkyl (especially tert-butyl);
$C_{3-6}$-cycloalkyl wherein said $C_{3-6}$-cycloalkyl independently is unsubstituted, mono- or di-substituted wherein the substituents independently are oxo, fluoro, or —NH—CO—$C_{1-4}$-alkoxy; or said $C_{3-6}$-cycloalkyl together with 1,3-dioxolan-2,2-diyl forms a spiro-compound;
4- to 6-membered heterocycloalkyl wherein said heterocycloalkyl contains one ring oxygen atom;
4- to 7-membered heterocycloalkyl wherein said heterocycloalkyl contains one ring nitrogen atom, wherein said nitrogen atom is unsubstituted or mono-substituted with $C_{1-6}$-alkyl, —CO—$C_{1-6}$-alkyl, —CO—$C_{4-6}$-cycloalkyl, —CO—$C_{1-3}$-fluoroalkyl, —CO—$C_{1-4}$-alkoxy, —CO—NH—$C_{1-4}$-alkyl, —$SO_2$—$C_{1-4}$-alkyl, —$SO_2$—NH—$C_{1-4}$-alkyl, —$CH_2$—$C_{3-6}$-cycloalkyl, —CO—$C_{1-6}$-alkyl wherein the $C_{1-6}$-alkyl is mono-substituted with amino, —$CH_2$-oxetanyl, thiazol-2-yl, oxazol-2-yl, or benzo[d]thiazol-2-yl;
L-OH, wherein L represents
$C_{1-6}$-alkylene;
$C_{4-6}$-cycloalkylene wherein said $C_{4-6}$-cycloalkylene independently is unsubstituted, mono- or di-substituted wherein the substituents independently are methyl, fluoro, or —CO—$R^{O2}$ wherein $R^{O2}$ represents hydroxy or $C_{1-4}$-alkoxy;
4- to 7-membered heterocycloalkylene wherein said heterocycloalkylene contains one ring oxygen atom;
4- to 7-membered heterocycloalkylene wherein said heterocycloalkylene contains one ring nitrogen atom, wherein said nitrogen atom is unsubstituted or mono-substituted with —CO—$C_{1-4}$-alkyl, or —CO—$C_{1-4}$-alkoxy;
5- or 6-membered heteroaryl (especially 1H-pyrazolyl, thiazolyl, pyridinyl, pyrimidinyl), wherein said 5- or 6-membered heteroaryl independently is unsubstituted or mono-substituted, wherein the substituents independently are $C_{1-4}$-alkyl (especially methyl), $C_{1-3}$-fluoroalkyl, halogen, $C_{1-4}$-alkoxy (especially methoxy), or $C_{1-4}$-fluoroalkoxy;
2-oxo-1,2-dihydropyridin-4-yl;
phenyl which is mono- or di-substituted, wherein the substituents independently are $C_{1-4}$-alkyl, $C_{1-3}$-fluoroalkyl, halogen, hydroxy, $C_{1-4}$-alkoxy (especially methoxy), or $C_{1-4}$-fluoroalkoxy;
benzyl;
9-membered heteroaryl (especially indazolyl and 1H-benzo[d]imidazolyl);
or $R^2$ represents a group of the structure ($R^{2-B}$):

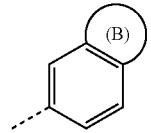

($R^{2-B}$)

wherein ring (B) represents a non-aromatic 5-membered ring fused to the phenyl group, wherein ring (B) comprises two heteroatoms independently selected from nitrogen and oxygen; wherein said ring (B) independently is mono- or di-substituted, wherein one of said substituents is oxo, and the other substituent, if present, is $C_{1-3}$-alkyl (especially methyl) [notably such group ($R^{2-B}$) is 1-methyl-2-oxo-2,3-dihydro-1H-benzo[d]imidazol-5-yl, or 2-oxo-2,3-dihydrobenzo[d]oxazol-6-yl];
wherein the characteristics disclosed in embodiments 2) to 20) are intended to apply mutatis mutandis also to the compounds of Formula ($I_P$) according to embodiment 21).

22) Another embodiment relates to compounds of Formula (I) according to embodiment 1), which are selected from the following compounds:

6-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one;

6-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one;

6-((S)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one;

tert-butyl 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate;

tert-butyl 4-((RS)-5-(((2R,3R,4S,5R,6R)-3-acetoxy-5-hydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;

tert-butyl 4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;

tert-butyl 4-(3-(((2R,3R,4S,5R,6R)-3-acetoxy-5-hydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate;

tert-butyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;

(2R,3R,4R,5R,6R)-2-((5-(tert-butyl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol;

tert-butyl (RS)-3-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate;

(2R,3R,4R,5R,6R)-2-(hydroxymethyl)-6-((5-(tetrahydro-2H-pyran-4-yl)isoxazol-3-yl)methyl)-4-(4-(3,4,5-trifluorophenyl)-1H-1,2,3-triazol-1-yl)tetrahydro-2H-pyran-3,5-diol;

tert-butyl 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)-4-hydroxypiperidine-1-carboxylate;

tert-butyl 4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)piperidine-1-carboxylate;

(2R,3R,4S,5R,6R)-2-(hydroxymethyl)-5-methoxy-6-((5-(tetrahydro-2H-pyran-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-6-((5-cyclopentylisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((5-(1-hydroxycyclohexyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((5-cyclobutylisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((5-(4,4-difluorocyclohexyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

tert-butyl ((1R,4R)-4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)cyclohexyl)carbamate;

tert-butyl ((1S,4S)-4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)cyclohexyl)carbamate;

(2R,3R,4R,5R,6R)-2-(hydroxymethyl)-6-((5-(1-(oxazol-2-yl)piperidin-4-yl)isoxazol-3-yl)methyl)-4-(4-(3,4,5-trifluorophenyl)-1H-1,2,3-triazol-1-yl)tetrahydro-2H-pyran-3,5-diol;

(2R,3R,4R,5R,6R)-2-((5-(1-(benzo[d]thiazol-2-yl)piperidin-4-yl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol;

(2R,3R,4R,5R,6R)-2-(hydroxymethyl)-6-((5-(1-(thiazol-2-yl)piperidin-4-yl)isoxazol-3-yl)methyl)-4-(4-(3,4,5-trifluorophenyl)-1H-1,2,3-triazol-1-yl)tetrahydro-2H-pyran-3,5-diol;

5-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one;

4-((S)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one;

4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one;

4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one;

4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)cyclohexan-1-one;

(2R,3R,4R,5R,6R)-2-((5-(4-hydroxycyclohexyl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol;

(2R,3R,4R,5R,6R)-2-((5-((1R,4R)-4-hydroxycyclohexyl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol;

tert-butyl 4-(3-(((2R,3R,4S,5R,6R)-5-hydroxy-6-(hydroxymethyl)-3-(propionyloxy)-4-(4-(3,4,5-trifluorophenyl)-1H-1,2,3-triazol-1-yl)tetrahydro-2H-pyran-2-yl)methyl)isoxazol-5-yl)piperidine-1-carboxylate;

(2R,3R,4S,5R,6R)-5-hydroxy-6-(hydroxymethyl)-2-((5-(piperidin-4-yl)isoxazol-3-yl)methyl)-4-(4-(3,4,5-trifluorophenyl)-1H-1,2,3-triazol-1-yl)tetrahydro-2H-pyran-3-yl propionate;

tert-butyl 4-(3-(((2R,3R,4S,5R,6R)-3-ethoxy-5-hydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate;

(2R,3R,4S,5R,6R)-5-hydroxy-6-(hydroxymethyl)-2-((5-(piperidin-4-yl)isoxazol-3-yl)methyl)-4-(4-(3,4,5-trifluorophenyl)-1H-1,2,3-triazol-1-yl)tetrahydro-2H-pyran-3-yl propionate;

tert-butyl 4-(3-(((2R,3R,4S,5R,6R)-5-hydroxy-6-(hydroxymethyl)-3-propoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;

2-(((2R,3R,4S,5R,6R)-2-((5-(1-(tert-butoxycarbonyl)piperidin-4-yl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid;

tert-butyl 4-(3-(((2R,3R,4S,5R,6R)-5-hydroxy-6-(hydroxymethyl)-3-(isobutyryloxy)-4-(4-(3,4,5-trifluorophenyl)-1H-1,2,3-triazol-1-yl)tetrahydro-2H-pyran-2-yl)methyl)isoxazol-5-yl)piperidine-1-carboxylate;

(2R,3R,4R,5R,6R)-2-(hydroxymethyl)-6-(((RS)-3-(piperidin-4-yl)-4,5-dihydroisoxazol-5-yl)methyl)-4-(4-(3,4,5-trifluorophenyl)-1H-1,2,3-triazol-1-yl)tetrahydro-2H-pyran-3,5-diol;

1-(4-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one;

1-(4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one;

(2R,3R,4S,5R,6R)-2-(hydroxymethyl)-5-methoxy-6-(((S)-3-(piperidin-4-yl)-4,5-dihydroisoxazol-5-yl)methyl)-4-(4-(3,4,5-trifluorophenyl)-1H-1,2,3-triazol-1-yl)tetrahydro-2H-pyran-3-ol;

(2R,3R,4R,5R,6R)-2-(hydroxymethyl)-6-((5-(piperidin-4-yl)isoxazol-3-yl)methyl)-4-(4-(3,4,5-trifluorophenyl)-1H-1,2,3-triazol-1-yl)tetrahydro-2H-pyran-3,5-diol;

1-(4-((S)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one;

1-(4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one;

(2R,3R,4S,5R,6R)-5-hydroxy-6-(hydroxymethyl)-2-((5-(piperidin-4-yl)isoxazol-3-yl)methyl)-4-(4-(3,4,5-trifluorophenyl)-1H-1,2,3-triazol-1-yl)tetrahydro-2H-pyran-3-yl acetate;

(2R,3R,4S,5R,6R)-2-(hydroxymethyl)-5-methoxy-6-((5-(piperidin-4-yl)isoxazol-3-yl)methyl)-4-(4-(3,4,5-trifluorophenyl)-1H-1,2,3-triazol-1-yl)tetrahydro-2H-pyran-3-ol;

1-(4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidin-1-yl)ethan-1-one;

1-(4-((RS)-3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-5-yl)piperidin-1-yl)ethan-1-one;

1-(4-((S)-3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-5-yl)piperidin-1-yl)ethan-1-one;

1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)ethan-1-one;

(2R,3R,4S,5R,6R)-2-((5-(1-acetylpiperidin-4-yl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl acetate;

(2R,3R,4S,5R,6R)-2-(((RS)-5-(1-acetylpiperidin-4-yl)-4,5-dihydroisoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl acetate;

(2R,3R,4S,5R,6R)-2-(((S)-5-(1-acetylpiperidin-4-yl)-4,5-dihydroisoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl acetate;

ethyl 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate;

4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)-N-ethylpiperidine-1-carboxamide;

(2R,3R,4R,5R,6R)-2-(hydroxymethyl)-6-((5-(1-(methylsulfonyl)piperidin-4-yl)isoxazol-3-yl)methyl)-4-(4-(3,4,5-trifluorophenyl)-1H-1,2,3-triazol-1-yl)tetrahydro-2H-pyran-3,5-diol;

(2R,3R,4R,5R,6R)-2-(hydroxymethyl)-6-((5-(1-methylpiperidin-4-yl)isoxazol-3-yl)methyl)-4-(4-(3,4,5-trifluorophenyl)-1H-1,2,3-triazol-1-yl)tetrahydro-2H-pyran-3,5-diol;

1-(4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidin-1-yl)-2,2-dimethylpropan-1-one;

ethyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;

methyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;

1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-2-methylpropan-1-one;

1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-2,2-dimethylpropan-1-one;

1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)butan-1-one;

N-ethyl-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxamide;

4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N-isopropylpiperidine-1-carboxamide;

(2R,3R,4S,5R,6R)-2-(hydroxymethyl)-5-methoxy-6-((5-(1-methylpiperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((5-(1-isobutylpiperidin-4-yl)isoxazol-3-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((5-(1-(3,3-dimethylbutyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((5-(1-(cyclopropylmethyl)piperidin-4-yl)isoxazol-3-yl)methyl)-2-(hydroxymethyl)-5-methoxy-4- (4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(methylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(propylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((5-(1-(isopropylsulfonyl)piperidin-4-yl)isoxazol-3-yl)methyl)-5-methoxy-4- (4-(3,4,5-trifluorophenyl)-1H-1,2,3-triazol-1-yl)tetrahydro-2H-pyran-3-ol;

1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-3-methylbutan-1-one;

cyclopentyl(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)methanone;

cyclobutyl(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)methanone;

3,3,3-trifluoro-1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)propan-1-one;

N-(tert-butyl)-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxamide;

(RS)-1-(4-(3-(((2R,3R,4S,5R,6R)-5-hydroxy-6-(hydroxymethyl)-3-methoxy-4-(4-(3,4,5-trifluorophenyl)-1H- 1,2,3-triazol-1-yl)tetrahydro-2H-pyran-2-yl)methyl)isoxazol-5-yl)piperidin-1-yl)-2-methylbutan-1-one;

(2R,3R,4S,5R,6R)-2-(hydroxymethyl)-5-methoxy-6-((1-(tetrahydro-2H-pyran-4-yl)-1H-1,2,3-triazol-4-yl)methyl)- 4-(4-(3,4,5-trifluorophenyl)-1H-1,2,3-triazol-1-yl)tetrahydro-2H-pyran-3-ol;

1-(4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidin-1-yl)ethan-1-one;

tert-butyl 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxylate;

1-(4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidin-1-yl)ethan-1-one;

(2R,3R,4S,5R,6R)-2-(hydroxymethyl)-5-methoxy-6-((1-(1-(methylsulfonyl)piperidin-4-yl)-1H-1,2,3-triazol-4-yl)methyl)-4-(4-(3,4,5-trifluorophenyl)-1H-1,2,3-triazol-1-yl)tetrahydro-2H-pyran-3-ol;

N-(tert-butyl)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxamide;

(2R,3R,4S,5R,6R)-2-(hydroxymethyl)-5-methoxy-6-((1-(1-(propylsulfonyl)piperidin-4-yl)-1H-1,2,3-triazol-4-yl)methyl)-4-(4-(3,4,5-trifluorophenyl)-1H-1,2,3-triazol-1-yl)tetrahydro-2H-pyran-3-ol; and (2R,3R,4S,5R,6R)-2-(hydroxymethyl)-6-((1-(1-(isopropylsulfonyl)piperidin-4-yl)-1H-1,2,3-triazol-4-yl)methyl)-5-methoxy-4-(4-(3,4,5-trifluorophenyl)-1H-1,2,3-triazol-1-yl)tetrahydro-2H-pyran-3-ol. 23) In addition to the compounds listed in embodiment 22), further compounds according to embodiment 1) are selected from the following compounds:

tert-butyl 4-((RS)-5-(((2R,3R,4R,5R,6R)-4-(4-(4-chloro-3,5-difluorophenyl)-1H-1,2,3-triazol-1-yl)-3,5- dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(4-chloro-2,3-difluorophenyl)-1H-1,2,3-triazol-1-yl)-3,5- dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(3,4-dichlorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(3,4-difluoro-5-methoxyphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(4-chloro-3-methoxyphenyl)-1H-1,2,3-triazol-1-yl)-3,5- dihydroxy-6-(hydroxymethyl)tetrahydro-2H-pyran-2-yl)methyl)-4,5-dihydroisoxazol-3-yl)piperidine-1-carboxylate;

(RS)-5-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)piperidin-2-one;

tert-butyl 4-((RS)-5-(((2R,3R,4S,5R,6R)-4-(4-(4-chloro-3-fluorophenyl)-1H-1,2,3-triazol-1-yl)-5- hydroxy-6-(hydroxymethyl)-3-methoxytetrahydro-2H-pyran-2-yl)methyl)-4,5-dihydroisoxazol-3-yl)piperidine-1-carboxylate;

4-(3-(((2R,3R,4S,5R,6R)-5-hydroxy-6-(hydroxymethyl)-3-methoxy-4-(4-(3,4,5-trifluorophenyl)-1H-1,2,3- triazol-1-yl)tetrahydro-2H-pyran-2-yl)methyl)isoxazol-5-yl)-1-methylpyridin-2(1H)-one;

(2R,3R,4S,5R,6R)-6-((3-cyclohexylisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

tert-butyl 4-(3-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

tert-butyl 4-(3-(((2R,3R,4S,5R,6R)-4-(4-(3,5-difluorophenyl)-1H-1,2,3-triazol-1-yl)-5-hydroxy-6- (hydroxymethyl)-3-methoxytetrahydro-2H-pyran-2-yl)methyl)isoxazol-5-yl)piperidine-1-carboxylate;

tert-butyl 4-(5-(((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate;

tert-butyl 4-(5-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate;

tert-butyl 4-(5-(((2R,3R,4S,5R,6R)-4-(4-(4-bromo-3-fluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate;

tert-butyl 4-(5-(((2R,3R,4S,5R,6R)-4-(4-(3,5-difluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate;

(2R,3R,4S,5R,6R)-6-((5-(4-bromothiazol-2-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-(((S)-5-cyclohexyl-4,5-dihydroisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

tert-butyl (4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)bicyclo[2.2.2]octan-1-yl)carbamate;

(2R,3R,4S,5R,6R)-6-((5-(4-aminobicyclo[2.2.2]octan-1-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol formate;

tert-butyl 4-hydroxy-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;

4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-4-ol formate;

tert-butyl ((1R,4r)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclohexyl)carbamate;

tert-butyl 4-((RS)-5-(((2R,3R,4S,5R,6R)-4-(4-(3,5-difluoro-4-methylphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-4-(4-(3-fluoro-4-methylphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

(2R,3R,4S,5R,6R)-2-(hydroxymethyl)-5-methoxy-6-((5-((S)-1-(N-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-((R)-1-(N-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol;

tert-butyl 4-((RS)-5-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-4-(4-(4-bromo-2,3-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

(2R,3R,4S,5R,6R)-4-(4-(4-bromo-2,3-difluorophenyl)-1H-1,2,3-triazol-1-yl)-2-(hydroxymethyl)-5-methoxy-6-(((RS)-3-(piperidin-4-yl)-4,5-dihydroisoxazol-5-yl)methyl)tetrahydro-2H-pyran-3-ol formate;

tert-butyl 4-((RS)-5-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-4,5-dihydroisoxazol-3-yl)piperidine-1-carboxylate;

(2R,3R,4S,5R,6R)-2-(hydroxymethyl)-5-methoxy-6-(((RS)-3-(piperidin-4-yl)-4,5-dihydroisoxazol-5-yl)methyl)-4-(4-(2,3,4-trifluorophenyl)-1H-1,2,3-triazol-1-yl)tetrahydro-2H-pyran-3-ol formate;

tert-butyl 4-((RS)-5-(((2R,3R,4S,5R,6R)-4-(4-(4-chloro-3,5-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

(2R,3R,4S,5R,6R)-4-(4-(4-chloro-3,5-difluorophenyl)-1H-1,2,3-triazol-1-yl)-2-(hydroxymethyl)-5-methoxy-6-(((RS)-3-(piperidin-4-yl)-4,5-dihydroisoxazol-5-yl)methyl)tetrahydro-2H-pyran-3-ol formate;

(1R,4r)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-1-(isopropylimino)hexahydro-1l6-thiopyran 1-oxide;

(1S,4s)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-1-(isopropylimino)hexahydro-1l6-thiopyran 1-oxide;

ethyl 4-(3-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

ethyl 4-(3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-5-yl)piperidine-1-carboxylate;

ethyl 4-(3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

(2R,3R,4S,5R,6R)-4-(4-(3,5-difluoro-4-methylphenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(3-fluoro-4-methylphenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(4-bromo-2,3-difluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(4-chloro-3-fluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-2-(hydroxymethyl)-5-methoxy-6-((5-(1-(methylsulfonyl)piperidin-4-yl)isoxazol-3-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(4-chloro-3,5-difluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(3-chloro-5-fluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

1-(4-(3-(((2R,3R,4S,5R,6R)-4-(4-(3,5-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(3-fluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(4-bromo-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-5-yl)piperidin-1-yl)ethan-1-one;

1-(4-(3-(((2R,3R,4S,5R,6R)-4-(4-(4-chloro-3,5-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(3-chloro-5-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

(2R,3R,4S,5R,6R)-4-(4-(4-chloro-2,3-difluorophenyl)-1H-1,2,3-triazol-1-yl)-6-((5-cyclohexylisoxazol-3-yl)methyl)-2-(hydroxymethyl)-5-methoxytetrahydro-2H-pyran-3-ol;

(2R,3R,4S,5R,6R)-6-((5-cyclohexylisoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-4-(4-(3,5-difluoro-4-methylphenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(3-fluoro-4-methylphenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(4-bromo-2,3-difluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(4-chloro-3-fluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-2-(hydroxymethyl)-5-methoxy-6-((5-(tetrahydro-2H-pyran-4-yl)isoxazol-3-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(4-chloro-3,5-difluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-6-((5-(tert-butyl)isoxazol-3-yl)methyl)-4-(4-(3,5-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(3-fluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

(2R,3R,4S,5R,6R)-4-(4-(4-bromo-2,3-difluorophenyl)-1H-1,2,3-triazol-1-yl)-6-((5-(tert-butyl)isoxazol-3-yl)methyl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(4-chloro-3-fluorophenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((5-(tert-butyl)isoxazol-3-yl)methyl)-4-(4-(4-chloro-3,5-difluorophenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-2-(hydroxymethyl)-6-((5-(1-(N-isopropylpropan-2-ylsulfonimidoyl)piperidin-4-yl)isoxazol-3-yl)methyl)-5-methoxy-4-(4-(3,4,5-trifluorophenyl)-1H-1,2,3-triazol-1-yl)tetrahydro-2H-pyran-3-ol;

ethyl 4-(3-(((2R,3R,4S,5R,6R)-4-(4-(4-bromo-2,3-difluorophenyl)-1H-1,2,3-triazol-1-yl)-5-hydroxy-6-(hydroxymethyl)-3-methoxytetrahydro-2H-pyran-2-yl)methyl) isoxazol-5-yl)piperidine-1-carboxylate;

ethyl 4-(3-(((2R,3R,4S,5R,6R)-4-(4-(4-chloro-3,5-difluorophenyl)-1H-1,2,3-triazol-1-yl)-5-hydroxy-6-(hydroxymethyl)-3-methoxytetrahydro-2H-pyran-2-yl)methyl) isoxazol-5-yl)piperidine-1-carboxylate;

ethyl 4-(3-(((2R,3R,4S,5R,6R)-4-(4-(3-chloro-5-fluorophenyl)-1H-1,2,3-triazol-1-yl)-5-hydroxy-6- (hydroxymethyl)-3-methoxytetrahydro-2H-pyran-2-yl)methyl) isoxazol-5-yl)piperidine-1-carboxylate;

ethyl 4-(3-(((2R,3R,4S,5R,6R)-4-(4-(3-fluoro-4-methylphenyl)-1H-1,2,3-triazol-1-yl)-5-hydroxy-6- (hydroxymethyl)-3-methoxytetrahydro-2H-pyran-2-yl)methyl) isoxazol-5-yl)piperidine-1-carboxylate;

ethyl 4-(3-(((2R,3R,4S,5R,6R)-4-(4-(3,5-difluoro-4-methylphenyl)-1H-1,2,3-triazol-1-yl)-5-hydroxy-6-(hydroxymethyl)-3-methoxytetrahydro-2H-pyran-2-yl) methyl)isoxazol-5-yl)piperidine-1-carboxylate;

ethyl 4-(3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl) isoxazol-5-yl)piperidine-1-carboxylate;

(2R,3R,4S,5R,6R)-2-((5-(tert-butyl)isoxazol-3-yl)methyl)-4-(4-(2,3-difluoro-4-methylphenyl)-1H-1,2,3- triazol-1-yl)-5-hydroxy-6-(hydroxymethyl)tetrahydro-2H-pyran-3-yl acetate;

(2R,3R,4R,5R,6R)-2-((5-(tert-butyl)isoxazol-3-yl)methyl)-4-(4-(2,3-difluoro-4-methylphenyl)-1H-1,2,3- triazol-1-yl)-6-(hydroxymethyl)tetrahydro-2H-pyran-3,5-diol;

(2R,3R,4S,5R,6R)-6-((3-(tert-butyl)isoxazol-5-yl)methyl)-2-(hydroxymethyl)-5-methoxy-4-(4-(3,4,5-trifluorophenyl)- 1H-1,2,3-triazol-1-yl)tetrahydro-2H-pyran-3-ol;

(2R,3R,4S,5R,6R)-6-((3-(1-hydroxy-2-methylpropan-2-yl) isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

ethyl 3-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-3-methylbutanoate;

(2R,3R,4S,5R,6R)-2-(hydroxymethyl)-5-methoxy-6-((3-(1-methoxycyclopentyl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(1-methoxycyclohexyl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(3-methyloxetan-3-yl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-6-((3-(3-ethyloxetan-3-yl)isoxazol-5-yl) methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((3-(1-fluorocyclopropyl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((3-(1-(difluoromethyl)cyclopropyl) isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(1-methylcyclopropyl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-6-((3-(2-aminopropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

1-(4-(3-(((2R,3R,4S,5R,6R)-4-(4-(3-chloro-4,5-difluorophenyl)-1H-1,2,3-triazol-1-yl)-5-hydroxy- 6-(hydroxymethyl)-3-methoxytetrahydro-2H-pyran-2-yl)methyl) isoxazol-5-yl)piperidin-1-yl)ethan-1-one;

ethyl 4-(3-(((2R,3R,4S,5R,6R)-4-(4-(3-chloro-4,5-difluorophenyl)-1H-1,2,3-triazol-1-yl)-5-hydroxy-6-(hydroxymethyl)-3-methoxytetrahydro-2H-pyran-2-yl)methyl) isoxazol-5-yl)piperidine-1-carboxylate;

(2R,3R,4S,5R,6R)-6-((5-(tert-butyl)isoxazol-3-yl)methyl)-4-(4-(3-chloro-4,5-difluorophenyl)-1H-1,2,3- triazol-1-yl)-2-(hydroxymethyl)-5-methoxytetrahydro-2H-pyran-3-ol;

(2R,3R,4S,5R,6R)-6-((3-cyclopentylisoxazol-5-yl)methyl)-2-(hydroxymethyl)-5-methoxy-4-(4-(3,4,5-trifluorophenyl)- 1H-1,2,3-triazol-1-yl)tetrahydro-2H-pyran-3-ol;

(2R,3R,4S,5R,6R)-6-((3-cyclobutylisoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((3-cyclobutylisoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-4-(4-(4-chloro-2,3-difluorophenyl)-1H-1,2,3-triazol-1-yl)-6-((5-cyclobutylisoxazol-3-yl)methyl)-2-(hydroxymethyl)-5-methoxytetrahydro-2H-pyran-3-ol;

tert-butyl 4-(3-(((2R,3R,4S,5R,6R)-4-(4-(3-fluorophenyl)-1H-1,2,3-triazol-1-yl)-5-hydroxy-6- (hydroxymethyl)-3-methoxytetrahydro-2H-pyran-2-yl)methyl)isoxazol-5-yl) piperidine-1-carboxylate;

(2R,3R,4S,5R,6R)-2-(hydroxymethyl)-6-((5-(2-hydroxypropan-2-yl)isoxazol-3-yl)methyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((5-(1-hydroxycyclohexyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((5-(1-hydroxycyclopentyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((5-cyclopentylisoxazol-3-yl)methyl)-2-(hydroxymethyl)-5-methoxy-4-(4-(2,3,4-trifluorophenyl)- 1H-1,2,3-triazol-1-yl)tetrahydro-2H-pyran-3-ol;

(2R,3R,4S,5R,6R)-6-((5-(1-hydroxycyclobutyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-((5-(2-hydroxypropan-2-yl)isoxazol-3-yl)methyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-(1- hydroxycyclohexyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-(1- hydroxycyclopentyl)isoxazol-3-yl)methyl)-2-(hydroxymethyl)-5-methoxytetrahydro-2H-pyran-3-ol;

(2R,3R,4S,5R,6R)-6-((5-cyclopentylisoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-(1- hydroxycyclobutyl)isoxazol-3-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-6-((5-(2-hydroxypropan-2-yl)isoxazol-3-yl)methyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((5-(1- hydroxycyclohexyl)isoxazol-3-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((5-(1- hydroxycyclopentyl)isoxazol-3-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((5-cyclopentylisoxazol-3-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((5-(1- hydroxycyclobutyl)isoxazol-3-yl)methyl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(2,5-difluoro-4-methylphenyl)-1H-1,2,3- triazol-1-yl)-2-(hydroxymethyl)-5-methoxytetrahydro-2H-pyran-3-ol;

tert-butyl 4-(3-(((2R,3R,4S,5R,6R)-4-(4-(3-fluorophenyl)-1H-1,2,3-triazol-1-yl)-5-hydroxy-6- (hydroxymethyl)-3-methoxytetrahydro-2H-pyran-2-yl)methyl)isoxazol-5-yl)piperidine-1-carboxylate;

(2R,3R,4S,5R,6R)-6-((3-(tert-butyl)isoxazol-5-yl)methyl)-2-(hydroxymethyl)-5-methoxy-4-(4-(2,3,4-trifluorophenyl)- 1H-1,2,3-triazol-1-yl)tetrahydro-2H-pyran-3-ol;

(2R,3R,4S,5R,6R)-2-(hydroxymethyl)-5-methoxy-6-((3-(1-methylcyclopropyl)isoxazol-5-yl)methyl)-4-(4-(2,3,4-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(3-methyloxetan-3-yl)isoxazol-5-yl)methyl)-4-(4-(2,3,4-trifluorophenyl)-1H-1,2,3-triazol-1-yl)tetrahydro-2H-pyran-3-ol;

(2R,3R,4S,5R,6R)-6-((3-(1-hydroxy-2-methylpropan-2-yl)isoxazol-5-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((3-(tert-butyl)isoxazol-5-yl)methyl)-4-(4-(2,3-difluoro-4-methylphenyl)-1H-1,2,3- triazol-1-yl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((3-(1-methylcyclopropyl)isoxazol-5-yl)methyl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((3-(3-methyloxetan-3-yl)isoxazol-5-yl)methyl)tetrahydro-2H-pyran-3-ol;

(2R,3R,4S,5R,6R)-4-(4-(2,3-difluoro-4-methylphenyl)-1H-1,2,3-triazol-1-yl)-6-((3-(1-hydroxy-2- methylpropan-2-yl)isoxazol-5-yl)methyl)-2-(hydroxymethyl)-5-methoxytetrahydro-2H-pyran-3-ol;

(2R,3R,4S,5R,6R)-6-((3-(tert-butyl)isoxazol-5-yl)methyl)-4-(4-(4-chloro-2,3-difluorophenyl)-1H-1,2,3- triazol-1-yl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((3-(1-methylcyclopropyl)isoxazol-5-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((3-(3-methyloxetan-3-yl)isoxazol-5-yl)methyl)tetrahydro-2H-pyran-3-ol;

(2R,3R,4S,5R,6R)-4-(4-(4-chloro-2,3-difluorophenyl)-1H-1,2,3-triazol-1-yl)-6-((3-(1-hydroxy-2- methylpropan-2-yl)isoxazol-5-yl)methyl)-2-(hydroxymethyl)-5-methoxytetrahydro-2H-pyran-3-ol;

(2R,3R,4S,5R,6R)-6-((3-(1-chloro-3-hydroxy-2-methylpropan-2-yl)isoxazol-5-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((3-(1-chloro-3-hydroxy-2-methylpropan-2-yl)isoxazol-5-yl)methyl)-4-(4-(2,3- difluoro-4-methylphenyl)-1H-1,2,3-triazol-1-yl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((3-(1-chloro-3- hydroxy-2-methylpropan-2-yl)isoxazol-5-yl)methyl)-2-(hydroxymethyl)-5-methoxytetrahydro-2H-pyran-3-ol;

(2R,3R,4S,5R,6R)-6-(((RS)-3-(tert-butyl)-4,5-dihydroisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-(((RS)-3-(tert-butyl)-4,5-dihydroisoxazol-5-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

4-(1-((2R,3R,4S,5R,6R)-2-((5-(tert-butyl)isoxazol-3-yl)methyl)-5-hydroxy-6-(hydroxymethyl)-3-methoxytetrahydro-2H-pyran-4-yl)-1H-1,2,3-triazol-4-yl)-2,3-difluorobenzonitrile;

(2R,3R,4S,5R,6R)-2-(hydroxymethyl)-5-methoxy-6-((5-(4-methyltetrahydro-2H-pyran-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(4-methyltetrahydro-2H-pyran-4-yl)isoxazol-3-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(4-methyltetrahydro-2H-pyran-4-yl)isoxazol-3-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((5-(4-methyltetrahydro-2H-pyran-4-yl)isoxazol-3-yl)methyl)tetrahydro-2H-pyran-3-ol;

(2R,3R,4S,5R,6R)-2-(hydroxymethyl)-5-methoxy-6-((5-(1-methylcyclopentyl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-methylcyclopentyl)isoxazol-3-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(1-methylcyclopentyl)isoxazol-3-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((5-(1-methylcyclopentyl)isoxazol-3-yl)methyl)tetrahydro-2H-pyran-3-ol;

1-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)cyclopentane-1-carbonitrile;

1-(3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-5-yl)cyclopentane-1-carbonitrile;

1-(3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)cyclopentane-1-carbonitrile;

1-(3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)cyclopentane-1-carbonitrile;

(2R,3R,4S,5R,6R)-4-(4-(4-chloro-2,3-difluorophenyl)-1H-1,2,3-triazol-1-yl)-6-(((RS)-3-(1-hydroxy-2-methylpropan-2-yl)-4,5-dihydroisoxazol-5-yl)methyl)-2-(hydroxymethyl)-5-methoxytetrahydro-2H-pyran-3-ol;

(2R,3R,4S,5R,6R)-2-(hydroxymethyl)-5-methoxy-6-((3-(4-methyltetrahydro-2H-pyran-4-yl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(4-methyltetrahydro-2H-pyran-4-yl)isoxazol-5-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((3-(4-methyltetrahydro-2H-pyran-4-yl)isoxazol-5-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((3-(4-methyltetrahydro-2H-pyran-4-yl)isoxazol-5-yl)methyl)tetrahydro-2H-pyran-3-ol;

(2R,3R,4S,5R,6R)-2-(hydroxymethyl)-5-methoxy-6-((3-(1-methylcyclopentyl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(1-methylcyclopentyl)isoxazol-5-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((3-(1-methylcyclopentyl)isoxazol-5-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((3-(1-methylcyclopentyl)isoxazol-5-yl)methyl)tetrahydro-2H-pyran-3-ol;

1-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclopentane-1-carbonitrile;

1-(5-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-3-yl)cyclopentane-1-carbonitrile;

1-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)cyclopentane-1-carbonitrile;

1-(5-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-3-yl)cyclopentane-1-carbonitrile;

(2R,3R,4R,5R,6R)-2-((3-(tert-butyl)isoxazol-5-yl)methyl)-4-(4-(4-chloro-2,3-difluorophenyl)-1H-1,2,3-triazol-1-yl)-6-(hydroxymethyl)tetrahydro-2H-pyran-3,5-diol;

(2R,3R,4S,5R,6R)-6-((3-(1,1-difluoro-2-methylpropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((3-isopropylisoxazol-5-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((3-(1-hydroxycyclopentyl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

2-(1-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclopropyl)acetonitrile;

(2R,3R,4S,5R,6R)-2-(hydroxymethyl)-5-methoxy-6-((3-(1-methoxy-2-methylpropan-2-yl)isoxazol-5-yl)methyl)-4-(4-(3,4,5-trifluorophenyl)-1H-1,2,3-triazol-1-yl)tetrahydro-2H-pyran-3-ol;

tert-butyl (2-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-2-methylpropyl)carbamate;

(2R,3R,4S,5R,6R)-6-((3-(1-amino-2-methylpropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-6-((5-((RS)-1-hydroxy-1-phenylethyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-(1-hydroxycyclopropyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(3-methyloxetan-3-yl)isoxazol-3-yl)methyl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-((5-(1-(hydroxymethyl)cyclopropyl)isoxazol-3-yl)methyl)-5-methoxytetrahydro-2H-pyran-3-ol;

ethyl 4-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)-4-methylpiperidine-1-carboxylate;

(2R,3R,4S,5R,6R)-4-(4-(2,3-difluoro-4-methylphenyl)-1H-1,2,3-triazol-1-yl)-6-((3-(1-hydroxycyclopentyl)isoxazol-5-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((3-(2-ethoxypropan-2-yl)isoxazol-5-yl)methyl)-2-(hydroxymethyl)-5-methoxytetrahydro-2H-pyran-3-ol;

tert-butyl 4-((RS)-5-(((2R,3R,4S,5R,6R)-4-(4-(2,3-difluoro-4-methoxyphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-4-(4-(2,3-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

(2R,3R,4S,5R,6R)-4-(4-(2,3-difluoro-4-methylphenyl)-1H-1,2,3-triazol-1-yl)-2-(hydroxymethyl)-5-methoxy-6-((3-(1-methoxy-2-methylpropan-2-yl)isoxazol-5-yl)methyl)tetrahydro-2H-pyran-3-ol;

tert-butyl (2-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)-2-methylpropyl)carbamate;

2-(1-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)cyclopropyl)acetonitrile;

(2R,3R,4R,5R,6R)-4-(4-(2,3-difluoro-4-methylphenyl)-1H-1,2,3-triazol-1-yl)-2-(hydroxymethyl)-6-((3-(1-methylcyclopropyl)isoxazol-5-yl)methyl)tetrahydro-2H-pyran-3,5-diol;

(2R,3R,4R,5R,6R)-4-(4-(2,3-difluoro-4-methylphenyl)-1H-1,2,3-triazol-1-yl)-2-((3-(1-hydroxy-2-methylpropan-2-yl)isoxazol-5-yl)methyl)-6-(hydroxymethyl)tetrahydro-2H-pyran-3,5-diol;

(2R,3R,4R,5R,6R)-4-(4-(2,3-difluoro-4-methylphenyl)-1H-1,2,3-triazol-1-yl)-2-(hydroxymethyl)-6-((3-(3-methyloxetan-3-yl)isoxazol-5-yl)methyl)tetrahydro-2H-pyran-3,5-diol;

(2R,3R,4S,5R,6R)-6-((3-(1-amino-2-methylpropan-2-yl)isoxazol-5-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(RS)-5-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)azepan-2-one;

4-(1-((2R,3R,4S,5R,6R)-2-((3-(tert-butyl)isoxazol-5-yl)methyl)-5-hydroxy-6-(hydroxymethyl)-3-methoxytetrahydro-2H-pyran-4-yl)-1H-1,2,3-triazol-4-yl)-2,3-difluorobenzonitrile;

(2R,3R,4S,5R,6R)-4-(4-(2,3-difluoro-4-methylphenyl)-1H-1,2,3-triazol-1-yl)-6-((5-((R)-1-hydroxy-1-phenylethyl)isoxazol-3-yl)methyl)-2-(hydroxymethyl)-5-methoxytetrahydro-2H-pyran-3-ol;

5-(((4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxin-6-yl)methyl)-3-((RS)-1-phenylethyl)isoxazole;

(2R,3R,4S,5R,6R)-4-(4-(2,3-difluoro-4-methylphenyl)-1H-1,2,3-triazol-1-yl)-6-((5-((1RS,2RS)-2-hydroxycyclobutyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-5-hydroxy-2-((5-((1RS,2RS)-2-hydroxycyclopentyl)isoxazol-3-yl)methyl)-6-(hydroxymethyl)tetrahydro-2H-pyran-3-yl acetate;

(RS)-5-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)-1-methylazepan-2-one;

(2R,3R,4S,5R,6R)-4-(4-(2,3-difluoro-4-methylphenyl)-1H-1,2,3-triazol-1-yl)-6-((5-((1S,2S)-2-hydroxycyclobutyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-((1R,2R)-2-hydroxycyclobutyl)isoxazol-3-yl)methyl)-2-(hydroxymethyl)-5-methoxytetrahydro-2H-pyran-3-ol;

(RS)-5-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)azepan-2-one;

(2R,3R,4S,5R,6R)-4-(4-(2,3-difluoro-4-methylphenyl)-1H-1,2,3-triazol-1-yl)-6-((5-((1S,2R)-2-hydroxycyclopropyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-((1R,2R)-2-hydroxycyclopropyl)isoxazol-3-yl)methyl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(2,3-difluorophenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(2,3-difluoro-4-methoxyphenyl)-1H-1,2,3-triazol-1-yl)-2-(hydroxymethyl)-5-methoxytetrahydro-2H-pyran-3-ol;

(RS)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-1-methylpiperidin-2-one;

(RS)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)piperidin-2-one;

(RS)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)pyrrolidin-2-one;

tert-butyl 4-((RS)-5-(((2R,3R,4R,5R,6R)-4-(4-(4-chloro-2,5-difluorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(2,3-difluoro-4-methylphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl 4-(3-(((2R,3R,4S,5R,6R)-5-hydroxy-6-(hydroxymethyl)-3-isopropoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;

tert-butyl 4-(3-(((2R,3R,4S,5R,6R)-3-(2,2-difluoroethoxy)-5-hydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate;

(2R,3R,4S,5R,6R)-5-(2,2-difluoroethoxy)-2-(hydroxymethyl)-6-((5-(piperidin-4-yl)isoxazol-3-yl)methyl)-4-(4-(3,4,5-trifluorophenyl)-1H-1,2,3-triazol-1-yl)tetrahydro-2H-pyran-3-ol;

2-(((2R,3R,4S,5R,6R)-2-((5-(tert-butyl)isoxazol-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetic acid;

2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one;

tert-butyl ((S)-1-(((1R,4S)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclohexyl)amino)-3-methyl-1-oxobutan-2-yl)carbamate;

(S)-2-amino-N-((1R,4S)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclohexyl)-3-methylbutanamide;

tert-butyl 4-((RS)-5-(((2R,3R,4S,5R,6R)-3-ethoxy-5-hydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;

2-(((2R,3R,4S,5R,6R)-2-(((RS)-3-(1-(tert-butoxycarbonyl)piperidin-4-yl)-4,5-dihydroisoxazol-5-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid;

tert-butyl 4-((RS)-5-(((2R,3R,4S,5R,6R)-5-hydroxy-6-(hydroxymethyl)-3-(2-(methylamino)-2-oxoethoxy)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-5-hydroxy-6-(hydroxymethyl)-3-(2-morpholino-2-oxoethoxy)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;

2-(((2R,3R,4S,5R,6R)-2-((3-(tert-butyl)isoxazol-5-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid;

2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-N-methylacetamide;

2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-((R)-3-hydroxypyrrolidin-1-yl)ethan-1-one;

2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(3-hydroxyazetidin-1-yl)ethan-1-one;

2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(4-hydroxypiperidin-1-yl)ethan-1-one;

2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-((S)-3-hydroxypyrrolidin-1-yl)ethan-1-one;

2-(((2R,3R,4S,5R,6R)-2-((3-(tert-butyl)isoxazol-5-yl)methyl)-5-hydroxy-6-(hydroxymethyl)-4-(4-(2,3,4-trifluorophenyl)-1H-1,2,3-triazol-1-yl)tetrahydro-2H-pyran-3-yl)oxy)acetic acid;

2-(((2R,3R,4S,5R,6R)-5-hydroxy-6-(hydroxymethyl)-2-((3-(1-methylcyclopropyl)isoxazol-5-yl)methyl)-4-(4-(2,3,4-trifluorophenyl)-1H-1,2,3-triazol-1-yl)tetrahydro-2H-pyran-3-yl)oxy)acetic acid;

(2R,3R,4S,5R,6R)-2-((3-(tert-butyl)isoxazol-5-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl carbamate;

2-(((2R,3R,4S,5R,6R)-5-hydroxy-2-((3-(1-hydroxy-2-methylpropan-2-yl)isoxazol-5-yl)methyl)-6-(hydroxymethyl)-4-(4-(2,3,4-trifluorophenyl)-1H-1,2,3-triazol-1-yl)tetrahydro-2H-pyran-3-yl)oxy)acetic acid;

(2R,3R,4S,5R,6R)-6-((5-(tert-butyl)isoxazol-3-yl)methyl)-4-(4-(4-ethynyl-2,3-difluorophenyl)-1H-1,2,3-triazol-1-yl)-2-(hydroxymethyl)-5-methoxytetrahydro-2H-pyran-3-ol;

(2R,3R,4R,5R,6R)-2-((3-(tert-butyl)isoxazol-5-yl)methyl)-6-(hydroxymethyl)-4-(4-(3,4,5-trifluorophenyl)-1H-1,2,3-triazol-1-yl)tetrahydro-2H-pyran-3,5-diol;

(2R,3R,4R,5R,6R)-2-((3-(tert-butyl)isoxazol-5-yl)methyl)-6-(hydroxymethyl)-4-(4-(2,3,4-trifluorophenyl)-1H-1,2,3-triazol-1-yl)tetrahydro-2H-pyran-3,5-diol;

(2R,3R,4R,5R,6R)-2-((3-(tert-butyl)isoxazol-5-yl)methyl)-4-(4-(2,3-difluoro-4-methylphenyl)-1H-1,2,3-triazol-1-yl)-6-(hydroxymethyl)tetrahydro-2H-pyran-3,5-diol;

(2R,3R,4S,5R,6R)-2-((3-(tert-butyl)isoxazol-5-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl ethylcarbamate;

(2R,3R,4S,5R,6R)-6-((3-(tert-butyl)isoxazol-5-yl)methyl)-4-(4-(2,3-difluoro-4-methylphenyl)-1H-1,2,3-triazol-1-yl)-2-(hydroxymethyl)-5-((1-methyl-1H-imidazol-2-yl)methoxy)tetrahydro-2H-pyran-3-ol;

(2R,3R,4S,5R,6R)-6-((3-(tert-butyl)isoxazol-5-yl)methyl)-4-(4-(2,3-difluoro-4-methylphenyl)-1H-1,2,3-triazol-1-yl)-2-(hydroxymethyl)-5-(thiazol-2-ylmethoxy)tetrahydro-2H-pyran-3-ol;

(2R,3R,4S,5R,6R)-6-((3-(tert-butyl)isoxazol-5-yl)methyl)-4-(4-(2,3-difluoro-4-methylphenyl)-1H-1,2,3-triazol-1-yl)-2-(hydroxymethyl)-5-(thiazol-4-ylmethoxy)tetrahydro-2H-pyran-3-ol;

(2R,3R,4S,5R,6R)-6-((3-(tert-butyl)isoxazol-5-yl)methyl)-4-(4-(2,3-difluoro-4-methylphenyl)-1H-1,2,3-triazol-1-yl)-2-(hydroxymethyl)-5-(oxazol-5-ylmethoxy)tetrahydro-2H-pyran-3-ol;

(2R,3R,4S,5R,6R)-4-(4-(2,3-difluoro-4-methylphenyl)-1H-1,2,3-triazol-1-yl)-6-((3-(1-hydroxycyclobutyl)isoxazol-5-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((3-(1-hydroxycyclobutyl)isoxazol-5-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((3-(1-hydroxycyclobutyl)isoxazol-5-yl)methyl)-2-(hydroxymethyl)-5-methoxytetrahydro-2H-pyran-3-ol;

(2R,3R,4S,5R,6R)-2-(hydroxymethyl)-6-((3-(2-hydroxypropan-2-yl)isoxazol-5-yl)methyl)-5-methoxy-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-((3-(2-hydroxypropan-2-yl)isoxazol-5-yl)methyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-6-((3-(2-hydroxypropan-2-yl)isoxazol-5-yl)methyl)-5-methoxytetrahydro-2H-pyran-3-ol;

(2R,3R,4S,5R,6R)-6-((5-(1-((S)-tert-butylsulfinyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(2-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(N-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol;

4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N,N-dimethylpiperidine-1-sulfonamide;

N-cyclopropyl-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxamide;

(2R,3R,4S,5R,6R)-2-(hydroxymethyl)-6-(((S)-3-(1-(isopropylsulfonyl)piperidin-4-yl)-4,5-dihydroisoxazol-5-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(morpholinosulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(piperidin-1-ylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(pyrrolidin-1-ylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-6-((5-(1-((4,4-difluoropiperidin-1-yl)sulfonyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)(piperidin-1-yl)methanone;

(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)(pyrrolidin-1-yl)methanone;

N-ethyl-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N-methylpiperidine-1-carboxamide;

4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N,N-dimethylpiperidine-1-carboxamide;

(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)(4-methylpiperazin-1-yl)methanone;

benzyl 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxylate;

(2R,3R,4S,5R,6R)-2-(hydroxymethyl)-5-methoxy-6-((1-(tetrahydro-2H-thiopyran-4-yl)-1H-1,2,3-triazol-4-yl)methyl)-4-(4-(3,4,5-trifluorophenyl)-1H-1,2,3-triazol-1-yl)tetrahydro-2H-pyran-3-ol;

4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)tetrahydro-2H-thiopyran 1-oxide;

4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)tetrahydro-2H-thiopyran 1,1-dioxide;

4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)-1-iminohexahydro-1l6-thiopyran 1-oxide;

4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)-1-(methylimino)hexahydro-1l6-thiopyran 1-oxide;

(2R,3R,4S,5R,6R)-6-((1-(1-((S)-tert-butylsulfinyl)piperidin-4-yl)-1H-1,2,3-triazol-4-yl)methyl)-2-(hydroxymethyl)-5-methoxy-4-(4-(3,4,5-trifluorophenyl)-1H-1,2,3-triazol-1-yl)tetrahydro-2H-pyran-3-ol;

benzyl 4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidine-1-carboxylate;

(2R,3R,4S,5R,6R)-2-(hydroxymethyl)-5-methoxy-6-((1-(1-(2-methylpropan-2-ylsulfonimidoyl)piperidin-4-yl)-1H-1,2,3-triazol-4-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((4-(1-(isopropylsulfonyl)piperidin-4-yl)-1H-1,2,3-triazol-1-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((4-(1-tosylpiperidin-4-yl)-1H-1,2,3-triazol-1-yl)methyl)-4-(4-(3,4,5-trifluorophenyl)-1H-1,2,3-triazol-1-yl)tetrahydro-2H-pyran-3-ol;

1-(ethylimino)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)hexahydro-1l6-thiopyran 1-oxide;

(2R,3R,4S,5R,6R)-2-(hydroxymethyl)-5-methoxy-6-((4-(1-(N-methylpropan-2-ylsulfonimidoyl)piperidin-4-yl)-1H-1,2,3-triazol-1-yl)methyl)-4-(4-(3,4,5-trifluorophenyl)-1H-1,2,3-triazol-1-yl)tetrahydro-2H-pyran-3-ol;

4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)-N,N-dimethylpiperidine-1-sulfonamide;

N-(tert-butyl)-4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidine-1-carboxamide;

1-(benzylimino)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)hexahydro-1l6-thiopyran 1-oxide;

(2R,3R,4S,5R,6R)-6-((1-cyclohexyl-1H-1,2,3-triazol-4-yl)methyl)-2-(hydroxymethyl)-5-methoxy-4-(4-(3,4,5-trifluorophenyl)-1H-1,2,3-triazol-1-yl)tetrahydro-2H-pyran-3-ol;

4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)-1-(isopropylimino)hexahydro-1l6-thiopyran 1-oxide;

N-cyclopropyl-4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidine-1-carboxamide;

1-((4,4-difluorocyclohexyl)imino)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)hexahydro-1l6-thiopyran 1-oxide;

benzyl 4-(4-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)-1H-1,2,3-triazol-1-yl)piperidine-1-carboxylate;

benzyl 4-(4-(((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)methyl)-1H-1,2,3-triazol-1-yl)piperidine-1-carboxylate;

benzyl 4-(4-(((2R,3R,4S,5R,6R)-4-(4-(4-bromo-3-fluorophenyl)-1H-1,2,3-triazol-1-yl)-5-hydroxy-6-(hydroxymethyl)-3-methoxytetrahydro-2H-pyran-2-yl)methyl)-1H-1,2,3-triazol-1-yl)piperidine-1-carboxylate;

benzyl 4-(4-(((2R,3R,4S,5R,6R)-4-(4-(3,5-difluorophenyl)-1H-1,2,3-triazol-1-yl)-5-hydroxy-6-(hydroxymethyl)-3-methoxytetrahydro-2H-pyran-2-yl)methyl)-1H-1,2,3-triazol-1-yl)piperidine-1-carboxylate;

(2R,3R,4S,5R,6R)-6-((4-(tert-butyl)-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol;

ethyl 4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidine-1-carboxylate;

(2R,3R,4S,5R,6R)-2-(hydroxymethyl)-5-methoxy-6-((4-(tetrahydro-2H-pyran-4-yl)-1H-1,2,3-triazol-1-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((4-(2-hydroxypropan-2-yl)-1H-1,2,3-triazol-1-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((1-(tert-butyl)-1H-1,2,3-triazol-4-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((1-(tert-butyl)-1H-1,2,3-triazol-4-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((4-cyclopentyl-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((4-(1-methylcyclopentyl)-1H-1,2,3-triazol-1-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((4-(4-methyltetrahydro-2H-pyran-4-yl)-1H-1,2,3-triazol-1-yl)methyl)-4-(4-(3,4,5-trifluorophenyl)-1H-1,2,3-triazol-1-yl)tetrahydro-2H-pyran-3-ol;

(2R,3R,4S,5R,6R)-6-((1-(tert-butyl)-1H-1,2,3-triazol-4-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((1-(tert-butyl)-1H-1,2,3-triazol-4-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

(2R,3R,4S,5R,6R)-6-((4-(tert-butyl)-1H-1,2,3-triazol-1-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((4-(tert-butyl)-1H-1,2,3-triazol-1-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

(RS)-3-(1-acetylpiperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one;

(RS)-5-(((2R,3R,4S,5R,6R)-5-hydroxy-6-(hydroxymethyl)-3-methoxy-4-(4-(3,4,5-trifluorophenyl)-1H-1,2,3- triazol-1-yl)tetrahydro-2H-pyran-2-yl)methyl)-3-(1-(methylsulfonyl)piperidin-4-yl)oxazolidin-2-one;

(S)-3-(1-acetylpiperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one;

(S)-5-(((2R,3R,4S,5R,6R)-5-hydroxy-6-(hydroxymethyl)-3-methoxy-4-(4-(3,4,5-trifluorophenyl)-1H-1,2,3- triazol-1-yl)tetrahydro-2H-pyran-2-yl)methyl)-3-(1-(methylsulfonyl)piperidin-4-yl)oxazolidin-2-one;

(R)-5-(((2R,3R,4S,5R,6R)-5-hydroxy-6-(hydroxymethyl)-3-methoxy-4-(4-(3,4,5-trifluorophenyl)-1H-1,2,3- triazol-1-yl)tetrahydro-2H-pyran-2-yl)methyl)-3-(1-(methylsulfonyl)piperidin-4-yl)oxazolidin-2-one;

tert-butyl 4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-3-yl)piperidine-1-carboxylate;

(RS)-5-(((2R,3R,4S,5R,6R)-5-hydroxy-6-(hydroxymethyl)-3-methoxy-4-(4-(3,4,5-trifluorophenyl)-1H-1,2,3- triazol-1-yl)tetrahydro-2H-pyran-2-yl)methyl)-3-(1-isobutyrylpiperidin-4-yl)oxazolidin-2-one;

4-((RS)_5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-3-yl)-N,N-dimethylpiperidine-1-carboxamide;

(S)-5-(((2R,3R,4S,5R,6R)-5-hydroxy-6-(hydroxymethyl)-3-methoxy-4-(4-(3,4,5-trifluorophenyl)-1H-1,2,3- triazol-1-yl)tetrahydro-2H-pyran-2-yl)methyl)-3-(1-isobutyrylpiperidin-4-yl)oxazolidin-2-one;

tert-butyl 4-((R)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-3-yl)piperidine-1-carboxylate;

(RS)-5-(((2R,3R,4S,5R,6R)-5-hydroxy-6-(hydroxymethyl)-3-methoxy-4-(4-(3,4,5-trifluorophenyl)-1H-1,2,3- triazol-1-yl)tetrahydro-2H-pyran-2-yl)methyl)-3-(tetrahydro-2H-pyran-4-yl)oxazolidin-2-one;

(RS)-5-(((2R,3R,4S,5R,6R)-5-hydroxy-6-(hydroxymethyl)-3-methoxy-4-(4-(3,4,5-trifluorophenyl)-1H-1,2,3- triazol-1-yl)tetrahydro-2H-pyran-2-yl)methyl)-3-(1-(isobutylsulfonyl)piperidin-4-yl)oxazolidin-2-one;

(RS)-3-(1-(3,3-dimethylbutanoyl)piperidin-4-yl)-5-(((2R,3R,4S,5R,6R)-5-hydroxy-6-(hydroxymethyl)-3- methoxy-4-(4-(3,4,5-trifluorophenyl)-1H-1,2,3-triazol-1-yl)tetrahydro-2H-pyran-2-yl)methyl)oxazolidin-2-one;
(RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-((trifluoromethyl)sulfonyl)piperidin-4-yl)oxazolidin-2-one;
(RS)-3-(1-(tert-butylsulfonyl)piperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one;
(RS)-3-cyclohexyl-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one;
tert-butyl 4-((RS)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-5-yl)piperidine-1-carboxylate;
tert-butyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isothiazol-5-yl)piperidine-1-carboxylate;
(2R,3R,4S,5R,6R)-2-(hydroxymethyl)-5-methoxy-6-((5-(piperidin-4-yl)isothiazol-3-yl)methyl)-4-(4-(3,4,5-trifluorophenyl)-1H-1,2,3-triazol-1-yl)tetrahydro-2H-pyran-3-ol;
(2R,3R,4S,5R,6R)-6-((4-(tert-butyl)-1H-imidazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol;
5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-phenyloxazol-2(3H)-one;
3-cyclohexyl-1-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)imidazolidin-4-one;
1-(1-acetylpiperidin-4-yl)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)imidazolidin-4-one;
3-(1-acetylpiperidin-4-yl)-1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)imidazolidin-4-one;
3-cyclohexyl-1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)imidazolidin-4-one;
1-(((2R,3R,4S,5R, 6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(tetrahydro-2H-pyran-4-yl)imidazolidin-4-one; and
ethyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-5-oxoimidazolidin-1-yl)piperidine-1-carboxylate.

The compounds of Formula (I) according to embodiments 1) to 23) and their pharmaceutically acceptable salts can be used as medicaments, e.g. in the form of pharmaceutical compositions for enteral (such especially oral e.g. in form of a tablet or a capsule) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention/prophylaxis or treatment of a disease or disorder mentioned herein comprising administering to a subject a pharmaceutically active amount of a compound of Formula (I) according to embodiments 1) to 23). In a sub-embodiment of the invention, the administered amount is comprised between 1 mg and 1000 mg per day.

For avoidance of any doubt, if compounds are described as useful for the prevention/prophylaxis or treatment of certain diseases, such compounds are likewise suitable for use in the preparation of a medicament for the prevention/prophylaxis or treatment of said diseases. Likewise, such compounds are also suitable in a method for the prevention/prophylaxis or treatment of such diseases, comprising administering to a subject (mammal, especially human) in need thereof, an effective amount of such compound.

24) Another embodiment relates to the compounds of formula (I) as defined in any one of embodiments 1) to 23) which are useful for the prevention/prophylaxis or treatment of diseases and disorders that are related to galectin-3 binding to natural ligands.

Such diseases and disorders that are related to Gal-3 binding to natural ligands are especially diseases and disorders in which inhibition of the physiological activity of Gal-3 is useful, such as diseases in which a Gal-3 receptor participates, is involved in the etiology or pathology of the disease, or is otherwise associated with at least one symptom of the disease.

Diseases or disorders that are related to galectin-3 binding to natural ligands may in particular be defined as including:
fibrosis of organs comprising:
all forms of lung/pulmonary fibrosis including all forms of fibrosing interstitial lung diseases, especially idiopathic pulmonary fibrosis (alternatively named cryptogenic fibrosing alveolitis); pulmonary fibrosis secondary to systemic inflammatory disease such as rheumatoid arthritis, scleroderma (systemic sclerosis, SSc), lupus (systemic lupus erythematosus, SLE), polymyositis, or mixed connective tissue disease (MCTD); pulmonary fibrosis secondary to sarcoidosis; iatrogenic pulmonary fibrosis including radiation-induced fibrosis; silicosis-induced pulmonary fibrosis; asbestos-induced pulmonary fibrosis; and pleural fibrosis;
renal/kidney fibrosis, including renal fibrosis caused by/associated with chronic kidney disease (CKD), (acute or chronic) renal failure, tubulointerstitial nephritis, and/or chronic nephropathies such as (primary) glomerulonephritis and glomerulonephritis secondary to systemic inflammatory diseases such as SLE or SSc, diabetes, focal segmental glomerular sclerosis, IgA nephropathy, hypertension, renal allograft, and Alport syndrome;
all forms of liver/hepatic fibrosis (associated or not with portal hypertension) including cirrhosis, alcohol-induced liver fibrosis, nonalcoholic steatohepatitis, biliary duct injury, primary biliary cirrhosis (also known as primary biliary cholangitis), infection- or viral-induced liver fibrosis (e.g. chronic HCV infection), and autoimmune hepatitis;

all forms of heart/cardiac fibrosis, including heart/cardiac fibrosis associated with cardiovascular diseases, heart failure, Fabry disease, CKD; diabetes, hypertension, or hypercholesterolemia;

gut fibrosis, including gut fibrosis secondary to SSc, and radiation-induced gut fibrosis;

skin fibrosis, including SSc and skin scarring;

head and neck fibrosis, including radiation-induced head and neck fibrosis;

eye/corneal fibrosis, including scarring (e.g. sequelae of laser-assisted in situ keratomileusis, or trabeculectomy);

hypertrophic scarring and keloids, including burn-induced or surgical hypertrophic scarring and keloids;

fibrosis sequelae of organ transplant (including corneal transplant);

and other fibrotic diseases including endometriosis, spinal cord fibrosis, myelofibrosis, perivascular and arterial fibrosis; as well as formation of scar tissue, Peyronie's disease, abdominal or bowel adhesions, bladder fibrosis, fibrosis of the nasal passages, and fibrosis mediated by fibroblasts;

(acute or chronic) liver diseases and disorders including acute and chronic viral hepatitis; cirrhosis caused by/associated with arthritis and vasculitis; metabolic liver diseases caused by/associated with arthritis, myocarditis, diabetes, or neurologic symptoms; cholestatic diseases caused by/associated with hyperlipidaemia, inflammatory bowel disease (IBD), or ulcerative colitis; liver tumors; autoimmune hepatitis and cirrhosis caused by/associated with celiac disease, autoimmune haemolytic anaemia, IBD, autoimmune thyroiditis, ulcerative colitis, diabetes, glomerulonephritis, pericarditis, autoimmune thyroiditis, hyperthyroidism, polymyositis, Sjörgen syndrome, panniculitis, alveolitis or alcoholic steatosis; cirrhosis associated with dementia; cirrhosis associated with peripheral neuropathy; cirrhosis caused by/associated with oral or oesophageal cancer; non-alcoholic fatty liver disease (especially non-alcoholic steatohepatitis) caused by/associated with obesity, metabolic syndrome or type 2 diabetes; hepatic blood vessel disorders (including Budd-Chiari syndrome, portal vein thrombosis, sinusoidal obstruction syndrome); acute and chronic liver failure (associated or not with portal hypertension); liver hypofunction;

acute kidney injury and chronic kidney disease (CKD) [especially CKD of stages 1 to 5 as defined by the Kidney Disease Improving Global Outcomes (KDIGO) Guidelines], in particular CKD (notably of these stages) caused by/associated with cardiac diseases (also referred to as cardio-renal syndrome type 1 and type 2), or caused by/associated with hypertension, or caused by/associated with diabetes (also referred to as diabetic kidney disease (DKD), including DKD associated with hypertension), wherein such diabetes especially is type 1 or type 2 diabetes), or caused by/associated with inflammatory diseases and disorders (such as glomerulonephritis and glomerulonephritis secondary to systemic inflammatory diseases such as SLE or SSc, tubulo-interstitial nephritis, vasculitis, sepsis, urinary tract infection), or caused by/associated with polycystic kidney disease, or caused by/associated with obstructive nephropathy (including calculi, benign prostatic hyperplasia, prostate cancer, retroperitoneal pelvic tumor), or caused by/associated with symptoms associated with neuropathic bladder disease); as well as acute and chronic renal failure;

cardiovascular diseases and disorders (including atherosclerosis caused by/associated with hypertension, hypercholesterolemia, diabetes, inflammation, obesity, elderly/age; peripheral arterial disease caused by/associated with hypertension, hypercholesterolemia, diabetes, elderly/age; deep venous thrombosis; pulmonary embolism caused by/associated with obesity or cancer; aortic aneurysm and dissection caused by/associated with elderly/age, hypertension, Marfan syndrome, congenital heart disorders, inflammatory or infectious disorders; cerebrovascular disease caused by/associated with hypertension, atrial fibrillation, hypercholesterolemia, diabetes, elderly/age; coronary heart disease caused by/associated with hypertension, hypercholesterolemia, diabetes, elderly/age, or CKD (especially CKD of stages 1 to 5 as defined by the Kidney Disease Improving Global Outcomes (KDIGO) Guidelines); rheumatic heart disease caused by/associated with bacterial infection; heart and vascular tumors; cardiomyopathy and arrythmias; valvular heart disease (including valvular calcification and degenerative aortic stenosis); inflammatory heart disease caused by/associated with infection, carditis, glomerulonephritis, cancer; heart failure (HF) defined as including especially congestive HF, including in particular systolic HF/HF with reduced ejection fraction (HFrEF), and diastolic HF/HF with preserved ejection fraction (HFpEF);

interstitial lung diseases and disorders (including smoking-related interstitial lung disease; interstitial lung disease associated with/caused by chronic obstructive pulmonary disease; interstitial pneumonia associated with collagen vascular disease (including usual interstitial pneumonia), or pneumonia);

cell proliferative diseases and cancers (including solid tumors, solid tumor metastasis, carcinoma, sarcoma, myeloma (and multiple myeloma), leukemia, lymphoma, mixed types of cancers, vascular fibroma, Kaposi's sarcoma, chronic lymphocytic leukemia (CLL), spinal cord tumors and invasive metastasis of cancer cells);

inflammatory and autoimmune diseases and disorders including chronic and acute inflammatory and autoimmune diseases and disorders (in particular including sepsis, Q-fever, asthma, rheumatoid arthritis, multiple sclerosis, SLE, SSc, polymyositis, plaque psoriasis (including psoriasis caused by/associated with NASH), atopic dermatitis, inflammatory renal/kidney diseases such as nephropathy (including diabetic nephropathy, glomerulonephritis, tubulointerstitial nephritis), inflammatory cardiac/heart diseases, inflammatory lung/lung related diseases; inflammatory liver/liver related diseases; diabetes (type 1 or type 2) and diabetes related diseases such as diabetic vasculopathy, diabetic nephropathy, diabetic retinopathy, diabetic peripheral neuropathy or skin related condition; viral encephalitis; and COVID-19 and sequelae thereof);

gastrointestinal tract diseases and disorders (including irritable bowel syndrome (IBS), inflammatory bowel disease (IBD), gastritis, and abnormal pancreatic secretion);

pancreatic diseases and disorders (including pancreatitis, e.g. associated with cystic fibrosis);

abnormal angiogenesis-associated diseases and disorders (including arterial obstruction);

brain-associated diseases and disorders (including stroke and cerebral haemorrhage);

neuropathic pain and peripheral neuropathy;

ocular diseases and disorders (including dry eye disease (dry eye syndrome), macular degeneration (AMD associated with age, diabetes related disease (diabetic retinopathy), proliferative vitreoretinopathy (PVR), cicatricial pemphigoid, and glaucoma (including glaucoma associated with elevated intraocular pressure, and ocular scarring after glaucoma filtration surgery), and corneal angiogenesis/neovascularization); and transplant rejection comprising rejection of transplanted organs such as kidney, liver, heart, lung, pancreas, cornea, and skin; graft-versus-host diseases brought about by hematopoietic stem cell transplantation; chronic allograft rejection and chronic allograft vasculopathy; and sequelae of such transplant rejection.

25) A further embodiment relates to the compounds of formula (I) for use according to embodiment 24) wherein said compounds are for use in the prevention/prophylaxis or treatment of fibrosis of organs including liver/hepatic fibrosis, renal/kidney fibrosis, lung/pulmonary fibrosis, heart/cardiac fibrosis, eye/corneal fibrosis, and skin fibrosis; as well as gut fibrosis, head and neck fibrosis, hypertrophic scarring and keloids; and fibrosis sequelae of organ transplant.

26) A further embodiment relates to the compounds of formula (I) for use according to embodiment 24) wherein said compounds are for use in the prevention/prophylaxis or treatment of cardiovascular diseases and disorders.

27) A further embodiment relates to the compounds of formula (I) for use according to embodiment 24) wherein said compounds are for use in the prevention/prophylaxis or treatment of acute kidney injury and chronic kidney disease (CKD).

28) A further embodiment relates to the compounds of formula (I) for use according to embodiment 24) wherein said compounds are for use in the prevention/prophylaxis or treatment of (acute or chronic) liver diseases and disorders.

29) A further embodiment relates to the compounds of formula (I) for use according to embodiment 24) wherein said compounds are for use in the prevention/prophylaxis or treatment of interstitial lung diseases and disorders.

30) A further embodiment relates to the compounds of formula (I) for use according to embodiment 24) wherein said compounds are for use in the prevention/prophylaxis or treatment of ocular diseases and disorders.

31) A further embodiment relates to the compounds of formula (I) for use according to embodiment 24) wherein said compounds are for use in the prevention/prophylaxis or treatment of cell proliferative diseases and cancers.

32) A further embodiment relates to the compounds of formula (I) for use according to embodiment 24) wherein said compounds are for use in the prevention/prophylaxis or treatment of chronic or acute inflammatory and autoimmune diseases and disorders.

33) A further embodiment relates to the compounds of formula (I) for use according to embodiment 24) wherein said compounds are for use in the prevention/prophylaxis or treatment of gastrointestinal tract diseases and disorders.

34) A further embodiment relates to the compounds of formula (I) for use according to embodiment 24) wherein said compounds are for use in the prevention/prophylaxis or treatment of pancreatic diseases and disorders.

35) A further embodiment relates to the compounds of formula (I) for use according to embodiment 24) wherein said compounds are for use in the prevention/prophylaxis or treatment of abnormal angiogenesis-associated diseases and disorders.

36) A further embodiment relates to the compounds of formula (I) for use according to embodiment 24) wherein said compounds are for use in the prevention/prophylaxis or treatment of brain-associated diseases and disorders.

37) A further embodiment relates to the compounds of formula (I) for use according to embodiment 24) wherein said compounds are for use in the prevention/prophylaxis or treatment of neuropathic pain and peripheral neuropathy.

38) A further embodiment relates to the compounds of formula (I) for use according to embodiment 24) wherein said compounds are for use in the treatment of transplant rejection.

Preparation of Compounds of Formula (I):

The compounds of Formula (I) can be prepared by well-known literature methods, by the methods given below, by the methods given in the experimental part below or by analogous methods. Optimum reaction conditions may vary with the particular reactants or solvents used, but such conditions can be determined by a person skilled in the art by routine optimisation procedures. In some cases, the order of carrying out the following reaction schemes, and/or reaction steps, may be varied to facilitate the reaction or to avoid unwanted reaction products. In the general sequence of reactions outlined below, the generic groups $R^1$, $R^2$, A, and $Ar^1$ are as defined for Formula (I). Other abbreviations used herein are explicitly defined, or are as defined in the experimental section. In some instances, the generic groups $R^1$, $R^2$, A, and $Ar^1$ might be incompatible with the assembly illustrated in the schemes below and so will require the use of protecting groups (Pg). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases, the final product may be further modified, for example, by manipulation of substituents to give a new final product. These manipulations may include, but are not limited to, reduction, oxidation, alkylation, acylation, hydrolysis and transition-metal catalysed cross-coupling reactions which are commonly known to those skilled in the art. The compounds obtained may also be converted into salts, especially pharmaceutically acceptable salts, in a manner known per se.

Compounds of the Formula (I) of the present invention can be prepared according to the general sequence of reactions outlined below. Only a few of the synthetic possibilities leading to compounds of Formula (I) are described.

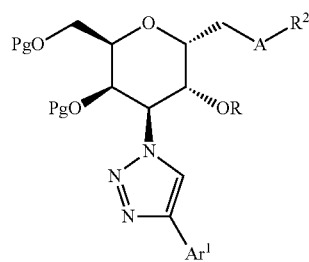

Structure 1

Compounds of Formula (I) are prepared by deprotecting a compound of Structure 1 in which R represents, hydrogen, a suitable protective group such as acetyl, trimethylsilyl, TBDMS or $R^1$, as defined in Formula (I).

Compounds of Structure 1 in which A represents a 3,5-disubstituted isoxazole or 4,5-dihydroisoxazole (Structure 1a or Structure 1b) are synthesised as shown below by 1,3-dipolar cycloadditions of nitrile oxides with dipolarophiles such as alkynes and alkenes of Structure 2a, 2b, 5 or 6. As precursors of nitrile oxides serve oximes such as Structures 3a or 4 which are oxidised in situ with N-chlorosuccinimide followed by elimination with a tertiary amine base such as $NEt_3$ or DIPEA in a suitable solvent such as DCM or DMF at temperatures ranging between rt and 50° C. Alternatively, nitrile oxides can be generated by dehydration of aliphatic nitrocompounds of Structure 3b using an aryl isocyanate and a catalytic amount of base (Mukaiyama conditions, T. Mukaiyama and T. Hoshino, J. Am. Chem. Soc., 1960, 82, 5339-5342).

Structure 1a

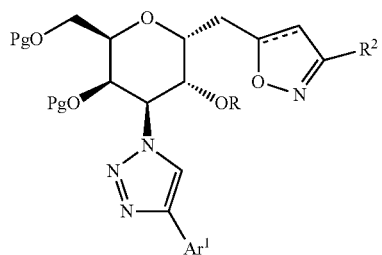

A = isoxazole, isoxazoline

Structure 2a

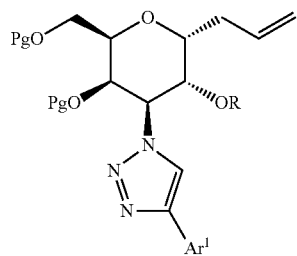

Structure 2b

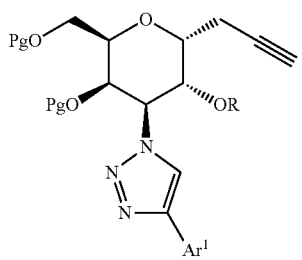

Structure 3a

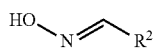

Structure 3b

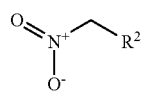

Structure 1b

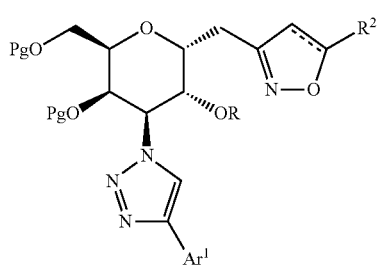

(A = isoxazole, isoxazoline)

Structure 4

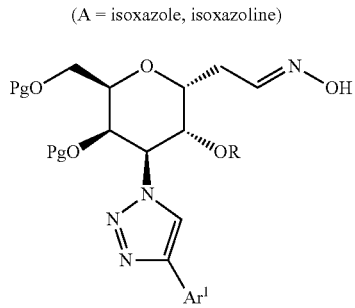

Structure 5

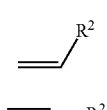

Structure 6

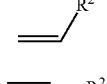

Compounds of Structure 1 in which A represents a 1,4-disubstituted 1,2,3-triazole (Structure 9a or Structure 9b) can be prepared by copper-catalysed 1,3-dipolar cycloadditions of alkynes of structures 2b or 6 with azides of structures 7 or 8 (*Click Chemistry in Glycoscience: New Development and Strategies*, 1st Edition, 2013, John Wiley& Sons) following a batch procedure, alternatively the reaction can be run on a commercial continuous-flow reactor (Vapourtec) using a copper coil in a solvent such as THF and as shown below.

Structure 9a

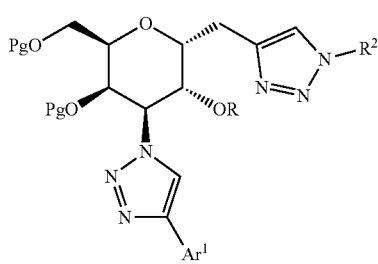

(A=triazole)

Structure 2b

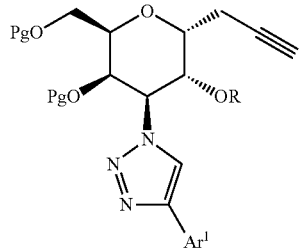

Structure 8

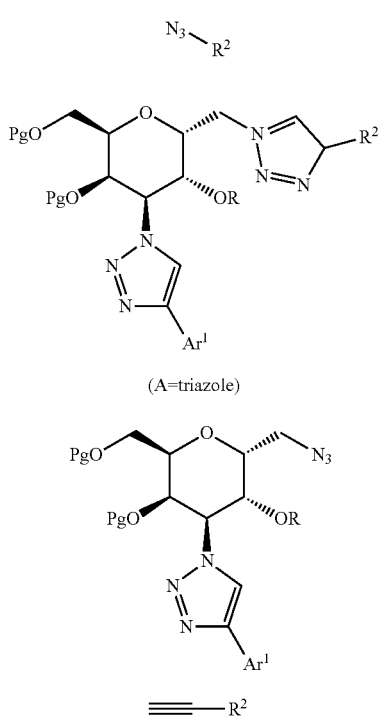

(A=triazole)

Structure 7

Structure 6

≡—R²

Structure 12a

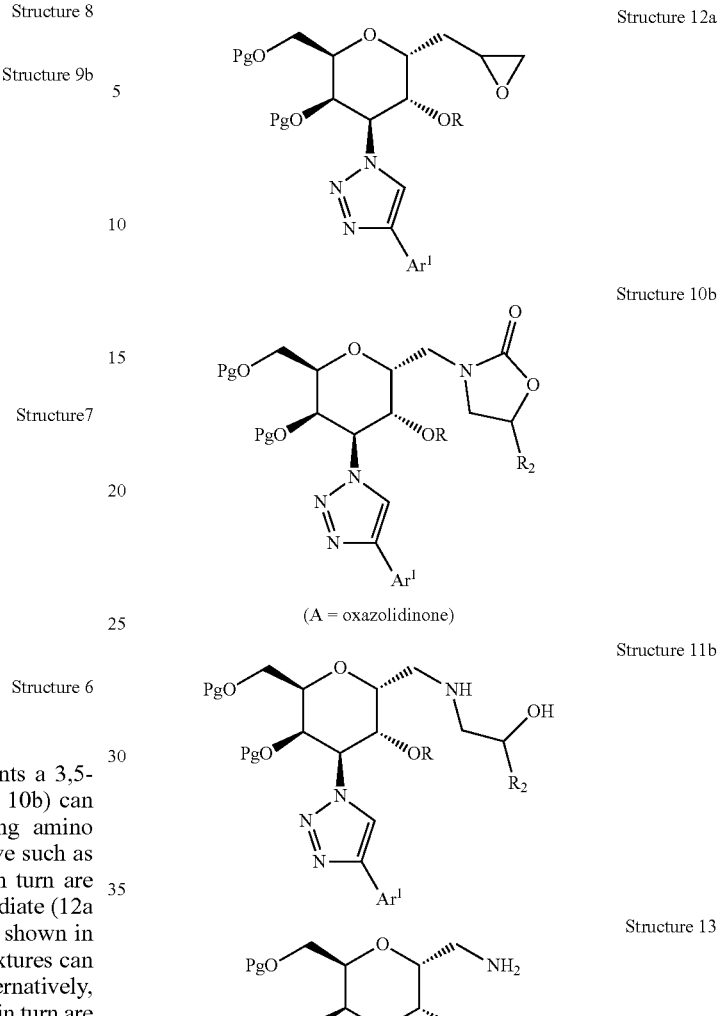

Structure 10b (A = oxazolidinone)

Structure 11b

Structure 13

Structure 12b

Compounds of structure 1 in which A represents a 3,5-disubstituted oxazolidin-2-one (Structures 10a or 10b) can be obtained by cyclisation of the corresponding amino alcohols 11a or 11b with a carbonic acid derivative such as CDI or phosgene. The required aminoalcohols in turn are obtained by reaction of a suitable epoxide intermediate (12a or 12b) with a primary amine (13a or $H_2NR^2$) as shown in the figure below. The resulting diastereomeric mixtures can be separated by chiral preparative HPLC. Alternatively, chiral epoxides can be used in the synthesis which in turn are prepared from alkene precursors following methods known to people skilled in the art.

Structure 10a

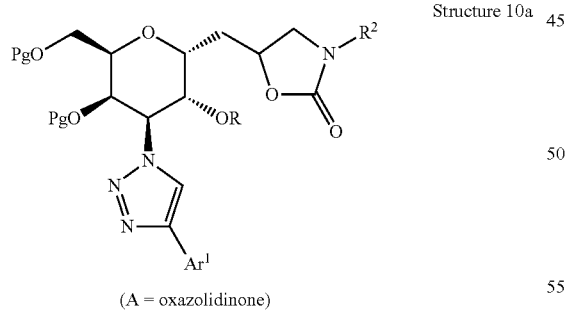

(A = oxazolidinone)

Structure 11a

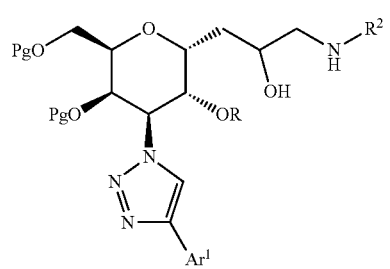

Compounds of structure 1 in which A represents a 1,3-disubstituted imidazolidin-4-one (Structures 14a or 14b) can be obtained by cyclisation of the corresponding amino acid amides 15a or 15b with formaldehyde. The required amino acid amide 15a is obtained by alkylation with the corresponding chloro acetamides of structure 16 or by reductive amination with a glyoxalamide derivative of structure 17. Amino acid amides of structure 15b are obtained by reaction of a chloroacetamide derivative of structure 18 (obtained by acylation of amines of structure 13 with chloroacetyl chloride) with a primary amine as shown in the Figure below.

Structure 14a

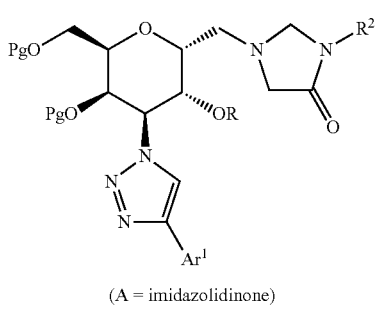

(A = imidazolidinone)

Structure 15a

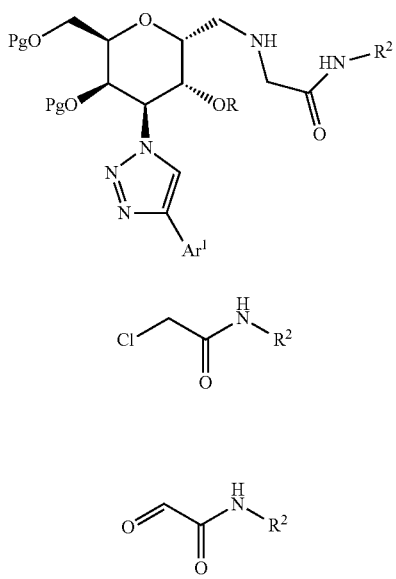

Structure 16

Structure 17

Structure 14b

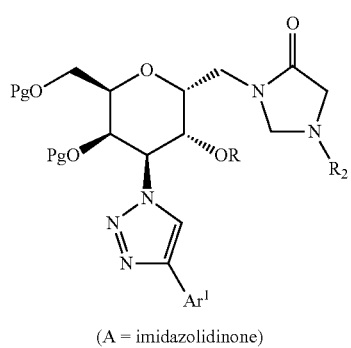

(A = imidazolidinone)

Structure 15b

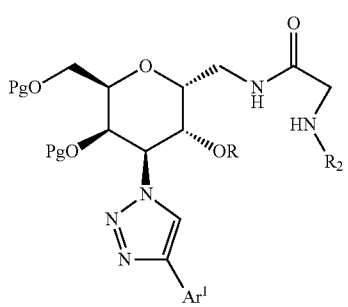

Structure 18

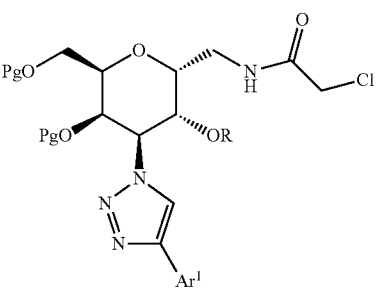

EXPERIMENTAL PART

The following examples illustrate the invention but do not at all limit the scope thereof.

All temperatures are stated in ° C. Commercially available starting materials were used as received without further purification. Unless otherwise specified, all reactions were carried out under an atmosphere of nitrogen or argon. Compounds were purified by flash chromatography on silica gel (Biotage), by prep TLC (TLC-plates from Merck, Silica gel 60 $F_{254}$) or by preparative HPLC. Compounds described in the invention are characterized by $^1$H-NMR (400 MHz or 500 MHz Bruker; chemical shifts are given in ppm relative to the solvent used; multiplicities: s=singlet, d=doublet, t=triplet, q=quadruplet, quint=quintuplet, hex=hexet, hept=heptet, m=multiplet, br=broad, coupling constants are given in Hz) and/or by LCMS (retention time $t_R$ is given in min; molecular weight obtained for the mass spectrum is given in g/mol) using the conditions listed below.

Characterization methods used:

The LC-MS retention times have been obtained using the following elution conditions:

A) LC-MS (A):

Zorbax RRHD SB-Aq, 1.8 μm, 2.1×50 mm column thermostated at 40° C. The two elution solvents were as follows: solvent A=water+0.04% TFA; solvent B=acetonitrile. The eluent flow rate was 0.8 mL/min and the characteristics of the eluting mixture proportion in function of the time t from start of the elution are summarized in the table below (a linear gradient being used between two consecutive time points):

| t (min) | 0 | 0.01 | 1.20 | 1.90 | 2.10 |
|---|---|---|---|---|---|
| Solvent A (%) | 95 | 95 | 5 | 5 | 95 |
| Solvent B (%) | 5 | 5 | 95 | 95 | 5 |

Detection: UV at 210 nm.

B) LC-MS (B):

Waters BEH C18, 1.8 μm, 1.2*50 mm column thermostated at 40° C. The two elution solvents were as follows: solvent A=water+13 mM NH$_4$OH; solvent B=acetonitrile. The eluent flow rate was 0.8 mL/min and the characteristics of the eluting mixture proportion in function of the time t from start of the elution are summarized in the table below (a linear gradient being used between two consecutive time points):

| t (min)       | 0  | 0.01 | 1.20 | 1.90 | 2.00 |
|---------------|----|------|------|------|------|
| Solvent A (%) | 95 | 95   | 5    | 5    | 95   |
| Solvent B (%) | 5  | 5    | 95   | 95   | 5    |

Detection: UV at 210 nm.

The purifications by preparative LC-MS have been performed using the conditions described hereafter.

C) Preparative LC-MS (1):

A Waters column (Waters XBridge C18, 10 μm OBD, 30×75 mm) was used. The two elution solvents were as follows: solvent A=water+0.5% of a solution of 25% $NH_4OH$ in water; solvent B=acetonitrile. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 4.0 | 6.0 | 6.2 | 6.6 |
|---------------|----|------|-----|-----|-----|-----|
| Solvent A (%) | 90 | 90   | 5   | 5   | 90  | 90  |
| Solvent B (%) | 10 | 10   | 95  | 95  | 10  | 10  |

Detection 210 nm.

D) Preparative LC-MS (10:

A Waters column (Waters XBridge C18, 10 μm OBD, 30×75 mm) was used. The two elution solvents were as follows: solvent A=water+HCOOH 0.5%; solvent B=acetonitrile. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 4.0 | 6.0 | 6.2 | 6.6 |
|---------------|----|------|-----|-----|-----|-----|
| Solvent A (%) | 90 | 90   | 5   | 5   | 90  | 90  |
| Solvent B (%) | 10 | 10   | 95  | 95  | 10  | 10  |

Detection 210 nm.

E) Preparative LC-MS (III):

A Waters column (Zorbax SB-AQ 30×75 mm 5 μm) was used. The two elution solvents were as follows: solvent A=water+HCOOH 0.5%; solvent B=acetonitrile. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 4.0 | 6.0 | 6.2 | 6.6 |
|---------------|----|------|-----|-----|-----|-----|
| Solvent A (%) | 90 | 90   | 5   | 5   | 90  | 90  |
| Solvent B (%) | 10 | 10   | 95  | 95  | 10  | 10  |

Detection 210 nm.

Chiral Preparative HPLC Methods Used:

The separation of epimers has been performed by preparative chiral column chromatography using the conditions described hereafter. The separation was done either at the final stage or with the protective group still present.

Chiral Preparative HPLC (I):

ChiralPack IC, 5 μm, 30×250 mm was used, column thermostated at 40° C. The two elution solvents were as follows: solvent A=CO2; solvent B=DCM/MeOH/DEA 50:50:0.1. The eluent flow rate was 160 mL/min. The elution was done using 60% of the solvent A and 40% of the solvent B. The injection V=1.0 mL, 10 mg/mL EtOH (Examples 1.03/1.04 (protected)).

Chiral Preparative HPLC (II):

ChiralPack IC, 5 μm, 30×250 mm was used, column thermostated at 40° C. The two elution solvents were as follows: solvent A=CO2; solvent B=DCM/MeOH 1:1. The eluent flow rate was 160 mL/min. The elution was done using 65% of the solvent A and 35% of the solvent B. The injection V=1.0 mL, 10 mg/mL EtOH (Examples 1.06/1.07 (acetate protected)).

Chiral Preparative HPLC (III):

ChiralPack IC, 5 μm, 30×250 mm was used, column thermostated at 40° C. The two elution solvents were as follows: solvent A=CO2; solvent B=EtOH. The eluent flow rate was 160 mL/min. The elution was done using 65% of the solvent A and 35% of the solvent B. The injection V=1.0 mL, 10 mg/mL EtOH. (examples 2.04/2.05)

Chiral Preparative HPLC (IV):

ChiralPack IH, 5 μm, 30×250 mm was used, column thermostated at 40° C. The two elution solvents were as follows: solvent A=CO2; solvent B=EtOH. The eluent flow rate was 160 mL/min. The elution was done using 65% of the solvent A and 35% of the solvent B. The injection V=1.0 mL, 10 mg/mL EtOH. (examples 1.09/1.10 (protected))

Chiral Preparative HPLC (V):

ChiralPack AD-H, 5 μm, 30×250 mm was used, column thermostated at 40° C. The two elution solvents were as follows: solvent A=CO2; solvent B=MeCN/EtOH 1:1. The eluent flow rate was 160 mL/min. The elution was done using 65% of the solvent A and 35% of the solvent B. The injection V=1.0 mL, 10 mg/mL EtOH. (examples 1.128/1.129 (protected))

Chiral Preparative HPLC (VI):

ChiralPack AD-H, 5 μm, 30×250 mm was used, column thermostated at 40° C. The two elution solvents were as follows: solvent A=CO2; solvent B=MeCN/EtOH/D EA 50:50:0.1. The eluent flow rate was 160 mL/min. The elution was done using 65% of the solvent A and 35% of the solvent B. The injection V=1.0 mL, 10 mg/mL EtOH. (examples 1.138/1.139)

Chiral Preparative HPLC (VII):

ChiralPack IE, 5 μm, 30×250 mm was used, column thermostated at 40° C. The two elution solvents were as follows: solvent A=CO2; solvent B=ACN/EtOH/DEA 50:50:0.1. The eluent flow rate was 160 mL/min. The elution was done using 55% of the solvent A and 45% of the solvent B. The injection V=1.0 mL, 10 mg/mL EtOH (Examples 1.147/1.148)

Chiral Preparative HPLC (VIII):

ChiralCel OD-H, 5 μm, 30×250 mm was used, column thermostated at 40° C. The two elution solvents were as follows: solvent A=CO2; solvent B=EtOH/. The eluent flow rate was 160 mL/min. The elution was done using 65% of the solvent A and 35% of the solvent B. The injection V=1.0 mL, 10 mg/mL EtOH (Examples 1.339/1.340)

Chiral Preparative HPLC (IX):

ChiralPack AD-H, 5 μm, 30×250 mm was used, column thermostated at 40° C. The two elution solvents were as follows: solvent A=CO2; solvent B=EtOH. The eluent flow rate was 160 mL/min. The elution was done using 65% of the solvent A and 35% of the solvent B. The injection V=1.0 mL, 10 mg/mL EtOH. (examples 1.47/1.48)

Chiral Preparative HPLC (X):

ChiralPack IC, 5 μm, 30×250 mm was used, column thermostated at 40° C. The two elution solvents were as follows: solvent A=CO2; solvent B=MeCN/D EA 50:50:0.1. The eluent flow rate was 160 mL/min. The elution was done using 60% of the solvent A and 40% of the solvent B. The injection V=1.0 mL, 10 mg/mL EtOH (Examples 3.06/3.07 (protected); 3.10/3.11 (protected); 3.12/3.13 (protected))

Chiral Preparative HPLC (XI):

ChiralPack IB, 5 μm, 30×250 mm was used, column thermostated at 40° C. The two elution solvents were as follows: solvent A=CO2; solvent B=EtOH. The eluent flow rate was 160 mL/min. The elution was done using 65% of the solvent A and 35% of the solvent B. The injection V=1.0 mL, 10 mg/mL EtOH. (examples 3.19/3.20 (protected))

Chiral Preparative HPLC (XII):

ChiralPack IE, 5 μm, 30×250 mm was used, column thermostated at 40° C. The two elution solvents were as follows: solvent A=CO2; solvent B=EtOH. The eluent flow rate was 160 mL/min. The elution was done using 55% of the solvent A and 45% of the solvent B. The injection V=1.0 mL, 10 mg/mL EtOH (Examples 3.24/3.25, Chiral Preparative HPLC (XIII):

ChiralPack IB, 5 μm, 30×250 mm was used, column thermostated at 40° C. The two elution solvents were as follows: solvent A=CO2; solvent B=MeCN/EtOH 1:1. The eluent flow rate was 160 mL/min. The elution was done using 75% of the solvent A and 25% of the solvent B. The injection V=1.0 mL, 10 mg/mL EtOH. (examples 3.60/3.61 (protected); 5.14/5.15)

Chiral Preparative HPLC (XIV):

ChiralPack IE, 5 μm, 30×250 mm was used, column thermostated at 40° C. The two elution solvents were as follows: solvent A=CO2; solvent B=ACN/MeOH 50:50. The eluent flow rate was 160 mL/min. The elution was done using 55% of the solvent A and 45% of the solvent B. The injection V=1.0 mL, 10 mg/mL EtOH (Examples 5.05/5.06)

Chiral Preparative HPLC (XV):

ChiralCel OJ-H, 5 μm, 30×250 mm was used, column thermostated at 40° C. The two elution solvents were as follows: solvent A=CO2; solvent B=ACN/MeOH 50:50. The eluent flow rate was 160 mL/min. The elution was done using 55% of the solvent A and 45% of the solvent B. The injection V=1.0 mL, 10 mg/mL EtOH (Examples 5.07/5.08)

Chiral Preparative HPLC (XVI):

ChiralPack ID, 5 μm, 30×250 mm was used, column thermostated at 40° C. The two elution solvents were as follows: solvent A=CO2; solvent B=ACN/EtOH/DEA 50:50:0.1. The eluent flow rate was 160 mL/min. The elution was done using 55% of the solvent A and 45% of the solvent B. The injection V=1.0 mL, 10 mg/mL EtOH (Examples 512/513 (precursor))

Chiral Preparative HPLC (XVII):

ChiralPack IH, 5 μm, 30×250 mm was used, column thermostated at 40° C. The two elution solvents were as follows: solvent A=CO2; solvent B=MeCN/EtOH/DEA 50:50:0.1. The eluent flow rate was 160 mL/min. The elution was done using 55% of the solvent A and 45% of the solvent B. The injection V=1.0 mL, 10 mg/mL EtOH. (examples 2.07a/2.07b (protected))

NMR:

1H-NMR spectra are recorded on a Bruker Avance II, 400 MHz Ultra Shield™ or Brooker Avance III HD, Ascend 500 MHz; chemical shifts are given in ppm relative to the solvent used; multiplicities: s=singlet, d=doublet, t=triplet, q=quadruplet, quint=quintuplet, hex=hextet, hept=heptet, m=multiplet, br=broad, coupling constants are given in Hz).

Abbreviations (as Used Herein):
  Ac₂O acetic anhydride
  AcOH acetic acid
  aq. aqueous
  BB building block
  BF₃OEt₂ boron trifluoride diethyletherate
  Boc tert-butoxycarbonyl
  BOP benzotriazol-1-yloxytris(dimethylamino)phosphonium hexafluorophosphate
  Bu butyl (such as in nBuLi=n-butyl lithium)
  CC column chromatography on silica
  conc. Concentrated
  CSA (+)-camphor-10-sulfonic acid
  DCM dichloromethane
  dil. dilute
  DIPEA N-ethyl diisopropyl amine
  DMAP 4-dimethylamino pyridine
  DMF dimethylformamide
  DMSO dimethylsulfoxide
  EA ethyl acetate
  EDC HCl N-(3-dimethylaminopropyl)-N'-ethylcarbodiimide hydrochloride
  eq (molar) equivalent(s)
  Et ethyl
  EtOH ethanol
  Et₂O diethyl ether
  FC flash chromatography
  h hour(s)
  HATU 1-[Bis(dimethylamino)methylene]-1H-1,2,3-triazolo[4,5-b]pyridinium 3-oxid hexafluorophosphate
  Hept heptane
  HOBt 1-hydroxybenzotriazole hydrate
  HPLC high performance liquid chromatography
  M molarity [mol L⁻¹]
  mCPBA 3-chloro perbenzoic acid
  Me methyl
  MeCN acetonitrile
  MeOH methanol
  Ms methane sulfonyl
  MS mass spectroscopy
  min. minute(s)
  N normality
  NaOAc sodium acetate
  NaOMe sodium methoxide
  NaOtBu sodium tert. (tertiary) butoxide
  NBS N-bromosuccinimide
  NCS N-chlorosuccinimide
  NEt₃ triethylamine
  o/n over night
  org. organic
  Pg protective group
  Ph phenyl
  PTSA p-Toluenesulfonic acid
  rt room temperature
  sat. saturated
  TBME tert-butylmethylether
  TBTU O-benzotriazol-1-yl-N,N,N',N'-tetramethyluronium tetrafluoroborate
  tBu tert-butyl=tertiary butyl
  TFA trifluoroacetic acid
  THF tetrahydrofuran
  TMEDA tetramethylethylenediamine
  TMSCl trimethylsilyl chloride
  T3P propylphosphonic anhydride
  $t_R$ retention time A—Preparation of Precursors and Intermediates

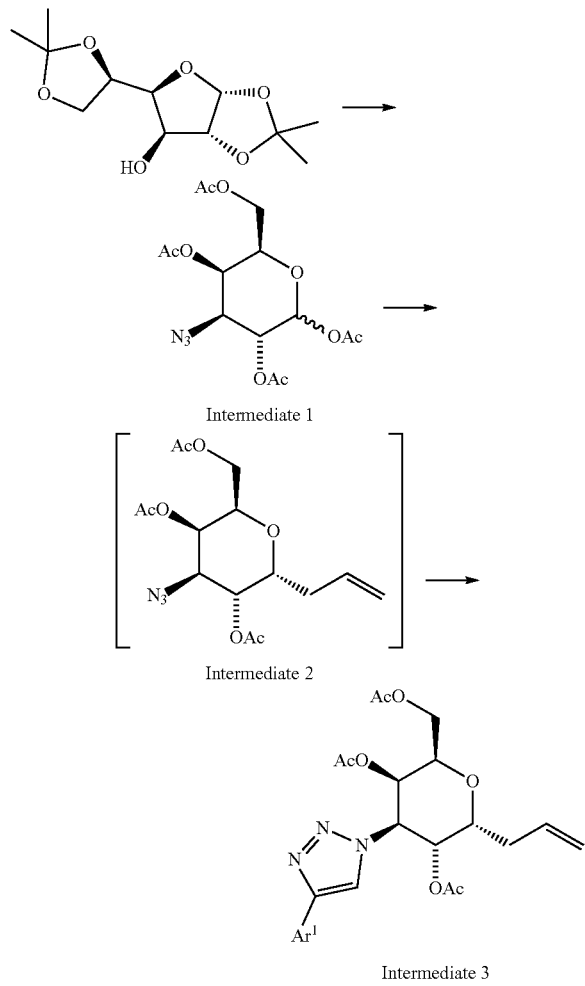

Intermediate 1

Intermediate 2

Intermediate 3

Intermediate 1: (3R,4S,5R,6R)-6-(Acetoxymethyl)-4-azidotetrahydro-2H-pyran-2,3,5-triyl triacetate (3R,4S,5R,6R)-6-(acetoxymethyl)-4-azidotetrahydro-2H-pyran-2,3,5-triyl triacetate is synthesized from (3aR,5S,6S,6aR)-5-((R)-2,2-dimethyl-1,3-dioxolan-4-yl)-2,2-dimethyltetrahydrofuro[2,3-d][1,3]dioxol-6-ol following the literature procedures from Ref: Carbohydrate Research 1994, 251, 33-67 and references cited therein.

Intermediate 2: (2R,3R,4R,5R,6R)-2-(acetoxymethyl)-6-allyl-4-azidotetrahydro-2H-pyran-3,5-diyl diacetate A solution of Intermediate 1 (10 g, 26.8 mmol, 1 eq) in MeCN (100 mL) is cooled to 0° C. and allyltrimethylsilane 98% (13 mL, 80.4 mmol, 3 eq) and dropwise trimethylsilyl trifluoromethanesulfonate 99% (2.45 mL, 13.4 mmol, 0.5 eq) are added (not exothermic). The ice bath is removed and the mixture stirred at rt for 72 h. The mixture is poured on sat. NaHCO$_3$ solution and extracted with TBME. Org. phase is washed with brine, dried over MgSO$_4$ and concentrated. The crude is purified by filtration over SiO$_2$ (DCM/TBME 9:1) to give the title intermediate (as a 9:1 mixture of alpha/beta isomers) as a colourless oil which is used in the next step without further purification.

major isomer: $^1$H NMR (500 MHz, DMSO) δ: 5.70-5.78 (m, 2H), 5.31 (dd, J$^1$=1.6 Hz, J$^2$=3.4 Hz, 1H), 5.06-5.14 (m, 2H), 4.98-5.04 (m, 1H), 4.39 (dd, J$^1$=3.4 Hz, J$^2$=10.6 Hz, 1H), 4.15 (m, 1H), 3.91-4.09 (m, 4H), 2.56-2.65 (m, 1H), 2.22-2.28 (m, 1H), 2.11 (s, 3H), 2.09 (s, 3H), 1.99 (s, 3H)

Intermediate 3a: (2R,3R,4R,5R,6R)-2-(acetoxymethyl)-6-allyl-4-(4-(3,4,5-trifluorophenyl)-1H-1,2,3-triazol-1-yl)tetrahydro-2H-pyran-3,5-diyl diacetate To a solution of Intermediate 2 (15 g, 42.5 mmol, 1 eq) in DMF (160 mL) are added 5-ethynyl-1,2,3-trifluorobenzene (9950 mg, 63.7 mmol, 1.5 eq), copper(I) iodide (809 mg, 4.25 mmol, 0.1 eq) and NEt$_3$ (17.8 mL, 127 mmol, 3 eq) and stirred at rt o/n. The mixture is diluted with EA and dil. HCl. Org. phase is washed with water and brine, dried over MgSO$_4$ and concentrated. The crude is crystallized from EA (20 mL) and TBME (200 mL) to give the desired pure alpha isomer as a colourless solid. LCMS (A): t$_R$=1.02 min; [M+H]$^+$=512.15

$^1$H NMR (500 MHz, DMSO-d6) δ: 8.78 (s, 1H), 7.83-7.88 (m, 2H), 5.75-5.84 (m, 1H), 5.70-5.74 (m, 2H), 5.36 (s, 1H), 5.18-5.21 (m, 1H), 5.10-5.14 (m, 1H), 4.41 (m, 1H), 4.35 (m, 1H), 4.00-4.04 (m, 1H), 3.94 (dd, J$^1$=7.1 Hz, J$^2$=11.3 Hz, 1H), 2.84-2.91 (m, 1H), 2.30-2.35 (m, 1H), 2.02 (s, 3H), 1.98 (s, 3H), 1.86 (s, 3H)

Intermediate 3b (reference example): (2R,3R,4R,5R,6S)-2-(acetoxymethyl)-6-allyl-4-(4-(3,4,5-trifluorophenyl)-1H-1,2,3-triazol-1-yl)tetrahydro-2H-pyran-3,5-diyl diacetate This intermediate is isolated as by-product in the synthesis of Intermediate 3a (from mother liquors) LCMS (A): t$_R$=1.04 min; [M+H]$^+$=512.15

1H NMR (500 MHz, DMSO-d6) δ: 8.76-8.79 (m, 1H), 7.85 (m, 2H), 5.86 (m, 1H), 5.57 (dd, J$^1$=3.2 Hz, J$^2$=11.0 Hz, 1H), 5.47 (m, 1H), 5.39-5.41 (m, 1H), 5.08-5.15 (m, 2H), 4.28 (m, 1H), 4.03 (m, 2H), 3.82 (m, 1H), 2.35-2.40 (m, 1H), 2.21-2.27 (m, 1H), 2.08 (s, 3H), 2.00 (s, 3H), 1.83 (s, 3H)

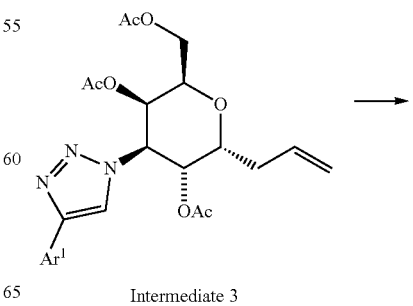

Intermediate 3

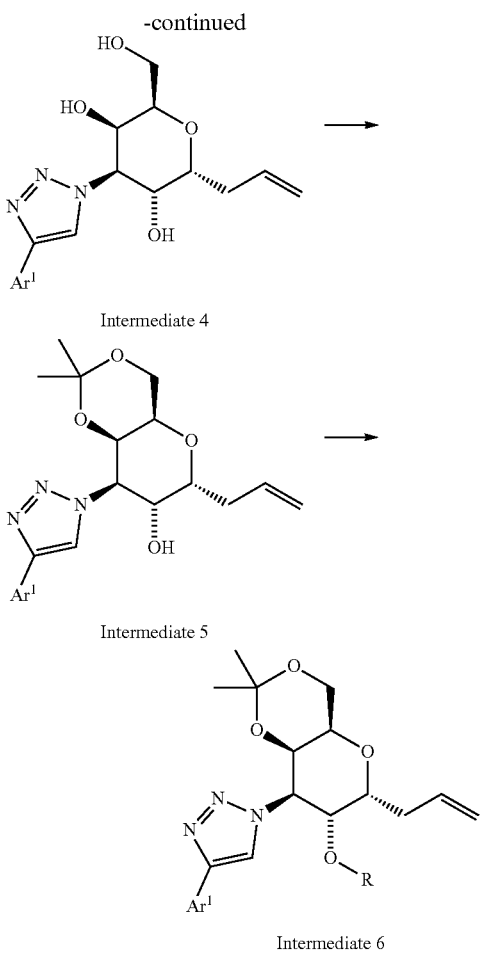

Intermediate 4

Intermediate 5

Intermediate 6

Intermediate 4a: (2R,3R,4R,5R,6R)-2-allyl-6-(hydroxymethyl)-4-(4-(3,4,5-trifluorophenyl)-1H-1,2,3-triazol-1-yl)tetrahydro-2H-pyran-3,5-diol To a solution of Intermediate 3a (12 g, 23.5 mmol, 1 eq) in methanol (240 mL) is added K$_2$CO$_3$ (324 mg, 2.35 mmol, 0.1 eq). The reaction mixture is stirred at rt for 2 h. The mixture is concentrated in vacuo to afford a beige foam. The crude compound is purified by FC (DCM/MeOH 9:1) to give the desired product as a colourless solid.

LCMS (A): $t_R$=0.7 min; [M+H]$^+$=385.76

$^1$H NMR (500 MHz, DMSO-d6) δ: 8.72 (s, 1H), 7.82-7.87 (m, 2H), 5.88 (m, 1H), 5.26 (d, J=5.7 Hz, 1H), 5.14-5.19 (m, 2H), 5.05-5.07 (m, 1H), 4.90 (dd, J$^1$=2.9 Hz, J$^2$=11.4 Hz, 1H), 4.58 (t, J=5.5 Hz, 1H), 4.52 (m, 1H), 4.02 (m, 1H), 3.93 (dd, J$^1$=2.6 Hz, J$^2$=6.4 Hz, 1H), 3.78 (t, J=6.2 Hz, 1H), 3.49 (m, 1H), 3.42 (m, 1H), 2.68-2.75 (m, 1H), 2.33-2.38 (m, 1H)

Intermediate 5a: (4aR,6R,7R,8R,8aR)-6-allyl-2,2-dimethyl-8-(4-(3,4,5-trifluorophenyl)-1H-1,2,3-triazol-1-yl)hexahydropyrano[3,2-d][1,3]dioxin-7-ol A solution of Intermediate 4a (15 g, 38.9 mmol, 1 eq) in THF (180 mL) is treated with 2,2-dimethoxypropane (19.1 mL, 156 mmol, 4 eq) and PTSA monohydrate (0.378 g, 1.95 mmol, 0.05 eq) and the light yellow solution is stirred at rt o/n. The mixture is diluted with EA and the org. layer is washed with sat. NaHCO$_3$ solution, water and brine, dried over MgSO$_4$, filtered and concentrated under reduced pressure to give the title intermediate as a colourless solid.

LCMS (A): $t_R$=0.93 min; [M+H]$^+$=426.13

$^1$H NMR (500 MHz, DMSO-d6) δ: 8.72 (s, 0H), 8.58-8.64 (m, 1H), 7.80-7.94 (m, 2H), 5.81-5.90 (m, 1H), 5.33-5.38 (m, 1H), 5.11-5.20 (m, 1H), 5.00-5.11 (m, 2H), 4.41-4.52 (m, 1H), 4.26-4.31 (m, 1H), 4.12 (ddd, J$^1$=11.5 Hz, J$^2$=5.7 Hz, J$^3$=3.2 Hz, 1H), 4.01 (dd, J$^1$=12.7 Hz, J$^2$=2.0 Hz, 1H), 3.66-3.71 (m, 1H), 3.57-3.65 (m, 1H), 2.64-2.72 (m, 1H), 2.34-2.41 (m, 1H), 1.32 (s, 3H), 1.20 (s, 3H)

Intermediate 6a: 1-((4aR,6R,7R,8R,8aR)-6-allyl-7-methoxy-2,2-dimethylhexahydropyrano[3,2-d][1,3]dioxin-8-yl)-4-(3,4,5-trifluorophenyl)-1H-1,2,3-triazole To a solution of Intermediate 5a (7.3 g, 17.2 mmol, 1 eq) in dry THF (50 mL) cooled to 0° C. is added dimethyl sulfate (2 mL, 20.6 mmol, 1.2 eq) followed by NaH [55% dispersion in paraffin] (824 mg, 20.6 mmol, 1.2 eq) portion wise. The mixture is stirred at 0° C. for 3 h. The mixture is quenched with sat. NH$_4$Cl and extracted twice with TBME. The combined org. layers are washed with brine, dried over MgSO$_4$, filtered and concentrated under reduced pressure to afford a colourless solid. LCMS (A): $t_R$=1.03 min; [M+H]$^+$=440.22

$^1$H NMR (500 MHz, DMSO-d6) δ: 8.71 (s, 1H), 7.68-7.98 (m, 2H), 5.70-5.97 (m, 1H), 5.14-5.21 (m, 2H), 5.09 (m, 1H), 4.48 (ddd, J$^1$=3.5 Hz, J$^2$=5.5 Hz, J$^3$=11.4 Hz, 1H), 4.30 (d, J=2.9 Hz, 1H), 4.22 (dd, J$^1$=5.7 Hz, J$^2$=11.5 Hz, 1H), 3.93-4.10 (m, 1H), 3.56-3.74 (m, 2H), 3.21 (s, 3H), 2.70-2.78 (m, 1H), 2.20-2.31 (m, 1H), 1.32 (s, 3H), 1.20 (s, 3H)

Intermediate 6b: (4aR,6R,7R,8S,8aR)-6-allyl-2,2-dimethyl-8-(4-(3,4,5-trifluorophenyl)-1H-1,2,3-triazol-1-yl)hexahydropyrano[3,2-d][1,3]dioxin-7-yl acetate Intermediate 5a (725 mg, 1.7 mmol, 1 eq) is dissolved in DCM (10 mL) and Ac$_2$O (0.193 mL, 2.05 mmol, 1.2 eq), DIPEA (0.438 mL, 2.56 mmol, 1.5 eq) and DMAP (10.4 mg, 0.0852 mmol, 0.05 eq) are added. The mixture is stirred at rt for 1 h. The mixture is partitioned between EA and NaHCO$_3$ solution. The org. phase is washed with sat NH$_4$Cl and brine, dried over MgSO$_4$ and concentrated. Purification by FC (hept/EA 2:1, 1:1, 1:2) gives the title intermediate as a colourless foam. LCMS (A): $t_R$=1.04 min; [M+H]+=467.98

$^1$H NMR (500 MHz, DMSO-d6) δ: 8.63 (s, 1H), 7.89 (m, 2H), 5.81 (m, 1H), 5.59 (dd, J$^1$=5.7 Hz, J$^2$=11.4 Hz, 1H), 5.47 (dd, J$^1$=3.2 Hz, J$^2$=11.4 Hz, 1H), 5.19 (dd, J$^1$=1.9 Hz, J$^2$=17.2 Hz, 1H), 5.09 (m, 1H), 4.36-4.41 (m, 2H), 4.03-4.06 (m, 1H), 3.76 (d, J=1.0 Hz, 1H), 3.66 (dd, J$^1$=1.7 Hz, J$^2$=12.8 Hz, 1H), 2.80 (m, 1H), 2.28-2.33 (m, 1H), 1.84 (s, 3H), 1.38 (s, 3H), 1.25 (s, 3H)

Intermediate 6c: ((2R,3R,4R,5R,6R)-3-acetoxy-6-allyl-5-methoxy-4-(4-(3,4,5-trifluorophenyl)-1H-1,2,3-triazol-1-yl)tetrahydro-2H-pyran-2-yl)methyl acetate Step 1: (2R,3R,4S,5R,6R)-6-allyl-2-(hydroxymethyl)-5-methoxy-4-(4-(3,4,5-trifluorophenyl)-1H-1,2,3-triazol-1-yl)tetrahydro-2H-pyran-3-ol To a mixture of Intermediate 6a (3050 mg, 6.94 mmol, 1 eq) in water (15 mL) was added acetic acid (30 mL) and the suspension was stirred at 55° C. for 3 h. The solution was concentrated under reduced pressure and the residue was dried under hv o/n. The crude (light yellow solid) was used in the next step without further purification.

Step 2

To a solution of Intermediate of step 1 (3340 mg, 8.36 mmol, 1 eq) and Et$_3$N (6.99 mL, 50.2 mmol, 6 eq) in DCM (40 mL) at 0° C. under N$_2$ was added Ac$_2$O (2.42 mL, 25.1 mmol, 3 eq) and the solution was stirred at rt for o/n. Water was added and the mixture was extracted with DCM. The org. layer was dried over MgSO$_4$ and was then concentrated under reduced pressure to give the title intermediate as a colourless solid.

LCMS (A): t$_R$=1.03 min; [M+H]+=484.20

$^1$H NMR (500 MHz, DMSO-d6) δ: 9.72 (m, 1H), 8.73 (s, 1H), 7.87 (dd, J$^1$=9.0 Hz, J$^2$=6.8 Hz, 2H), 5.11-5.18 (m, 2H), 4.24-4.30 (m, 2H), 4.01-4.04 (m, 1H), 3.57-3.69 (m, 2H), 3.32 (s), 3.20 (s, 3H), 2.98 (ddd, J$^1$=16.2 Hz, J$^2$=9.2 Hz, J$^3$=3.0 Hz, 1H), 2.83 (ddd, J$^1$=16.2 Hz, J$^2$=5.0 Hz, J$^3$=1.4 Hz, 1H), 1.18-1.33 (m, 6H)

Intermediate 7b: (4aR,6R,7R,8S,8aR)-2,2-dimethyl-6-(2-oxoethyl)-8-(4-(3,4,5-trifluorophenyl)-1H-1,2,3-triazol-1-yl)hexahydropyrano[3,2-d][1,3]dioxin-7-yl acetate Preparation in analogy to Intermediate 7a, starting from Intermediate 6b. LCMS (A): t$_R$=0.92 min; [M+H]$^+$=469.96

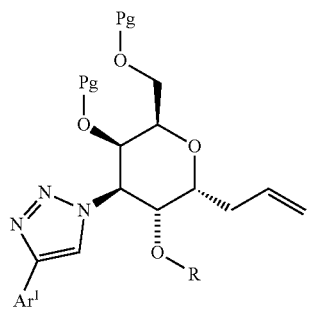  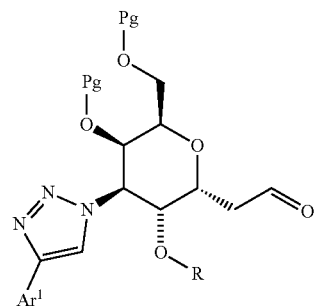

Intermediate 6   Intermediate 7

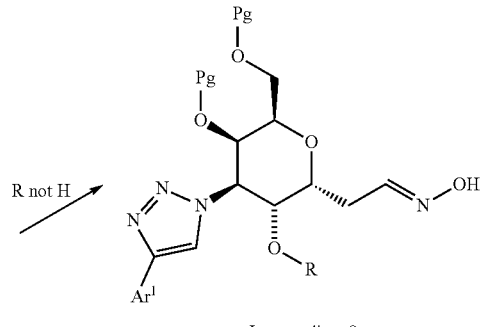

Intermediate 8

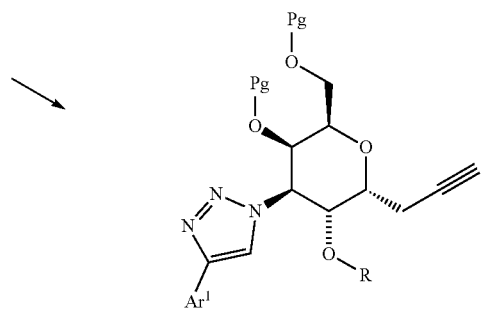

Intermediate 9

Intermediate 7a: 2-((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)acetaldehyde Intermediate 6a (4270 mg, 9.72 mmol, 1 eq) is suspended in 1,4-dioxane (50 mL) and water (15 mL). 2,6-lutidine (1.24 mL, 10.6 mmol, 3 eq) and sodium periodate (6235 mg, 29.2 mmol, 3 eq) are added, followed by the addition of potassium osmate dihydrate (15 mg, 0.0408 mmol, 0.0042 eq). The suspension is vigorously stirred at rt o/n. The mixture is diluted with water and EA and adjusted carefully to pH 2-3 with HCl (1N). The two layers are separated and the org. layer is washed with brine, dried over MgSO$_4$ and concentrated under reduced pressure. The crude is purified by FC using CombiFlash (40 g SiO$_2$ column; gradient: 0-100% EA in hept) to give the desired aldehyde as a colourless solid. LCMS (A): t$_R$=0.91 min; [M+H]$^+$=442.12

Intermediate 7c: (2R,3R,4R,5R,6R)-2-(acetoxymethyl)-6-(2-oxoethyl)-4-(4-(3,4,5-trifluorophenyl)-1H-1,2,3-triazol-1-yl)tetrahydro-2H-pyran-3,5-diyl diacetate Preparation in analogy to Intermediate 7a, starting from Intermediate 3a. LCMS (A): t$_R$=0.93 min; [M+H]$^+$=514.10

Intermediate 8a: 2-((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)acetaldehyde oxime Intermediate 7a (1390 mg, 3.15 mmol, 1 eq), hydroxylamine HCl (328 mg, 4.72 mmol, 1.5 eq) and NaOAc (775 mg, 9.45 mmol, 3 eq) are charged into a flask and suspended in EtOH (5 mL) and H$_2$O (5 mL). THF (5 mL) is added and the mixture is stirred at rt for 1.5 h. The mixture is partitioned between EA and water. The org. layer is washed with brine, dried over MgSO$_4$ and concentrated under reduced pressure. The crude is triturated in TBME and hept 3/1 (20 mL), treated with ultrasonic sound and off-white crystals are filtered off and dried at hv.

The desired oxime (E/Z mixture) is isolated as an off-white solid. LCMS (A): $t_R$=0.88 min; [M+H]$^+$=457.16

Intermediate 8b: (4aR,6R,7R,8S,8aR)-6-(2-(hydroxyimino)ethyl)-2,2-dimethyl-8-(4-(3,4,5-trifluorophenyl)-1H-1,2,3-triazol-1-yl)hexahydropyrano[3,2-d][1,3]dioxin-7-yl acetate Preparation in analogy to Intermediate 8a, starting from Intermediate 7b. LCMS (A): $t_R$=0.90 min; [M+H]$^+$=485.18

Intermediate 8c: (2R,3R,4R,5R,6R)-2-(acetoxymethyl)-6-(2-(hydroxyimino)ethyl)-4-(4-(3,4,5-trifluorophenyl)-1H-1,2,3-triazol-1-yl)tetrahydro-2H-pyran-3,5-diyl diacetate Preparation in analogy to Intermediate 8a, starting from Intermediate 7c. LCMS (A): $t_R$=0.89 min; [M+H]$^+$=529.05

Intermediate 9a: 1-((4aR,6R,7R,8R,8aR)-7-methoxy-2,2-dimethyl-6-(prop-2-yn-1-yl)hexahydropyrano[3,2-d][1,3]dioxin-8-yl)-4-(3,4,5-trifluorophenyl)-1H-1,2,3-triazole Intermediate 7a (750 mg, 1.7 mmol, 1 eq) is suspended in MeOH (15 mL) and dimethyl (1-diazo-2-oxopropyl)phosphonate (10% solution in MeCN) (4.61 mL, 2.04 mmol, 1.2 eq) is added, followed by K$_2$CO$_3$ (470 mg, 3.4 mmol, 2 eq). The mixture is stirred at rt for 3 h. The mixture is partitioned between DCM and sat. NH$_4$Cl solution. The aq. phase is extracted once more with DCM. The combined org. phases are dried over MgSO$_4$ and concentrated. The crude product is purified by FC (CombiFlash 24 g cartridge, 30-100% EA in hept) to give the desired intermediate as a colourless solid. LCMS (A): $t_R$=0.99 min; [M+H]$^+$=437.91

$^1$H NMR (500 MHz, DMSO-d6) δ: 8.71 (s, 1H), 7.86 (dd, J$^1$=6.8 Hz, J$^2$=9.0 Hz, 2H), 5.19-5.21 (m, 1H), 4.59 (m, 1H), 4.27 (d, J=3.4 Hz, 1H), 4.23 (dd, J$^1$=5.7 Hz, J$^2$=11.4 Hz, 1H), 4.06 (d, J=11.0 Hz, 1H), 3.67-3.70 (m, 2H), 3.22 (s, 3H), 2.95 (ddd, J$^1$=2.5 Hz, J$^2$=10.8 Hz, J$^3$=17.6 Hz, 1H), 2.84 (t, J=2.6 Hz, 1H), 2.45 (m, 1H), 1.32 (s, 3H), 1.20 (s, 3H)

Intermediate 9b (reference example): 1-((4aR,6S,7R,8R,8aR)-7-methoxy-2,2-dimethyl-6-(prop-2-yn-1-yl)hexahydropyrano[3,2-d][1,3]dioxin-8-yl)-4-(3,4,5-trifluorophenyl)-1H-1,2,3-triazole The title intermediate was isolated in minor quantities in the synthesis of Intermediate 9a. LCMS (A): $t_R$=1.00 min; [M+H]$^+$=437.91

$^1$H NMR (500 MHz, DMSO-d6) δ: 8.77 (s, 1H), 7.92 (dd, J$^1$=9.0 Hz, J$^2$=6.8 Hz, 2H), 5.11 (dd, J$^1$=10.6 Hz, J$^2$=3.2 Hz, 1H), 4.33 (d, J=2.9 Hz, 1H), 4.01 (dd, J$^1$=12.7 Hz, J$^2$=1.7 Hz, 1H), 3.90 (m, 1H), 3.75 (dd, J$^1$=12.8 Hz, J$^2$=1.4 Hz, 1H), 3.61-3.65 (m, 2H), 3.06 (s, 3H), 2.91 (t, J=2.6 Hz, 1H), 1.31 (d, J=69.7 Hz, 7H)

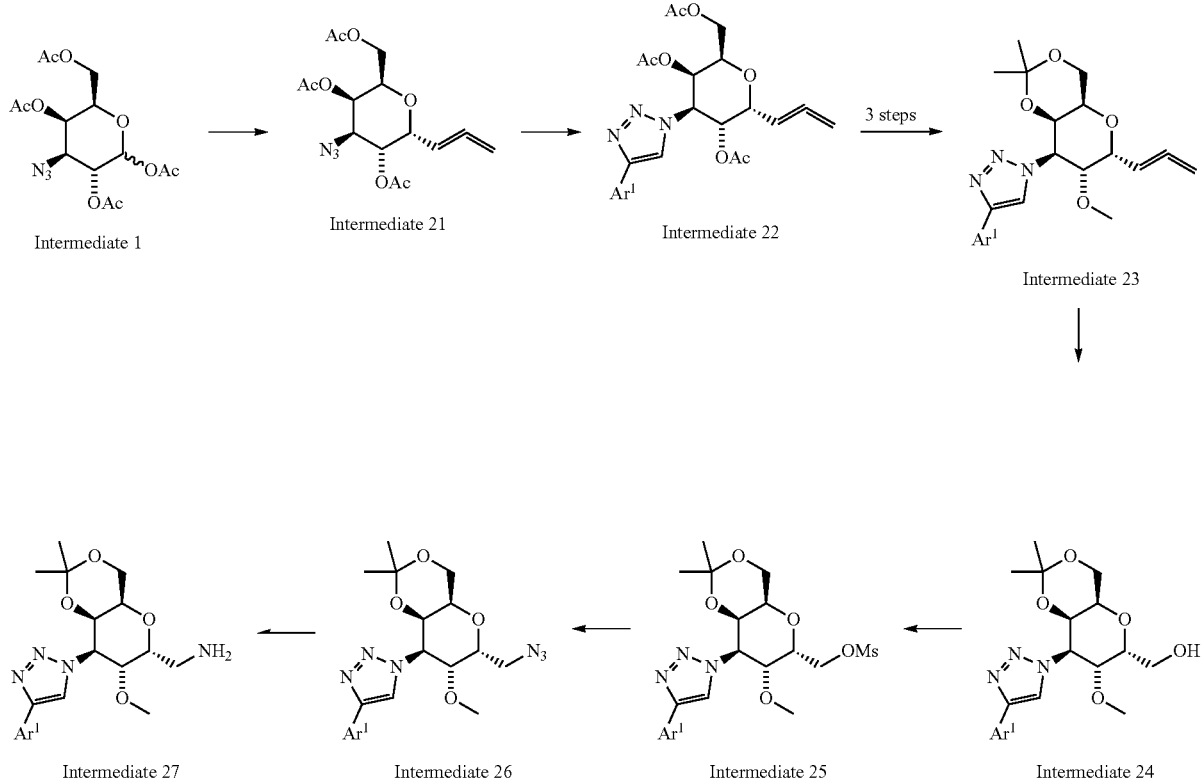

Intermediate 21: (2R,3R,4R,5R,6R)-2-(acetoxymethyl)-4-azido-6-(propa-1,2-dien-1-yl)tetrahydro-2H-pyran-3,5-diyl diacetate Intermediate 1 (3733 mg, 10 mmol, 1 eq) is dissolved in MeCN (20 mL) and cooled to 3° C. Trimethyl(propargyl) silane (3.73 mL, 25 mmol, 2.5 eq) is added followed by BF$_3$OEt$_2$ (3.7 mL, 30 mmol, 3 eq) and trimethylsilyl trifluoromethanesulfonate (3.66 mL, 20 mmol, 2 eq) dropwise. The mixture is stirred at 0° C. for 1.5 h and at rt for 1 h. Mixture is partitioned between TBME and sat NaHCO$_3$. The org. phase is washed with brine, dried over MgSO$_4$ and concentrated. The crude product is purified by FC (hept/EA 2:1) to give the desired allene intermediate as a yellowish oil.

$^1$H NMR (500 MHz, DMSO-D6) δ: 5.56 (q, J=6.7 Hz, 1H), 5.35 (d, J=2.2 Hz, 1H), 4.98-5.05 (m, 3H), 4.74 (m, 1H), 4.35 (dd, J$^1$=3.3 Hz, J$^2$=11.2 Hz, 1H), 4.20-4.23 (m, 1H), 4.00-4.03 (m, 1H), 3.90 (dd, J$^1$=7.0 Hz, J$^2$=11.4 Hz, 1H), 2.12 (s, 3H), 2.09 (s, 3H), 2.00-2.02 (m, 4H)

Intermediate 22a: (2R,3R,4R,5R,6R)-2-(acetoxymethyl)-6-(propa-1,2-dien-1-yl)-4-(4-(3,4,5-trifluorophenyl)-1H-1,2,3-triazol-1-yl)tetrahydro-2H-pyran-3,5-diyl diacetate The title compound is prepared in analogy to Intermediate 3a, starting from Intermediate 21. LCMS (A): t$_R$=1.02 min; [M+H]$^+$=510.24

$^1$H NMR (500 MHz, DMSO-d6) δ: 8.81 (s, 1H), 7.82-7.86 (m, 2H), 5.80 (q, J=6.8 Hz, 1H), 5.65-5.72 (m, 2H), 5.40 (d, J=1.5 Hz, 1H), 5.06 (dd, J$^1$=6.6 Hz, J$^2$=2.3 Hz, 2H), 4.96-4.99 (m, 1H), 4.50 (t, J=6.3 Hz, 1H), 4.01 (m, 2H), 2.00-2.04 (m, 6H), 1.87 (s, 3H)

Intermediate 23a: 1-((4aR,6R,7R,8R,8aR)-7-methoxy-2,2-dimethyl-6-(propa-1,2-dien-1-yl)hexahydropyrano[3,2-d][1,3]dioxin-8-yl)-4-(3,4,5-trifluorophenyl)-1H-1,2,3-triazole The title intermediate is prepared starting from Intermediate 22a and following the procedures of Intermediates 4a, 5a and 6a. LCMS (A): t$_R$=1.02 min; [M+H]$^+$=438.21

$^1$H NMR (500 MHz, DMSO-d6) δ: 8.71 (s, 1H), 7.87 (dd, J$^1$=6.8 Hz, J$^2$=9.0 Hz, 2H), 5.75 (m, 1H), 5.13 (dd, J$^1$=3.3 Hz, J$^2$=11.4 Hz, 1H), 5.07 (m, 1H), 4.98 (m, 2H), 4.34-4.34 (m, 1H), 4.26 (dd, J$^1$=5.6 Hz, J$^2$=11.5 Hz, 1H), 4.04 (dd, J$^1$=2.0 Hz, J$^2$=12.9 Hz, 1H), 3.82 (d, J=0.7 Hz, 1H), 3.68 (dd, J$^1$=1.5 Hz, J$^2$=12.9 Hz, 1H), 3.22 (s, 3H), 1.32 (s, 3H), 1.21 (s, 3H)

Intermediate 24a: ((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)methanol Intermediate 23a (1000 mg, 2.29 mmol, 1 eq) is dissolved in DCM/MeOH 4:1 (60 mL) and cooled to −70° C. Ozone is bubbled through the solution until the KI solution in the scrubber turned brown (~60 min). Excess O$_3$ is purged by bubbling N$_2$ through for 10 min. NaBH$_4$ (86.5 mg, 2.29 mmol, 1 eq) is added at −78° C., the dry ice bath is removed and the mixture is allowed to warm up to rt within 1 h. The mixture is then carefully quenched with water (25 mL), the layers are separated, the org. layer is dried over MgSO$_4$ and concentrated under reduced pressure.

The crude solid is purified by FC using CombiFlash (24 g SiO$_2$ column; gradient from hept/EA 2/1 to 100% EA in 20 min) to give the title intermediate as a colourless solid. LCMS (A): t$_R$=0.84 min; [M+H]$^+$=430.29

$^1$H NMR (500 MHz, DMSO-d6) δ: 8.69 (s, 1H), 7.86 (m, 2H), 5.29 (dd, J$^1$=11.4 Hz, J$^2$=3.4 Hz, 1H), 4.80 (t, J=5.5 Hz, 1H), 4.34 (m, 2H), 4.24 (dd, J$^1$=11.4 Hz, J$^2$=6.1 Hz, 1H), 3.96-4.07 (m, 2H), 3.91 (s, 1H), 3.71 (dd, J$^1$=12.7 Hz, J$^2$=1.4 Hz, 1H), 3.63 (ddd, J$^1$=12.3 Hz, J$^2$=5.8 Hz, J$^3$=2.9 Hz, 1H), 3.23 (s, 3H), 1.32 (s, 3H), 1.20 (s, 3H)

Intermediate 25a: ((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)methyl methanesulfonate Intermediate 24a (400 mg, 0.932 mmol, 1 eq) is dissolved in DCM (8 mL) and cooled to 0° C. At this temperature MsCl (0.0736 mL, 0.932 mmol, 1 eq) and DIPEA (0.191 mL, 1.12 mmol, 1.2 eq) are added and the mixture is stirred at 0° C. for 30 min. More MsCl (0.0144 mL, 0.186 mmol, 0.2 eq) is added and the mixture is stirred at 0° C. for further 30 min. The mixture is diluted with DCM and washed with water. The org. layer is dried over a phase separator and concentrated under reduced pressure. The crude foam is purified by FC using CombiFlash (12 g SiO$_2$ column; gradient from hept to hept/EA 1/2 in 16 min) to give the desired intermediate as a colourless solid. LCMS (A): t$_R$=0.96 min; [M+H]$^+$=508.14

$^1$H NMR (500 MHz, DMSO-d6) δ: 8.72-8.74 (m, 1H), 7.83-7.90 (m, 2H), 5.18-5.27 (m, 1H), 4.89-4.98 (m, 1H), 4.75-4.84 (m, 1H), 4.27-4.37 (m, 3H), 4.06-4.09 (m, 1H), 3.83 (s, 1H), 3.73 (dd, J$^1$=12.9 Hz, J$^2$=1.5 Hz, 1H), 3.26 (d, J=6.1 Hz, 6H), 1.34 (s, 3H), 1.22 (s, 3H)

Intermediate 26a: 1-((4aR,6R,7R,8R,8aR)-6-(azidomethyl)-7-methoxy-2,2-dimethylhexahydropyrano[3,2-d][1,3]dioxin-8-yl)-4-(3,4,5-trifluorophenyl)-1H-1,2,3-triazole To a solution of Intermediate 25a (409 mg, 0.806 mmol, 1 eq) in dry DMF (10 mL) under N$_2$ is added sodium azide (62.9 mg, 0.967 mmol, 1.2 eq). The reaction mixture is heated at 70° C. for 5 h. The temperature is increased to 80° C. and the mixture stirred at this temperature until completion of the reaction. The mixture is allowed to cool to rt, diluted with EA and water and the layers are separated. The aq. layer is extracted once more with EA. The combined org. layers are washed twice with water, brine, dried over MgSO$_4$, filtered and concentrated under reduced pressure. The crude colorless solid is purified by FC using CombiFlash (12 g SiO$_2$ column; gradient: hept to hept/EA 1/1 in 17 min) to give the desired intermediate as a colourless solid. LCMS (A): t$_R$=1.01 min; [M+H]$^+$=455.19

$^1$H NMR (500 MHz, DMSO) δ: 8.68-8.74 (m, 1H), 7.82-7.91 (m, 2H), 5.13-5.23 (m, 1H), 4.67-4.74 (m, 1H), 4.27-4.33 (m, 2H), 4.17-4.25 (m, 1H), 4.05-4.12 (m, 1H), 3.78-3.86 (m, 1H), 3.66-3.74 (m, 1H), 3.23-3.26 (m, 1H), 3.22 (s, 3H), 1.34 (s, 3H), 1.23 (s, 3H)

Intermediate 27a: ((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)methanamine To a solution of Intermediate 26a (500 mg, 1.1 mmol, 1 eq) in THF (7.5 mL) was added PPh$_3$ (583 mg, 2.2 mmol, 2 eq) and water (1.5 mL). The resulting mixture was then heated under N₂ at 60° C. for 3 h. The mixture was diluted with EA and was then extracted with 10% citric acid (3 times) until all amine was removed from org phase. The combined aq. layers were once more extracted with EA and were then basified with aq. sat. NaHCO₃. The basic aq. layer was extracted twice with EA. The combined org. layers were dried over MgSO₄, filtered and concentrated under reduced pressure. Used as such.

LCMS (A): $t_R$=0.72 min; [M+H]⁺=429.09

¹H NMR (500 MHz, DMSO) δ: 8.42-8.90 (m, 1H), 7.77-7.89 (m, 2H), 5.09 (dd, $J^1$=11.4 Hz, $J^2$=3.4 Hz, 1H), 4.27-4.31 (m, 2H), 4.23 (m, 1H), 3.99-4.03 (m, 1H), 3.74 (dd, $J^1$=1.5 Hz, $J^2$=12.8 Hz, 1H), 3.68 (s, 1H), 3.21 (s, 3H), 3.11 (dd, $J^1$=13.8 Hz, $J^2$=10.5 Hz, 1H), 2.67 (dd, $J^1$=13.8 Hz, $J^2$=3.4 Hz, 1H), 1.32 (s, 3H)

All further analogs of Intermediates 3-27 with different Ar¹-substituents have been prepared in analogy to above procedures starting from known or commercially available substituted aryl acetylenes.

The following most important analogs of Intermediates of 6, 8, 9, 26 and 27 were namely prepared and used in the synthesis of final examples:

| Intermediate | Compound | $t_R$ [min] (LC-MS method A) | MS Data m/z [M + H]⁺ |
|---|---|---|---|
| 6d | 1-((4aR,6R,7R,8R,8aR)-6-allyl-7-methoxy-2,2-dimethylhexahydropyrano[3,2-d][1,3]dioxin-8-yl)-4-(3,5-difluoro-4-methylphenyl)-1H-1,2,3-triazol | 1.04 | 436.23 |
| 6e | 1-((4aR,6R,7R,8R,8aR)-6-allyl-7-methoxy-2,2-dimethylhexahydropyrano[3,2-d][1,3]dioxin-8-yl)-4-(4-chloro-3,5-difluorophenyl)-1H-1,2,3-triazole | 1.06 | 456.16 |
| 6f | ((2R,3R,4R,5R,6R)-3-acetoxy-6-allyl-4-(4-(3,5-difluoro-4-methylphenyl)-1H-1,2,3-triazol-1-yl)-5-methoxytetrahydro-2H-pyran-2-yl)methyl acetate | 1.03 | 480.16 |
| 6g | ((2R,3R,4R,5R,6R)-3-acetoxy-6-allyl-4-(4-(4-chloro-3,5-difluorophenyl)-1H-1,2,3-triazol-1-yl)-5-methoxytetrahydro-2H-pyran-2-yl)methyl acetate | 1.05 | 500.07 |
| 6h | 1-((4aR,6R,7R,8R,8aR)-6-allyl-7-methoxy-2,2-dimethylhexahydropyrano[3,2-d][1,3]dioxin-8-yl)-4-(3-fluoro-4-methylphenyl)-1H-1,2,3-triazole | 1.00 | 418.25 |
| 6i | 1-((4aR,6R,7R,8R,8aR)-6-allyl-7-methoxy-2,2-dimethylhexahydropyrano[3,2-d][1,3]dioxin-8-yl)-4-(2,3-difluoro-4-methylphenyl)-1H-1,2,3-triazole | 1.06 | 436.25 |
| 6j | 1-((4aR,6R,7R,8R,8aR)-6-allyl-7-methoxy-2,2-dimethylhexahydropyrano[3,2-d][1,3]dioxin-8-yl)-4-(4-chloro-2,3-difluorophenyl)-1H-1,2,3-triazole | 1.08 | 456.17 |
| 6k | 1-((4aR,6R,7R,8R,8aR)-6-allyl-7-methoxy-2,2-dimethylhexahydropyrano[3,2-d][1,3]dioxin-8-yl)-4-(4-bromo-2,3-difluorophenyl)-1H-1,2,3-triazole | 1.06 | 500.10 |
| 6l | 1-((4aR,6R,7R,8R,8aR)-6-allyl-7-methoxy-2,2-dimethylhexahydropyrano[3,2-d][1,3]dioxin-8-yl)-4-(4-chloro-3-fluorophenyl)-1H-1,2,3-triazole | 1.02 | 438.16 |
| 6m | 1-((4aR,6R,7R,8R,8aR)-6-allyl-7-methoxy-2,2-dimethylhexahydropyrano[3,2-d][1,3]dioxin-8-yl)-4-(2,3,4-trifluorophenyl)-1H-1,2,3-triazole | 1.02 | 440.20 |
| 6n | (4aR,6R,7R,8S,8aR)-6-allyl-8-(4-(2,3-difluoro-4-methylphenyl)-1H-1,2,3-triazol-1-yl)-2,2-dimethylhexahydropyrano[3,2-d][1,3]dioxin-7-yl acetate | 1.05 | 464.20 |
| 6o | 1-((4aR,6R,7R,8R,8aR)-6-allyl-7-methoxy-2,2-dimethylhexahydropyrano[3,2-d][1,3]dioxin-8-yl)-4-(3-chloro-4,5-difluorophenyl)-1H-1,2,3-triazole | 1.05 | 456.21 |
| 6p | 1-((4aR,6R,7R,8R,8aR)-6-allyl-7-methoxy-2,2-dimethylhexahydropyrano[3,2-d][1,3]dioxin-8-yl)-4-(2,5-difluoro-4-methylphenyl)-1H-1,2,3-triazole | 1.04 | 436.21 |
| 6q | 4-(1-((4aR,6R,7R,8R,8aR)-6-allyl-7-methoxy-2,2-dimethylhexahydropyrano[3,2-d][1,3]dioxin-8-yl)-1H-1,2,3-triazol-4-yl)-2,6-difluorobenzonitrile | 1.03 | 447.22 |
| 6r | 4-(1-((4aR,6R,7R,8R,8aR)-6-allyl-7-methoxy-2,2-dimethylhexahydropyrano[3,2-d][1,3]dioxin-8-yl)-1H-1,2,3-triazol-4-yl)-2,3-difluorobenzonitrile | 1.03 | 452.24 |
| 6s | 1-((4aR,6R,7R,8R,8aR)-6-allyl-7-methoxy-2,2-dimethylhexahydropyrano[3,2-d][1,3]dioxin-8-yl)-4-(2,3-difluoro-4-methoxyphenyl)-1H-1,2,3-triazole | 1.01 | 452.24 |
| 8d | ((2R,3R,4R,5R,6R)-3-acetoxy-6-(2-(hydroxyimino)ethyl)-5-methoxy-4-(4-(3,4,5-trifluorophenyl)-1H-1,2,3-triazol-1-yl)tetrahydro-2H-pyran-2-yl)methyl acetate | 0.89 | 501.16 |
| 8e | ((2R,3R,4R,5R,6R)-3-acetoxy-4-(4-(3,5-difluoro-4-methylphenyl)-1H-1,2,3-triazol-1-yl)-6-(2-(hydroxyimino)ethyl)-5-methoxytetrahydro-2H-pyran-2-yl)methyl acetate | 0.89 | 497.11 |
| 8f | ((2R,3R,4R,5R,6R)-3-acetoxy-4-(4-(4-chloro-3,5-difluorophenyl)-1H-1,2,3-triazol-1-yl)-6-(2-(hydroxyimino)ethyl)-5-methoxytetrahydro-2H-pyran-2-yl)methyl acetate | 0.91 | 517.01 |
| 8g | 2-((4aR,6R,7R,8R,8aR)-8-(4-(3-fluorophenyl)-1H-1,2,3-triazol-1-yl)-7-methoxy-2,2-dimethylhexahydropyrano[3,2-d][1,3]dioxin-6-yl)acetaldehyde oxime | 0.81 | 421.12 |

-continued

| Intermediate | Compound | $t_R$ [min] (LC-MS method A) | MS Data m/z [M + H]⁺ |
|---|---|---|---|
| 8h | 2-((4aR,6R,7R,8R,8aR)-8-(4-(4-chloro-3-fluorophenyl)-1H-1,2,3-triazol-1-yl)-7-methoxy-2,2-dimethylhexahydropyrano[3,2-d][1,3]dioxin-6-yl)acetaldehyde oxime | 0.88 | 455.07 |
| 8i | 2-((4aR,6R,7R,8R,8aR)-8-(4-(3,5-difluorophenyl)-1H-1,2,3-triazol-1-yl)-7-methoxy-2,2-dimethylhexahydropyrano[3,2-d][1,3]dioxin-6-yl)acetaldehyde oxime | 0.85 | 439.10 |
| 8j | 2-((4aR,6R,7R,8R,8aR)-8-(4-(4-bromo-3-fluorophenyl)-1H-1,2,3-triazol-1-yl)-7-methoxy-2,2-dimethylhexahydropyrano[3,2-d][1,3]dioxin-6-yl)acetaldehyde oxime | 0.89 | 500.99 |
| 8k | 2-((4aR,6R,7R,8R,8aR)-8-(4-(3,5-difluoro-4-methylphenyl)-1H-1,2,3-triazol-1-yl)-7-methoxy-2,2-dimethylhexahydropyrano[3,2-d][1,3]dioxin-6-yl)acetaldehyde oxime | 0.89 | 453.18 |
| 8l | 2-((4aR,6R,7R,8R,8aR)-8-(4-(3-fluoro-4-methylphenyl)-1H-1,2,3-triazol-1-yl)-7-methoxy-2,2-dimethylhexahydropyrano[3,2-d][1,3]dioxin-6-yl)acetaldehyde oxime | 0.86 | 435.18 |
| 8m | 2-((4aR,6R,7R,8R,8aR)-8-(4-(4-chloro-2,3-difluorophenyl)-1H-1,2,3-triazol-1-yl)-7-methoxy-2,2-dimethylhexahydropyrano[3,2-d][1,3]dioxin-6-yl)acetaldehyde oxime | 0.93 | 473.19 |
| 8n | 2-((4aR,6R,7R,8R,8aR)-8-(4-(4-bromo-2,3-difluorophenyl)-1H-1,2,3-triazol-1-yl)-7-methoxy-2,2-dimethylhexahydropyrano[3,2-d][1,3]dioxin-6-yl)acetaldehyde oxime | 0.93 | 519.14 |
| 8o | 2-((4aR,6R,7R,8R,8aR)-8-(4-(4-chloro-3,5-difluorophenyl)-1H-1,2,3-triazol-1-yl)-7-methoxy-2,2-dimethylhexahydropyrano[3,2-d][1,3]dioxin-6-yl)acetaldehyde oxime | 0.92 | 473.12 |
| 8p | 2-((4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxin-6-yl)acetaldehyde oxime | 0.89 | 453.19 |
| 8q | 2-((4aR,6R,7R,8R,8aR)-8-(4-(3-chloro-5-fluorophenyl)-1H-1,2,3-triazol-1-yl)-7-methoxy-2,2-dimethylhexahydropyrano[3,2-d][1,3]dioxin-6-yl)acetaldehyde oxime | 0.89 | 455.19 |
| 8r | (4aR,6R,7R,8S,8aR)-8-(4-(2,3-difluoro-4-methylphenyl)-1H-1,2,3-triazol-1-yl)-6-(2-(hydroxyimino)ethyl)-2,2-dimethylhexahydropyrano[3,2-d][1,3]dioxin-7-yl acetate | 0.91 | 481.21 |
| 8s | 2-((4aR,6R,7R,8R,8aR)-7-methoxy-2,2-dimethyl-8-(4-(2,3,4-trifluorophenyl)-1H-1,2,3-triazol-1-yl)hexahydropyrano[3,2-d][1,3]dioxin-6-yl)acetaldehyde oxime | 0.88 | 457.19 |
| 8t | 2-((4aR,6R,7R,8R,8aR)-8-(4-(3-chloro-4,5-difluorophenyl)-1H-1,2,3-triazol-1-yl)-7-methoxy-2,2-dimethylhexahydropyrano[3,2-d][1,3]dioxin-6-yl)acetaldehyde oxime | 0.92 | 473.18 |
| 8u | 2-((4aR,6R,7R,8R,8aR)-8-(4-(2,5-difluoro-4-methylphenyl)-1H-1,2,3-triazol-1-yl)-7-methoxy-2,2-dimethylhexahydropyrano[3,2-d][1,3]dioxin-6-yl)acetaldehyde oxime | 0.89 | 453.23 |
| 8v | 2-((4aR,6R,7R,8R,8aR)-8-(4-(2,3-difluorophenyl)-1H-1,2,3-triazol-1-yl)-7-methoxy-2,2-dimethylhexahydropyrano[3,2-d][1,3]dioxin-6-yl)acetaldehyde oxime | 0.84 | 439.2 |
| 9c | 4-(3-fluorophenyl)-1-((4aR,6R,7R,8R,8aR)-7-methoxy-2,2-dimethyl-6-(prop-2-yn-1-yl)hexahydropyrano[3,2-d][1,3]dioxin-8-yl)hexahydropyrano[3,2-d][1,3]dioxin-8-yl)-1H-1,2,3-triazole | 0.93 | 402.15 |
| 9d | 4-(4-bromo-3-fluorophenyl)-1-((4aR,6R,7R,8R,8aR)-7-methoxy-2,2-dimethyl-6-(prop-2-yn-1-yl)hexahydropyrano[3,2-d][1,3]dioxin-8-yl)-1H-1,2,3-triazole | 1.00 | 482.00 |
| 9e | 4-(4-chloro-3-fluorophenyl)-1-((4aR,6R,7R,8R,8aR)-7-methoxy-2,2-dimethyl-6-(prop-2-yn-1-yl)hexahydropyrano[3,2-d][1,3]dioxin-8-yl)-1H-1,2 | 0.99 | 435.84 |
| 9f | 4-(3,5-difluorophenyl)-1-((4aR,6R,7R,8R,8aR)-7-methoxy-2,2-dimethyl-6-(prop-2-yn-1-yl)hexahydropyrano[3,2-d][1,3]dioxin-8-yl)-1H-1,2,3-triazole | 0.96 | 419.89 |
| 9g | (4aR,6R,7R,8R,8aR)-2,2-dimethyl-6-(prop-2-yn-1-yl)-8-(4-(3,4,5-trifluorophenyl)-1H-1,2,3-triazol-1-yl)hexahydropyrano[3,2-d][1,3]dioxin-7-ol | 0.90 | 424.17 |
| 9h | 1-((4aR,6R,7R,8R,8aR)-7-methoxy-2,2-dimethyl-6-(prop-2-yn-1-yl)hexahydropyrano[3,2-d][1,3]dioxin-8-yl)-4-(2,3,4-trifluorophenyl)-1H-1,2,3-triazole | 0.99 | 438.07 |
| 9i | (4aR,6R,7R,8R,8aR)-8-(4-(2,3-difluoro-4-methylphenyl)-1H-1,2,3-triazol-1-yl)-2,2-dimethyl-6-(prop-2-yn-1-yl)hexahydropyrano[3,2-d][1,3]dioxin-7-ol | 0.92 | 420.22 |
| 9j | (4aR,6R,7R,8R,8aR)-8-(4-(4-chloro-2,3-difluorophenyl)-1H-1,2,3-triazol-1-yl)-2,2-dimethyl-6-(prop-2-yn-1-yl)hexahydropyrano[3,2-d][1,3]dioxin-7-ol | 0.94 | 440.19 |
| 9k | 4-(4-chloro-2,3-difluorophenyl)-1-((4aR,6R,7R,8R,8aR)-7-methoxy-2,2-dimethyl-6-(prop-2-yn-1-yl)hexahydropyrano[3,2-d][1,3]dioxin-8-yl)-1H-1,2,3-triazole | 1.04 | 453.89 |
| 9l | 4-(2,3-difluoro-4-methylphenyl)-1-((4aR,6R,7R,8R,8aR)-7-methoxy-2,2-dimethyl-6-(prop-2-yn-1-yl)hexahydropyrano[3,2-d][1,3]dioxin-8-yl)-1H-1,2,3-triazole | 1.02 | 434.22 |
| 9m | (4aR,6R,7R,8R,8aR)-2,2-dimethyl-6-(prop-2-yn-1-yl)-8-(4-(2,3,4-trifluorophenyl)-1H-1,2,3-triazol-1-yl)hexahydropyrano[3,2-d][1,3]dioxin-7-ol | 0.88 | 424.19 |

-continued

| Intermediate | Compound | $t_R$ [min] (LC-MS method A) | MS Data m/z [M + H]$^+$ |
|---|---|---|---|
| 9n | 4-(4-bromo-2,3-difluorophenyl)-1-((4aR,6R,7R,8R,8aR)-7-methoxy-2,2-dimethyl-6-(prop-2-yn-1-yl)hexahydropyrano[3,2-d][1,3]dioxin-8-yl)-1H-1,2,3-triazole | 1.04 | 497.87 |
| 26c | 1-((4aR,6R,7R,8R,8aR)-6-(azidomethyl)-7-methoxy-2,2-dimethylhexahydropyrano[3,2-d][1,3]dioxin-8-yl)-4-(4-chloro-2,3-difluorophenyl)-1H-1,2,3-triazole | 1.06 | 471.17 |
| 27b | ((4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxin-6-yl)methanamine | 0.70 | 425.31 |
| 27c | ((4aR,6R,7R,8R,8aR)-8-(4-(4-chloro-2,3-difluorophenyl)-1H-1,2,3-triazol-1-yl)-7-methoxy-2,2-dimethylhexahydropyrano[3,2-d][1,3]dioxin-6-yl)methanamine | 0.71 | 445.18 |

Preparation of Other Non-Commercial Intermediates:
The following intermediates were prepared according to the procedure of Intermediate 8a:

| Intermediate | Compound | $t_R$ [min] (LC-MS method) | MS Data m/z [M + H]$^+$ |
|---|---|---|---|
| 31 | 3-((tert-butyldimethylsilyl)oxy)-4-methoxybenzaldehyde oxime | 1.05 (A) | 282.21 |
| 32 | 1-methyl-2-oxo-2,3-dihydro-1H-benzo[d]imidazole-5-carbaldehyde oxime | 0.53 (A) | 192.34 |
| 37 | tert-butyl 4-((hydroxyimino)methyl)piperidine-1-carboxylate | 0.73 (A) | 229.29 |

Intermediate 33: 2-(4-ethynylpiperidin-1-yl)oxazole

4-Ethynylpiperidine hydrochloride (118 mg, 0.81 mmol, 1 eq) and 2-bromo-1,3-oxazole (126 mg, 0.81 mmol, 1 eq) are dissolved in DMF (2 mL) and $Cs_2CO_3$ (660 mg, 2.03 mmol, 2.5 eq) is added at rt. The mixture is stirred at rt for 2 h and at 100° C. for 1 h. The mixture is diluted with water and extracted twice with EA. The org. layers are washed with brine, before they are combined, dried over $MgSO_4$, filtered and evaporated. The product is purified by FC (CombiFlash, 4 g redisep column, 0-100% EA in hept) to give the desired intermediate as a pinkish oil.
LCMS (A): $t_R$=0.47 min; [M+H]$^+$=177.33

Intermediate 34: 2-(4-ethynylpiperidin-1-yl)benzo[d]thiazole

This intermediate is prepared in analogy to Intermediate 33. LCMS (A): $t_R$=0.78 min; [M+H]$^+$=243.12

Intermediate 35: 2-(4-ethynylpiperidin-1-yl)thiazole

This intermediate is prepared in analogy to Intermediate 33. LCMS (A): $t_R$=0.50 min; [M+H]$^+$=193.25

Intermediate 36: benzyl 4-azidopiperidine-1-carboxylate

This intermediate is prepared in analogy to literature procedures (WO 2017007689). LCMS (A): $t_R$=0.96 min; [M+H]$^+$=261.15

Intermediate 38: 1-(isopropylimino)hexahydro-1l6-thiopyran-4-carbaldehyde 1-oxide oxime A solution of tetrahydrothiopyran-4-carbaldehyde (1 eq) in EtOH (1 mL/mmol) and CSA (tip of spatula) is stirred in a sealed flask until completion of reaction.

The ethylacetal intermediate is oxidized according to the general procedure N.

The sulfoxide intermediate is oxidized according to the general procedure M.

The sulfoximine intermediate is alkylated according to the general procedure J.

The acetal is deprotected according to the general procedure C.

$^1$H NMR (500 MHz, DMSO) δ: 9.33-9.72 (m, 1H), 3.44-3.62 (m, 2H), 3.18-3.23 (m, 2H), 3.02-3.08 (m, 1H), 2.62-2.67 (m, 1H), 2.16-2.20 (m, 2H), 1.73-1.81 (m, 2H), 1.05-1.07 (m, 6H)

The aldehyde is transformed into the title oxime in analogy to Intermediate 8a and used without purification

Intermediate 39: ethyl 4-ethynylpiperidine-1-carboxylate

This intermediate is prepared from 4-ethynylpiperidine hydrochloride according to the general procedure G. LCMS (A): $t_R$=0.80; [M+H]$^+$=182.32.

Intermediate 40: 4-ethynyl-1-(N-isopropylpropan-2-ylsulfonimidoyl)piperidine To a solution of diisopropyl disulfide (1 eq) in acetic acid (2 eq) cooled to −40° C. is added slowly sulfuryl chloride (3 eq). The reaction mixture is stirred at rt until completion of reaction, concentrated and used as such in the next step.

The sulfinamide is prepared according to the general procedure H.

The sulfonimidamide is prepared according to the general procedure M.

The sulfonimidamide is alkylated according to the general procedure J. LCMS (A): $t_R$=0.67; [M+H]$^+$=257.24.

Intermediate 41:
trimethyl(propa-1,2-dien-1-yl)silane

The desired intermediate was prepared following literature procedures (OL 2009, 11, 5458)
$^1$H NMR (500 MHz, CDCl3) δ: 0.13 (s, 11H), 4.33 (d, J=7.1 Hz, 2H), 4.90 (t, J=7.1 Hz, 1H)

Intermediate 42:
1-ethynylcyclopentane-1-carbonitrile

To a solution of 1-formylcyclopentane-1-carbonitrile (1 eq) in MeOH (5 mL/mmol) are added $K_2CO_3$ (2 eq) and 1-diazo-1-dimethoxyphosphoryl-propan-2-one (1.1 eq). The suspension is stirred at rt for 2 h. After aq. Workup (NaHCO$_3$ sat./pentane), the crude product is dried and used without further purification.
1H NMR (500 MHz, DMSO) δ: 1.70-1.88 (m, 4H), 2.03-2.12 (m, 2H), 2.17-2.32 (m, 2H), 3.58-3.64 (m, 1H)

Intermediate 43:
N-cyclohexyl-2,2-dihydroxyacetamide

Step 1: (2R,3R)—N1,N4-dicyclohexyl-2,3-dihydroxysuccinamide (+)-Dimethyl L-tartrate (1 eq) and cyclohexylamine (2.5 eq) are stirred in a sealed flask at 80° C. for 1 h. TBME is added and the suspension is filtered. The solid is dried. LCMS (A): $t_R$=0.71; [M+H]$^+$=313.28.

Step 2: N-cyclohexyl-2,2-dihydroxyacetamide

Intermediate of step 1 (1 eq) is dissolved in dioxane/H$_2$O 5:1 (5 mL/mmol) and sodium (meta)periodate (1.2 eq) is added.
The reaction mixture is stirred at rt o/n. The suspension is filtered, the solid is washed with EA and dried. Used without purification in the next step. LCMS (A): $t_R$=0.45; [M+H]$^+$=174.25

Intermediate 44:
N-(1-acetylpiperidin-4-yl)-2,2-dihydroxyacetamide

In analogy to Intermediate 43, but using 4-amino N-acetyl piperidine instead of cyclohexylamine.

Intermediate 45: 2,2-dihydroxy-N-(tetrahydro-2H-pyran-4-yl)acetamide

In analogy to Intermediate 43, but using 4-aminotetrahydropyrane instead of cyclohexylamine.

Intermediate 46: ethyl 4-(2,2-dihydroxyacetamido)piperidine-1-carboxylate

In analogy to Intermediate 43, but using ethyl 4-aminopiperidine-1-carboxylate instead of cyclohexylamine. LCMS (A): $t_R$=0.45; [M+H]$^+$=247.26

Intermediate 47:
trimethyl(1-(nitromethyl)cyclobutoxy)silane

Step 1: 1-(nitromethyl)cyclobutan-1-ol

Nitromethane (2.75 mL, 50 mmol, 1 eq) was treated with 1,1,3,3-tetramethylguanidine (0.35 mL, 2.76 mmol, 0.05 eq)), followed by dropwise addition of cyclobutanone (3613 mg, 50 mmol, 1 eq) over 1 h. The mixture was stirred at rt o/n, diluted with EA and washed with water (2 times) and brine, dried over MgSO$_4$ and concentrated. The crude product was used as such in the next step Step 2: trimethyl(1-(nitromethyl)cyclobutoxy)silane Imidazole (1744 mg, 25.6 mmol, 1.2 eq) was dissolved in DMF (5 mL) and chlorotrimethylsilane (2.98 mL, 23.5 mmol, 1.1 eq) was added. Intermediate of step 1 (2800 mg, 21.4 mmol, 1 eq) was added dropwise over 15 min. The mixture was stirred at rt for 3 h and partitioned between TBME and water. The org. phase was washed with water and brine, dried over MgSO$_4$ and concentrated under reduced pressure (100 mbar, 40° C.) to give the desired intermediate as a liquid. $^1$H NMR (500 MHz, DMSO) δ: 4.71 (s, 2H), 3.08 (s), 2.30 (m, 2H), 2.16-2.23 (m, 2H), 1.58-1.77 (m, 2H), 1.11 (s), 0.11 (m, 9H)

Intermediate 48: 1-cyclopropyl-1-(pyridin-2-yl)prop-2-yn-1-ol

A solution of trimethylsilyl acetylene (0.252 ml, 1.73 mmol) in THF (5 ml) was cooled to 0° C. and a solution of nBuLi (2.5M in hexanes) (0.676 mL, 1.18 eq) was added dropwise under an Ar atmosphere. The clear solution stirred at 0° C. for 1 h, before a solution of cyclopropyl(2-pyridyl)methanone (250 mg, 1.65 mmol) in THF (1.5 ml) was added dropwise. The mixture was stirred at 0° C. for 1 h. The mixture was partitioned between water and DCM. The organic phase was dried over MgSO$_4$ and concentrated. The crude intermediate was dissolved in MeOH (5 mL) and K$_2$CO$_3$ (342 mg, 1.94 mmol) was added at rt and stirred until completion of reaction. The product isolated by prep HPLC (I) (yellowish foam)
$^1$H NMR (500 MHz, MeOD) δ: 8.53 (ddd, $J^1$=0.9 Hz, $J^2$=1.7 Hz, $J^3$=4.9 Hz, 1H), 7.86 (m, 1H), 7.78 (m, 1H), 7.35 (ddd, $J^1$=1.2 Hz, $J^2$=4.9 Hz, $J^3$=7.4 Hz, 1H), 2.98 (s, 1H), 1.42 (tt, $J^1$=5.1 Hz, $J^2$=8.2 Hz, 1H), 0.68-0.78 (m, 2H), 0.48-0.53 (m, 2H). LCMS (A): $t_R$=0.42; [M+H]$^+$=174.13.

Intermediate 49:
3-bromo-5-((3-ethynyloxetan-3-yl)oxy)pyridine

This intermediate was prepared in analogy to J. Med. Chem. 2011, 54, 8471-8489 (preparation of compound 22) starting from 3-ethynyloxetan-3-ol and 3-bromo-5-hydroxypyridine.
$^1$H NMR (400 MHz, MeOD) δ: 8.36 (d, J=1.8 Hz, 1H), 8.21 (d, J=2.5 Hz, 1H), 7.57 (dd, $J^1$=1.9 Hz, $J^2$=2.5 Hz, 1H), 5.02 (dd, $J^1$=0.9 Hz, $J^2$=7.2 Hz, 2H), 4.89-4.93 (m, 5H), 3.58 (s, 1H). LCMS (A): $t_R$=0.79; [M+H]$^+$=254.04

B—Preparation of Examples

General Procedure A: Cycloadditions of Nitrile Oxides with Alkenes or Alkynes

A solution of oxime intermediate (1 eq) and NCS (1.5 eq) in DMF (5 mL/mmol) is stirred at rt until complete conversion to hydroximoyl chloride. Alkene or alkyne (1-3 eq) and DIPEA or 2,6-lutidine (3-4 eq) are added and the mixture stirred at rt or 50° C. until complete conversion of intermediate. The products are isolated after aqueous workup (dil. HCl/EA) and purified as described in the general methods. Reactions with alkenes leads to formation of diastereomers which can be separated by chiral preparative HPLC as described in the general methods.

General Procedure A': Cycloadditions in One Pot Procedure from Aldehydes and Alkynes or Alkenes $K_2CO_3$ (3 eq) is added to a solution of aldehyde (4 eq) and hydroxyl amine HCl (4 eq) in DMF (5 ml/mmol) at rt. The mixture is stirred at rt o/n. NCS (5 eq) is added and the mixture further stirred at rt for 2 h. Alkyne or alkene (1 eq) and 2,6-lutidine (4 eq) are added and the mixture stirred at 55° C. until completion of reaction. The products are isolated after aqueous workup (dil. HCl/EA) and purified as described in the general methods.

General Procedure B: Copper-Catalyzed Cyloadditions of Azides with Alkynes (Click Chemistry)

A mixture of azide (1 eq), alkyne (1 eq), CuI (0.1 eq) and DIPEA (3 eq) in DMF or THF (5 mL/mmol) is heated at 50° C. until complete conversion. The products are isolated after aqueous workup (dil. HCl/EA) and purified as described in the general methods.

General Procedure C: Deprotection with aq. AcOH

The protected intermediate (acetal and/or silyl Pg) (1 eq) is refluxed in $AcOH/H_2O$ 1:1 or $AcOH/H_2O$/THF or dioxane 1:1:1 (5 ml/mmol) until completion of reaction. The products are purified as described in the general methods.

General Procedure D: Acetate deprotection with $K_2CO_3$ in MeOH $K_2CO_3$ (0.1 eq) is added to the acetate protected intermediate (1 eq) in MeOH (5 mL/mmol) and stirred at rt until completion of reaction. The products are purified as described in the general methods.

General Procedure E: Boc Deprotection with TFA

TFA (10-20 eq) is added to a solution of Boc-protected intermediate (1 eq) in DCM (5 mL/mmol). The mixture is stirred at rt until complete conversion. Volatiles are removed under reduced pressure and the residue partitioned between DCM and dil. $NH_4OH$ solution. The org. phase is dried over $MgSO_4$ and concentrated in vacuo. If necessary, the product is further purified as described in the general methods

General Procedure F: Boc Deprotection with HCl

A solution of Boc-protected amine (1 eq) in dioxane (5 mL/mmol) is treated with a solution of HCl in dioxane (4 M, 10-20 eq) and the resulting mixture is stirred at rt until completion of reaction. Volatiles are removed under reduced pressure and the crude product isolated by trituration with TBME.

General Procedure G: Schotten Baumann Acylation

Acyl chloride or anhydride (1.2 eq) is added at 0° C. to a biphasic mixture of amine (1 eq) in DCM (5 mL/mmol) and sat. $NaHCO_3$ solution (5 mL/mmol) under vigorous stirring. The mixture is further stirred at rt until complete conversion. The phases are separated and the org. phase dried over $MgSO_4$ and concentrated. The product is purified as described in the general methods.

General Procedure H: Derivatization with Sulfonyl Chlorides, Chloroformates, Isocyanates, Sulfinyl Chloride, Sulfamoyl Chloride or Carbamoyl Chloride The electrophile (sulfonyl chloride, chloroformate, isocyanate, sulfinyl chloride, sulfamoyl chloride or carbamoyl chloride 1.1 eq) is added to a mixture of starting amine (1 eq, either free base or as TFA or HCl salt) in DCM (5 mL/mmol), with or without DMF (1 mL/mmol) and a base ($NEt_3$ or DIPEA, 5 eq) at 0° C. or rt. The mixture is stirred at rt until completion of reaction. The product is purified as described in the general methods.

General Procedure I: Standard Amide Coupling

To a solution of acid BB (1.1 eq) and amine intermediate (1 eq) in DMF (5 mL/mmol) is added DIPEA (3-5 eq) and coupling reagent (HATU, DCC, EDC HCl, BOP/HOBt or $T_3P$ (50% solution in EA)) (1.5 eq) and the mixture is stirred at rt until complete conversion. After aqueous workup (EA/dil. HCl) the products are purified as described in the general methods.

General Procedure J: Reductive Amination

A mixture of amine intermediate (1 eq) and aldehyde BB or ketone (1-2 eq) in DCM is treated with $NaBH(OAc)_3$ (3 eq) and the mixture stirred at rt until complete conversion. After aqueous workup (DCM/dil. $NH_4OH$) the desired products are isolated as described in the general methods.

General Procedure K: Acetal Protection

A mixture of diol, 2,2-dimethoxypropane (3 eq) and pTsOH or CSA (0.05 eq) in THF is stirred at rt until completion of reaction. After aqueous workup (EA/sat. $NaHCO_3$), the crude product is used as such in the next step

General Procedure L: O/N-alkylation

To a solution of the hydroxy or amine intermediate (1 eq) and alkylating agent (chloride, bromide or mesylate) (1.2 eq) in DMF cooled to 0° C. is added sodium hydride (1.2 eq). The mixture is stirred at 0° C. for 20 minutes and at rt until completion of reaction. After aqueous workup (EA/sat $NH_4Cl$), the product is purified as described in the general methods.

General Procedure M: Sulfonimidamide or Sulfoximine Formation

A mixture of diacetoxyiodobenzene (3 eq), ammonium carbamate (4 eq) and the sulfur derivative (1 eq) in MeOH is stirred at rt until completion of reaction. After aqueous workup (EA/sat. $NaHCO_3$), the crude product is used as such in the next step.

General Procedure N: Oxidation (Sulfoxide Formation)

The sulfur derivative (1 eq) in MeOH and dioxane is cooled to 0° C. A solution of sodium periodate (1.1 eq) in $H_2O$ is added dropwise and the reaction mixture is stirred at rt until completion of reaction. After aqueous workup (EA/H$_2$O), the product is purified as described in the general methods.

General Procedure O: Oxidation (Sulfone Formation)

A mixture of mCPBA (2.5 eq) and sulfur derivative (1 eq) in DCM is stirred at rt until completion of reaction. The mixture is used as such in the next step.

General Procedure P: Cbz Deprotection

The Cbz protected intermediate (1 eq) in MeOH (5 mL/mmol) is stirred with Pd/C 10% (0.1 eq) under hydrogen atmosphere (1 bar) until completion of reaction. After filtration, the liquid is concentrated under reduced pressure and the crude product is used as such in the next step.

General Procedure Q: Saponification

The ester (1 eq) in THF/H$_2$O 1:1 or THF/MeOH/H$_2$O 3:2:1 (1 mL/mmol) and LiOH·H$_2$O (1.5-3 eq) are stirred at rt until completion of reaction. After aqueous workup (EA/H$_2$O), the product is purified as described in the general methods.

General Procedure R: Epoxidation mCPBA (1.5 eq) in DCM (5 mL/mmol) is dried over MgSO$_4$ and filtered. The alkene (1 eq) in DCM (5 mL/mmol) is cooled to 0° C. and the mCPBA solution is added. The reaction mixture is stirred at rt until completion of reaction. After aqueous workup (DCM/H$_2$O or 10% Na$_2$S$_2$O$_3$), the crude product is purified as described in the general methods.

General Procedure S: Epoxide Opening

Amine (5 eq) is added to the epoxide (1 eq) in MeOH (5 mL/mmol). The mixture is stirred at 70° C. until completion of reaction. After aqueous workup (EA/sat. NH$_4$Cl), the product is purified as described in the general methods.

General Procedure S': Epoxide Opening

Amine (1 eq) is added to the epoxide (1 eq) in DMF (5 mL/mmol). Lithium tert-butoxide solution 1M in THF (1.5-2 eq) is added and the mixture is stirred at rt until completion of reaction. After aqueous workup (EA/H$_2$O), the product is purified as described in the general methods.

General Procedure T: Cyclization with Triphosgene or Diphosgene

DIPEA or NEt$_3$ (4-10 eq) and triphosgene (0.4-0.8 eq) or a 1M solution of bis(trichloromethyl)carbonate (1 eq) are added dropwise to the 1,2-aminoalcohol (1 eq) in DCM (5-10 mL/mmol) at 0° C. The reaction mixture is stirred at rt until completion of reaction. After aqueous workup (DCM/sat. NaHCO$_3$), the product is purified as described in the general methods.

General Procedure U: Nitrile Oxide Formation by Dehydration of Nitro Derivatives (Mukaiyama Conditions) and Cycloaddition with Alkynes (*J. Am. Chem. Soc.* 1960, 82, 20, 5339-5342)

To a solution of alkyne derivative (1 eq) and alkyl nitro derivative (3 eq) in toluene (10 ml/mmol) is added phenyl isocyanate (2.5 eq) followed by 2,6-lutidine (3 eq) and NEt$_3$ (0.2 eq). The mixture is stirred at 50-55° C. until completion of reaction. After aqueous workup (water/EA), the product is purified as described in the general methods.

Compounds of Examples 1.01-1.352 listed in Table 1 below are prepared by applying General procedure A or A' to the appropriate Intermediates of the preceding section or commercially available building blocks, followed by deprotection according to General Procedure C or D to give isoxazoles or isoxazolines.

TABLE 1

| Ex. | Compound | t$_R$ [min] (LC-MS method) | MS Data m/z [M + H]$^+$ |
|---|---|---|---|
| 1.01 | (2R,3R,4R,5R,6R)-2-(((RS)-3-(4-fluorophenyl)-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.85 (A) | 523.23 |
| 1.02 | (2R,3R,4R,5R,6R)-2-(hydroxymethyl)-6-(((RS)-3-(4-methoxyphenyl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.85 (A) | 535.30 |
| 1.03 | (2R,3R,4R,5R,6R)-2-(hydroxymethyl)-6-(((S)-3-(4-methoxyphenyl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.82 (A) | 535.21 |
| 1.04 | (2R,3R,4R,5R,6R)-2-(hydroxymethyl)-6-(((R)-3-(4-methoxyphenyl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.82 (A) | 535.21 |
| 1.05 | (2R,3R,4R,5R,6R)-2-(((RS)-3-cyclohexyl-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.85 (A) | 511.27 |
| 1.06 | (2R,3R,4R,5R,6R)-2-(((R)-3-cyclohexyl-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.85 (A) | 511.31 |
| 1.07 | (2R,3R,4R,5R,6R)-2-(((S)-3-cyclohexyl-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.85 (A) | 511.30 |
| 1.08 | (2R,3R,4S,5R,6R)-6-(((RS)-3-cyclohexyl-4,5-dihydroisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.94 (A) | 525.31 |
| 1.09 | (2R,3R,4S,5R,6R)-6-(((R)-3-cyclohexyl-4,5-dihydroisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.95 (A) | 525.32 |

TABLE 1-continued

| Ex. | Compound | $t_R$ [min] (LC-MS method) | MS Data m/z [M + H]$^+$ |
|---|---|---|---|
| 1.10 | (2R,3R,4S,5R,6R)-6-(((S)-3-cyclohexyl-4,5-dihydroisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.95 (A) | 525.32 |
| 1.11 | (2R,3R,4R,5R,6R)-2-(((RS)-3-cyclopentyl-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.81 (A) | 497.24 |
| 1.12 | (2R,3R,4S,5R,6R)-6-(((RS)-3-cyclopentyl-4,5-dihydroisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.91 (A) | 511.27 |
| 1.13 | (2R,3R,4R,5R,6R)-2-(((RS)-3-(2-chloro-4-methoxyphenyl)-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.87 (A) | 569.17 |
| 1.14 | (2R,3R,4R,5R,6R)-2-(hydroxymethyl)-6-(((RS)-3-(pyrimidin-5-yl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.69 (A) | 507.22 |
| 1.15 | (2R,3R,4S,5R,6R)-2-(hydroxymethyl)-5-methoxy-6-(((RS)-3-(pyrimidin-5-yl)-4,5-dihydroisoxazol-5-yl)methyl)-4-(4-(3,4,5-trifluorophenyl)-1H-1,2,3-triazol-1-yl)tetrahydro-2H-pyran-3-ol | 0.80 (A) | 521.25 |
| 1.16 | (2R,3R,4R,5R,6R)-2-(hydroxymethyl)-6-(((RS)-3-(pyridin-4-yl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.61 (A) | 506.26 |
| 1.17 | (2R,3R,4S,5R,6R)-2-(hydroxymethyl)-5-methoxy-6-(((RS)-3-(pyridin-4-yl)-4,5-dihydroisoxazol-5-yl)methyl)-4-(4-(3,4,5-trifluorophenyl)-1H-1,2,3-triazol-1-yl)tetrahydro-2H-pyran-3-ol | 0.69 (A) | 520.26 |
| 1.18 | (2R,3R,4R,5R,6R)-2-(((RS)-3-(3-chlorophenyl)-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.88 (A) | 539.28 |
| 1.19 | (2R,3R,4S,5R,6R)-2-(hydroxymethyl)-5-methoxy-6-(((RS)-3-(tetrahydro-2H-pyran-4-yl)-4,5-dihydroisoxazol-5-yl)methyl)-4-(4-(3,4,5-trifluorophenyl)-1H-1,2,3-triazol-1-yl)tetrahydro-2H-pyran-3-ol | 0.80 (A) | 527.40 |
| 1.20 | 6-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one | 0.84 (A) | 576.31 |
| 1.21 | 6-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one | 0.74 (A) | 562.34 |
| 1.22 | (2R,3R,4R,5R,6R)-2-(hydroxymethyl)-6-(((RS)-3-(tetrahydro-2H-pyran-4-yl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.70 (A) | 513.36 |
| 1.23 | (2R,3R,4R,5R,6R)-2-(hydroxymethyl)-6-(((RS)-3-(6-methoxypyridin-3-yl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.79 (A) | 536.15 |
| 1.24 | (2R,3R,4R,5R,6R)-2-(hydroxymethyl)-6-(((RS)-3-(2-methoxypyridin-4-yl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.79 (A) | 536.16 |
| 1.25 | (2R,3R,4R,5R,6R)-2-(((RS)-3-(3-hydroxy-4-methoxyphenyl)-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.75 (A) | 551.14 |
| 1.26 | (2R,3R,4R,5R,6R)-2-(((RS)-3-(1H-benzo[d]imidazol-5-yl)-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.61 (A) | 545.14 |
| 1.27 | (2R,3R,4R,5R,6R)-2-(((RS)-3-(1H-pyrazol-4-yl)-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.65 (A) | 495.14 |
| 1.28 | 5-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)-1-methyl-1,3-dihydro-2H-benzo[d]imidazol-2-one | 0.73 (A) | 575.11 |
| 1.29 | 6-((R)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one | 0.83 (A) | 576.12 |
| 1.30 | 6-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one | 0.83 (A) | 576.11 |
| 1.31 | 6-((R)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one | 0.74 (A) | 562.10 |
| 1.32 | 6-((S)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one [1-(1,3-di-deoxy-3-[4-(3,4,5-trifluorophenyl)-1H-1,2,3-triazol-1-yl]-α-D-galacto-pyranose)-1-(3-(6-benzo[d]oxazol-2(3H)-onyl)-1H-(S)-4,5-dihydroisoxazol-5-yl)-methane] | 0.73 (A) | 562.07 |
| 1.33 | (2R,3R,4R,5R,6R)-2-(((RS)-3-(1H-indazol-6-yl)-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.77 (A) | 545.13 |

TABLE 1-continued

| Ex. | Compound | $t_R$ [min] (LC-MS method) | MS Data m/z [M + H]$^+$ |
|---|---|---|---|
| 1.34 | (2R,3R,4R,5R,6R)-2-(((RS)-3-(1H-indazol-5-yl)-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.75 (A) | 545.16 |
| 1.35 | (2R,3R,4R,5R,6R)-2-(((RS)-5-cyclohexyl-4,5-dihydroisoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.87 (A) | 511.23 |
| 1.36 | (2R,3R,4R,5R,6R)-2-(((RS)-5-benzyl-4,5-dihydroisoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.84 (A) | 519.21 |
| 1.37 | (2R,3R,4R,5R,6R)-2-(hydroxymethyl)-6-(((RS)-5-(4-methylthiazol-5-yl)-4,5-dihydroisoxazol-3-yl)methyl)-4-(4-(3,4,5-trifluorophenyl)-1H-1,2,3-triazol-1-yl)tetrahydro-2H-pyran-3,5-diol | 0.71 (A) | 526.12 |
| 1.38 | (2R,3R,4R,5R,6R)-2-(((RS)-5-(2-hydroxyethyl)-4,5-dihydroisoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.62 (A) | 473.19 |
| 1.39 | (2R,3R,4R,5R,6R)-2-(hydroxymethyl)-6-(((RS)-5-(2-hydroxypropan-2-yl)-4,5-dihydroisoxazol-3-yl)methyl)-4-(4-(3,4,5-trifluorophenyl)-1H-1,2,3-triazol-1-yl)tetrahydro-2H-pyran-3,5-diol | 0.66 (A) | 487.20 |
| 1.40 | tert-butyl 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate [1-(1,3-di-deoxy-3-[4-(3,4,5-trifluorophenyl)-1H-1,2,3-triazol-1-yl]-α-D-galacto-pyranose)-1-(5-((1-tert-butyloxy-carbonyl)piperidin-4-yl)-1H-isoxazol-3-yl)-methane] | 0.90 (A) | 610.18 |
| 1.41 | tert-butyl 4-((RS)-3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-5-yl)piperidine-1-carboxylate | 0.86 (A) | 611.97 |
| 1.42 | (2R,3R,4R,5R,6R)-2-(((RS)-5-(2-hydroxy-2-methylpropyl)-4,5-dihydroisoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.67 (A) | 501.22 |
| 1.43 | (2R,3R,4R,5R,6R)-2-(hydroxymethyl)-6-((5-(hydroxymethyl)isoxazol-3-yl)methyl)-4-(4-(3,4,5-trifluorophenyl)-1H-1,2,3-triazol-1-yl)tetrahydro-2H-pyran-3,5-diol | 0.64 (A) | 457.14 |
| 1.44 | tert-butyl 4-((RS)-5-(((2R,3R,4S,5R,6R)-3-acetoxy-5-hydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate | 0.95 (A) | 654.22 |
| 1.45 | tert-butyl 4-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate | 0.86 (A) | 612.11 |
| 1.46 | tert-butyl 4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate | 0.94 (A) | 626.22 |
| 1.47 | tert-butyl 4-((R)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate | 0.94 (A) | 626.21 |
| 1.48 | tert-butyl 4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate | 0.94 (A) | 626.21 |
| 1.49 | tert-butyl 4-(3-(((2R,3R,4S,5R,6R)-3-acetoxy-5-hydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate | 0.99 (A) | 652.17 |
| 1.50 | tert-butyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate | 0.99 (A) | 624.20 |
| 1.51 | (2R,3R,4R,5R,6R)-2-((5-(tert-butyl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.85 (A) | 483.13 |
| 1.52 | (2R,3R,4R,5R,6R)-2-((5-cyclopropylisoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.78 (a) | 467.08 |
| 1.53 | tert-butyl 3-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)azetidine-1-carboxylate | 0.86 (A) | 582.15 |
| 1.54 | tert-butyl (RS)-3-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate | 0.91 (A) | 610.18 |
| 1.55 | tert-butyl (RS)-3-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)pyrrolidine-1-carboxylate | 0.88 (A) | 596.14 |
| 1.56 | (2R,3R,4R,5R,6R)-2-((5-cyclohexylisoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.91 (A) | 509.21 |
| 1.57 | (2R,3R,4R,5R,6R)-2-((5-cyclopentylisoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.87 (A) | 495.22 |
| 1.58 | (2R,3R,4R,5R,6R)-2-((5-(1-hydroxycyclopentyl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.75 (A) | 511.18 |
| 1.59 | (2R,3R,4R,5R,6R)-2-(hydroxymethyl)-6-((5-(3-hydroxyoxetan-3-yl)isoxazol-3-yl)methyl)-4-(4-(3,4,5-trifluorophenyl)-1H-1,2,3-triazol-1-yl)tetrahydro-2H-pyran-3,5-diol | 0.65 (A) | 499.14 |

TABLE 1-continued

| Ex. | Compound | $t_R$ [min] (LC-MS method) | MS Data m/z [M + H]$^+$ |
|---|---|---|---|
| 1.60 | (2R,3R,4R,5R,6R)-2-(hydroxymethyl)-6-((5-(tetrahydro-2H-pyran-4-yl)isoxazol-3-yl)methyl)-4-(4-(3,4,5-trifluorophenyl)-1H-1,2,3-triazol-1-yl)tetrahydro-2H-pyran-3,5-diol | 0.75 (A) | 511.17 |
| 1.61 | tert-butyl 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)-4-hydroxypiperidine-1-carboxylate | 0.82 (A) | 626.16 |
| 1.62 | tert-butyl 4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)piperidine-1-carboxylate | 0.99 (A) | 624.19 |
| 1.63 | (2R,3R,4S,5R,6R)-6-((5-(tert-butyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.95 (A) | 497.20 |
| 1.64 | (2R,3R,4S,5R,6R)-2-(hydroxymethyl)-5-methoxy-6-((5-(tetrahydro-2H-pyran-4-yl)isoxazol-3-yl)methyl)-4-(4-(3,4,5-trifluorophenyl)-1H-1,2,3-triazol-1-yl)tetrahydro-2H-pyran-3-ol | 0.85 (A) | 525.16 |
| 1.65 | (2R,3R,4S,5R,6R)-6-((5-cyclohexylisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 1.00 (A) | 523.16 |
| 1.66 | (2R,3R,4S,5R,6R)-6-(((RS)-5-(tert-butyl)-4,5-dihydroisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.92 (A) | 499.23 |
| 1.67 | tert-butyl 4-((RS)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-5-yl)piperidine-1-carboxylate | 0.96 (A) | 626.17 |
| 1.68 | (2R,3R,4S,5R,6R)-2-(hydroxymethyl)-6-(((RS)-5-(2-hydroxypropan-2-yl)-4,5-dihydroisoxazol-3-yl)methyl)-5-methoxy-4-(4-(3,4,5-trifluorophenyl)-1H-1,2,3-triazol-1-yl)tetrahydro-2H-pyran-3-ol | 0.79 (A) | 499.17 |
| 1.69 | (2R,3R,4S,5R,6R)-2-(hydroxymethyl)-6-((5-(3-hydroxyoxetan-3-yl)isoxazol-3-yl)methyl)-5-methoxy-4-(4-(3,4,5-trifluorophenyl)-1H-1,2,3-triazol-1-yl)tetrahydro-2H-pyran-3-ol | 0.74 (A) | 513.11 |
| 1.70 | tert-butyl (RS)-3-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)pyrrolidine-1-carboxylate | 0.96 (A) | 610.13 |
| 1.71 | (2R,3R,4S,5R,6R)-6-((5-cyclopentylisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.97 (A) | 509.15 |
| 1.72 | (2R,3R,4S,5R,6R)-6-((5-(1-hydroxycyclopentyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.85 (A) | 525.11 |
| 1.73 | (2R,3R,4S,5R,6R)-6-((5-(1-hydroxycyclohexyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.88 (A) | 539.10 |
| 1.74 | (2R,3R,4S,5R,6R)-6-((5-cyclobutylisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.94 (A) | 495.14 |
| 1.75 | (2R,3R,4S,5R,6R)-2-(hydroxymethyl)-6-((5-(4-hydroxytetrahydro-2H-pyran-4-yl)isoxazol-3-yl)methyl)-5-methoxy-4-(4-(3,4,5-trifluorophenyl)-1H-1,2,3-triazol-1-yl)tetrahydro-2H-pyran-3-ol | 0.76 (A) | 541.04 |
| 1.76 | tert-butyl (RS)-4-hydroxy-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)azepane-1-carboxylate | 0.92 (A) | 654.15 |
| 1.77 | (2R,3R,4R,5R,6R)-2-((5-(1,4-dioxaspiro[4.5]decan-8-yl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.81 (A) | 567.05 |
| 1.78 | ethyl (1S,4s)-4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)-4-hydroxycyclohexane-1-carboxylate | 0.79 (A9 | 597.02 |
| 1.79 | (2R,3R,4S,5R,6R)-6-((5-(4,4-difluorocyclohexyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.97 (A) | 559.07 |
| 1.80 | tert-butyl ((1R,4r)-4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)cyclohexyl)carbamate | 0.91 (A) | 624.1 |
| 1.81 | tert-butyl ((1S,4s)-4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)cyclohexyl)carbamate0.91 (A) | 0.91 (A) | 624.10 |
| 1.82 | (2R,3R,4S,5R,6R)-6-((5-(1-hydroxy-4,4-dimethylcyclohexyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.95 (A) | 567.08 |
| 1.83 | (2R,3R,4S,5R,6R)-6-((5-(4,4-difluoro-1-hydroxycyclohexyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.89 (A) | 575.03 |
| 1.84 | (2R,3R,4S,5R,6R)-2-(hydroxymethyl)-5-methoxy-6-((5-(oxetan-3-yl)isoxazol-3-yl)methyl)-4-(4-(3,4,5-trifluorophenyl)-1H-1,2,3-triazol-1-yl)tetrahydro-2H-pyran-3-ol | 0.80 (A) | 497.08 |

TABLE 1-continued

| Ex. | Compound | t_R [min] (LC-MS method) | MS Data m/z [M + H]+ |
|---|---|---|---|
| 1.85 | (2R,3R,4R,5R,6R)-2-(hydroxymethyl)-6-((5-(1-(oxazol-2-yl)piperidin-4-yl)isoxazol-3-yl)methyl)-4-(4-(3,4,5-trifluorophenyl)-1H-1,2,3-triazol-1-yl)tetrahydro-2H-pyran-3,5-diol | 0.67 (A) | 577.02 |
| 1.86 | (2R,3R,4R,5R,6R)-2-((5-(1-(benzo[d]thiazol-2-yl)piperidin-4-yl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol | 0.82 (A) | 643.02 |
| 1.87 | (2R,3R,4R,5R,6R)-2-(hydroxymethyl)-6-((5-(1-(thiazol-2-yl)piperidin-4-yl)isoxazol-3-yl)methyl)-4-(4-(3,4,5-trifluorophenyl)-1H-1,2,3-triazol-1-yl)tetrahydro-2H-pyran-3,5-diol | 0.68 (A) | 593.02 |
| 1.88 (Ref. Ex.) | (2R,3R,4R,5R,6S)-2-(hydroxymethyl)-6-(((RS)-3-(4-methoxyphenyl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.84 (A) | 535.0 |
| 1.89 | (RS)-4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)-1-methylpiperidin-2-one | 0.74 (A) | 554.18 |
| 1.90 | (RS)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-1-methylpiperidin-2-one | 0.79 (A) | 552.18 |
| 1.91 | (RS)-4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidin-2-one | 0.71 (A) | 539.97 |
| 1.92 | (RS)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)piperidin-2-one | 0.76 (A) | 537.96 |
| 1.93 | (RS)-4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)pyrrolidin-2-one | 0.70 (A) | 526.00 |
| 1.94 | (RS)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)pyrrolidin-2-one | 0.74 (A) | 524.00 |
| 1.95 | tert-butyl 4-((RS)-5-(((2R,3R,4R,5R,6R)-4-(4-(4-chloro-2,5-difluorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.87 (A) | 628.13 |
| 1.96 | tert-butyl 4-((RS)-5-(((2R,3R,4R,5R,6R)-4-(4-(5-fluoro-2-methoxyphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.82 (A) | 606.21 |
| 1.97 | tert-butyl 4-((RS)-5-(((2R,3R,4R,5R,6R)-4-(4-(2,3-difluoro-4-methylphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.85 (A) | 608.21 |
| 1.98 | tert-butyl 4-((RS)-5-(((2R,3R,4R,5R,6R)-4-(4-(benzo[d]thiazol-6-yl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.76 (A) | 615.16 |
| 1.99 | tert-butyl 4-((RS)-5-(((2R,3R,4R,5R,6R)-4-(4-(4-fluoro-3-methylphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.83 (A) | 590.21 |
| 1.100 | tert-butyl 4-((RS)-5-(((2R,3R,4R,5R,6R)-4-(4-(4-cyano-3-fluorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.81 (A) | 601.20 |
| 1.101 | tert-butyl 4-((RS)-5-(((2R,3R,4R,5R,6R)-4-(4-(4-chloro-3,5-difluorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.88 (A) | 628.14 |
| 1.102 | tert-butyl 4-((RS)-5-(((2R,3R,4R,5R,6R)-4-(4-(4-chloro-2,3-difluorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.87 (A) | 628.15 |
| 1.103 | tert-butyl-4-((RS)-5-(((2R,3R,4R,5R,6R)-4-(4-(3-fluoro-4-(trifluoromethyl)phenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.89 (A) | 644.18 |
| 1.104 | tert-butyl 4-((RS)-5-(((2R,3R,4R,5R,6R)-4-(4-(5-fluoropyridin-2-yl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.73 (A) | 577.19 |
| 1.105 | tert-butyl 4-((RS)-5-(((2R,3R,4R,5R,6R)-4-(4-(2,5-dichlorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.87 (A) | 626.12 |
| 1.106 | tert-butyl-4-((RS)-5-(((2R,3R,4R,5R,6R)-4-(4-(4,5-difluoro-2-methoxyphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.85 (A) | 624.20 |
| 1.107 | tert-butyl-4-((RS)-5-(((2R,3R,4R,5R,6R)-4-(4-(3,4-dichlorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.88 (A) | 626.11 |
| 1.108 | tert-butyl-4-((RS)-5-(((2R,3R,4R,5R,6R)-4-(4-(3,4-difluoro-5-methoxyphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.84 (A) | 624.17 |

TABLE 1-continued

| Ex. | Compound | $t_R$ [min] (LC-MS method) | MS Data m/z [M + H]+ |
|---|---|---|---|
| 1.109 | tert-butyl-4-((RS)-5-(((2R,3R,4R,5R,6R)-4-(4-(benzo[d]thiazol-2-yl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.82 (A) | 615.16 |
| 1.110 | tert-butyl 4-((RS)-5-(((2R,3R,4R,5R,6R)-4-(4-(4-chloro-3-methoxyphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.84 (A) | 622.18 |
| 1.111 | tert-butyl 4-((RS)-5-(((2R,3R,4R,5R,6R)-4-(4-(5-fluoro-2,4-dimethoxyphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.82 (A) | 636.21 |
| 1.112 | tert-butyl 4-((RS)-5-(((2R,3R,4R,5R,6R)-4-(4-(3-fluoro-2-methylphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.82 (A) | 590.21 |
| 1.113 | tert-butyl 4-((RS)-5-(((2R,3R,4R,5R,6R)-3,5-dihydroxy-6-(hydroxymethyl)-4-(4-(4-methoxyphenyl)-1H-1,2,3-triazol-1-yl)tetrahydro-2H-pyran-2-yl)methyl)-4,5-dihydroisoxazol-3-yl)piperidine-1-carboxylate | 0.78 (A) | 588.23 |
| 1.114 | (RS)-5-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)piperidin-2-one | 0.76 (A) | 538.00 |
| 1.115 | tert-butyl 4-((RS)-5-(((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.89 (A) | 590.12 |
| 1.116 | tert-butyl 4-((RS)-5-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.94 (A) | 624.10 |
| 1.117 | tert-butyl 4-((RS)-5-(((2R,3R,4S,5R,6R)-4-(4-(4-bromo-3-fluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.95 (A) | 670.00 |
| 1.118 | tert-butyl 4-((RS)-5-(((2R,3R,4S,5R,6R)-4-(4-(3,5-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.92 (A) | 608.10 |
| 1.119 | 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-1-methyl pyridin-2(1H)-one | 0.82 (A) | 548.01 |
| 1.120 | (2R,3R,4S,5R,6R)-6-((3-cyclohexylisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.99 (A) | 523.12 |
| 1.121 | tert-butyl 4-(3-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.99 (A) | 622.17 |
| 1.122 | tert-butyl 4-(3-(((2R,3R,4S,5R,6R)-4-(4-(3,5-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.97 (A) | 606.17 |
| 1.123 | tert-butyl 4-(5-(((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate | 0.94 (A) | 588.12 |
| 1.124 | tert-butyl 4-(5-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate | 0.99 (A) | 622.15 |
| 1.125 | tert-butyl 4-(5-(((2R,3R,4S,5R,6R)-4-(4-(4-bromo-3-fluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate | 0.99 (A) | 666.06 |
| 1.126 | tert-butyl 4-(5-(((2R,3R,4S,5R,6R)-4-(4-(3,5-difluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate | 0.96 (A) | 606.16 |
| 1.127 | (2R,3R,4S,5R,6R)-6-((5-(4-bromothiazol-2-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.95 (A) | 602.00 |
| 1.128 | (2R,3R,4S,5R,6R)-6-(((R)-5-cyclohexyl-4,5-dihydroisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.97 (A) | 525.19 |
| 1.129 | (2R,3R,4S,5R,6R)-6-(((S)-5-cyclohexyl-4,5-dihydroisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.97 (A) | 525.19 |
| 1.130 | tert-butyl (4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)bicyclo[2.2.2]octan-1-yl)carbamate | 1.03 (A) | 664.24 |
| 1.131 | (2R,3R,4S,5R,6R)-6-((5-(4-aminobicyclo[2.2.2]octan-1-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol (by-product in synthesis of Example 1.130) | 0.70 (A) | 563.93 |
| 1.132 | tert-butyl 4-hydroxy-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate | 0.91 (A) | 640.20 |
| 1.133 | 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2- | 0.64 (A) | 540.12 |

TABLE 1-continued

| Ex. | Compound | t_R [min] (LC-MS method) | MS Data m/z [M + H]+ |
|---|---|---|---|
| | yl)methyl)isoxazol-5-yl)piperidin-4-ol (by-product in synthesis of Example 1.132) | | |
| 1.134 | tert-butyl ((1R,4r)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclohexyl)carbamate | 0.99 (A) | 638.25 |
| 1.135 | tert-butyl 4-((RS)-5-(((2R,3R,4S,5R,6R)-4-(4-(3,5-difluoro-4-methylphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.95 (A) | 622.27 |
| 1.136 | tert-butyl 4-((RS)-5-(((2R,3R,4S,5R,6R)-4-(4-(3-fluoro-4-methylphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.92 (A) | 604.27 |
| 1.137 | tert-butyl 4-((RS)-5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.94 (A) | 622.27 |
| 1.138 | (2R,3R,4S,5R,6R)-2-(hydroxymethyl)-5-methoxy-6-((5-((S)-1-(N-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol | 0.77 (A) | 643.21 |
| 1.139 | (2R,3R,4S,5R,6R)-2-(hydroxymethyl)-5-methoxy-6-((5-((R)-1-(N-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol | 0.77 (A) | 643.22 |
| 1.140 | tert-butyl 4-((RS)-5-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.96 (A) | 642.24 |
| 1.141 | tert-butyl 4-((RS)-5-(((2R,3R,4S,5R,6R)-4-(4-(4-bromo-2,3-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.97 (A) | 688.15 |
| 1.142 | (2R,3R,4S,5R,6R)-4-(4-(4-bromo-2,3-difluorophenyl)-1H-1,2,3-triazol-1-yl)-2-(hydroxymethyl)-5-methoxy-6-(((RS)-3-(piperidin-4-yl)-4,5-dihydroisoxazol-5-yl)methyl)tetrahydro-2H-pyran-3-ol (by-product of synthesis of example 1.141) | 0.66 (A) | 588.10 |
| 1.143 | tert-butyl 4-((RS)-5-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-4,5-dihydroisoxazol-3-yl)piperidine-1-carboxylate | 0.93 (A) | 626.25 |
| 1.144 | (2R,3R,4S,5R,6R)-2-(hydroxymethyl)-5-methoxy-6-(((RS)-3-(piperidin-4-yl)-4,5-dihydroisoxazol-5-yl)methyl)-4-(4-(2,3,4-trifluorophenyl)-1H-1,2,3-triazol-1-yl)tetrahydro-2H-pyran-3-ol (by-product of synthesis of example 1.143) | 0.62 (A) | 526.20 |
| 1.145 | tert-butyl 4-((RS)-5-(((2R,3R,4S,5R,6R)-4-(4-(4-chloro-3,5-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.97 (A) | 642.19 |
| 1.146 | (2R,3R,4S,5R,6R)-4-(4-(4-chloro-3,5-difluorophenyl)-1H-1,2,3-triazol-1-yl)-2-(hydroxymethyl)-5-methoxy-6-(((RS)-3-(piperidin-4-yl)-4,5-dihydroisoxazol-5-yl)methyl)tetrahydro-2H-pyran-3-o (by-product of synthesis of example 1.145) | 0.67 (A) | 542.14 |
| 1.147 | (1R,4r)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-1-(isopropylimino)hexahydro-1l6-thiopyran 1-oxide | 0.74 (A) | 614.19 |
| 1.148 | (1S,4s)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-1-(isopropylimino)hexahydro-1l6-thiopyran 1-oxide | 0.75 (A) | 614.19 |
| 1.149 | ethyl 4-(3-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.93 (A) | 594.19 |
| 1.150 | ethyl 4-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-5-yl)piperidine-1-carboxylate | 0.92 (A) | 596.00 |
| 1.151 | ethyl 4-(3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.93 (A) | 592.22 |
| 1.152 | (2R,3R,4S,5R,6R)-4-(4-(3,5-difluoro-4-methylphenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol | 0.87 (A) | 597.86 |
| 1.153 | (2R,3R,4S,5R,6R)-4-(4-(3-fluoro-4-methylphenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol | 0.82 (A) | 580.14 |
| 1.154 | (2R,3R,4S,5R,6R)-4-(4-(4-chloro-2,3-difluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol | 0.88 (A) | 618.04 |
| 1.155 | (2R,3R,4S,5R,6R)-4-(4-(4-bromo-2,3-difluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol | 0.90 (A) | 661.64 |
| 1.156 | (2R,3R,4S,5R,6R)-4-(4-(4-chloro-3-fluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol | 0.85 (A) | 600.06 |
| 1.157 | (2R,3R,4S,5R,6R)-2-(hydroxymethyl)-5-methoxy-6-((5-(1-(methylsulfonyl)piperidin-4-yl)isoxazol-3-yl)methyl)-4-(4-(2,3,4-trifluorophenyl)-1H-1,2,3-triazol-1-yl)tetrahydro-2H-pyran-3-ol | 0.83 (A) | 602.07 |

TABLE 1-continued

| Ex. | Compound | $t_R$ [min] (LC-MS method) | MS Data m/z [M + H]$^+$ |
|---|---|---|---|
| 1.158 | (2R,3R,4S,5R,6R)-4-(4-(4-chloro-3,5-difluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol | 0.89 (A) | 618.02 |
| 1.159 | (2R,3R,4S,5R,6R)-4-(4-(2,3-difluoro-4-methylphenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol | 0.85 (A) | 597.90 |
| 1.160 | (2R,3R,4S,5R,6R)-4-(4-(3-chloro-5-fluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol | 0.87 (A) | 600.05 |
| 1.161 | 1-(4-(3-(((2R,3R,4S,5R,6R)-4-(4-(3,5-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one | 0.81 (A) | 562.11 |
| 1.162 | 1-(4-(3-(((2R,3R,4S,5R,6R)-4-(4-(3-fluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one | 0.77 (A) | 544.17 |
| 1.163 | 1-(4-(3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one | 0.83 (A) | 581.69 |
| 1.164 | 1-(4-(3-(((2R,3R,4S,5R,6R)-4-(4-(4-bromo-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one | 0.84 (A) | 626.06 |
| 1.165 | 1-(4-(3-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one | 0.80 (A) | 564.08 |
| 1.166 | 1-(4-(3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-5-yl)piperidin-1-yl)ethan-1-one | 0.77 (A) | 565.88 |
| 1.167 | 1-(4-(3-(((2R,3R,4S,5R,6R)-4-(4-(4-chloro-3,5-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one | 0.84 (A) | 581.81 |
| 1.168 | 1-(4-(3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one | 0.80 (A) | 562.16 |
| 1.169 | 1-(4-(3-(((2R,3R,4S,5R,6R)-4-(4-(3-chloro-5-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one | 0.81 (A) | 564.16 |
| 1.170 | (2R,3R,4S,5R,6R)-6-((5-cyclohexylisoxazol-3-yl)methyl)-4-(4-(3,5-difluoro-4-methylphenyl)-1H-1,2,3-triazol-1-yl)-2-(hydroxymethyl)-5-methoxytetrahydro-2H-pyran-3-ol | 1.06 (A) | 519.19 |
| 1.171 | (2R,3R,4S,5R,6R)-6-((5-cyclohexylisoxazol-3-yl)methyl)-4-(4-(3-fluoro-4-methylphenyl)-1H-1,2,3-triazol-1-yl)-2-(hydroxymethyl)-5-methoxytetrahydro-2H-pyran-3-ol | 1.02 (A) | 501.05 |
| 1.172 | (2R,3R,4S,5R,6R)-4-(4-(4-chloro-2,3-difluorophenyl)-1H-1,2,3-triazol-1-yl)-6-((5-cyclohexylisoxazol-3-yl)methyl)-2-(hydroxymethyl)-5-methoxytetrahydro-2H-pyran-3-ol | 1.09 (A) | 539.12 |
| 1.173 | (2R,3R,4S,5R,6R)-4-(4-(4-bromo-2,3-difluorophenyl)-1H-1,2,3-triazol-1-yl)-6-((5-cyclohexylisoxazol-3-yl)methyl)-2-(hydroxymethyl)-5-methoxytetrahydro-2H-pyran-3-ol | 1.10 (A) | 583.02 |
| 1.174 | (2R,3R,4S,5R,6R)-4-(4-(4-chloro-3-fluorophenyl)-1H-1,2,3-triazol-1-yl)-6-((5-cyclohexylisoxazol-3-yl)methyl)-2-(hydroxymethyl)-5-methoxytetrahydro-2H-pyran-3-ol | 1.05 (A) | 521.14 |
| 1.175 | (2R,3R,4S,5R,6R)-6-((5-cyclohexylisoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol | 1.05 (A) | 523.16 |
| 1.176 | (2R,3R,4S,5R,6R)-4-(4-(4-chloro-3,5-difluorophenyl)-1H-1,2,3-triazol-1-yl)-6-((5-cyclohexylisoxazol-3-yl)methyl)-2-(hydroxymethyl)-5-methoxytetrahydro-2H-pyran-3-ol | 1.09 (A) | 539.13 |
| 1.177 | (2R,3R,4S,5R,6R)-6-((5-cyclohexylisoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 1.06 (A) | 519.14 |
| 1.178 | (2R,3R,4S,5R,6R)-4-(4-(3-chloro-5-fluorophenyl)-1H-1,2,3-triazol-1-yl)-6-((5-cyclohexylisoxazol-3-yl)methyl)-2-(hydroxymethyl)-5-methoxytetrahydro-2H-pyran-3-ol | 1.07 (A) | 521.02 |
| 1.179 | (2R,3R,4S,5R,6R)-4-(4-(3,5-difluoro-4-methylphenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol | 0.87 (A) | 521.16 |
| 1.180 | (2R,3R,4S,5R,6R)-4-(4-(3-fluoro-4-methylphenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol | 0.82 (A) | 503.13 |
| 1.181 | (2R,3R,4S,5R,6R)-4-(4-(4-chloro-2,3-difluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol | 0.89 (A) | 541.06 |
| 1.182 | (2R,3R,4S,5R,6R)-4-(4-(4-bromo-2,3-difluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol | 0.90 (A) | 585.06 |

TABLE 1-continued

| Ex. | Compound | t_R [min] (LC-MS method) | MS Data m/z [M + H]+ |
|---|---|---|---|
| 1.183 | (2R,3R,4S,5R,6R)-4-(4-(4-chloro-3-fluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol | 0.85 (A) | 523.09 |
| 1.184 | (2R,3R,4S,5R,6R)-2-(hydroxymethyl)-5-methoxy-6-((5-(tetrahydro-2H-pyran-4-yl)isoxazol-3-yl)methyl)-4-(4-(2,3,4-trifluorophenyl)-1H-1,2,3-triazol-1-yl)tetrahydro-2H-pyran-3-ol | 0.83 (A) | 525.12 |
| 1.185 | (2R,3R,4S,5R,6R)-4-(4-(4-chloro-3,5-difluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol | 0.90 (A) | 541.10 |
| 1.186 | (2R,3R,4S,5R,6R)-4-(4-(2,3-difluoro-4-methylphenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol | 0.85 (A) | 521.10 |
| 1.187 | (2R,3R,4S,5R,6R)-4-(4-(3-chloro-5-fluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol | 0.87 (A) | 523.12 |
| 1.188 | (2R,3R,4S,5R,6R)-6-((5-(tert-butyl)isoxazol-3-yl)methyl)-4-(4-(3,5-difluoro-4-methylphenyl)-1H-1,2,3-triazol-1-yl)-2-(hydroxymethyl)-5-methoxytetrahydro-2H-pyran-3-ol | 0.99 (A) | 493.10 |
| 1.189 | (2R,3R,4S,5R,6R)-6-((5-(tert-butyl)isoxazol-3-yl)methyl)-4-(4-(3-fluoro-4-methylphenyl)-1H-1,2,3-triazol-1-yl)-2-(hydroxymethyl)-5-methoxytetrahydro-2H-pyran-3-ol | 0.95 (A) | 475.03 |
| 1.190 | (2R,3R,4S,5R,6R)-6-((5-(tert-butyl)isoxazol-3-yl)methyl)-4-(4-(4-chloro-2,3-difluorophenyl)-1H-1,2,3-triazol-1-yl)-2-(hydroxymethyl)-5-methoxytetrahydro-2H-pyran-3-ol | 1.02 (A) | 513.04 |
| 1.191 | (2R,3R,4S,5R,6R)-4-(4-(4-bromo-2,3-difluorophenyl)-1H-1,2,3-triazol-1-yl)-6-((5-(tert-butyl)isoxazol-3-yl)methyl)-2-(hydroxymethyl)-5-methoxytetrahydro-2H-pyran-3-ol | 1.03 (A) | 556.98 |
| 1.192 | (2R,3R,4S,5R,6R)-6-((5-(tert-butyl)isoxazol-3-yl)methyl)-4-(4-(4-chloro-3-fluorophenyl)-1H-1,2,3-triazol-1-yl)-2-(hydroxymethyl)-5-methoxytetrahydro-2H-pyran-3-ol | 0.98 (A) | 495.06 |
| 1.193 | (2R,3R,4S,5R,6R)-6-((5-(tert-butyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.96 (A) | 497.15 |
| 1.194 | (2R,3R,4S,5R,6R)-6-((5-(tert-butyl)isoxazol-3-yl)methyl)-4-(4-(4-chloro-3,5-difluorophenyl)-1H-1,2,3-triazol-1-yl)-2-(hydroxymethyl)-5-methoxytetrahydro-2H-pyran-3-ol | 1.02 (A) | 513.12 |
| 1.195 | (2R,3R,4S,5R,6R)-6-((5-(tert-butyl)isoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.98 (A) | 493.12 |
| 1.196 | (2R,3R,4S,5R,6R)-6-((5-(tert-butyl)isoxazol-3-yl)methyl)-4-(4-(3-chloro-5-fluorophenyl)-1H-1,2,3-triazol-1-yl)-2-(hydroxymethyl)-5-methoxytetrahydro-2H-pyran-3-ol | 0.99 (A) | 495.13 |
| 1.197 | (2R,3R,4S,5R,6R)-2-(hydroxymethyl)-6-((5-(1-(N-isopropylpropan-2-ylsulfonimidoyl)piperidin-4-yl)isoxazol-3-yl)methyl)-5-methoxy-4-(4-(3,4,5-trifluorophenyl)-1H-1,2,3-triazol-1-yl)tetrahydro-2H-pyran-3-ol (mixture of isomers at sulfur) | 0.82 (A) | 671.24 |
| 1.198 | ethyl 4-(3-(((2R,3R,4S,5R,6R)-4-(4-(4-bromo-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.97 (A) | 658.13 |
| 1.199 | ethyl 4-(3-(((2R,3R,4S,5R,6R)-4-(4-(4-chloro-3,5-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.97 (A) | 611.97 |
| 1.200 | ethyl 4-(3-(((2R,3R,4S,5R,6R)-4-(4-(3-chloro-5-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.95 (A) | 594.15 |
| 1.201 | ethyl 4-(3-(((2R,3R,4S,5R,6R)-4-(4-(3-fluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.92 (A) | 574.22 |
| 1.202 | ethyl 4-(3-(((2R,3R,4S,5R,6R)-4-(4-(3,5-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.95 (A) | 592.21 |
| 1.203 | ethyl 4-(3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.96 (A) | 612.00 |
| 1.204 | (2R,3R,4S,5R,6R)-2-((5-(tert-butyl)isoxazol-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl acetate | 0.96 (A) | 521.23 |
| 1.205 | (2R,3R,4R,5R,6R)-2-((5-(tert-butyl)isoxazol-3-yl)methyl)-4-(4-(2,3-difluoro-4-methylphenyl)-1H-1,2,3-triazol-1-yl)-6-(hydroxymethyl)tetrahydro-2H-pyran-3,5-diol | 0.86 (A) | 479.22 |
| 1.206 | (2R,3R,4S,5R,6R)-6-((3-(tert-butyl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.95 (A) | 497.25 |
| 1.207 | (2R,3R,4S,5R,6R)-6-((3-(1-hydroxy-2-methylpropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.82 (A) | 513.23 |

TABLE 1-continued

| Ex. | Compound | $t_R$ [min] (LC-MS method) | MS Data m/z [M + H]$^+$ |
|---|---|---|---|
| 1.208 | ethyl 3-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-3-methylbutanoate | 0.96 (A) | 569.23 |
| 1.209 | (2R,3R,4S,5R,6R)-2-(hydroxymethyl)-5-methoxy-6-((3-(1-methoxycyclopentyl)isoxazol-5-yl)methyl)-4-(4-(3,4,5-trifluorophenyl)-1H-1,2,3-triazol-1-yl)tetrahydro-2H-pyran-3-ol | 0.94 (A) | 539.22 |
| 1.210 | (2R,3R,4S,5R,6R)-2-(hydroxymethyl)-5-methoxy-6-((3-(1-methoxycyclohexyl)isoxazol-5-yl)methyl)-4-(4-(3,4,5-trifluorophenyl)-1H-1,2,3-triazol-1-yl)tetrahydro-2H-pyran-3-ol | 0.98 (A) | 553.22 |
| 1.211 | (2R,3R,4S,5R,6R)-2-(hydroxymethyl)-5-methoxy-6-((3-(3-methyloxetan-3-yl)isoxazol-5-yl)methyl)-4-(4-(3,4,5-trifluorophenyl)-1H-1,2,3-triazol-1-yl)tetrahydro-2H-pyran-3-ol | 0.85 (A) | 511.20 |
| 1.212 | (2R,3R,4S,5R,6R)-6-((3-(3-ethyloxetan-3-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.88 (A) | 525.22 |
| 1.213 | (2R,3R,4S,5R,6R)-6-((3-(1-fluorocyclopropyl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.92 (A) | 499.20 |
| 1.214 | (2R,3R,4S,5R,6R)-6-((3-(1-(difluoromethyl)cyclopropyl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.94 (A) | 531.19 |
| 1.215 | (2R,3R,4S,5R,6R)-2-(hydroxymethyl)-5-methoxy-6-((3-(1-methylcyclopropyl)isoxazol-5-yl)methyl)-4-(4-(3,4,5-trifluorophenyl)-1H-1,2,3-triazol-1-yl)tetrahydro-2H-pyran-3-ol | 0.93 (A) | 495.22 |
| 1.216 | tert-butyl (2-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)propan-2-yl)carbamate | 0.95 (A) | 598.04 |
| 1.217 | (2R,3R,4S,5R,6R)-6-((3-(2-aminopropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol (byproduct of synthesis of example 1.216) | 0.66 (A) | 498.23 |
| 1.218 | (2R,3R,4S,5R,6R)-4-(4-(3-chloro-4,5-difluorophenyl)-1H-1,2,3-triazol-1-yl)-6-((5-cyclohexylisoxazol-3-yl)methyl)-2-(hydroxymethyl)-5-methoxytetrahydro-2H-pyran-3-ol | 1.04 (A) | 539.17 |
| 1.219 | 1-(4-(3-(((2R,3R,4S,5R,6R)-4-(4-(3-chloro-4,5-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one | 0.86 (A) | 582.17 |
| 1.220 | ethyl 4-(3-(((2R,3R,4S,5R,6R)-4-(4-(3-chloro-4,5-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.96 (A) | 612.19 |
| 1.221 | (2R,3R,4S,5R,6R)-6-((5-(tert-butyl)isoxazol-3-yl)methyl)-4-(4-(3-chloro-4,5-difluorophenyl)-1H-1,2,3-triazol-1-yl)-2-(hydroxymethyl)-5-methoxytetrahydro-2H-pyran-3-ol | 0.98 (A) | 513.02 |
| 1.222 | (2R,3R,4S,5R,6R)-6-((3-cyclopentylisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.97 (A) | 509.22 |
| 1.223 | tert-butyl 4-((RS)-5-(((2R,3R,4S,5R,6R)-4-(4-(4-cyano-3,5-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.94 (A) | 633.32 |
| 1.224 | (2R,3R,4S,5R,6R)-6-((5-cyclobutylisoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.94 (A) | 491.23 |
| 1.225 | (2R,3R,4S,5R,6R)-6-((5-(1-hydroxycyclobutyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.81 (A) | 511.19 |
| 1.226 | (2R,3R,4S,5R,6R)-6-((5-cyclobutylisoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.93 (A) | 495.21 |
| 1.227 | (2R,3R,4S,5R,6R)-4-(4-(4-chloro-2,3-difluorophenyl)-1H-1,2,3-triazol-1-yl)-6-((5-cyclobutylisoxazol-3-yl)methyl)-2-(hydroxymethyl)-5-methoxytetrahydro-2H-pyran-3-ol | 0.96 (A) | 511.15 |
| 1.228 | tert-butyl 4-(3-(((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 0.94 (A) | 588.15 |
| 1.229 | (2R,3R,4S,5R,6R)-4-(4-(2,3-difluoro-4-methylphenyl)-1H-1,2,3-triazol-1-yl)-2-(hydroxymethyl)-5-methoxy-6-((5-(2,3,4-trifluorophenyl)isoxazol-3-yl)methyl)tetrahydro-2H-pyran-3-ol | 1.02 (A) | 567.16 |
| 1.230 | (2R,3R,4S,5R,6R)-2-(hydroxymethyl)-5-methoxy-4-(4-(2,3,4-trifluorophenyl)-1H-1,2,3-triazol-1-yl)-6-((5-(2,3,4-trifluorophenyl)isoxazol-3-yl)methyl)tetrahydro-2H-pyran-3-ol | 1.01 (A) | 1141.44 [2M + 1] |
| 1.231 | (2R,3R,4S,5R,6R)-4-(4-(4-chloro-2,3-difluorophenyl)-1H-1,2,3-triazol-1-yl)-2-(hydroxymethyl)-5-methoxy-6-((5-(2,3,4-trifluorophenyl)isoxazol-3-yl)methyl)tetrahydro-2H-pyran-3-ol | 1.04 (A) | 587.09 |
| 1.232 | (2R,3R,4S,5R,6R)-2-(hydroxymethyl)-6-((5-(2-hydroxypropan-2-yl)isoxazol-3-yl)methyl)-5-methoxy-4-(4-(2,3,4-trifluorophenyl)-1H-1,2,3-triazol-1-yl)tetrahydro-2H-pyran-3-ol [1-(1,3-di-deoxy-2-O-methyl-3-[4-(2,3,4-trifluorophenyl)-1H-1,2,3-triazol-1- | 0.77 (A) | 499.19 |

TABLE 1-continued

| Ex. | Compound | $t_R$ [min] (LC-MS method) | MS Data m/z [M + H]$^+$ |
|---|---|---|---|
| | yl]-a-D-galacto-pyranose)-1-(5-(2-hydroxypropan-2-yl)1H-isoxazol-3-yl)-methane] | | |
| 1.233 | (2R,3R,4S,5R,6R)-6-((5-(1-hydroxycyclohexyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.86 (A) | 539.19 |
| 1.234 | (2R,3R,4S,5R,6R)-6-((5-(1-hydroxycyclopentyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.83 (A) | 525.19 |
| 1.235 | (2R,3R,4S,5R,6R)-6-((5-cyclopentylisoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.96 (A) | 509.19 |
| 1.236 | (2R,3R,4S,5R,6R)-6-((5-(1-hydroxycyclobutyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.80 (A) | 511.16 |
| 1.237 | (2R,3R,4S,5R,6R)-4-(4-(2,3-difluoro-4-methylphenyl)-1H-1,2,3-triazol-1-yl)-2-(hydroxymethyl)-6-((5-(2-hydroxypropan-2-yl)isoxazol-3-yl)methyl)-5-methoxytetrahydro-2H-pyran-3-ol | 0.79 (A) | 495.22 |
| 1.238 | (2R,3R,4S,5R,6R)-4-(4-(2,3-difluoro-4-methylphenyl)-1H-1,2,3-triazol-1-yl)-6-((5-(1-hydroxycyclohexyl)isoxazol-3-yl)methyl)-2-(hydroxymethyl)-5-methoxytetrahydro-2H-pyran-3-ol | 0.88 (A) | 535.21 |
| 1.239 | (2R,3R,4S,5R,6R)-4-(4-(2,3-difluoro-4-methylphenyl)-1H-1,2,3-triazol-1-yl)-6-((5-(1-hydroxycyclopentyl)isoxazol-3-yl)methyl)-2-(hydroxymethyl)-5-methoxytetrahydro-2H-pyran-3-ol | 0.85 (A) | 521.20 |
| 1.240 | (2R,3R,4S,5R,6R)-6-((5-cyclopentylisoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.97 (A) | 505.26 |
| 1.241 | (2R,3R,4S,5R,6R)-4-(4-(2,3-difluoro-4-methylphenyl)-1H-1,2,3-triazol-1-yl)-6-((5-(1-hydroxycyclobutyl)isoxazol-3-yl)methyl)-2-(hydroxymethyl)-5-methoxytetrahydro-2H-pyran-3-ol | 0.82 (A) | 507.24 |
| 1.242 | (2R,3R,4S,5R,6R)-4-(4-(4-chloro-2,3-difluorophenyl)-1H-1,2,3-triazol-1-yl)-2-(hydroxymethyl)-6-((5-(2-hydroxypropan-2-yl)isoxazol-3-yl)methyl)-5-methoxytetrahydro-2H-pyran-3-ol | 0.81 (A) | 515.16 |
| 1.243 | (2R,3R,4S,5R,6R)-4-(4-(4-chloro-2,3-difluorophenyl)-1H-1,2,3-triazol-1-yl)-6-((5-(1-hydroxycyclohexyl)isoxazol-3-yl)methyl)-2-(hydroxymethyl)-5-methoxytetrahydro-2H-pyran-3-ol | 0.90 (A) | 555.19 |
| 1.244 | (2R,3R,4S,5R,6R)-4-(4-(4-chloro-2,3-difluorophenyl)-1H-1,2,3-triazol-1-yl)-6-((5-(1-hydroxycyclopentyl)isoxazol-3-yl)methyl)-2-(hydroxymethyl)-5-methoxytetrahydro-2H-pyran-3-ol | 0.87 (A) | 541.16 |
| 1.245 | (2R,3R,4S,5R,6R)-4-(4-(4-chloro-2,3-difluorophenyl)-1H-1,2,3-triazol-1-yl)-6-((5-cyclopentylisoxazol-3-yl)methyl)-2-(hydroxymethyl)-5-methoxytetrahydro-2H-pyran-3-ol | 0.99 (A) | 525.16 |
| 1.246 | (2R,3R,4S,5R,6R)-4-(4-(4-chloro-2,3-difluorophenyl)-1H-1,2,3-triazol-1-yl)-6-((5-(1-hydroxycyclobutyl)isoxazol-3-yl)methyl)-2-(hydroxymethyl)-5-methoxytetrahydro-2H-pyran-3-ol | 0.84 (A) | 527.16 |
| 1.247 | (2R,3R,4S,5R,6R)-6-((5-(tert-butyl)isoxazol-3-yl)methyl)-4-(4-(2,5-difluoro-4-methylphenyl)-1H-1,2,3-triazol-1-yl)-2-(hydroxymethyl)-5-methoxytetrahydro-2H-pyran-3-ol | 0.95 (A) | 493.28 |
| 1.248 | (2R,3R,4S,5R,6R)-6-((5-cyclohexylisoxazol-3-yl)methyl)-4-(4-(2,5-difluoro-4-methylphenyl)-1H-1,2,3-triazol-1-yl)-2-(hydroxymethyl)-5-methoxytetrahydro-2H-pyran-3-ol | 1.01 (A) | 519.28 |
| 1.249 | tert-butyl 4-(3-(((2R,3R,4S,5R,6R)-4-(4-(4-bromo-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate | 1.00 (A) | 668.07 |
| 1.250 | (2R,3R,4S,5R,6R)-6-((3-(tert-butyl)isoxazol-5-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.93 (A) | 497.21 |
| 1.251 | (2R,3R,4S,5R,6R)-2-(hydroxymethyl)-5-methoxy-6-((3-(1-methylcyclopropyl)isoxazol-5-yl)methyl)-4-(4-(2,3,4-trifluorophenyl)-1H-1,2,3-triazol-1-yl)tetrahydro-2H-pyran-3-ol | 0.91 (A) | 495.21 |
| 1.252 | (2R,3R,4S,5R,6R)-2-(hydroxymethyl)-5-methoxy-6-((3-(3-methyloxetan-3-yl)isoxazol-5-yl)methyl)-4-(4-(2,3,4-trifluorophenyl)-1H-1,2,3-triazol-1-yl)tetrahydro-2H-pyran-3-ol | 0.81 (A) | 511.06 |
| 1.253 | (2R,3R,4S,5R,6R)-6-((3-(1-hydroxy-2-methylpropan-2-yl)isoxazol-5-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.81 (A) | 513.24 |
| 1.254 | (2R,3R,4S,5R,6R)-6-((3-(tert-butyl)isoxazol-5-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.95 (A) | 493.25 |
| 1.255 | (2R,3R,4S,5R,6R)-4-(4-(2,3-difluoro-4-methylphenyl)-1H-1,2,3-triazol-1-yl)-2-(hydroxymethyl)-5-methoxy-6-((3-(1-methylcyclopropyl)isoxazol-5-yl)methyl)tetrahydro-2H-pyran-3-ol | 0.93 (A) | 491.23 |

TABLE 1-continued

| Ex. | Compound | t_R [min] (LC-MS method) | MS Data m/z [M + H]+ |
|---|---|---|---|
| 1.256 | (2R,3R,4S,5R,6R)-4-(4-(2,3-difluoro-4-methylphenyl)-1H-1,2,3-triazol-1-yl)-2-(hydroxymethyl)-5-methoxy-6-((3-(3-methyloxetan-3-yl)isoxazol-5-yl)methyl)tetrahydro-2H-pyran-3-ol [1-(1,3-di-deoxy-2-O-methyl-3-[4-(2,3-difluoro-4-methylphenyl)-1H-1,2,3-triazol-1-yl]-a-D-galacto-pyranose)-1-(3-(3-methyloxetan-3-yl)1H-isoxazol-5-yl)-methane] | 0.83 (A) | 507.07 |
| 1.257 | (2R,3R,4S,5R,6R)-4-(4-(2,3-difluoro-4-methylphenyl)-1H-1,2,3-triazol-1-yl)-6-((3-(1-hydroxy-2-methylpropan-2-yl)isoxazol-5-yl)methyl)-2-(hydroxymethyl)-5-methoxytetrahydro-2H-pyran-3-ol | 0.82 (A) | 509.25 |
| 1.258 | (2R,3R,4S,5R,6R)-6-((3-(tert-butyl)isoxazol-5-yl)methyl)-4-(4-(4-chloro-2,3-difluorophenyl)-1H-1,2,3-triazol-1-yl)-2-(hydroxymethyl)-5-methoxytetrahydro-2H-pyran-3-ol | 0.97 (A) | 513.20 |
| 1.259 | (2R,3R,4S,5R,6R)-4-(4-(4-chloro-2,3-difluorophenyl)-1H-1,2,3-triazol-1-yl)-2-(hydroxymethyl)-5-methoxy-6-((3-(1-methylcyclopropyl)isoxazol-5-yl)methyl)tetrahydro-2H-pyran-3-ol | 0.95 (A) | 511.18 |
| 1.260 | (2R,3R,4S,5R,6R)-4-(4-(4-chloro-2,3-difluorophenyl)-1H-1,2,3-triazol-1-yl)-2-(hydroxymethyl)-5-methoxy-6-((3-(3-methyloxetan-3-yl)isoxazol-5-yl)methyl)tetrahydro-2H-pyran-3-ol | 0.87 (A) | 527.09 |
| 1.261 | (2R,3R,4S,5R,6R)-4-(4-(4-chloro-2,3-difluorophenyl)-1H-1,2,3-triazol-1-yl)-6-((3-(1-hydroxy-2-methylpropan-2-yl)isoxazol-5-yl)methyl)-2-(hydroxymethyl)-5-methoxytetrahydro-2H-pyran-3-ol | 0.84 (A) | 529.21 |
| 1.262 | (RS)-(2R,3R,4S,5R,6R)-6-((3-(1-chloro-3-hydroxy-2-methylpropan-2-yl)isoxazol-5-yl)methyl)-2-(hydroxymethyl)-5-methoxy-4-(4-(2,3,4-trifluorophenyl)-1H-1,2,3-triazol-1-yl)tetrahydro-2H-pyran-3-ol (by-product in synthesis of Example 1.252) | 0.84 (A) | 547.08 |
| 1.263 | (RS)-(2R,3R,4S,5R,6R)-6-((3-(1-chloro-3-hydroxy-2-methylpropan-2-yl)isoxazol-5-yl)methyl)-4-(4-(2,3-difluoro-4-methylphenyl)-1H-1,2,3-triazol-1-yl)-2-(hydroxymethyl)-5-methoxytetrahydro-2H-pyran-3-ol (by-product in synthesis of Example 1.256) | 0.86 (A) | 543.06 |
| 1.264 | (RS)-(2R,3R,4S,5R,6R)-4-(4-(4-chloro-2,3-difluorophenyl)-1H-1,2,3-triazol-1-yl)-6-((3-(1-chloro-3-hydroxy-2-methylpropan-2-yl)isoxazol-5-yl)methyl)-2-(hydroxymethyl)-5-methoxytetrahydro-2H-pyran-3-ol (by-product in synthesis of Example 1.260) | 0.88 (A) | 563.17 |
| 1.265 | (2R,3R,4S,5R,6R)-6-(((RS)-3-(tert-butyl)-4,5-dihydroisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.90 (A) | 499.25 |
| 1.266 | (2R,3R,4S,5R,6R)-6-(((RS)-3-(tert-butyl)-4,5-dihydroisoxazol-5-yl)methyl)-4-(4-(4-chloro-2,3-difluorophenyl)-1H-1,2,3-triazol-1-yl)-2-(hydroxymethyl)-5-methoxytetrahydro-2H-pyran-3-ol | 0.93 (A) | 515.23 |
| 1.267 | 4-(1-((2R,3R,4S,5R,6R)-2-((5-(tert-butyl)isoxazol-3-yl)methyl)-5-hydroxy-6-(hydroxymethyl)-3-methoxytetrahydro-2H-pyran-4-yl)-1H-1,2,3-triazol-4-yl)-2,3-difluorobenzonitrile | 0.95 (A) | 504.26 |
| 1.268 | (2R,3R,4S,5R,6R)-2-(hydroxymethyl)-5-methoxy-6-((5-(4-methyltetrahydro-2H-pyran-4-yl)isoxazol-3-yl)methyl)-4-(4-(3,4,5-trifluorophenyl)-1H-1,2,3-triazol-1-yl)tetrahydro-2H-pyran-3-ol | 0.89 (A) | 539.23 |
| 1.269 | (2R,3R,4S,5R,6R)-2-(hydroxymethyl)-5-methoxy-6-((5-(4-methyltetrahydro-2H-pyran-4-yl)isoxazol-3-yl)methyl)-4-(4-(2,3,4-trifluorophenyl)-1H-1,2,3-triazol-1-yl)tetrahydro-2H-pyran-3-ol | 0.87 (A) | 539.22 |
| 1.270 | (2R,3R,4S,5R,6R)-4-(4-(2,3-difluoro-4-methylphenyl)-1H-1,2,3-triazol-1-yl)-2-(hydroxymethyl)-5-methoxy-6-((5-(4-methyltetrahydro-2H-pyran-4-yl)isoxazol-3-yl)methyl)tetrahydro-2H-pyran-3-ol | 0.89 (A) | 535.26 |
| 1.271 | (2R,3R,4S,5R,6R)-4-(4-(4-chloro-2,3-difluorophenyl)-1H-1,2,3-triazol-1-yl)-2-(hydroxymethyl)-5-methoxy-6-((5-(4-methyltetrahydro-2H-pyran-4-yl)isoxazol-3-yl)methyl)tetrahydro-2H-pyran-3-ol | 0.91 (A) | 555.18 |
| 1.272 | (2R,3R,4S,5R,6R)-2-(hydroxymethyl)-5-methoxy-6-((5-(1-methylcyclopentyl)isoxazol-3-yl)methyl)-4-(4-(3,4,5-trifluorophenyl)-1H-1,2,3-triazol-1-yl)tetrahydro-2H-pyran-3-ol | 1.01 (A) | 523.23 |
| 1.273 | (2R,3R,4S,5R,6R)-2-(hydroxymethyl)-5-methoxy-6-((5-(1-methylcyclopentyl)isoxazol-3-yl)methyl)-4-(4-(2,3,4-trifluorophenyl)-1H-1,2,3-triazol-1-yl)tetrahydro-2H-pyran-3-ol | 1.00 (A) | 523.24 |
| 1.274 | (2R,3R,4S,5R,6R)-4-(4-(2,3-difluoro-4-methylphenyl)-1H-1,2,3-triazol-1-yl)-2-(hydroxymethyl)-5-methoxy-6-((5-(1-methylcyclopentyl)isoxazol-3-yl)methyl)tetrahydro-2H-pyran-3-ol | 1.01 (A) | 519.26 |
| 1.275 | (2R,3R,4S,5R,6R)-4-(4-(4-chloro-2,3-difluorophenyl)-1H-1,2,3-triazol-1-yl)-2-(hydroxymethyl)-5-methoxy-6-((5-(1-methylcyclopentyl)isoxazol-3-yl)methyl)tetrahydro-2H-pyran-3-ol | 1.03 (A) | 539.15 |
| 1.276 | 1-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)cyclopentane-1-carbonitrile | 0.95 (A) | 533.89 |
| 1.277 | 1-(3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-5-yl)cyclopentane-1-carbonitrile | 0.92 (A) | 533.79 |
| 1.278 | 1-(3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)cyclopentane-1-carbonitrile | 0.94 (A) | 530.07 |

TABLE 1-continued

| Ex. | Compound | $t_R$ [min] (LC-MS method) | MS Data m/z [M + H]$^+$ |
|---|---|---|---|
| 1.279 | 1-(3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)cyclopentane-1-carbonitrile | 0.97 (A) | 549.69 |
| 1.280 | (2R,3R,4S,5R,6R)-4-(4-(4-chloro-2,3-difluorophenyl)-1H-1,2,3-triazol-1-yl)-6-(((RS)-3-(1-hydroxy-2-methylpropan-2-yl)-4,5-dihydroisoxazol-5-yl)methyl)-2-(hydroxymethyl)-5-methoxytetrahydro-2H-pyran-3-ol | 0.80 (A) | 531.17 |
| 1.281 | (2R,3R,4S,5R,6R)-6-(((RS)-3-(1-hydroxy-2-methylpropan-2-yl)-4,5-dihydroisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.77 (A) | 515.21 |
| 1.282 | (2R,3R,4S,5R,6R)-2-(hydroxymethyl)-5-methoxy-6-((3-(4-methyltetrahydro-2H-pyran-4-yl)isoxazol-5-yl)methyl)-4-(4-(3,4,5-trifluorophenyl)-1H-1,2,3-triazol-1-yl)tetrahydro-2H-pyran-3-ol | 0.89 (A) | 539.15 |
| 1.283 | (2R,3R,4S,5R,6R)-2-(hydroxymethyl)-5-methoxy-6-((3-(4-methyltetrahydro-2H-pyran-4-yl)isoxazol-5-yl)methyl)-4-(4-(2,3,4-trifluorophenyl)-1H-1,2,3-triazol-1-yl)tetrahydro-2H-pyran-3-ol | 0.87 (A) | 539.15 |
| 1.284 | (2R,3R,4S,5R,6R)-4-(4-(2,3-difluoro-4-methylphenyl)-1H-1,2,3-triazol-1-yl)-2-(hydroxymethyl)-5-methoxy-6-((3-(4-methyltetrahydro-2H-pyran-4-yl)isoxazol-5-yl)methyl)tetrahydro-2H-pyran-3-ol | 0.89 (A) | 535.15 |
| 1.285 | (2R,3R,4S,5R,6R)-4-(4-(4-chloro-2,3-difluorophenyl)-1H-1,2,3-triazol-1-yl)-2-(hydroxymethyl)-5-methoxy-6-((3-(4-methyltetrahydro-2H-pyran-4-yl)isoxazol-5-yl)methyl)tetrahydro-2H-pyran-3-ol | 0.91 (A) | 555.13 |
| 1.286 | (2R,3R,4S,5R,6R)-2-(hydroxymethyl)-5-methoxy-6-((3-(1-methylcyclopentyl)isoxazol-5-yl)methyl)-4-(4-(3,4,5-trifluorophenyl)-1H-1,2,3-triazol-1-yl)tetrahydro-2H-pyran-3-ol | 1.00 (A) | 523.18 |
| 1.287 | (2R,3R,4S,5R,6R)-2-(hydroxymethyl)-5-methoxy-6-((3-(1-methylcyclopentyl)isoxazol-5-yl)methyl)-4-(4-(2,3,4-trifluorophenyl)-1H-1,2,3-triazol-1-yl)tetrahydro-2H-pyran-3-ol | 0.99 (A) | 523.18 |
| 1.288 | (2R,3R,4S,5R,6R)-4-(4-(2,3-difluoro-4-methylphenyl)-1H-1,2,3-triazol-1-yl)-2-(hydroxymethyl)-5-methoxy-6-((3-(1-methylcyclopentyl)isoxazol-5-yl)methyl)tetrahydro-2H-pyran-3-ol | 1.00 (A) | 519.21 |
| 1.289 | (2R,3R,4S,5R,6R)-4-(4-(4-chloro-2,3-difluorophenyl)-1H-1,2,3-triazol-1-yl)-2-(hydroxymethyl)-5-methoxy-6-((3-(1-methylcyclopentyl)isoxazol-5-yl)methyl)tetrahydro-2H-pyran-3-ol | 1.02 (A) | 539.17 |
| 1.290 | 1-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclopentane-1-carbonitrile | 0.94 (A) | 534.06 |
| 1.291 | 1-(5-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-3-yl)cyclopentane-1-carbonitrile | 0.93 (A) | 534.08 |
| 1.292 | 1-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)cyclopentane-1-carbonitrile | 0.94 (A) | 530.20 |
| 1.293 | 1-(5-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-3-yl)cyclopentane-1-carbonitrile | 0.97 (A) | 550.05 |
| 1.294 | (2R,3R,4S,5R,6R)-2-(hydroxymethyl)-5-methoxy-6-(((RS)-3-(4-methoxyphenyl)-4,5-dihydroisoxazol-5-yl)methyl)-4-(4-(3,4,5-trifluorophenyl)-1H-1,2,3-triazol-1-yl)tetrahydro-2H-pyran-3-ol | 0.92 (A) | 549.27 |
| 1.295 | (2R,3R,4R,5R,6R)-2-(((RS)-3-(2,5-dichlorophenyl)-4,5-dihydroisoxazol-5-yl)methyl)-6-(hydroxymethyl)-4-(4-(3,4,5-trifluorophenyl)-1H-1,2,3-triazol-1-yl)tetrahydro-2H-pyran-3,5-diol | 0.91 (A) | 573.26 |
| 1.296 | (2R,3R,4R,5R,6R)-2-(hydroxymethyl)-6-((5-(4-methoxyphenyl)isoxazol-3-yl)methyl)-4-(4-(3,4,5-trifluorophenyl)-1H-1,2,3-triazol-1-yl)tetrahydro-2H-pyran-3,5-diol | 0.88 (A) | 533.13 |
| 1.298 | tert-butyl 4-((RS)-5-(((2R,3R,4R,5R,6R)-4-(4-(2,6-difluorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate | 0.78 (A) | 594.17 |
| 1.299 | tert-butyl 4-((RS)-5-(((2R,3R,4R,5R,6R)-3,5-dihydroxy-6-(hydroxymethyl)-4-(4-(2-methylbenzo[d]thiazol-6-yl)-1H-1,2,3-triazol-1-yl)tetrahydro-2H-pyran-2-yl)methyl)-4,5-dihydroisoxazol-3-yl)piperidine-1-carboxylate | 0.79 (A) | 626.96 |
| 1.300 | tert-butyl 4-((RS)-5-(((2R,3R,4R,5R,6R)-3,5-dihydroxy-6-(hydroxymethyl)-4-(4-(3-methoxyphenyl)-1H-1,2,3-triazol-1-yl)tetrahydro-2H-pyran-2-yl)methyl)-4,5-dihydroisoxazol-3-yl)piperidine-1-carboxylate | 0.79 (A) | 588.22 |
| 1.301 | tert-butyl 4-((RS)-5-(((2R,3R,4R,5R,6R)-3,5-dihydroxy-6-(hydroxymethyl)-4-(4-(3-(trifluoromethyl)phenyl)-1H-1,2,3-triazol-1-yl)tetrahydro-2H-pyran-2-yl)methyl)-4,5-dihydroisoxazol-3-yl)piperidine-1-carboxylate | 0.87 (A) | 626.18 |
| 1.302 | (2R,3R,4R,5R,6R)-2-((3-(tert-butyl)isoxazol-5-yl)methyl)-4-(4-(4-chloro-2,3-difluorophenyl)-1H-1,2,3-triazol-1-yl)-6-(hydroxymethyl)tetrahydro-2H-pyran-3,5-diol | 0.86 (A) | 497.07 |
| 1.303 | (2R,3R,4S,5R,6R)-6-((3-(1,1-difluoro-2-methylpropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.95 (A) | 533.08 |
| 1.304 | tert-butyl 4-((RS)-5-(((2R,3R,4S,5R,6R)-5-hydroxy-6-(hydroxymethyl)-3-methoxy-4-(4-(naphthalen-2-yl)-1H-1,2,3-triazol-1-yl)tetrahydro-2H-pyran-2-yl)methyl)-4,5-dihydroisoxazol-3-yl)piperidine-1-carboxylate | 0.95 (A) | 622.26 |

TABLE 1-continued

| Ex. | Compound | $t_R$ [min] (LC-MS method) | MS Data m/z [M + H]+ |
|---|---|---|---|
| 1.305 | tert-butyl 4-((RS)-5-(((2R,3R,4S,5R,6R)-5-hydroxy-6-(hydroxymethyl)-3-methoxy-4-(4-(naphthalen-1-yl)-1H-1,2,3-triazol-1-yl)tetrahydro-2H-pyran-2-yl)methyl)-4,5-dihydroisoxazol-3-yl)piperidine-1-carboxylate | 0.93 (A) | 622.25 |
| 1.306 | (2R,3R,4S,5R,6R)-2-(hydroxymethyl)-5-methoxy-6-((3-methylisoxazol-5-yl)methyl)-4-(4-(3,4,5-trifluorophenyl)-1H-1,2,3-triazol-1-yl)tetrahydro-2H-pyran-3-ol | 0.83 (A) | 455.19 |
| 1.307 | (2R,3R,4S,5R,6R)-6-((3-ethylisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.88 (A) | 469.20 |
| 1.308 | (2R,3R,4S,5R,6R)-2-(hydroxymethyl)-6-((3-isopropylisoxazol-5-yl)methyl)-5-methoxy-4-(4-(3,4,5-trifluorophenyl)-1H-1,2,3-triazol-1-yl)tetrahydro-2H-pyran-3-ol | 0.91 (A) | 483.21 |
| 1.309 | (2R,3R,4S,5R,6R)-6-((3-(2-ethoxypropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.92 (A) | 527.20 |
| 1.310 | tert-butyl 4-((RS)-5-(((2R,3R,4S,5R,6R)-5-hydroxy-6-(hydroxymethyl)-3-methoxy-4-(4-phenyl-1H-1,2,3-triazol-1-yl)tetrahydro-2H-pyran-2-yl)methyl)-4,5-dihydroisoxazol-3-yl)piperidine-1-carboxylate | 0.87 (A) | 572.32 |
| 1.311 | tert-butyl 4-((RS)-5-(((2R,3R,4S,5R,6R)-4-(4-(4-bromothiazol-2-yl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.88 (A) | 657.13 |
| 1.312 | (2R,3R,4S,5R,6R)-6-((3-(1-hydroxycyclopentyl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.86 (A) | 525.2 |
| 1.313 | 2-(1-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclopropyl)acetonitrile | 0.89 (A) | 520.19 |
| 1.314 | (2R,3R,4S,5R,6R)-2-(hydroxymethyl)-5-methoxy-6-((3-(1-methoxy-2-methylpropan-2-yl)isoxazol-5-yl)methyl)-4-(4-(3,4,5-trifluorophenyl)-1H-1,2,3-triazol-1-yl)tetrahydro-2H-pyran-3-ol | 0.92 (A) | 527.22 |
| 1.315 | tert-butyl (2-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-2-methylpropyl)carbamate | 0.98 (A) | 612.22 |
| 1.316 | (2R,3R,4S,5R,6R)-6-((3-(1-amino-2-methylpropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol (by-product in the synthesis of example 1.315) | 0.67 (A) | 512.23 |
| 1.317 | (2R,3R,4S,5R,6R)-6-((5-((RS)-cyclopropyl(hydroxy)(pyridin-2-yl)methyl)isoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.78 (A) | 584.20 |
| 1.318 | (2R,3R,4S,5R,6R)-4-(4-(2,3-difluoro-4-methylphenyl)-1H-1,2,3-triazol-1-yl)-6-((5-((RS)-1-hydroxy-1-phenylethyl)isoxazol-3-yl)methyl)-2-(hydroxymethyl)-5-methoxytetrahydro-2H-pyran-3-ol | 0.91 (A) | 557.20 |
| 1.319 | (2R,3R,4S,5R,6R)-4-(4-(2,3-difluoro-4-methylphenyl)-1H-1,2,3-triazol-1-yl)-6-((5-(1-hydroxycyclopropyl)isoxazol-3-yl)methyl)-2-(hydroxymethyl)-5-methoxytetrahydro-2H-pyran-3-ol | 0.80 | 493.20 |
| 1.320 | (2R,3R,4S,5R,6R)-4-(4-(2,3-difluoro-4-methylphenyl)-1H-1,2,3-triazol-1-yl)-2-(hydroxymethyl)-5-methoxy-6-((5-(3-methyloxetan-3-yl)isoxazol-3-yl)methyl)tetrahydro-2H-pyran-3-ol | 0.84 (A) | 507.23 |
| 1.321 | (2R,3R,4S,5R,6R)-4-(4-(2,3-difluoro-4-methylphenyl)-1H-1,2,3-triazol-1-yl)-6-((5-((RS)-1-(2-fluorophenyl)-1-hydroxyethyl)isoxazol-3-yl)methyl)-2-(hydroxymethyl)-5-methoxytetrahydro-2H-pyran-3-ol | 0.92 (A) | 575.17 |
| 1.322 | (2R,3R,4S,5R,6R)-6-((5-(3-((5-bromopyridin-3-yl)oxy)oxetan-3-yl)isoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.94 (A) | 666.05 |
| 1.323 | (2R,3R,4S,5R,6R)-4-(4-(2,3-difluoro-4-methylphenyl)-1H-1,2,3-triazol-1-yl)-2-(hydroxymethyl)-6-((5-(3-hydroxypentan-3-yl)isoxazol-3-yl)methyl)-5-methoxytetrahydro-2H-pyran-3-ol | 0.88 (A) | 523.23 |
| 1.324 | (2R,3R,4S,5R,6R)-4-(4-(2,3-difluoro-4-methylphenyl)-1H-1,2,3-triazol-1-yl)-2-(hydroxymethyl)-6-((5-(1-(hydroxymethyl)cyclopropyl)isoxazol-3-yl)methyl)-5-methoxytetrahydro-2H-pyran-3-ol | 0.80 (A) | 507.22 |
| 1.325 | ethyl 4-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)-4-methylpiperidine-1-carboxylate | 0.97 (A) | 606.22 |
| 1.326 | (2R,3R,4S,5R,6R)-4-(4-(2,3-difluoro-4-methylphenyl)-1H-1,2,3-triazol-1-yl)-6-((3-(1-hydroxycyclopentyl)isoxazol-5-yl)methyl)-2-(hydroxymethyl)-5-methoxytetrahydro-2H-pyran-3-ol | 0.85 (A) | 521.23 |
| 1.327 | (2R,3R,4S,5R,6R)-4-(4-(2,3-difluoro-4-methylphenyl)-1H-1,2,3-triazol-1-yl)-6-((3-(2-ethoxypropan-2-yl)isoxazol-5-yl)methyl)-2-(hydroxymethyl)-5-methoxytetrahydro-2H-pyran-3-ol | 0.92 (A) | 523.24 |
| 1.328 | tert-butyl 4-((RS)-5-(((2R,3R,4S,5R,6R)-4-(4-(2,3-difluoro-4-methoxyphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.92 (A) | 638.22 |
| 1.329 | tert-butyl 4-((RS)-5-(((2R,3R,4S,5R,6R)-4-(4-(2,3-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate | 0.91 (A) | 608.15 |

TABLE 1-continued

| Ex. | Compound | $t_R$ [min] (LC-MS method) | MS Data m/z [M + H]$^+$ |
|---|---|---|---|
| 1.330 | (2R,3R,4S,5R,6R)-4-(4-(2,3-difluoro-4-methylphenyl)-1H-1,2,3-triazol-1-yl)-2-(hydroxymethyl)-5-methoxy-6-((3-(1-methoxy-2-methylpropan-2-yl)isoxazol-5-yl)methyl)tetrahydro-2H-pyran-3-ol | 0.92 (A) | 523.25 |
| 1.331 | tert-butyl (2-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)-2-methylpropyl)carbamate | 0.99 (A) | 608.22 |
| 1.332 | 2-(1-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)cyclopropyl)acetonitrile | 0.89 (A) | 516.22 |
| 1.333 | (2R,3R,4R,5R,6R)-4-(4-(2,3-difluoro-4-methylphenyl)-1H-1,2,3-triazol-1-yl)-2-(hydroxymethyl)-6-((3-(1-methylcyclopropyl)isoxazol-5-yl)methyl)tetrahydro-2H-pyran-3,5-diol | 0.82 (A) | 477.23 |
| 1.334 | (2R,3R,4R,5R,6R)-4-(4-(2,3-difluoro-4-methylphenyl)-1H-1,2,3-triazol-1-yl)-2-((3-(1-hydroxy-2-methylpropan-2-yl)isoxazol-5-yl)methyl)-6-(hydroxymethyl)tetrahydro-2H-pyran-3,5-diol | 0.72 (A) | 495.23 |
| 1.335 | (2R,3R,4R,5R,6R)-4-(4-(2,3-difluoro-4-methylphenyl)-1H-1,2,3-triazol-1-yl)-2-(hydroxymethyl)-6-((3-(3-methyloxetan-3-yl)isoxazol-5-yl)methyl)tetrahydro-2H-pyran-3,5-diol | 0.74 (A) | 493.22 |
| 1.336 | (2R,3R,4S,5R,6R)-6-((3-(1-amino-2-methylpropan-2-yl)isoxazol-5-yl)methyl)-4-(4-(2,3-difluoro-4-methylphenyl)-1H-1,2,3-triazol-1-yl)-2-(hydroxymethyl)-5-methoxytetrahydro-2H-pyran-3-ol (by-product of example 1.331) | 0.87 (A) | 508.26 |
| 1.337 | (RS)-5-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)azepan-2-one | 0.78 (A) | 552.20 |
| 1.338 | 4-(1-((2R,3R,4S,5R,6R)-2-((3-(tert-butyl)isoxazol-5-yl)methyl)-5-hydroxy-6-(hydroxymethyl)-3-methoxytetrahydro-2H-pyran-4-yl)-1H-1,2,3-triazol-4-yl)-2,3-difluorobenzonitrile | 0.93 (A) | 504.24 |
| 1.339 | (2R,3R,4S,5R,6R)-4-(4-(2,3-difluoro-4-methylphenyl)-1H-1,2,3-triazol-1-yl)-6-((5-(1-hydroxy-1-phenylethyl)isoxazol-3-yl)methyl)-2-(hydroxymethyl)-5-methoxytetrahydro-2H-pyran-3-ol (diastereomer 1, chiral separation of example 1.318) | 0.91 (A) | 557.21 |
| 1.340 | (2R,3R,4S,5R,6R)-4-(4-(2,3-difluoro-4-methylphenyl)-1H-1,2,3-triazol-1-yl)-6-((5-(1-hydroxy-1-phenylethyl)isoxazol-3-yl)methyl)-2-(hydroxymethyl)-5-methoxytetrahydro-2H-pyran-3-ol (diastereomer 2, chiral separation of example 1.318) | 0.90 (A) | 557.19 |
| 1.341 | 5-(((4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxin-6-yl)methyl)-3-((RS)-1-phenylethyl)isoxazole | 1.00 (A) | 541.22 |
| 1.342 | (2R,3R,4S,5R,6R)-4-(4-(2,3-difluoro-4-methylphenyl)-1H-1,2,3-triazol-1-yl)-2-(hydroxymethyl)-5-methoxy-6-((3-((RS)-1-phenylethyl)isoxazol-5-yl)methyl)tetrahydro-2H-pyran-3-ol | 1.00 (A) | 541.20 |
| 1.343 | (2R,3R,4S,5R,6R)-4-(4-(2,3-difluoro-4-methylphenyl)-1H-1,2,3-triazol-1-yl)-6-((5-((1RS,2RS)-2-hydroxycyclobutyl)isoxazol-3-yl)methyl)-2-(hydroxymethyl)-5-methoxytetrahydro-2H-pyran-3-ol | 0.80 (A) | 507.23 |
| 1.344 | (2R,3R,4S,5R,6R)-4-(4-(2,3-difluoro-4-methylphenyl)-1H-1,2,3-triazol-1-yl)-5-hydroxy-2-((5-((1RS,2RS)-2-hydroxycyclopentyl)isoxazol-3-yl)methyl)-6-(hydroxymethyl)tetrahydro-2H-pyran-3-yl acetate | 0.83 (A) | 549.08 |
| 1.345 | (RS)-5-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)-1-methylazepan-2-one | 0.81 (A) | 562.22 |
| 1.346 | (2R,3R,4S,5R,6R)-4-(4-(2,3-difluoro-4-methylphenyl)-1H-1,2,3-triazol-1-yl)-6-((5-(-2-hydroxycyclobutyl)isoxazol-3-yl)methyl)-2-(hydroxymethyl)-5-methoxytetrahydro-2H-pyran-3-ol (diastereomer 1, separation of example 1.343) | 0.80 (A) | 507.23 |
| 1.347 | (2R,3R,4S,5R,6R)-4-(4-(2,3-difluoro-4-methylphenyl)-1H-1,2,3-triazol-1-yl)-6-((5-(-2-hydroxycyclobutyl)isoxazol-3-yl)methyl)-2-(hydroxymethyl)-5-methoxytetrahydro-2H-pyran-3-ol (diastereomer 2, separation of example 1.343) | 0.80 (A) | 507.23 |
| 1.348 | (RS)-5-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)azepan-2-one | 0.77 (A) | 548.20 |
| 1.349 | (2R,3R,4S,5R,6R)-4-(4-(2,3-difluoro-4-methylphenyl)-1H-1,2,3-triazol-1-yl)-6-((5-((1S,2R)-2-hydroxycyclopropyl)isoxazol-3-yl)methyl)-2-(hydroxymethyl)-5-methoxytetrahydro-2H-pyran-3-ol | 0.79 (A) | 493.20 |
| 1.350 | (2R,3R,4S,5R,6R)-4-(4-(2,3-difluoro-4-methylphenyl)-1H-1,2,3-triazol-1-yl)-6-((5-((1R,2R)-2-hydroxycyclopropyl)isoxazol-3-yl)methyl)-2-(hydroxymethyl)-5-methoxytetrahydro-2H-pyran-3-ol | 0.79 (A) | 493.21 |
| 1.351 | (2R,3R,4S,5R,6R)-6-((5-(tert-butyl)isoxazol-3-yl)methyl)-4-(4-(2,3-difluorophenyl)-1H-1,2,3-triazol-1-yl)-2-(hydroxymethyl)-5-methoxytetrahydro-2H-pyran-3-ol | 0.92 (A) | 479.23 |
| 1.352 | (2R,3R,4S,5R,6R)-6-((5-(tert-butyl)isoxazol-3-yl)methyl)-4-(4-(2,3-difluoro-4-methoxyphenyl)-1H-1,2,3-triazol-1-yl)-2-(hydroxymethyl)-5-methoxytetrahydro-2H-pyran-3-ol | 0.92 (A) | 509.24 |

Example 2.01: (2R,3R,4R,5R,6R)-2-(hydroxymethyl)-6-((3-(4-methoxyphenyl)isoxazol-5-yl)methyl)-4-(4-(3,4,5-trifluorophenyl)-1H-1,2,3-triazol-1-yl)tetrahydro-2H-pyran-3,5-diol Step 1

To a mixture of (2R,3R,4R,5R,6R)-2-(acetoxymethyl)-6-(((RS)-3-(4-methoxyphenyl)-4,5-dihydroisoxazol-5-yl)methyl)-4-(4-(3,4,5-trifluorophenyl)-1H-1,2,3-triazol-1-yl)tetrahydro-2H-pyran-3,5-diyl diacetate (intermediate in the synthesis of Example 1.02, 270 mg, 0.409 mmol, 1 eq) in dry toluene (8 mL) is added manganese(IV) oxide (632 mg, 6.54 mmol, 16 eq) and the resulting suspension is heated to 100° C. and stirred at this temperature o/n. More manganese(IV) oxide (355 mg, 4.09 mmol, 10 eq) is added and the black suspension is stirred at 100° C. for another 24 h. The black suspension is filtered, the solid is washed with EA and the filtrate is concentrated under reduced pressure. The crude is purified by prep. HPLC (LCMS III) to give the acetate-protected title compound. LCMS (A): $t_R$=1.09 min; [M+H]$^+$=659.20

Step 2

Deprotection following General procedure D gives the title compound. LCMS (A): tR=0.87 min; [M+H]+=533.24

Example 2.02 5-(RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one Step 1

To a solution of (2R,3R,4R,5R,6R)-2-(acetoxymethyl)-6-(((RS)-3-(6-methoxypyridin-3-yl)-4,5-dihydroisoxazol-5-yl)methyl)-4-(4-(3,4,5-trifluorophenyl)-1H-1,2,3-triazol-1-yl)tetrahydro-2H-pyran-3,5-diyl diacetate (Intermediate in the synthesis of Example 1.23, 49 mg, 0.0741 mmol, 1 eq) in acetonitrile dry (1 mL) under N$_2$ is added chlorotrimethylsilane (0.047 mL, 0.37 mmol, 5 eq) and sodium iodide (55.5 mg, 0.37 mmol, 5 eq) and the resulting yellow suspension is stirred at 80° C. for 2 h. The suspension is diluted with EA and washed twice with 10% aq. Na$_2$S$_2$O$_3$ solution, once with water and once with brine. The org. layer is dried over MgSO$_4$, filtered and concentrated under reduced pressure. LCMS (A): $t_R$=0.90 min; [M+H]$^+$=648.11

Step 2

Deprotection following General procedure D gives the title compound. LCMS (A): $t_R$=0.64 min; [M+H]$^+$=522.15
Example 2.03: 4-(RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one Step 1: 4-(RS)-5-(((4aR,6R,7R,8R,8aR)-7-hydroxy-2,2-dimethyl-8-(4-(3,4,5-trifluorophenyl)-1H-1,2,3-triazol-1-yl)hexahydropyrano[3,2-d][1,3]dioxin-6-yl)methyl)-4,5-dihydroisoxazol-3-yl)pyridin-2(1H)-one This intermediate is prepared in analogy to Example 2.02, step 1 starting from the intermediate of Example 1.24. LCMS (A): $t_R$=0.83 min; [M+H]$^+$=561.91

Step 2

Deprotection following General procedure C gives the title compound.
LCMS (A): $t_R$=0.65 min; [M+H]$^+$=522.15

Example 2.04. and 2.05

The diastereomers of compound of Example 2.03 are separated on chiral HPLC (chiral prep HPLC (III)). First eluting compound: S-isomer. Second eluting compound: R-isomer.
Both compounds are deprotected following General procedure C to give Example 2.04 4-((R)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one LCMS (A): $t_R$=0.65 min; [M+H]$^+$=522.15
1H NMR (500 MHz, DMSO-d6) δ: 11.54-11.71 (m, 1H), 8.56-8.85 (m, 1H), 7.83-7.87 (m, 2H), 7.34-7.44 (m, 1H), 6.37-6.61 (m, 2H), 5.10-5.35 (m, 2H), 4.83-5.04 (m, 2H), 4.49-4.65 (m, 2H), 4.05-4.26 (m, 1H), 3.82- 3.92 (m, 2H), 3.41-3.48 (m, 3H), 3.16-3.21 (m, 1H), 2.39-2.43 (m, 1H), 1.74-2.02 (m, 1H)

Example 2.05. 4-((S)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one LCMS (A): $t_R$=0.66 min; [M+H]$^+$=522.14
$^1$H NMR (500 MHz, DMSO-d6) δ: 11.58-11.68 (m, 1H), 8.72-8.76 (m, 1H), 7.84 (m, 2H), 7.38 (d, J=6.8 Hz, 1H), 6.28-6.67 (m, 2H), 5.28 (m, 2H), 4.85-4.93 (m, 2H), 4.71 (t, J=5.8 Hz, 1H), 4.54 (m, 1H), 4.23 (ddd, J$_1$=11.7 Hz, J$_2$=6.1 Hz, J$_3$=2.4 Hz, 1H), 3.81-3.90 (m, 2H), 3.45-3.55 (m, 3H), 3.12 (dd, J$_1$=17.3 Hz, J$_2$=7.9 Hz, 1H), 2.25-2.31 (m, 1H), 1.95 (m, 1H)

Example 2.06: 4-(RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one The title example is prepared in analogy to Example 2.03. LCMS (A): $t_R$=0.75 min; [M+H]$^+$=536.14

Example 2.07a: 4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one The title example is prepared by chiral separation of Example 2.06.
LCMS (A): $t_R$=0.75 min; [M+H]$^+$=536.17
$^1$H NMR (500 MHz, DMSO-d6) δ: 11.57-11.70 (m, 1H), 8.72-8.90 (m, 1H), 7.73-7.94 (m, 2H), 7.35-7.41 (m, 1H), 6.46-6.53 (m, 2H), 5.24-5.36 (m, 2H), 4.84-5.04 (m, 2H), 4.74 (m, 1H), 4.45-4.61 (m, 1H), 4.25-4.31 (m, 1H), 3.74-

3.96 (m, 2H), 3.45-3.56 (m, 3H), 3.21 (s, 3H), 3.14 (dd, $J^1$=17.3 Hz, $J^2$=8.2 Hz, 1H), 2.37 (m, 2H), 1.75-1.81 (m, 1H)

Example 2.07b: 4-((R)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one The title example is obtained by chiral separation of Example 2.06.
LCMS (A): $t_R$=0.75 min; [M+H]$^+$=536.15

Example 2.08: (2R,3R,4S,5R,6R)-2-(hydroxymethyl)-5-methoxy-6-((5-((RS)-pyrrolidin-3-yl)isoxazol-3-yl)methyl)-4-(4-(3,4,5-trifluorophenyl)-1H-1,2,3-triazol-1-yl)tetrahydro-2H-pyran-3-ol The intermediate of Example 1.70 is deprotected using General procedure E. LCMS (A): $t_R$=0.66 min; [M+H]$^+$=510.14

Example 2.09: 1-(RS)-3-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)pyrrolidin-1-yl)ethan-1-one Example 2.08 is acylated with acetic anhydride following General Procedure G. LCMS (A): $t_R$=0.79 min; [M+H]$^+$=552.08

Example 2.10: 1-(RS)-4-hydroxy-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)azepan-1-yl)ethan-1-one The title example is prepared starting from the intermediate of Example 1.76 and following general procedures E and G. LCMS (A): $t_R$=0.76 min; [M+H]$^+$=596.11

Example 2.11: (1S,4s)-4-(3-(((2R,3R,4R,5R,6R)-3,5-dihydroxy-6-(hydroxymethyl)-4-(4-(3,4,5- trifluorophenyl)-1H-1,2,3-triazol-1-yl)tetrahydro-2H-pyran-2-yl)methyl)isoxazol-5-yl)-4-hydroxycyclohexane-1-carboxylic acid Example 1.78 is saponified using general procedure Q. LCMS (A): $t_R$=0.63 min; [M+H]$^+$=569.01

Example 2.12: 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)cyclohexan-1-one The compound of Example 1.77 is deprotected using general procedure C. LCMS (A): $t_R$=0.76 min; [M+H]$^+$=523.04

Example 2.13: (2R,3R,4R,5R,6R)-2-((5-(4-hydroxycyclohexyl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol (cis/trans mixture 1:1)

A solution of Example 2.12 (25 mg, 0.0478 mmol, 1 eq) in MeOH (1.5 mL) is treated with sodium borohydride (1.83 mg, 0.0478 mmol, 1 eq) and the mixture is stirred at rt for 20 min. The product is recovered after aqueous workup as a mixture of isomers.
LCMS (A): $t_R$=0.72/0.73 min; [M+H]$^+$=525.05

Example 2.14: (2R,3R,4R,5R,6R)-2-((5-((1r,4r)-4-hydroxycyclohexyl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol Example 2.13 is further purified by prep HPLC (Prep LC-MS III) to give the pure trans-configured compound.
LCMS (A): $t_R$=0.72 min; [M+H]$^+$=525.05
$^1$H NMR (500 MHz, DMSO-d6) δ: 8.76 (s, 1H), 7.85 (m, 2H), 6.34 (d, 1H), 5.47 (d, J=5.5 Hz, 1H), 5.26 (d, J=6.4 Hz, 1H), 5.02 (dd, $J^1$=11.4 Hz, $J^2$=2.9 Hz, 1H), 4.71 (t, J=5.5 Hz, 1H), 4.62 (d, J=4.4 Hz, 1H), 4.57 (m, 1H), 4.17 (ddd, $J^1$=11.9 Hz, $J^2$=6.0 Hz, $J^3$=2.6 Hz, 1H), 3.93-3.98 (m, 2H), 3.39-3.51 (m, 3H), 3.27 (dd, $J^1$=15.2 Hz, $J^2$=12.0 Hz, 1H), 2.93 (dd, $J^1$=15.2 Hz, $J^2$=2.6 Hz, 1H), 2.65-2.72 (m, 1H), 1.98-2.01 (m, 2H), 1.90 (dd, $J^1$=12.9 Hz, $J^2$=3.3 Hz, 2H), 1.37-1.45 (m, 2H), 1.28 (m, 3H)

Example 2.15: tert-butyl 4-(3-(((2R,3R,4S,5R,6R)-5-hydroxy-6-(hydroxymethyl)-3-(propionyloxy)-4-(4-(3,4,5-trifluorophenyl)-1H-1,2,3-triazol-1-yl)tetrahydro-2H-pyran-2-yl)methyl)isoxazol-5-yl)piperidine-1-carboxylate Step 1: tert-butyl 4-(3-(((4aR,6R,7R,8S,8aR)-7-acetoxy-2,2-dimethyl-8-(4-(3,4,5-trifluorophenyl)-1H-1,2,3-triazol-1-yl)hexahydropyrano[3,2-d][1,3]dioxin-6-yl)methyl)isoxazol-5-yl)piperidine-1-carboxylate Intermediate 8b and 1-Boc-4-ethynylpiperidine are coupled according to general procedure A. LCMS (A): $t_R$=1.12 min; [M+H]$^+$=692.20

Step 2: tert-butyl 4-(3-(((4aR,6R,7R,8R,8aR)-7-hydroxy-2,2-dimethyl-8-(4-(3,4,5-trifluorophenyl)-1H-1,2,3-triazol-1-yl)hexahydropyrano[3,2-d][1,3]dioxin-6-yl)methyl)isoxazol-5-yl)piperidine-1-carboxylate The acetate group of Intermediate of Step 1 is removed following general procedure D.
LCMS (A): $t_R$=1.05 min; [M+H]$^+$=650.19

Step 3: tert-butyl 4-(3-(((4aR,6R,7R,8S,8aR)-2,2-dimethyl-7-(propionyloxy)-8-(4-(3,4,5-trifluorophenyl)-1H- 1,2,3-triazol-1-yl)hexahydropyrano[3,2-d][1,3]dioxin-6-yl)methyl)isoxazol-5-yl)piperidine-1-carboxylate Pyridine (0.17 mL, 0.215 mmol, 4 eq), DMAP (3.32 mg, 0.5 eq) and propionyl chloride (0.0057 mL, 1.2 eq) are added to a solution of Intermediate of step 2 (35 mg, 0.0539 mmol, 1 eq) in DCM (1 mL) and the mixture is stirred at rt for 2 days. The mixture is partitioned between DCM and water and the aq. phase is extracted twice more with DCM. The combined org phases are washed with brine, dried over MgSO$_4$ and concentrated under reduced pressure.
LCMS (A): t$_R$=1.14 min; [M+H]$^+$=706.21

Step 4: tert-butyl 4-(3-(((2R,3R,4S,5R,6R)-5-hydroxy-6-(hydroxymethyl)-3-(propionyloxy)-4-(4-(3, 4,5- trifluorophenyl)-1H-1,2,3-triazol-1-yl)tetrahydro-2H-pyran-2-yl)methyl)isoxazol-5-yl) piperidine-1-carboxylate Intermediate of step 3 is deprotected according to general procedure C. LCMS (A): t$_R$=1.01 min; [M+H]$^+$=666.17

Example 2.16: (2R,3R,4S,5R,6R)-5-hydroxy-6-(hydroxymethyl)-2-((5-(piperidin-4-yl)isoxazol-3-yl) methyl)-4-(4-(3,4,5-trifluorophenyl)-1H-1,2,3-triazol-1-yl)tetrahydro-2H-pyran-3-yl propionate The title compound is obtained in minor amounts during the synthesis of Example 2.15, step 4
LCMS (A): t$_R$=0.71 min; [M+H]$^+$=566.16

Example 2.17: tert-butyl 4-(3-(((2R,3R,4S,5R,6R)-3-ethoxy-5-hydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate Step 1: tert-butyl 4-(3-(((4aR,6R,7R,8R,8aR)-7-ethoxy-2,2-dimethyl-8-(4-(3,4,5-trifluorophenyl)-1H-1,2,3-triazol-1-yl)hexahydropyrano[3,2-d][1,3]dioxin-6-yl)methyl)isoxazol-5-yl)piperidine-1-carboxylate Intermediate of Example 2.15 step 2 is alkylated using general procedure L. LCMS (A): t$_R$=1.14 min; [M+H]$^+$=678.23

Step 2: Intermediate of step 1 is deprotected according to general procedure C. LCMS (A): t$_R$=1.01 min; [M+H]$^+$=638.17

Example 2.18: (2R,3R,4S,5R,6R)-5-hydroxy-6-(hydroxymethyl)-2-((5-(piperidin-4-yl)isoxazol-3-yl) methyl)-4-(4-(3,4,5-trifluorophenyl)-1H-1,2,3-triazol-1-yl)tetrahydro-2H-pyran-3-yl propionate The title compound is obtained in minor amounts during the synthesis of Example 2.17, step 2 LCMS (A): t$_R$=0.71 min; [M+H]$^+$=538.18

Example 2.19: tert-butyl 4-(3-(((2R,3R,4S,5R,6R)-5-hydroxy-6-(hydroxymethyl)-3-propoxy-4-(4-(3,4, 5-trifluorophenyl)-1H-1,2,3-triazol-1-yl)tetrahydro-2H-pyran-2-yl)methyl)isoxazol-5-yl)piperidine-1-carboxylate This example is prepared in analogy to Example 2.17 using 1-iodopropane instead of iodoethane.
LCMS (A): t$_R$=1.04 min; [M+H]$^+$=652.20

Example 2.20: tert-butyl 4-(3-(((2R,3R,4S,5R,6R)-3-butoxy-5-hydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate This example is prepared in analogy to Example 2.17 using 1-iodobutane instead of iodoethane. LCMS (A): t$_R$=1.06 min; [M+H]$^+$=666.23

Example 2.21: 2-(((2R,3R,4S,5R,6R)-2-((5-(1-(tert-butoxycarbonyl)piperidin-4-yl)isoxazol-3-yl) methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid This example is prepared in analogy to Example 2.17 using iodoacetic acid instead of iodoethane. LCMS (A): t$_R$=0.89 min; [M+H]$^+$=668.13

Example 2.22: tert-butyl 4-(3-(((2R,3R,4S,5R,6R)-5-hydroxy-6-(hydroxymethyl)-3-(isobutyryloxy)-4-(4-(3,4,5-trifluorophenyl)-1H-1,2,3-triazol-1-yl)tetrahydro-2H-pyran-2-yl)methyl)isoxazol-5-yl) piperidine-1-carboxylate This example is prepared in analogy to Example 2.15, steps 3-4, using isobutyryl chloride instead of propionyl chloride.
LCMS (A): t$_R$=1.04 min; [M+H]$^+$=680.19

Example 2.23: tert-butyl 4-(3-(((2R,3R,4S,5R,6R)-5-hydroxy-6-(hydroxymethyl)-3-isopropoxy-4-(4-(3, 4,5-trifluorophenyl)-1H-1,2,3-triazol-1-yl)tetrahydro-2H-pyran-2-yl)methyl)isoxazol-5-yl) piperidine-1-carboxylate Step 1: tert-butyl 4-(3-(((4aR,6R,7R,8R,8aR)-7-hydroxy-2,2-dimethyl-8-(4-(3,4,5-trifluorophenyl)-1H-1,2,3-triazol-1-yl)hexahydropyrano[3,2-d][1,3]dioxin-6-yl)methyl)isoxazol-5-yl)piperidine-1-carboxylate The example 1.40 is protected according to general procedure K. LCMS (A): t$_R$=1.05 min; [M+H]$^+$=650.18

Step 2: tert-butyl 4-(3-(((4aR,6R,7R,8R,8aR)-7-isopropoxy-2,2-dimethyl-8-(4-(3,4,5-trifluorophenyl)-1H-1,2,3-triazol-1-yl)hexahydropyrano[3,2-d][1,3]dioxin-6-yl)methyl)isoxazol-5-yl)piperidine-1-carboxylate Intermediate of step 1 is alkylated according to general procedure L using 2-iodopropane. LCMS (A): t$_R$=1.16 min; [M+H]$^+$=692.30

Step 3

Deprotection following General procedure C gives the title compound. LCMS (A): t$_R$=1.03 min; [M+H]$^+$=652.17

Example 2.24: (2R,3R,4S,5R,6R)-2-(hydroxymethyl)-5-isopropoxy-6-((5-(piperidin-4-yl)isoxazol-3-yl)methyl)-4-(4-(3,4,5-trifluorophenyl)-1H-1,2,3-triazol-1-yl)tetrahydro-2H-pyran-3-ol The title compound is obtained in minor amounts during the synthesis of Example 2.23, step 3. LCMS (A): t$_R$=0.73 min; [M+H]$^+$=552.16.

Example 2.25: tert-butyl 4-(3-(((2R,3R,4S,5R,6R)-3-(2,2-difluoroethoxy)-5-hydroxy-6-(hydroxymethyl)-4-(4-(3,4,5-trifluorophenyl)-1H-1,2,3-triazol-1-yl)tetrahydro-2H-pyran-2-yl)methyl)issoxazole-5-yl)piperidine-1-carboxylate This example is prepared in analogy to Example 2.23 using 2,2-difluoroethyl trifluoromethanesulfonic acid.
LCMS (A): t$_R$=1.00 min; [M+H]$^+$=673.94

Example 2.26: (2R,3R,4S,5R,6R)-5-(2,2-difluoroethoxy)-2-(hydroxymethyl)-6-((5-(piperidin-4-yl)isoxazol-3-yl)methyl)-4-(4-(3,4,5-trifluorophenyl)-1H-1,2,3-triazol-1-yl)tetrahydro-2H-pyran-3-ol The title compound is obtained in minor amounts during the synthesis of Example 2.25, step 3. LCMS (A): $t_R$=0.72 min; [M+H]$^+$=574.15.

Example 2.27: 2-(((2R,3R,4S,5R,6R)-2-((5-(tert-butyl)isoxazol-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetic acid Step 1: (4aR,6R,7R,8R,8aR)-6-((5-(tert-butyl)isoxazol-3-yl)methyl)-8-(4-(2,3-difluoro-4-methylphenyl)-1H-1,2,3-triazol-1-yl)-2,2-dimethylhexahydropyrano[3,2-d][1,3]dioxin-7-ol Hydrolysis of the acetate protective group of acetate-protected example 1.204 is was performed following general procedure D. LCMS (A): $t_R$=1.04 min; [M+H]$^+$=519.29

Step 2: methyl 2-(((4aR,6R,7R,8R,8aR)-6-((5-(tert-butyl)isoxazol-3-yl)methyl)-8-(4-(2,3-difluoro-4-methylphenyl)-1H-1,2,3-triazol-1-yl)-2,2-dimethylhexahydropyrano[3,2-d][1,3]dioxin-7-yl)oxy)acetate Alkylation of intermediate of step 1 with methyl chloroacetate was performed following general procedure L. LCMS (A): $t_R$=1.11 min; [M+H]$^+$=591.25

Step 3: 2-(((4aR,6R,7R,8R,8aR)-6-((5-(tert-butyl)isoxazol-3-yl)methyl)-8-(4-(2,3-difluoro-4-methylphenyl)-1H-1,2,3-triazol-1-yl)-2,2-dimethylhexahydropyrano[3,2-d][1,3]dioxin-7-yl)oxy)acetic acid Ester hydrolysis was performed following general procedure Q. LCMS (A): $t_R$=1.01 min; [M+H]$^+$=577.22

Step 4

Deprotection following General procedure C gives the title compound. LCMS (A): $t_R$=0.84 min; [M+H]$^+$=537.22

Example 2.28: 2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one This example is prepared in analogy to Example 2.27, steps 2, and 4, using 4-(chloroacetyl)morpholine instead of methyl chloroacetate. LCMS (A): $t_R$=0.86 min; [M+H]$^+$=610.247

Example 2.29: tert-butyl ((S)-1-(((1R,4S)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclohexyl)amino)-3-methyl-1-oxobutan-2-yl)carbamate Step 1: (2R,3R,4S,5R,6R)-6-((3-((1r,4R)-4-aminocyclohexyl)isoxazol-5-yl)methyl)-2-(hydroxymethyl)-5-methoxy- 4-(4-(3,4,5-trifluorophenyl)-1H-1,2,3-triazol-1-yl)tetrahydro-2H-pyran-3-ol Example 1.134 is deprotected using general procedure E. LCMS (A): $t_R$=0.69 min; [M+H]$^+$=538.22

Step 2: tert-butyl ((S)-1-(((1R,4S)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclohexyl)amino)-3-methyl-1-oxobutan-2-yl)carbamate Intermediate of step 2 is coupled to Boc-Val-OH with HATU using general procedure I. LCMS (A): $t_R$=0.98 min; [M+H]$^+$=737.38

Example 2.30: (S)-2-amino-N-((1R,4S)-4-(5-(((2R,3R,4S,5R,6R)-5-hydroxy-6-(hydroxymethyl)-3-methoxy-4- (4-(3,4,5-trifluorophenyl)-1H-1,2,3-triazol-1-yl)tetrahydro-2H-pyran-2-yl)methyl)isoxazol-3-yl)cyclohexyl)-3-methylbutanamide The Boc group of the Example 2.29 is deprotected using general procedure E. LCMS (A): $t_R$=0.74 min; [M+H]$^+$=637.30

Example 2.31: tert-butyl 4-((RS)-5-(((2R,3R,4S,5R,6R)-3-ethoxy-5-hydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate Step 1: tert-butyl 4-((RS)-5-(((4aR,6R,7R,8R,8aR)-7-hydroxy-2,2-dimethyl-8-(4-(3,4,5-trifluorophenyl)-1H-1,2,3-triazol-1-yl)hexahydropyrano[3,2-d][1,3]dioxin-6-yl)methyl)-4,5-dihydroisoxazol-3-yl)piperidine-1-carboxylate Intermediates 5a is and intermediate 37 are coupled using general procedure A. LCMS (A): $t_R$=1.01 min; [M+H]$^+$=652.27

Step 2: tert-butyl 4-((RS)-5-(((4aR,6R,7R,8R,8aR)-7-ethoxy-2,2-dimethyl-8-(4-(3,4,5-trifluorophenyl)-1H-1,2,3-triazol-1-yl)hexahydropyrano[3,2-d][1,3]dioxin-6-yl)methyl)-4,5-dihydroisoxazol-3-yl)piperidine-1-carboxylate Intermediate of step 1 is alkylated with ethyl iodide according to general procedure L. LCMS (A): $t_R$=1.12 min; [M+H]$^+$=680.30

Step 3

Deprotection following General procedure C gives the title compound. LCMS (A): $t_R$=0.98 min; [M+H]$^+$=640.30

Example 2.32: tert-butyl 4-((RS)-5-(((2R,3R,4S,5R,6R)-3-(2,2-difluoroethoxy)-5-hydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate This example is prepared in analogy to Example 2.31 using 2,2-difluoroethyl trifluoromethanesulfonate instead of ethyl iodide. LCMS (A): $t_R$=0.97 min; [M+H]$^+$=676.20

Example 2.33: tert-butyl 4-((RS)-5-(((2R,3R,4S,5R,6R)-5-hydroxy-6-(hydroxymethyl)-3-(2-methoxy-2-oxoethoxy)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate This example is prepared in analogy to Example 2.31 using methyl bromoacetate instead of ethyl iodide. LCMS (A): $t_R$=0.95 min; [M+H]$^+$=684.30

Example 2.34: 2-(((2R,3R,4S,5R,6R)-2-(((RS)-3-(1-(tert-butoxycarbonyl)piperidin-4-yl)-4,5-dihydroisoxazol-5-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid Step 1: tert-butyl 4-((RS)-5-(((4aR,6R,7R,8R,8aR)-7-(2-methoxy-2-oxoethoxy)-2,2-dimethyl-8-(4-(3,4,5-trifluorophenyl)-1H-1,2,3-triazol-1-yl)hexahydropyrano[3,2-d][1,3]dioxin-6-yl)methyl)-4,5-dihydroisoxazol-3-yl)piperidine-1-carboxylate This intermediate is prepared in analogy to Example 2.31, steps 1 and 2. LCMS (A): $t_R$=1.09 min; [M+H]$^+$=724.26

Step 2: 2-(((4aR,6R,7R,8R,8aR)-6-(((RS)-3-(1-(tert-butoxycarbonyl)piperidin-4-yl)-4,5-dihydroisoxazol-5-yl)methyl)-2,2-dimethyl-8-(4-(3,4,5-trifluorophenyl)-1H-1,2,3-triazol-1-yl)hexahydropyrano[3,2-d][1,3]dioxin-7-yl)oxy)acetic acid Intermediate of step 1 is saponified using general procedure Q. LCMS (A): $t_R$=1.02 min; [M+H]$^+$=710.33

Step 3

Deprotection following General procedure C gives the title compound. LCMS (A): $t_R$=0.86 min; [M+H]$^+$=670.29

Example 2.35: tert-butyl 4-((RS)-5-(((2R,3R,4S,5R,6R)-5-hydroxy-6-(hydroxymethyl)-3-(2-(methylamino)-2-oxoethoxy)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate This example is prepared in analogy to Example 2.31 using 2-bromo-N-methylacetamine instead of ethyl iodide. LCMS (A): $t_R$=0.87 min; [M+H]$^+$=683.32

Example 2.36: tert-butyl 4-((RS)-5-(((2R,3R,4S,5R,6R)-5-hydroxy-6-(hydroxymethyl)-3-(2-morpholino-2-oxoethoxy)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate This example is prepared in analogy to Example 2.31 using 4-(chloroacetyl)-morpholine instead of ethyl iodide. LCMS (A): $t_R$=0.88 min; [M+H]$^+$=739.35

Example 2.37: 2-(((2R,3R,4S,5R,6R)-2-((3-(tert-butyl)isoxazol-5-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid This product is prepared in analogy to Example 2.34, steps 1, 2 and 3 starting with Intermediate 9 g and pivalaldehyde oxime. LCMS (A): $t_R$=0.83 min; [M+H]$^+$=541.19

Example 2.38: 2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-N-methylacetamide This product is prepared starting with Intermediate 8b in analogy to Example 2.27, using 2-bromo-N-methyl-acetamide. LCMS (A): $t_R$=0.85 min; [M+H]+=554.23

Example 2.39: 2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-((R)-3-hydroxypyrrolidin-1-yl)ethan-1-one Step 1: 2-(((4aR,6R,7R,8R,8aR)-6-((5-(tert-butyl)isoxazol-3-yl)methyl)-2,2-dimethyl-8-(4-(3,4,5-trifluorophenyl)- 1H-1,2,3-triazol-1-yl)hexahydropyrano[3,2-d][1,3]dioxin-7-yl)oxy)acetic acid This intermediate is prepared starting with Intermediate 8b in analogy to Example 2.27. LCMS (A): $t_R$=1.00 min; [M+H]+=581.16.

Step 2: 2-(((4aR,6R,7R,8R,8aR)-6-((5-(tert-butyl)isoxazol-3-yl)methyl)-2,2-dimethyl-8-(4-(3,4,5-trifluorophenyl)- 1H-1,2,3-triazol-1-yl)hexahydropyrano[3,2-d][1,3]dioxin-7-yl)oxy)-1-((R)-3-hydroxypyrrolidin-1-yl)ethan-1-one Intermediate of step 1 is coupled with (R)-3-pyrrolidinol according to general procedure I. LCMS (A): $t_R$=0.98 min; [M+H]+=650.30

Step 3

Deprotection following General procedure C gives the title compound. LCMS (A): $t_R$=0.80 min; [M+H]$^+$=610.24

Example 2.40: 2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(3-hydroxyazetidin-1-yl)ethan-1-one This product is prepared in analogy to Example 2.39 using azetidine-3-ol. LCMS (A): $t_R$=0.79 min; [M+H]+=596.24.

Example 2.41: 2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-(4-hydroxypiperidin-1-yl)ethan-1-one This product is prepared in analogy to Example 2.39 using hydroxypiperidine. LCMS (A): $t_R$=0.81 min; [M+H]+=624.25.

Example 2.42: 2-(((2R,3R,4S,5R,6R)-2-((5-(tert-butyl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-((S)-3-hydroxypyrrolidin-1-yl)ethan-1-one This product is prepared in analogy to Example 2.39 using (S)-3-pyrrolidinol. LCMS (A): $t_R$=0.80 min; [M+H]+=610.26.

Example 2.43: 2-(((2R,3R,4S,5R,6R)-2-((3-(tert-butyl)isoxazol-5-yl)methyl)-5-hydroxy-6-(hydroxymethyl)-4-(4-(2,3,4-trifluorophenyl)-1H-1,2,3-triazol-1-yl)tetrahydro-2H-pyran-3-yl)oxy)acetic acid This product is prepared starting with Intermediate 9h following general procedure A' using trimethylacetaldehyde, followed by alkylation with ethyl bromoacetate (general procedure L), saponification (general procedure Q) and deprotection (general procedure C). LCMS (A): $t_R$=0.82 min; [M+H]+=541.23.

Example 2.44: 2-(((2R,3R,4S,5R,6R)-5-hydroxy-6-(hydroxymethyl)-2-((3-(1-methylcyclopropyl)isoxazol-5-yl)methyl)-4-(4-(2,3,4-trifluorophenyl)-1H-1,2,3-triazol-1-yl)tetrahydro-2H-pyran-3-yl)oxy)acetic acid This product is prepared in analogy to Example 2.43 starting Intermediate 9h and 1-methylcyclopropane-1-carbaldehyde. LCMS (A): $t_R$=0.80 min; [M+H]+=539.14.

Example 2.45: (2R,3R,4S,5R,6R)-2-((3-(tert-butyl)isoxazol-5-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl carbamate Step 1: (4aR,6R,7R,8R,8aR)-6-((3-(tert-butyl)isoxazol-5-yl)methyl)-8-(4-(2,3-difluoro-4-methylphenyl)-1H-1,2,3-triazol-1-yl)-2,2-dimethylhexahydropyrano[3,2-d][1,3]dioxin-7-ol Intermediate 9i and trimethylacetaldehyde are coupled using general procedure A'. LCMS (A): $t_R$=1.04 min; [M+H]+=519.30.

Step 2

Intermediate of step 1 and trichloroacetyl isocyanate are coupled and deprotected using general procedure H, D and C. LCMS (A): $t_R$=0.83 min; [M+H]+=522.19.

Example 2.46: 2-(((2R,3R,4S,5R,6R)-5-hydroxy-2-((3-(1-hydroxy-2-methylpropan-2-yl)isoxazol-5-yl)methyl)-6-(hydroxymethyl)-4-(4-(2,3,4-trifluorophenyl)-1H-1,2,3-triazol-1-yl)tetrahydro-2H-pyran-3-yl)oxy)acetic acid This product is prepared in analogy to Example 2.43 starting Intermediate 9h and 3-hydroxy-2,2-dimethylpropanal. LCMS (A): $t_R$=0.70 min; [M+H]+=557.14.

Example 2.47: (2R,3R,4S,5R,6R)-6-((5-(tert-butyl)isoxazol-3-yl)methyl)-4-(4-(4-ethynyl-2,3-difluorophenyl)-1H-1,2,3-triazol-1-yl)-2-(hydroxymethyl)-5-methoxytetrahydro-2H-pyran-3-ol Step 1

To a mixture of Example 1.191 (1 eq), CuI (0.1 eq) and Bis(triphenylphosphine)palladium (0.1 eq) in 1,4-dioxane (5 mL/mmol) is added NEt₃ (5 eq) and trimethylsilylacetylene (5 eq). The resulting mixture is heated to 80° C. and stirred at this temperature for 3 h. More trimethylsilylacetylene (5 eq), CuI (0.1 eq) and bis(triphenylphoshine)palladium (0.1 eq) are added and the mixture is stirred at 80° C. o/n. EA is added and the suspension is filtered, the filtrate is washed with water. The org. layer is dried over MgSO₄, filtered and concentrated under reduced pressure. The crude is used without further purification. LCMS (A): $t_R$=1.13 min; [M+H]+=575.25

Step 2

Deprotection (TMS group) following General procedure D gives the title compound. LCMS (A): $t_R$=0.97 min; [M+H]+=503.25.

Example 2.48: (2R,3R,4R,5R,6R)-2-((3-(tert-butyl)isoxazol-5-yl)methyl)-6-(hydroxymethyl)-4-(4-(3,4,5-trifluorophenyl)-1H-1,2,3-triazol-1-yl)tetrahydro-2H-pyran-3,5-diol Step 1: (2R,3R,4R,5R,6R)-2-(acetoxymethyl)-4-azido-6-(prop-2-yn-1-yl)tetrahydro-2H-pyran-3,5-diyl diacetate Intermediate 1 (1 eq) is dissolved in MeOH and cooled to 0° C. Intermediate 41 (2 eq) is added followed by BF₃OEt₂ (3 eq) and trimethylsilyl trifluoromethanesulfonate (2 eq). The reaction mixture is stirred at 0° C. for 1 h and at rt for 2 h. After aqueous workup (NaHCO₃ sat./EA), the crude product is purified as described in the general methods.
¹H NMR (500 MHz, DMSO) b: 1.99-2.01 (m, 3H), 2.09-2.11 (m, 6H), 2.58 (m, 1H), 2.73 (ddd, J₁=17.4 Hz, J₂=9.4 Hz, J₃=2.6 Hz, 1H), 2.90 (t, J=2.6 Hz, 1H), 3.99-4.07 (m, 4H), 4.23 (m, 1H), 4.40 (dd, J¹=10.5 Hz, J₂=3.4 Hz, 1H), 5.02 (dd, J₁=10.5 Hz, J₂=5.6 Hz, 1H), 5.29 (dd, J¹=3.4 Hz, J₂=1.6 Hz, 1H)

Step 2: (2R,3R,4R,5R,6R)-2-(acetoxymethyl)-4-azido-6-((3-(tert-butyl)isoxazol-5-yl)methyl)tetrahydro-2H-pyran-3,5-diyl diacetate Intermediate of step 1 is coupled to trimethylacetaldehyde using General procedure A'. LCMS (A): $t_R$=1.00 min; [M+H]+=453.22.

Step 3: (2R,3R,4R,5R,6R)-2-(acetoxymethyl)-6-((3-(tert-butyl)isoxazol-5-yl)methyl)-4-(4-(3,4,5-trifluorophenyl)-1H-1,2,3-triazol-1-yl)tetrahydro-2H-pyran-3,5-diyl diacetate Intermediate of step 2 is coupled with 3,4,5-trifluorophenylacetylene using General procedure B. LCMS (A): $t_R$=1.10 min; [M+H]+=609.02.

Step 4

Deprotection following General procedure D gives the title compound. LCMS (A): $t_R$=0.84 min; [M+H]+=483.18.

Example 2.49: (2R,3R,4R,5R,6R)-2-((3-(tert-butyl)isoxazol-5-yl)methyl)-6-(hydroxymethyl)-4-(4-(2,3,4-trifluorophenyl)-1H-1,2,3-triazol-1-yl)tetrahydro-2H-pyran-3,5-diol This product is prepared in analogy of Example 2.48 using 2,3,4-trifluorophenylacetylene. LCMS (A): $t_R$=0.83 min; [M+H]+=483.19.

Example 2.50: (2R,3R,4R,5R,6R)-2-((3-(tert-butyl) isoxazol-5-yl)methyl)-4-(4-(2,3-difluoro-4-methylphenyl)-1H-1,2,3-triazol-1-yl)-6-(hydroxymethyl)tetrahydro-2H-pyran-3,5-diol This product is prepared in analogy of Example 2.48 using 1-ethynyl-2,3-difluoro-4-methyl-benzene. LCMS (A): $t_R$=0.85 min; [M+H]+=479.21.

Example 2.51: (2R,3R,4S,5R,6R)-2-((3-(tert-butyl) isoxazol-5-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl ethylcarbamate This product is prepared in analogy of Example 2.45 using ethyl isocyanate in step 2. LCMS (A): $t_R$=0.90 min; [M+H]+=550.15.

Example 2.52: (2R,3R,4S,5R,6R)-6-((3-(tert-butyl) isoxazol-5-yl)methyl)-4-(4-(2,3-difluoro-4-methylphenyl)-1H-1,2,3-triazol-1-yl)-2-(hydroxymethyl)-5-((1-methyl-1H-imidazol-2-yl)methoxy)tetrahydro-2H-pyran-3-ol This product was prepared starting from Example 2.45, step 1 and 2-(chloromethyl)-1-methyl-1H-imidazole following general procedure L (alkylation), followed by deprotection (general procedure C). $t_R$=0.69 min; [M+H]+=573.22.

Example 2.53: (2R,3R,4S,5R,6R)-6-((3-(tert-butyl) isoxazol-5-yl)methyl)-4-(4-(2,3-difluoro-4-methylphenyl)-1H-1,2,3-triazol-1-yl)-2-(hydroxymethyl)-5-(thiazol-2-ylmethoxy)tetrahydro-2H-pyran-3-ol This product was prepared starting from Example 2.45, step 1 and 2-(bromomethyl)thiazole following general procedure L (alkylation), followed by deprotection (general procedure C). $t_R$=0.94 min; [M+H]+=576.18.

Example 2.54: (2R,3R,4S,5R,6R)-6-((3-(tert-butyl) isoxazol-5-yl)methyl)-4-(4-(2,3-difluoro-4-methylphenyl)-1H-1,2,3-triazol-1-yl)-2-(hydroxymethyl)-5-(thiazol-4-ylmethoxy)tetrahydro-2H-pyran-3-ol This product was prepared starting from Example 2.45, step 1 and 4-(chloromethyl)thiazole following general procedure L (alkylation), followed by deprotection (general procedure C). $t_R$=0.94 min; [M+H]+=576.18.

Example 2.55: (2R,3R,4S,5R,6R)-6-((3-(tert-butyl) isoxazol-5-yl)methyl)-4-(4-(2,3-difluoro-4-methylphenyl)-1H-1,2,3-triazol-1-yl)-2-(hydroxymethyl)-5-(oxazol-5-ylmethoxy)tetrahydro-2H-pyran-3-ol This product was prepared starting from Example 2.45, step 1 and 5-(bromomethyl)oxazole following general procedure L (alkylation), followed by deprotection (general procedure C). $t_R$=0.92 min; [M+H]+=560.23.

Example 2.56: (2R,3R,4S,5R,6R)-6-((3-(1-hydroxycyclobutyl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol This product was prepared starting from Intermediates 9a and 47 and following general procedure U. Deprotection was performed following general procedure C. $t_R$=0.83 min; [M+H]+=511.20.

Example 2.57: (2R,3R,4S,5R,6R)-4-(4-(2,3-difluoro-4-methylphenyl)-1H-1,2,3-triazol-1-yl)-6-((3-(1-hydroxycyclobutyl)isoxazol-5-yl)methyl)-2-(hydroxymethyl)-5-methoxytetrahydro-2H-pyran-3-ol [1-(1,3-di-deoxy-2-O-methyl-3-[4-(2,3-difluoro-4-methylphenyl)-1H-1,2,3-triazol-1-yl]-α-D-galactopyranose)-1-(3-(1-hydroxycyclobutyl)1H-isoxazol-5-yl)-methane]

This product was prepared starting from Intermediates 9h and 47 and following general procedure U. Deprotection was performed following general procedure C. $t_R$=0.81 min; [M+H]+=511.19.

Example 2.58: (2R,3R,4S,5R,6R)-4-(4-(4-chloro-2,3-difluorophenyl)-1H-1,2,3-triazol-1-yl)-6-((3-(1-hydroxycyclobutyl)isoxazol-5-yl)methyl)-2-(hydroxymethyl)-5-methoxytetrahydro-2H-pyran-3-ol This product was prepared starting from intermediates 9l and 47 and following general procedure U. Deprotection was performed following general procedure C. $t_R$=0.83 min; [M+H]+=507.22

Example 2.59: (2R,3R,4S,5R,6R)-4-(4-(4-chloro-2,3-difluorophenyl)-1H-1,2,3-triazol-1-yl)-6-((3-(1-hydroxycyclobutyl)isoxazol-5-yl)methyl)-2-(hydroxymethyl)-5-methoxytetrahydro-2H-pyran-3-ol This product was prepared starting from Intermediates 9k and 47 and following general procedure U. Deprotection was performed following general procedure C. $t_R$=0.85 min; [M+H]+=527.13

Example 2.60: (2R,3R,4S,5R,6R)-2-(hydroxymethyl)-6-((3-(2-hydroxypropan-2-yl)isoxazol-5-yl)methyl)-5-methoxy-4-(4-(3,4,5-trifluorophenyl)-1H-1,2,3-triazol-1-yl)tetrahydro-2H-pyran-3-ol This product was prepared starting from trimethyl((2-methyl-1-nitropropan-2-yl)oxy)silane and following general procedure U. Deprotection was performed following general procedure C. $t_R$=0.80 min; [M+H]+=499.20

Example 2.61: (2R,3R,4S,5R,6R)-2-(hydroxymethyl)-6-((3-(2-hydroxypropan-2-yl)isoxazol-5-yl)methyl)-5-methoxy-4-(4-(2,3,4-trifluorophenyl)-1H-1,2,3-triazol-1-yl)tetrahydro-2H-pyran-3-ol This product was prepared starting from Intermediate 9h and trimethyl((2-methyl-1-nitropropan-2-yl)oxy)silane and following general procedure U. Deprotection was performed following general procedure C. $t_R$=0.78 min; [M+H]+=499.21

Example 2.62: (2R,3R,4S,5R,6R)-4-(4-(2,3-difluoro-4-methylphenyl)-1H-1,2,3-triazol-1-yl)-2-(hydroxymethyl)-6-((3-(2-hydroxypropan-2-yl)isoxazol-5-yl)methyl)-5-methoxytetrahydro-2H-pyran-3-ol This product was prepared starting from Intermediate 9l and trimethyl((2-methyl-1-nitropropan-2-yl)oxy)silane and following general procedure U. Deprotection was performed following general procedure C. $t_R$=0.80 min; [M+H]+=495.22

Example 2.63: (2R,3R,4S,5R,6R)-4-(4-(4-chloro-2,3-difluorophenyl)-1H-1,2,3-triazol-1-yl)-2-(hydroxymethyl)-6-((3-(2-hydroxypropan-2-yl)isoxazol-5-yl)methyl)-5-methoxytetrahydro-2H-pyran-3-ol This product was prepared starting from intermediate 9k and trimethyl((2-methyl-1-nitropropan-2-yl)oxy)silane and following general procedure U. Deprotection was performed following general procedure C. $t_R=0.82$ min; [M+H]+=515.17.

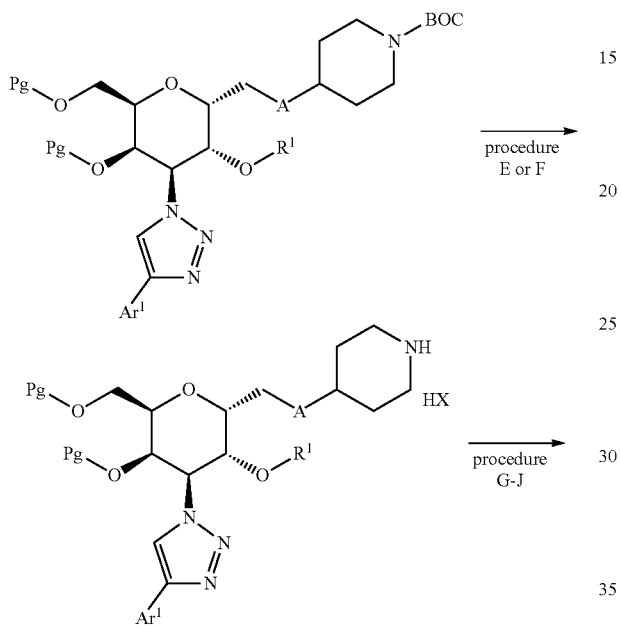

procedure E or F procedure G-J

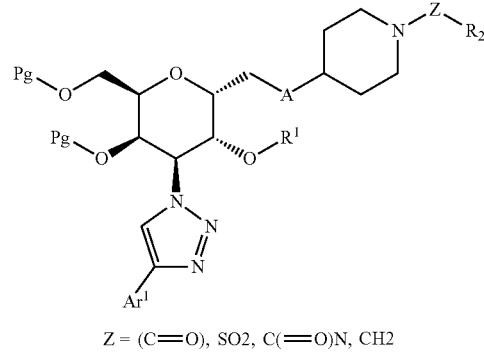

Z = (C=O), SO2, C(=O)N, CH2

Compounds of Examples 3.01-3.70 listed in Table 2 below are prepared by applying either one of the above-mentioned procedures E or F to Boc protected intermediates of examples of Table 1, followed by derivatization with electrophiles using procedures G, H, I, J and/or M

TABLE 2

| Ex. | Compound | $t_R$ [min] (LC-MS) | MS Data m/z [M + H]+ |
|---|---|---|---|
| 3.01 | (2R,3R,4R,5R,6R)-2-(hydroxymethyl)-6-(((RS)-3-(piperidin-4-yl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.56 (A) | 512.24 |
| 3.02 | (2R,3R,4R,5R,6R)-2-(hydroxymethyl)-6-(((RS)-3-(1-methylpiperidin-4-yl)-4,5-dihydroisoxazol-5-yl)methyl)-4-(4-(3,4,5-trifluorophenyl)-1H-1,2,3-triazol-1-yl)tetrahydro-2H-pyran-3,5-diol | 0.57 (A) | 526.22 |
| 3.03 | 1-(4-((RS)-5-((((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one | 0.68 (A) | 554.15 |
| 3.04 | (2R,3R,4S,5R,6R)-2-(hydroxymethyl)-5-methoxy-6-(((RS)-3-(piperidin-4-yl)-4,5-dihydroisoxazol-5-yl)methyl)-4-(4-(3,4,5-trifluorophenyl)-1H-1,2,3-triazol-1-yl)tetrahydro-2H-pyran-3-ol | 0.63 (A) | 526.22 |
| 3.05 | 1-(4-((RS)-5-((((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one | 0.78 (A) | 568.16 |
| 3.06 | (2R,3R,4S,5R,6R)-2-(hydroxymethyl)-5-methoxy-6-(((S)-3-(piperidin-4-yl)-4,5-dihydroisoxazol-5-yl)methyl)-4-(4-(3,4,5-trifluorophenyl)-1H-1,2,3-triazol-1-yl)tetrahydro-2H-pyran-3-ol (chiral separation of example 3.04) | 0.63 (A) | 526.22 |
| 3.07 | (2R,3R,4S,5R,6R)-2-(hydroxymethyl)-5-methoxy-6-(((R)-3-(piperidin-4-yl)-4,5-dihydroisoxazol-5-yl)methyl)-4-(4-(3,4,5-trifluorophenyl)-1H-1,2,3-triazol-1-yl)tetrahydro-2H-pyran-3-ol (chiral separation of example 3.04) | 0.63 (A) | 526.22 |
| 3.08 | (2R,3R,4R,5R,6R)-2-(hydroxymethyl)-6-((5-(piperidin-4-yl)isoxazol-3-yl)methyl)-4-(4-(3,4,5-trifluorophenyl)-1H-1,2,3-triazol-1-yl)tetrahydro-2H-pyran-3,5-diol | 0.59 (A) | 510.20 |
| 3.09 | (2R,3R,4R,5R,6R)-2-(hydroxymethyl)-6-(((RS)-5-(piperidin-4-yl)-4,5-dihydroisoxazol-3-yl)methyl)-4-(4-(3,4,5-trifluorophenyl)-1H-1,2,3-triazol-1-yl)tetrahydro-2H-pyran-3,5-diol | 0.57 (A) | 512.22 |

TABLE 2-continued

| Ex. | Compound | $t_R$ [min] (LC-MS) | MS Data m/z [M + H]$^+$ |
|---|---|---|---|
| 3.10 | 1-(4-((R)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one (chiral separation of example 3.05) | 0.68 (A) | 554.17 |
| 3.11 | 1-(4-((S)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one (chiral separation of example 3.05) | 0.68 (A) | 554.16 |
| 3.12 | 1-(4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one (chiral separation of example 3.03) | 0.78 (A) | 568.18 |
| 3.13 | 1-(4-((R)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one (chiral separation of example 3.03) | 0.78 (A) | 568.16 |
| 3.14 | (2R,3R,4S,5R,6R)-5-hydroxy-6-(hydroxymethyl)-2-(((RS)-3-(piperidin-4-yl)-4,5-dihydroisoxazol-5-yl)methyl)-4-(4-(3,4,5-trifluorophenyl)-1H-1,2,3-triazol-1-yl)tetrahydro-2H-pyran-3-yl acetate | 0.65 (A) | 554.18 |
| 3.15 | (2R,3R,4S,5R,6R)-5-hydroxy-6-(hydroxymethyl)-2-((5-(piperidin-4-yl)isoxazol-3-yl)methyl)-4-(4-(3,4,5-trifluorophenyl)-1H-1,2,3-triazol-1-yl)tetrahydro-2H-pyran-3-yl acetate | 0.67 (A) | 552.15 |
| 3.16 | (2R,3R,4S,5R,6R)-2-(hydroxymethyl)-5-methoxy-6-((5-(piperidin-4-yl)isoxazol-3-yl)methyl)-4-(4-(3,4,5-trifluorophenyl)-1H-1,2,3-triazol-1-yl)tetrahydro-2H-pyran-3-ol | 0.67 (A) | 524.17 |
| 3.17 | 1-(4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidin-1-yl)ethan-1-one | 0.73 (A) | 522.13 |
| 3.18 | 1-(4-((RS)-3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-5-yl)piperidin-1-yl)ethan-1-one | 0.69 (A) | 554.16 |
| 3.19 | 1-(4-((R)-3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-5-yl)piperidin-1-yl)ethan-1-one (chiral separation of example 3.18) | 0.69 (A) | 554.16 |
| 3.20 | 1-(4-((S)-3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-5-yl)piperidin-1-yl)ethan-1-one (chiral separation of example 3.18) | 0.69 (A) | 554.16 |
| 3.21 | 1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)ethan-1-one | 0.83 (A) | 565.90 |
| 3.22 | (2R,3R,4S,5R,6R)-2-((5-(1-acetylpiperidin-4-yl)isoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl acetate [1-(1,3-di-deoxy-2-O-acetyl-3-[4-(3,4,5-trifluorophenyl)-1H-1,2,3-triazol-1-yl]-α-D-galacto-pyranose)-1-(5-((1-acetyl)piperidin-4-yl)-1H-isoxazol-3-yl)-methane] | 0.83 (A) | 594.12 |
| 3.23 | (2R,3R,4S,5R,6R)-2-(((RS)-5-(1-acetylpiperidin-4-yl)-4,5-dihydroisoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl acetate | 0.80 (A) | 596.12 |
| 3.24 | (2R,3R,4S,5R,6R)-2-(((R)-5-(1-acetylpiperidin-4-yl)-4,5-dihydroisoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl acetate (chiral separation of example 3.23) | 0.80 (A) | 596.16 |
| 3.25 | (2R,3R,4S,5R,6R)-2-(((S)-5-(1-acetylpiperidin-4-yl)-4,5-dihydroisoxazol-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl acetate [1-(1,3-di-deoxy-2-O-acetyl-3-[4-(3,4,5-trifluorophenyl)-1H-1,2,3-triazol-1-yl]-α-D-galacto-pyranose)-1-((S)-5-((1-acetyl)piperidin-4-yl)-1H-4,5-dihydroisoxazol-3-yl)-methane] (chiral separation of example 3.23) | 0.80 (A) | 596.16 |
| 3.26 | ethyl 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate | 0.83 (A) | 581.90 |
| 3.27 | 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)-N-ethylpiperidine-1-carboxamide [1-(1,3-di-deoxy-3-[4-(3,4,5-trifluorophenyl)-1H-1,2,3-triazol-1-yl]-α-D-galacto-pyranose)-1-(5-((1-ethylamino-carbonyl)piperidin-4-yl)-1H-isoxazol-3-yl)-methane] | 0.74 (A) | 581.01 |
| 3.28 | (2R,3R,4R,5R,6R)-2-(hydroxymethyl)-6-((5-(1-(methylsulfonyl)piperidin-4-yl)isoxazol-3-yl)methyl)-4-(4-(3,4,5-trifluorophenyl)-1H-1,2,3-triazol-1-yl)tetrahydro-2H-pyran-3,5-diol | 0.76 (A) | 588.10 |
| 3.29 | (2R,3R,4R,5R,6R)-2-(hydroxymethyl)-6-((5-(1-methylpiperidin-4-yl)isoxazol-3-yl)methyl)-4-(4-(3,4,5-trifluorophenyl)-1H-1,2,3-triazol-1-yl)tetrahydro-2H-pyran-3,5-diol | 0.60 (A) | 524.16 |
| 3.30 | 1-(4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidin-1-yl)-2,2-dimethylpropan-1-one | 0.84 (A) | 594.16 |

TABLE 2-continued

| Ex. | Compound | $t_R$ [min] (LC-MS) | MS Data m/z [M + H]+ |
|---|---|---|---|
| 3.31 | ethyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate | 0.93 (A) | 596.14 |
| 3.32 | methyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate | 0.90 (A) | 582.12 |
| 3.33 | 1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-2-methylpropan-1-one | 0.89 (A) | 593.99 |
| 3.34 | 1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-2,2-dimethylpropan-1-one | 0.93 (A) | 608.17 |
| 3.35 | 1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)butan-1-one | 0.89 (A) | 593.97 |
| 3.36 | (2R,3R,4S,5R,6R)-2-(hydroxymethyl)-5-methoxy-6-(((RS)-5-(piperidin-4-yl)-4,5-dihydroisoxazol-3-yl)methyl)-4-(4-(3,4,5-trifluorophenyl)-1H-1,2,3-triazol-1-yl)tetrahydro-2H-pyran-3-ol | 0.64/0.65 (A) | 526.12 |
| 3.37 | N-ethyl-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxamide | 0.84 (A) | 595.13 |
| 3.38 | 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N-isopropylpiperidine-1-carboxamide | 0.87 (A) | 609.14 |
| 3.39 | (2R,3R,4S,5R,6R)-2-(hydroxymethyl)-5-methoxy-6-((5-(1-methylpiperidin-4-yl)isoxazol-3-yl)methyl)-4-(4-(3,4,5-trifluorophenyl)-1H-1,2,3-triazol-1-yl)tetrahydro-2H-pyran-3-ol | 0.67 (A) | 538.13 |
| 3.40 | 1-(4-((RS)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-5-yl)piperidin-1-yl)ethan-1-one | 0.79 (A) | 568.14 |
| 3.41 | (2R,3R,4S,5R,6R)-2-(hydroxymethyl)-6-((5-(1-isobutylpiperidin-4-yl)isoxazol-3-yl)methyl)-5-methoxy-4-(4-(3,4,5-trifluorophenyl)-1H-1,2,3-triazol-1-yl)tetrahydro-2H-pyran-3-ol | 0.74 (A) | 580.16 |
| 3.42 | (2R,3R,4S,5R,6R)-6-((5-(1-(3,3-dimethylbutyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.80 (A) | 608.17 |
| 3.43 | (2R,3R,4S,5R,6R)-6-((5-(1-(cyclopropylmethyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.73 (A) | 577.90 |
| 3.44 | (2R,3R,4S,5R,6R)-2-(hydroxymethyl)-5-methoxy-6-((5-(1-(oxetan-3-ylmethyl)piperidin-4-yl)isoxazol-3-yl)methyl)-4-(4-(3,4,5-trifluorophenyl)-1H-1,2,3-triazol-1-yl)tetrahydro-2H-pyran-3-ol | 0.68 (A) | 593.92 |
| 3.45 | (2R,3R,4S,5R,6R)-2-(hydroxymethyl)-5-methoxy-6-((5-(1-(methylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol | 0.86 (A) | 602.05 |
| 3.46 | (2R,3R,4S,5R,6R)-2-(hydroxymethyl)-5-methoxy-6-((5-(1-(propylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol | 0.93 (A) | 629.85 |
| 3.47 | (2R,3R,4S,5R,6R)-2-(hydroxymethyl)-6-((5-(1-(isopropylsulfonyl)piperidin-4-yl)isoxazol-3-yl)methyl)-5-methoxy-4-(4-(3,4,5-trifluorophenyl)-1H-1,2,3-triazol-1-yl)tetrahydro-2H-pyran-3-ol | 0.92 (A) | 629.85 |
| 3.48 | 1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-3-methylbutan-1-one | 0.92 (A) | 608.12 |
| 3.49 | cyclopentyl(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)methanone | 0.94 (A) | 620.11 |
| 3.50 | cyclobutyl(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)methanone | 0.91 (A) | 606.11 |
| 3.51 | 3,3,3-trifluoro-1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)propan-1-one | 0.90 (A) | 634.06 |
| 3.52 | N-(tert-butyl)-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxamide | 0.92 (A) | 623.16 |
| 3.53 | (RS)-1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-2-methylbutan-1-one | 0.92 (A) | 608.15 |
| 3.54 | (S)-2-amino-1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-3-methylbutan-1-one | 0.72 (A) | 623.12 |
| 3.55 | (2R,3R,4S,5R,6R)-6-((5-(1-((RS)-tert-butylsulfinyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.92 (A) | 628.03 |

TABLE 2-continued

| Ex. | Compound | $t_R$ [min] (LC-MS) | MS Data m/z [M + H]$^+$ |
|---|---|---|---|
| 3.56 | (RS)-(2R,3R,4S,5R,6R)-2-(hydroxymethyl)-5-methoxy-6-((5-(1-(2-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol | 0.81 (A) | 643.02 |
| 3.57 | (RS)-(2R,3R,4S,5R,6R)-2-(hydroxymethyl)-5-methoxy-6-((5-(1-(N-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol | 0.78 (A) | 643.08 |
| 3.58 | 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N,N-dimethylpiperidine-1-sulfonamide | 0.92 (A) | 631.07 |
| 3.59 | N-cyclopropyl-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxamide | 0.84 (A) | 607.14 |
| 3.60 | (2R,3R,4S,5R,6R)-2-(hydroxymethyl)-6-(((R)-3-(1-(isopropylsulfonyl)piperidin-4-yl)-4,5-dihydroisoxazol-5-yl)methyl)-5-methoxy-4-(4-(3,4,5-trifluorophenyl)-1H-1,2,3-triazol-1-yl)tetrahydro-2H-pyran-3-ol | 0.87 (A) | 632.17 |
| 3.61 | (2R,3R,4S,5R,6R)-2-(hydroxymethyl)-6-(((S)-3-(1-(isopropylsulfonyl)piperidin-4-yl)-4,5-dihydroisoxazol-5-yl)methyl)-5-methoxy-4-(4-(3,4,5-trifluorophenyl)-1H-1,2,3-triazol-1-yl)tetrahydro-2H-pyran-3-ol | 0.87 (A) | 632.20 |
| 3.62 | (2R,3R,4S,5R,6R)-2-(hydroxymethyl)-5-methoxy-6-((5-(1-(morpholinosulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol | 0.92 (A) | 673.25 |
| 3.63 | (2R,3R,4S,5R,6R)-2-(hydroxymethyl)-5-methoxy-6-((5-(1-(piperidin-1-ylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol | 1.00 (A) | 671.26 |
| 3.64 | (2R,3R,4S,5R,6R)-2-(hydroxymethyl)-5-methoxy-6-((5-(1-(pyrrolidin-1-ylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol | 0.96 (A) | 657.26 |
| 3.65 | (2R,3R,4S,5R,6R)-6-((5-(1-((4,4-difluoropiperidin-1-yl)sulfonyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 1.00 (A) | 707.26 |
| 3.66 | (4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)(piperidin-1-yl)methanone | 0.96 (A) | 635.35 |
| 3.67 | (4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)(pyrrolidin-1-yl)methanone | 0.91 (A) | 621.30 |
| 3.68 | N-ethyl-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N-methylpiperidine-1-carboxamide | 0.91 (A) | 609.32 |
| 3.69 | 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N,N-dimethylpiperidine-1-carboxamide | 0.88 (A) | 595.27 |
| 3.70 | (4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)(4-methylpiperazin-1-yl)methanone | 0.69 (A) | 650.35 |

Compounds of Examples 4.01-4.55 listed in Table 3 below are prepared by applying General procedure B (click chemistry) to the appropriate azide and alkyne building blocks (either commercially available or described as intermediate). Triazoles are then further deprotected (General Procedures C, D, E, F or P) and/or derivatised following General procedures G, H, I, J, M, N and/or O.

TABLE 3

| Ex. | Compound | $t_R$ [min] (LC-MS) | MS Data m/z [M + H]$^+$ |
|---|---|---|---|
| 4.01 | (2R,3R,4S,5R,6R)-6-((4-(3-fluorophenyl)-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.92 (A) | 535.26 |
| 4.02 | 6-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)benzo[d]oxazol-2(3H)-one | 0.82 (A) | 574.08 |
| 4.03 | (2R,3R,4S,5R,6R)-2-(hydroxymethyl)-5-methoxy-6-((1-(tetrahydro-2H-pyran-4-yl)-1H-1,2,3-triazol-4-yl)methyl)-4-(4-(3,4,5-trifluorophenyl)-1H-1,2,3-triazol-1-yl)tetrahydro-2H-pyran-3-ol | 0.76 (A) | 525.17 |
| 4.04 | 1-(4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidin-1-yl)ethan-1-one | 0.76 (A) | 566.15 |

TABLE 3-continued

| Ex. | Compound | $t_R$ [min] (LC-MS) | MS Data m/z [M + H]+ |
|---|---|---|---|
| 4.05 | tert-butyl 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxylate | 0.91 (A) | 624.16 |
| 4.06 | 1-(4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidin-1-yl)ethan-1-one [1-(1,3-di-deoxy-2-O-methyl-3-[4-(3,4,5-trifluorophenyl)-1H-1,2,3-triazol-1-yl]-α-D-galacto-pyranose)-1-(1-(1-acetylpiperidin-4-yl)-1H-1,2,3-triazol-4-yl)-methane] | 0.74 (A) | 565.81 |
| 4.07 | (2R,3R,4S,5R,6R)-2-(hydroxymethyl)-5-methoxy-6-((1-(1-(methylsulfonyl)piperidin-4-yl)-1H-1,2,3-triazol-4-yl)methyl)-4-(4-(3,4,5-trifluorophenyl)-1H-1,2,3-triazol-1-yl)tetrahydro-2H-pyran-3-ol | 0.78 (A) | 602.00 |
| 4.08 | N-(tert-butyl)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxamide | 0.84 (A) | 623.11 |
| 4.09 | (2R,3R,4S,5R,6R)-2-(hydroxymethyl)-5-methoxy-6-((1-(1-(propylsulfonyl)piperidin-4-yl)-1H-1,2,3-triazol-4-yl)methyl)-4-(4-(3,4,5-trifluorophenyl)-1H-1,2,3-triazol-1-yl)tetrahydro-2H-pyran-3-ol | 0.85 (A) | 629.82 |
| 4.10 | (2R,3R,4S,5R,6R)-2-(hydroxymethyl)-6-((1-(1-(isopropylsulfonyl)piperidin-4-yl)-1H-1,2,3-triazol-4-yl)methyl)-5-methoxy-4-(4-(3,4,5-trifluorophenyl)-1H-1,2,3-triazol-1-yl)tetrahydro-2H-pyran-3-ol | 0.84 (A) | 629.82 |
| 4.11 (Ref. Ex.) | tert-butyl 4-(4-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxylate | 0.91 (A) | 624.16 |
| 4.12 (Ref. Ex.) | 1-(4-(4-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidin-1-yl)ethan-1-one | 0.74 (A) | 565.86 |
| 4.13 | benzyl 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxylate | 0.93 (A) | 658.01 |
| 4.14 | (2R,3R,4S,5R,6R)-2-(hydroxymethyl)-5-methoxy-6-((1-(tetrahydro-2H-thiopyran-4-yl)-1H-1,2,3-triazol-4-yl)methyl)-4-(4-(3,4,5-trifluorophenyl)-1H-1,2,3-triazol-1-yl)tetrahydro-2H-pyran-3-ol | 0.84 (A) | 540.97 |
| 4.15 | 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)tetrahydro-2H-thiopyran 1-oxide (mixture of cis/trans isomers) | 0.69 (A) | 556.98 |
| 4.16 | 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)tetrahydro-2H-thiopyran 1,1-dioxide | 0.71 (A) | 572.99 |
| 4.17 | 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)-1-iminohexahydro-1l6-thiopyran 1-oxide (mixture of cis/trans isomers) | 0.66 (A) | 572.00 |
| 4.18 | 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)-1-(methylimino)hexahydro-1l6-thiopyran 1-oxide (mixture of cis/trans isomers) | 0.66 (A) | 586.03 |
| 4.19 | (2R,3R,4S,5R,6R)-6-((1-(1-(RS-tert-butylsulfinyl)piperidin-4-yl)-1H-1,2,3-triazol-4-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.84 (A) | 628.06 |
| 4.20 | benzyl 4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidine-1-carboxylate | 0.95 (A) | 658.06 |
| 4.21 | (2R,3R,4S,5R,6R)-2-(hydroxymethyl)-5-methoxy-6-((1-(1-(2-methylpropan-2-ylsulfonimidoyl)piperidin-4-yl)-1H-1,2,3-triazol-4-yl)methyl)-4-(4-(3,4,5-trifluorophenyl)-1H-1,2,3-triazol-1-yl)tetrahydro-2H-pyran-3-ol (mixture of isomers) | 0.75 (A) | 643.10 |
| 4.22 | (2R,3R,4S,5R,6R)-2-(hydroxymethyl)-6-((4-(1-(isopropylsulfonyl)piperidin-4-yl)-1H-1,2,3-triazol-1-yl)methyl)-5-methoxy-4-(4-(3,4,5-trifluorophenyl)-1H-1,2,3-triazol-1-yl)tetrahydro-2H-pyran-3-ol | 0.86 (A) | 629.80 |
| 4.23 | (2R,3R,4S,5R,6R)-2-(hydroxymethyl)-5-methoxy-6-((4-(1-tosylpiperidin-4-yl)-1H-1,2,3-triazol-1-yl)methyl)-4-(4-(3,4,5-trifluorophenyl)-1H-1,2,3-triazol-1-yl)tetrahydro-2H-pyran-3-ol | 0.95 (A) | 677.85 |
| 4.24 | 1-(ethylimino)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)hexahydro-1l6-thiopyran 1-oxide (mixture of cis/trans isomers) | 0.68 (A) | 600.09 |
| 4.25 | (2R,3R,4S,5R,6R)-2-(hydroxymethyl)-5-methoxy-6-((4-(1-(N-methylpropan-2-ylsulfonimidoyl)piperidin-4-yl)-1H-1,2,3-triazol-1-yl)methyl)-4-(4-(3,4,5-trifluorophenyl)-1H-1,2,3-triazol-1-yl)tetrahydro-2H-pyran-3-ol (mixture of isomers) | 0.73 (A) | 643.11 |
| 4.26 | 4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2- | 0.85 (A) | 631.07 |

TABLE 3-continued

| Ex. | Compound | $t_R$ [min] (LC-MS) | MS Data m/z [M + H]+ |
|---|---|---|---|
| | yl)methyl)-1H-1,2,3-triazol-4-yl)-N,N-dimethylpiperidine-1-sulfonamide | | |
| 4.27 | N-(tert-butyl)-4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidine-1-carboxamide | 0.86 (A) | 623.14 |
| 4.28 | 1-(benzylimino)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)hexahydro-1l6-thiopyran 1-oxide (mixture of cis/trans isomers) | 0.80 (A) | 661.94 |
| 4.29 | (2R,3R,4S,5R,6R)-6-((4-cyclohexyl-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.92 (A) | 523.13 |
| 4.30 | (2R,3R,4S,5R,6R)-6-(((1-cyclohexyl-1H-1,2,3-triazol-4-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.89 (A) | 523.10 |
| 4.31 | 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)-1-(isopropylimino)hexahydro-1l6-thiopyran 1-oxide (mixture of cis/trans isomers) | 0.70 (A) | 613.87 |
| 4.32 | N-cyclopropyl-4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidine-1-carboxamide | 0.78 (A) | 607.16 |
| 4.33 | 1-((4,4-difluorocyclohexyl)imino)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)hexahydro-1l6-thiopyran 1-oxide (mixture of cis/trans isomers) | 0.81 (A) | 690.15 |
| 4.34 | benzyl 4-(4-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)-1H-1,2,3-triazol-1-yl)piperidine-1-carboxylate | 0.92 (A) | 656.14 |
| 4.35 | benzyl 4-(4-(((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)methyl)-1H-1,2,3-triazol-1-yl)piperidine-1-carboxylate | 0.88 (A) | 622.16 |
| 4.36 | benzyl 4-(4-(((2R,3R,4S,5R,6R)-4-(4-(4-bromo-3-fluorophenyl)-1H-1,2,3-triazol-1-yl)-5-hydroxy-6-(hydroxymethyl)-3-methoxytetrahydro-2H-pyran-2-yl)methyl)-1H-1,2,3-triazol-1-yl)piperidine-1-carboxylate | 0.93 (A) | 702.20 |
| 4.37 | benzyl 4-(4-(((2R,3R,4S,5R,6R)-4-(4-(3,5-difluorophenyl)-1H-1,2,3-triazol-1-yl)-5-hydroxy-6-(hydroxymethyl)-3-methoxytetrahydro-2H-pyran-2-yl)methyl)-1H-1,2,3-triazol-1-yl)piperidine-1-carboxylate | 0.90 (A) | 640.30 |
| 4.38 | (2R,3R,4S,5R,6R)-6-(((4-(tert-butyl)-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.86 (A) | 497.22 |
| 4.39 | ethyl 4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidine-1-carboxylate | 0.86 (A) | 596.25 |
| 4.40 | (2R,3R,4S,5R,6R)-2-(hydroxymethyl)-5-methoxy-6-(((4-(tetrahydro-2H-pyran-4-yl)-1H-1,2,3-triazol-1-yl)methyl)-4-(4-(3,4,5-trifluorophenyl)-1H-1,2,3-triazol-1-yl)tetrahydro-2H-pyran-3-ol | 0.78 (A) | 525.26 |
| 4.41 | (2R,3R,4S,5R,6R)-6-(((4-(1-hydroxycyclopentyl)-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.78 (A) | 525.24 |
| 4.42 | (2R,3R,4S,5R,6R)-6-(((4-(cyclopent-1-en-1-yl)-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol (byproduct in the synthesis of Example 4.41) | 0.90 (A) | 507.27 |
| 4.43 | (2R,3R,4S,5R,6R)-6-(((4-(1-hydroxycyclobutyl)-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.76 (A) | 511.16 |
| 4.44 | (2R,3R,4S,5R,6R)-2-(hydroxymethyl)-6-(((4-(2-hydroxypropan-2-yl)-1H-1,2,3-triazol-1-yl)methyl)-5-methoxy-4-(4-(3,4,5-trifluorophenyl)-1H-1,2,3-triazol-1-yl)tetrahydro-2H-pyran-3-ol | 0.73 (A) | 499.25 |
| 4.45 | (2R,3R,4S,5R,6R)-6-(((1-(tert-butyl)-1H-1,2,3-triazol-4-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.83 (A) | 497.26 |
| 4.46 | (2R,3R,4S,5R,6R)-6-(((1-(tert-butyl)-1H-1,2,3-triazol-4-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.81 (A) | 497.27 |
| 4.47 | (2R,3R,4S,5R,6R)-6-(((4-(1-hydroxycyclohexyl)-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.82 (A) | 539.25 |
| 4.48 | (2R,3R,4S,5R,6R)-6-(((4-cyclopentyl-1H-1,2,3-triazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.89 (A) | 509.25 |
| 4.49 | (2R,3R,4S,5R,6R)-2-(hydroxymethyl)-5-methoxy-6-(((4-(1-methylcyclopentyl)-1H-1,2,3-triazol-1-yl)methyl)-4-(4-(3,4,5-trifluorophenyl)-1H-1,2,3-triazol-1-yl)tetrahydro-2H-pyran-3-ol | 0.92 (A) | 523.24 |

TABLE 3-continued

| Ex. | Compound | $t_R$ [min] (LC-MS) | MS Data m/z [M + H]+ |
|---|---|---|---|
| 4.50 | 1-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)cyclopentane-1-carbonitrile | 0.88 (A) | 534.25 |
| 4.51 | (2R,3R,4S,5R,6R)-2-(hydroxymethyl)-5-methoxy-6-((4-(4-methyltetrahydro-2H-pyran-4-yl)-1H-1,2,3-triazol-1-yl)methyl)-4-(4-(3,4,5-trifluorophenyl)-1H-1,2,3-triazol-1-yl)tetrahydro-2H-pyran-3-ol | 0.81 (A) | 539.24 |
| 4.52 | (2R,3R,4S,5R,6R)-6-((1-(tert-butyl)-1H-1,2,3-triazol-4-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.83 (A) | 493.29 |
| 4.53 | (2R,3R,4S,5R,6R)-6-((1-(tert-butyl)-1H-1,2,3-triazol-4-yl)methyl)-4-(4-(4-chloro-2,3-difluorophenyl)-1H-1,2,3-triazol-1-yl)-2-(hydroxymethyl)-5-methoxytetrahydro-2H-pyran-3-ol | 0.85 (A) | 513.22 |
| 4.54 | (2R,3R,4S,5R,6R)-6-((4-(tert-butyl)-1H-1,2,3-triazol-1-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.87 (A) | 493.25 |
| 4.55 | (2R,3R,4S,5R,6R)-6-((4-(tert-butyl)-1H-1,2,3-triazol-1-yl)methyl)-4-(4-(4-chloro-2,3-difluorophenyl)-1H-1,2,3-triazol-1-yl)-2-(hydroxymethyl)-5-methoxytetrahydro-2H-pyran-3-ol [1-(1,3-di-deoxy-2-O-methyl-3-[4-(4-chloro-2,3-difluorophenyl)-1H-1,2,3-triazol-1-yl]-a-D-galacto-pyranose)-1-(4-(tert-butyl)-1H-1,2,3-triazol-1-yl)-methane] | 0.89 (A) | 512.99 |

Compounds of Examples 5.01-5.26 listed in Table 4 below are prepared by applying General procedure R to the intermediate 6. Epoxides are then further opened with the appropriate amines (either commercially available or described as intermediate) following General Procedures S or S' and cyclized following T. Heterocycles are then further deprotected (General Procedures C, F) and/or derivatised following General procedures G, H or O.

TABLE 4

| Ex. | Compound | $t_R$ [min] (LC-MS) | MS Data m/z [M + H]+ |
|---|---|---|---|
| 5.01 | (RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(4-methoxyphenyl)oxazolidin-2-one | 0.90 (A) | 565.11 |
| 5.02 | (RS)-3-(4-(difluoromethoxy)phenyl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one | 0.95 (A) | 601.11 |
| 5.03 | (RS)-3-(1-acetylpiperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one | 0.75 (A) | 584.11 |
| 5.04 | (RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-(methylsulfonyl)piperidin-4-yl)oxazolidin-2-one | 0.78 (A) | 620.09. |
| 5.05 | (R)-3-(1-acetylpiperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one (chirale separation of example 5.03) | 0.74 (A) | 584.10 |
| 5.06 | (S)-3-(1-acetylpiperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one (chirale separation of example 5.03) | 0.74 (A) | 584.10 |
| 5.07 | (S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-(methylsulfonyl)piperidin-4-yl)oxazolidin-2-one (chirale separation of example 5.04) | 0.78 (A) | 620.07 |
| 5.08 | (R)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-(methylsulfonyl)piperidin-4-yl)oxazolidin-2-one (chirale separation of example 5.04) | 0.78 (A) | 620.07 |
| 5.09 | tert-butyl 4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-3-yl)piperidine-1-carboxylate | 0.90 (A) | 641.96 |
| 5.10 | (RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-isobutyrylpiperidin-4-yl)oxazolidin-2-one | 0.80 (A) | 612.15 |
| 5.11 | 4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-3-yl)-N,N-dimethylpiperidine-1-carboxamide | 0.79 (A) | 612.98 |

TABLE 4-continued

| Ex. | Compound | $t_R$ [min] (LC-MS) | MS Data m/z [M + H]+ |
|---|---|---|---|
| 5.12 | (S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-isobutyrylpiperidin-4-yl)oxazolidin-2-one (chirale separation of Example 5.10) | 0.80 (A) | 612.15 |
| 5.13 | (R)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-isobutyrylpiperidin-4-yl)oxazolidin-2-one (chirale separation of Example 5.10) | 0.80 (A) | 612.15 |
| 5.14 | tert-butyl 4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-3-yl)piperidine-1-carboxylate (chirale separation of Example 5.09) | 0.92 (A) | 642.17 |
| 5.15 | tert-butyl 4-((R)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-3-yl)piperidine-1-carboxylate (chirale separation of Example 5.09) | 0.91 (A) | 642.17 |
| 5.16 | tert-butyl 4-(((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-3-yl)methyl)piperidine-1-carboxylate | 0.92 (A) | 656.16 |
| 5.17 | (RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(tetrahydro-2H-pyran-4-yl)oxazolidin-2-one | 0.77 (A) | 542.99 |
| 5.18 | (RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-(isobutylsulfonyl)piperidin-4-yl)oxazolidin-2-one | 0.89 (A) | 662.12 |
| 5.19 | (RS)-3-(1-(3,3-dimethylbutanoyl)piperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one | 0.87 (A) | 640.19 |
| 5.20 | (RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-((trifluoromethyl)sulfonyl)piperidin-4-yl)oxazolidin-2-one | 0.93 (A) | 673.84 |
| 5.21 | (RS)-3-((RS)-1-(tert-butylsulfinyl)piperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one (mixture of 4 isomers) | 0.84 (A) | 646.14 |
| 5.22 | (RS)-3-(1-(tert-butylsulfonyl)piperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one | 0.87 (A) | 662.15 |
| 5.23 | (RS)-3-cyclohexyl-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one | 0.90 (A) | 541.17 |
| 5.25 | (RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-((1r,4R)-4-methoxycyclohexyl)oxazolidin-2-one | 0.82 (A) | 571.18 |
| 5.26 | (RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-((1s,4S)-4-methoxycyclohexyl)oxazolidin-2-one | 0.85 (A) | 571.18 |

Example 5.24: tert-butyl 4-((RS)-3-(((2R,3R,4S,5R, 6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-5-yl) piperidine-1-carboxylate This product is prepared starting with intermediate 27a using General procedures S, T and C. LCMS (A): $t_R$=0.93 min; [M+H]+=642.26.

Example 6.01: (2R,3R,4S,5R,6R)-6-((5-(4,4-difluorocyclohexyl)isothiazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol Step 1: 4-(4,4-difluorocyclohexyl)-1-((4aR,6R,7R, 8R,8aR)-7-methoxy-2,2-dimethyl-8-(4-(3,4,5-trifluorophenyl)-1H-1,2,3-triazol-1-yl)hexahydropyrano[3, 2-d][1,3]dioxin-6-yl)but-3-yn-2-ol 4-ethynyl-1,1-difluorocyclohexane (1.1 eq) in THF (5 mL/mmol) is cooled to −78° C. nBuLi 1.6M in hexanes (1.1 eq) is added dropwise under Nitrogen atmosphere. After stirring at −78° C. for 1 h, intermediate 7a (1 eq) in THF (5 mL/mmol) is added and the reaction mixture is stirred at −78° C. for 2 h. After aqueous workup (EA/NH₄Cl sat.), the crude product is used without further purification. LCMS (A): $t_R$=1.04 min; [M+H]+=586.15.

Step 2: 4-(4,4-difluorocyclohexyl)-1-((4aR,6R,7R, 8R,8aR)-7-methoxy-2,2-dimethyl-8-(4-(3,4,5-trifluorophenyl)-1H-1,2,3-triazol-1-yl)hexahydropyrano[3, 2-d][1,3]dioxin-6-yl)but-3-yn-2-one To a solution of intermediate of step 1 (1 eq) in acetone (5 mL/mmol) is added 8 times $MnO_2$ (5 eq). The reaction mixture is stirred at rt until completion of reaction. After filtration, the filtrate is concentrated under reduced pressure. The crude product is purified by FC (Heptane/EA 7:3) to give the desired product as a white solid. LCMS (A): $t_R$=1.10 min; [M+H]+=584.10.

Step 3: (2R,3R,4S,5R,6R)-6-((5-(4,4-difluorocyclohexyl)isothiazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol To a solution of intermediate of step 2 (1 eq) in $H_2O$ (5 mL/mmol) cooled to 0° C. is added hydroxylamine-O-sulfonic acid (1 eq). The mixture is stirred at rt o/n. NaHCO₃ (1 eq) and sodium hydrogen sulfide (1.1 eq) are added twice and the mixture is stirred until completion of reaction. After aqueous workup (TBME/$H_2O$), the product is purified as described in the general methods. LCMS (A): $t_R$=0.98 min; [M+H]+=574.86.

Example 6.02: tert-butyl 4-(3-(((2R,3R,4S,5R,6R)-5-hydroxy-6-(hydroxymethyl)-3-methoxy-4-(4-(3,4, 5-trifluorophenyl)-1H-1,2,3-triazol-1-yl)tetrahydro-2H-pyran-2-yl)methyl)isothiazol-5-yl)piperidine-1-carboxylate This product is prepared in analogy of Example 6.01 using tert-butyl 4-ethynylpiperidine-1-carboxylate instead of 4-ethynyl-1,1-difluorocyclohexane. LCMS (A): $t_R$=1.01 min; [M+H]+=639.92.

Example 6.03: (2R,3R,4S,5R,6R)-2-(hydroxymethyl)-5-methoxy-6-((5-(piperidin-4-yl)isothiazol-3-yl)methyl)-4-(4-(3,4,5-trifluorophenyl)-1H-1,2,3-triazol-1-yl)tetrahydro-2H-pyran-3-ol The Boc group of the Example 6.02 is deprotected during step 3. LCMS (A): $t_R$=0.68 min; [M+H]+=539.83.

Example 6.04: (2R,3R,4S,5R,6R)-6-((4-(tert-butyl)-1H-imidazol-1-yl)methyl)-2-(hydroxymethyl)-5-methoxy-4-(4-(3,4,5-trifluorophenyl)-1H-1,2,3-triazol-1-yl)tetrahydro-2H-pyran-3-ol To a solution of Intermediate 27a in toluene (5 mL/mmol) are added 1-bromopinacolone (1 eq), paraformaldehyde (1 eq) and ammonium acetate (1.5 eq). The reaction mixture is stirred at 110° C. until completion of reaction. After aqueous workup (EA/H2O), the crude product is purified as described in general methods. LCMS (A): $t_R$=0.73 min; [M+H]+=496.30.

Example 6.05: 5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-phenyloxazol-2(3H)-one Step 1: 1-((4aR,6R,7R,8R,8aR)-6-(3-bromoprop-2-yn-1-yl)-7-methoxy-2,2-dimethylhexahydropyrano [3,2-d][1,3]dioxin-8-yl)-4-(3,4,5-trifluorophenyl)-1H-1,2,3-triazole To a solution of Intermediate 9a (1 eq) in acetone (5 mL/mmol) are added NBS (1.3 eq) and silvernitrate (0.05 eq). The reaction mixture is stirred at rt until completion of reaction. After aqueous workup (EA, $H_2O$), the crude product is used without further purification. LCMS (A): $t_R$=1.06 min; [M+H]+=517.67.

Step 2: tert-butyl (3-((4aR,6R,7R,8R,8aR)-7-methoxy-2,2-dimethyl-8-(4-(3,4,5-trifluorophenyl)-1H-1,2,3- triazol-1-yl)hexahydropyrano[3,2-d][1,3] dioxin-6-yl)prop-1-yn-1-yl)(phenyl)carbamate To a solution of intermediate of step 1 (1.2 eq) and tert-butyl phenylcarbamate (1 eq) in toluene (5 mL/mmol) are added CuSO₄ (0.3 eq), potassium phosphate (2.6 eq) and 1,10-phenanthroline monohydrate (0.66 eq). The reaction mixture is stirred at 85° C. until completion of reaction. After aqueous workup (EA/$H_2O$), the crude product is purified as described in general methods. LCMS (A): $t_R$=1.18 min; [M+H]+=629.09.

Step 3: 5-(((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl) methyl)-3-phenyloxazol-2(3H)-one To a solution of Intermediate of step 2 (1 eq) in DCM (5 mL/mmol) are added Chloro(triphenylphosphine)gold(I) (0.08 eq) and Silver hexafluoroantimonate(V) (0.08 eq). The reaction mixture is stirred at 40° C. o/n. After aqueous workup (DCM/$H_2O$), the crude product is used without further purification. LCMS (A): $t_R$=1.06 min; [M+H]+=573.13.

Step 4: 5-(((2R,3R,4S,5R,6R)-5-hydroxy-6-(hydroxymethyl)-3-methoxy-4-(4-(3,4,5-trifluorophenyl)-1H-1,2,3- triazol-1-yl)tetrahydro-2H-pyran-2-yl)methyl)-3-phenyloxazol-2(3H)-one Intermediate of step 3 (1 eq) in THF/H$_2$O 1:2 (5 mL/mmol) is stirred with TFA o/n. The crude mixture is purified as described in general methods. LCMS (A): $t_R$=0.91 min; [M+H]$^+$=533.13.

Example 6.06: 3-cyclohexyl-1-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)imidazolidin-4-one Step 1: N-cyclohexyl-2-((((4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxin-6-yl)methyl)amino)acetamide To a solution of Intermediate 27b (1 eq) and Intermediate 43 (1.5 eq) in AcOH (2 eq) and DCM/MeOH 4:1 (5 mL/mmol) is added sodium cyanoborohydride (1.5 eq). The mixture is stirred at rt for 1.5 h. After aqueous workup (DCM/NH$_4$OH sat.), the crude product is purified by FC (DCM/MeOH 19:1). LCMS (A): $t_R$=0.82 min; [M+H]$^+$=564.29.

Step 2: 3-cyclohexyl-1-(((4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxin-6-yl)methyl)imidazolidin-4-one To a solution of Intermediate of step 1 (1 eq) in EtOH (5 mL/mmol) is added formaldehyde solution (37% in water, 10 eq). The mixture is stirred at 80° C. until completion of reaction. After aqueous workup (EA/H$_2$O), the crude product is purified by FC (DCM/MeOH 9:1). LCMS (A): $t_R$=0.93 min; [M+H]$^+$=576.23.

Step 3

Deprotection following General procedure C gives the title compound. LCMS (A): $t_R$=0.77 min; [M+H]$^+$=536.27.

Example 6.07: 1-(1-acetylpiperidin-4-yl)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)imidazolidin-4-one Step 1: 2-chloro-N-(((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)methyl)acetamide This intermediate is prepared starting from Intermediate 27a, following General procedure G. LCMS (A): $t_R$=0.92 min; [M+H]$^+$=505.13.

Step 2: 2-((1-acetylpiperidin-4-yl)amino)-N-(((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)methyl)acetamide Intermediate of step 1 (1 eq) is dissolved in DMF (5 mL/mmol). 1-Acetylpiperidin-4-amine (1.1 eq) and DIPEA (5 eq) are added and the reaction mixture is stirred at 50° C. until completion of reaction. After aqueous workup (EA/H$_2$O), the crude product is purified by FC (DCM/MeOH 9:1). LCMS (A): $t_R$=0.73 min; [M+H]$^+$=611.11.

Step 3

The title compound is obtained following step 2 and 3 of Example 6.06. LCMS (A): $t_R$=0.66 min; [M+H]$^+$=583.18.

Example 6.08: 3-(1-acetylpiperidin-4-yl)-1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)imidazolidin-4-one This product is prepared in analogy of Example 6.06 starting with Intermediate 27a and Intermediate 44. LCMS (A): $t_R$=0.67 min; [M+H]$^+$=583.21.

Example 6.09: 3-cyclohexyl-1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)imidazolidin-4-one This product is prepared in analogy of Example 6.06, starting with Intermediate 27a and Intermediate 43. LCMS (A): $t_R$=0.78 min; [M+H]$^+$=540.21.

Example 6.10: 1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(tetrahydro-2H-pyran-4-yl)imidazolidin-4-one This product is prepared in analogy of Example 6.06, starting with Intermediate 27a and Intermediate 45. LCMS (A): $t_R$=0.68 min; [M+H]$^+$=542.21.

Example 6.11: ethyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-5-oxoimidazolidin-1-yl)piperidine-1-carboxylate This product is prepared in analogy of Example 6.06 starting with Intermediate 27a and Intermediate 46. LCMS (A): $t_R$=0.76 min; [M+H]$^+$=613.11.

II. Biological Assays

Evaluation of Compound Inhibitory Activity (IC$_{50}$)

The inhibitory activity of compounds is determined in competitive binding assays. This spectrophotometric assay measures the binding of biotinylated human Gal-3 (hGal-3) or human Gal-1 (hGal-1), respectively, to a microplate-adsorbed glycoprotein, asialofetuin (ASF) (Proc Natl Acad Sci USA. 2013 Mar. 26; 110(13):5052-7.). Alternatively, and preferably, a human Gal-1 version in which all six cysteines are substituted by serines may be used.

Briefly, compounds are serially diluted in DMSO (working dilutions). ASF-coated 384 well plates are supplemented with 22.8 µL/well of biotinylated hGal-3 or hGal-1 in assay buffer (i.e. 300-1000 ng/mL biotinylated hGal-3 or hGal-1) to which 1.2 µL of compound working dilutions are added and mixed.

Plates are incubated for 3 hours at 4° C., then washed with cold assay buffer (3×50 uL), incubated for 1 hour with 25 µL/well of a streptavidin-peroxidase solution (diluted in assay buffer to 80 ng/mL) at 4° C., followed by further washing steps with assay buffer (3×50 uL). Finally, 25 µL/well of ABTS substrate is added. OD (410 nm) is recorded after 30 to 45 min and $IC_{50}$ values are calculated.

The calculated $IC_{50}$ values may fluctuate depending on the daily assay performance. Fluctuations of this kind are known to those skilled in the art. $IC_{50}$ values from several measurements are given as mean values.

Activity on hGal-3 ($IC_{50}$ in µM)

TABLE 5

| Ex | Gal-3 $IC_{50}$ | Ex | Gal-3 $IC_{50}$ | Ex | Gal-3 $IC_{50}$ | Ex | Gal-3 $IC_{50}$ |
|---|---|---|---|---|---|---|---|
| 1.01 | 0.70 | 1.02 | 0.49 | 1.03 | 0.31 | 1.04 | 0.58 |
| 1.05 | 0.48 | 1.06 | 1.80 | 1.07 | 0.52 | 1.08 | 1.08 |
| 1.09 | 2.15 | 1.10 | 0.56 | 1.11 | 0.51 | 1.12 | 0.67 |
| 1.13 | 1.11 | 1.14 | 0.68 | 1.15 | 0.65 | 1.16 | 0.43 |
| 1.17 | 0.70 | 1.18 | 0.97 | 1.19 | 0.53 | 1.20 | 0.24 |
| 1.21 | 0.15 | 1.22 | 0.43 | 1.23 | 0.70 | 1.24 | 0.80 |
| 1.25 | 0.67 | 1.26 | 1.15 | 1.27 | 0.41 | 1.28 | 0.47 |
| 1.29 | 2.14 | 1.30 | 0.33 | 1.31 | 1.13 | 1.32 | 0.053 |
| 1.33 | 0.80 | 1.34 | 0.88 | 1.35 | 1.00 | 1.36 | 2.54 |
| 1.37 | 0.44 | 1.38 | 1.42 | 1.39 | 0.71 | 1.40 | 0.043 |
| 1.41 | 0.45 | 1.42 | 1.06 | 1.43 | 1.90 | 1.44 | 0.065 |
| 1.45 | 0.11 | 1.46 | 0.29 | 1.47 | 0.66 | 1.48 | 0.089 |
| 1.49 | 0.078 | 1.50 | 0.063 | 1.51 | 0.15 | 1.52 | 0.50 |
| 1.53 | 0.35 | 1.54 | 0.29 | 1.55 | 0.66 | 1.56 | 0.34 |
| 1.57 | 0.40 | 1.58 | 0.49 | 1.59 | 0.40 | 1.60 | 0.29 |
| 1.61 | 0.036 | 1.62 | 0.076 | 1.63 | 0.34 | 1.64 | 0.27 |
| 1.65 | 0.56 | 1.66 | 1.08 | 1.67 | 0.43 | 1.68 | 0.47 |
| 1.69 | 0.45 | 1.70 | 1.98 | 1.71 | 0.23 | 1.72 | 0.36 |
| 1.73 | 0.19 | 1.74 | 0.18 | 1.75 | 0.40 | 1.76 | 4.62 |
| 1.77 | 0.71 | 1.78 | 1.00 | 1.79 | 0.27 | 1.80 | 0.11 |
| 1.81 | 0.20 | 1.82 | 1.35 | 1.83 | 0.40 | 1.84 | 0.35 |
| 1.85 | 0.047 | 1.86 | 0.089 | 1.87 | 0.080 | 1.88 (Ref. Ex.) | 6.23 |
| 1.89 | 0.99 | 1.90 | 0.26 | 1.91 | 0.48 | 1.92 | 0.26 |
| 1.93 | 0.55 | 1.94 | 0.14 | 1.95 | 0.19 | 1.96 | 1.74 |
| 1.97 | 0.031 | 1.98 | 1.56 | 1.99 | 0.40 | 1.100 | 0.65 |
| 1.101 | 0.18 | 1.102 | 0.082 | 1.103 | 0.45 | 1.104 | 1.84 |
| 1.105 | 1.68 | 1.106 | 0.49 | 1.107 | 0.11 | 1.108 | 0.18 |
| 1.109 | 1.60 | 1.110 | 0.25 | 1.111 | 1.66 | 1.112 | 1.00 |
| 1.113 | 1.06 | 1.114 | 0.075 | 1.115 | 0.44 | 1.116 | 0.17 |
| 1.117 | 0.33 | 1.118 | 0.33 | 1.119 | 0.26 | 1.120 | 0.29 |
| 1.121 | 0.082 | 1.122 | 0.14 | 1.123 | 0.14 | 1.124 | 0.031 |
| 1.125 | 0.14 | 1.126 | 0.081 | 1.127 | 0.30 | 1.128 | 0.87 |
| 1.129 | 0.27 | 1.130 | 0.26 | 1.131 | 0.14 | 1.132 | 0.069 |
| 1.133 | 0.23 | 1.134 | 0.084 | 1.135 | 0.10 | 1.136 | 0.112 |
| 1.137 | 0.048 | 1.138 | 0.13 | 1.139 | 0.042 | 1.140 | 0.049 |
| 1.141 | 0.097 | 1.142 | 0.071 | 1.143 | 0.10 | 1.144 | 0.18 |
| 1.145 | 0.17 | 1.146 | 0.24 | 1.147 | 0.17 | 1.148 | 0.059 |
| 1.149 | 0.084 | 1.150 | 0.023 | 1.151 | 0.019 | 1.152 | 0.039 |
| 1.153 | 0.067 | 1.154 | 0.033 | 1.155 | 0.022 | 1.156 | 0.031 |
| 1.157 | 0.030 | 1.158 | 0.066 | 1.159 | 0.057 | 1.160 | 0.078 |
| 1.161 | 0.034 | 1.162 | 0.037 | 1.163 | 0.043 | 1.164 | 0.038 |
| 1.165 | 0.059 | 1.166 | 0.026 | 1.167 | 0.040 | 1.168 | 0.029 |
| 1.169 | 0.154 | 1.170 | 0.40 | 1.171 | 0.44 | 1.172 | 0.26 |
| 1.173 | 0.44 | 1.174 | 0.90 | 1.175 | 0.31 | 1.176 | 0.87 |
| 1.177 | 0.18 | 1.178 | 0.98 | 1.179 | 0.15 | 1.180 | 0.18 |
| 1.181 | 0.056 | 1.182 | 0.082 | 1.183 | 0.28 | 1.184 | 0.13 |
| 1.185 | 0.19 | 1.186 | 0.085 | 1.187 | 0.45 | 1.188 | 0.18 |
| 1.189 | 0.17 | 1.190 | 0.071 | 1.191 | 0.15 | 1.192 | 0.20 |
| 1.193 | 0.12 | 1.194 | 0.18 | 1.195 | 0.060 | 1.196 | 0.40 |
| 1.197 | 0.11 | 1.198 | 0.047 | 1.199 | 0.052 | 1.200 | 0.12 |
| 1.201 | 0.067 | 1.202 | 0.033 | 1.203 | 0.026 | 1.204 | 0.041 |
| 1.205 | 0.041 | 1.206 | 0.083 | 1.207 | 0.11 | 1.208 | 0.13 |
| 1.209 | 0.26 | 1.210 | 0.29 | 1.211 | 0.094 | 1.212 | 0.16 |
| 1.213 | 0.16 | 1.214 | 0.13 | 1.215 | 0.10 | 1.216 | 0.34 |
| 1.217 | 0.18 | 1.218 | 0.42 | 1.219 | 0.023 | 1.220 | 0.035 |
| 1.221 | 0.16 | 1.222 | 0.11 | 1.223 | 0.38 | 1.224 | 0.070 |
| 1.225 | 0.53 | 1.226 | 0.13 | 1.227 | 0.077 | 1.228 | 0.20 |
| 1.229 | 0.53 | 1.230 | 0.54 | 1.231 | 0.91 | 1.232 | 0.10 |
| 1.233 | 0.088 | 1.234 | 0.057 | 1.235 | 0.10 | 1.236 | 0.057 |
| 1.237 | 0.075 | 1.238 | 0.045 | 1.239 | 0.072 | 1.240 | 0.10 |
| 1.241 | 0.079 | 1.242 | 0.068 | 1.243 | 0.042 | 1.244 | 0.11 |
| 1.245 | 0.067 | 1.246 | 0.073 | 1.247 | 0.21 | 1.248 | 0.70 |
| 1.249 | 0.15 | 1.250 | 0.057 | 1.251 | 0.044 | 1.252 | 0.069 |
| 1.253 | 0.058 | 1.254 | 0.031 | 1.255 | 0.032 | 1.256 | 0.055 |
| 1.257 | 0.044 | 1.258 | 0.037 | 1.259 | 0.033 | 1.260 | 0.063 |
| 1.261 | 0.042 | 1.262 | 0.070 | 1.263 | 0.058 | 1.264 | 0.071 |
| 1.265 | 0.25 | 1.266 | 0.091 | 1.267 | 0.16 | 1.268 | 0.11 |

TABLE 5-continued

| Ex | Gal-3 IC$_{50}$ | Ex | Gal-3 IC$_{50}$ | Ex | Gal-3 IC$_{50}$ | Ex | Gal-3 IC$_{50}$ |
|---|---|---|---|---|---|---|---|
| 1.269 | 0.049 | 1.270 | 0.038 | 1.271 | 0.049 | 1.272 | 0.25 |
| 1.273 | 0.066 | 1.274 | 0.11 | 1.275 | 0.11 | 1.276 | 0.097 |
| 1.277 | 0.140 | 1.278 | 0.093 | 1.279 | 0.12 | 1.280 | 0.30 |
| 1.281 | 0.53 | 1.282 | 0.11 | 1.283 | 0.049 | 1.284 | 0.15 |
| 1.285 | 0.051 | 1.286 | 0.23 | 1.287 | 0.069 | 1.288 | 0.063 |
| 1.289 | 0.059 | 1.290 | 0.27 | 1.291 | 0.14 | 1.292 | 0.051 |
| 1.293 | 0.093 | 1.294 | 1.54 | 1.295 | 1.80 | 1.296 | 1.41 |
|  |  | 1.298 | 2.50 | 1.299 | 4.04 | 1.300 | 1.41 |
| 1.301 | 2.70 | 1.302 | 0.036 | 1.303 | 0.14 | 1.304 | 1.62 |
| 1.305 | 1.86 | 1.306 | 1.22 | 1.307 | 0.67 | 1.308 | 0.18 |
| 1.309 | 0.69 | 1.310 | 3.62 | 1.311 | 2.38 | 1.312 | 0.14 |
| 1.313 | 0.13 | 1.314 | 0.13 | 1.315 | 0.27 | 1.316 | 0.19 |
| 1.317 | 0.31 | 1.318 | 0.16 | 1.319 | 0.14 | 1.320 | 0.075 |
| 1.321 | 0.40 | 1.322 | 0.31 | 1.323 | 0.62 | 1.324 | 0.14 |
| 1.325 | 0.017 | 1.326 | 0.057 | 1.327 | 0.076 | 1.328 | 0.077 |
| 1.329 | 0.069 | 1.330 | 0.061 | 1.331 | 0.058 | 1.332 | 0.043 |
| 1.333 | 0.010 | 1.334 | 0.024 | 1.335 | 0.026 | 1.336 | 0.023 |
| 1.337 | 0.055 | 1.338 | 0.15 | 1.339 | 0.28 | 1.340 | 0.33 |
| 1.341 | 0.20 | 1.342 | 0.55 | 1.343 | 0.093 | 1.344 | 0.040 |
| 1.345 | 0.044 | 1.346 | 0.10 | 1.347 | 0.11 | 1.348 | 0.068 |
| 1.349 | 0.18 | 1.350 | 0.27 | 1.351 | 0.18 | 1.352 | 0.10 |
| 2.01 | 0.84 | 2.02 | 0.25 | 2.03 | 0.30 | 2.04 | 0.91 |
| 2.05 | 0.19 | 2.06 | 0.24 | 2.07a | 0.26 | 2.07b | 1.70 |
| 2.08 | 0.65 | 2.09 | 0.66 | 2.10 | 0.45 | 2.11 | 2.54 |
| 2.12 | 0.19 | 2.13 | 0.21 | 2.14 | 0.19 | 2.15 | 0.095 |
| 2.16 | 0.16 | 2.17 | 0.13 | 2.18 | 0.22 | 2.19 | 0.17 |
| 2.20 | 0.39 | 2.21 | 0.022 | 2.22 | 0.20 | 2.23 | 0.22 |
| 2.24 | 0.99 | 2.25 | 0.17 | 2.26 | 0.20 | 2.27 | 0.024 |
| 2.28 | 0.11 | 2.29 | 0.017 | 2.30 | 0.072 | 2.31 | 0.30 |
| 2.32 | 0.35 | 2.33 | 0.31 | 2.34 | 0.068 | 2.35 | 0.14 |
| 2.36 | 0.12 | 2.37 | 0.071 | 2.38 | 0.19 | 2.39 | 0.11 |
| 2.40 | 0.13 | 2.41 | 0.10 | 2.42 | 0.18 | 2.43 | 0.047 |
| 2.44 | 0.040 | 2.45 | 0.022 | 2.46 | 0.029 | 2.47 | 0.23 |
| 2.48 | 0.098 | 2.49 | 0.053 | 2.50 | 0.13 | 2.51 | 0.046 |
| 2.52 | 0.078 | 2.53 | 0.053 | 2.54 | 0.052 | 2.55 | 0.12 |
| 2.56 | 0.49 | 2.57 | 0.081 | 2.58 | 0.060 | 2.59 | 0.084 |
| 2.60 | 0.40 | 2.61 | 0.11 | 2.62 | 0.036 | 2.63 | 0.074 |
| 3.01 | 0.30 | 3.02 | 0.34 | 3.03 | 0.15 | 3.04 | 0.55 |
| 3.05 | 0.29 | 3.06 | 0.28 | 3.07 | 1.86 | 3.08 | 0.29 |
| 3.09 | 0.84 | 3.10 | 0.62 | 3.11 | 0.15 | 3.12 | 0.070 |
| 3.13 | 0.67 | 3.14 | 0.32 | 3.15 | 0.14 | 3.16 | 0.22 |
| 3.17 | 0.046 | 3.18 | 0.18 | 3.19 | 0.43 | 3.20 | 0.24 |
| 3.21 | 0.046 | 3.22 | 0.028 | 3.23 | 0.23 | 3.24 | 0.34 |
| 3.25 | 0.17 | 3.26 | 0.068 | 3.27 | 0.032 | 3.28 | 0.038 |
| 3.29 | 0.27 | 3.30 | 0.16 | 3.31 | 0.073 | 3.32 | 0.046 |
| 3.33 | 0.065 | 3.34 | 0.12 | 3.35 | 0.048 | 3.36 | 1.16 |
| 3.37 | 0.097 | 3.38 | 0.043 | 3.39 | 0.26 | 3.40 | 0.31 |
| 3.41 | 0.23 | 3.42 | 0.14 | 3.43 | 0.13 | 3.44 | 0.56 |
| 3.45 | 0.037 | 3.46 | 0.044 | 3.47 | 0.050 | 3.48 | 0.041 |
| 3.49 | 0.057 | 3.50 | 0.045 | 3.51 | 0.071 | 3.52 | 0.031 |
| 3.53 | 0.19 | 3.54 | 0.44 | 3.55 | 0.090 | 3.56 | 0.020 |
| 3.57 | 0.097 | 3.58 | 0.061 | 3.59 | 0.042 | 3.60 | 0.37 |
| 3.61 | 0.072 | 3.62 | 0.045 | 3.63 | 0.069 | 3.64 | 0.025 |
| 3.65 | 0.045 | 3.66 | 0.14 | 3.67 | 0.069 | 3.68 | 0.11 |
| 3.69 | 0.17 | 3.70 | 0.084 |  |  |  |  |
| 4.01 | 1.24 | 4.02 | 0.69 | 4.03 | 0.076 | 4.04 | 0.044 |
| 4.05 | 0.035 | 4.06 | 0.052 | 4.07 | 0.012 | 4.08 | 0.010 |
| 4.09 | 0.013 | 4.10 | 0.025 | 4.11 (Ref. Ex.) | 1.20 | 4.12 (Ref. Ex.) | 0.70 |
| 4.13 | 0.017 | 4.14 | 0.036 | 4.15 | 0.21 | 4.16 | 0.035 |
| 4.17 | 0.025 | 4.18 | 0.057 | 4.19 | 0.034 | 4.20 | 0.021 |
| 4.21 | 0.019 | 4.22 | 0.045 | 4.23 | 0.038 | 4.24 | 0.054 |
| 4.25 | 0.12 | 4.26 | 0.061 | 4.27 | 0.034 | 4.28 | 0.013 |
| 4.29 | 0.31 | 4.30 | 0.085 | 4.31 | 0.027 | 4.32 | 0.065 |
| 4.33 | 0.071 | 4.34 | 0.025 | 4.35 | 0.040 | 4.36 | 0.019 |
| 4.37 | 0.015 | 4.38 | 0.093 | 4.39 | 0.044 | 4.40 | 0.16 |
| 4.41 | 0.34 | 4.42 | 0.79 | 4.43 | 0.30 | 4.44 | 0.24 |
| 4.45 | 0.085 | 4.46 | 0.045 | 4.47 | 0.33 | 4.48 | 0.25 |
| 4.49 | 0.24 | 4.50 | 0.33 | 4.51 | 0.16 | 4.52 | 0.053 |
| 4.53 | 0.034 | 4.54 | 0.046 | 4.55 | 0.031 |  |  |
| 5.01 | 1.57 | 5.02 | 1.56 | 5.03 | 0.12 | 5.04 | 0.18 |
| 5.05 | 0.33 | 5.06 | 0.096 | 5.07 | 0.28 | 5.08 | 0.018 |
| 5.09 | 0.083 | 5.10 | 0.19 | 5.11 | 0.26 | 5.12 | 0.13 |
| 5.13 | 0.59 | 5.14 | 0.34 | 5.15 | 0.050 | 5.16 | 0.63 |
| 5.17 | 0.19 | 5.18 | 0.035 | 5.19 | 0.10 | 5.20 | 0.14 |
| 5.21 | 0.35 | 5.22 | 0.067 | 5.23 | 0.14 | 5.24 | 0.29 |
| 5.25 | 0.74 | 5.26 | 1.24 |  |  |  |  |
| 6.01 | 0.56 | 6.02 | 0.11 | 6.03 | 0.22 | 6.04 | 0.18 |

TABLE 5-continued

| Ex | Gal-3 IC$_{50}$ | Ex | Gal-3 IC$_{50}$ | Ex | Gal-3 IC$_{50}$ | Ex | Gal-3 IC$_{50}$ |
|---|---|---|---|---|---|---|---|
| 6.05 | 0.25 | 6.06 | 0.042 | 6.07 | 0.15 | 6.08 | 0.022 |
| 6.09 | 0.059 | 6.10 | 0.037 | 6.11 | 0.026 | | |

Activities on hGal-1 IC50 (μM)

TABLE 6

| Ex | Gal-1 IC$_{50}$ | Ex | Gal-1 IC$_{50}$ | Ex | Gal-1 IC$_{50}$ | Ex | Gal-1 IC$_{50}$ |
|---|---|---|---|---|---|---|---|
| 1.01 | 6.16 | 1.02 | 53.9 | 1.03 | 5.45 | 1.04 | >100 |
| 1.05 | 7.18 | 1.06 | 22.2 | 1.07 | 4.9 | 1.08 | 8.74 |
| 1.09 | 27.5 | 1.10 | 5.39 | 1.11 | 5.61 | 1.12 | 3.55 |
| 1.13 | 6.34 | 1.14 | 2.27 | 1.15 | 3.20 | 1.16 | 6.62 |
| 1.17 | 8.79 | 1.18 | 14.1 | 1.19 | 5.58 | 1.20 | 4.27 |
| 1.21 | 4.77 | 1.22 | 4.48 | 1.23 | 6.80 | 1.24 | 13.3 |
| 1.25 | 4.97 | 1.26 | 17.5 | 1.27 | 6.54 | 1.28 | 18.9 |
| 1.29 | >100 | 1.30 | 3.09 | 1.31 | 13.5 | 1.32 | 1.15 |
| 1.33 | 7.94 | 1.34 | 10.6 | 1.35 | 5.58 | 1.36 | 10.9 |
| 1.37 | 7.70 | 1.38 | 15.9 | 1.39 | 9.94 | 1.40 | 0.74 |
| 1.41 | 6.29 | 1.42 | 3.61 | 1.43 | 15.8 | 1.44 | 1.71 |
| 1.45 | 1.02 | 1.46 | 1.00 | 1.47 | 6.54 | 1.48 | 0.56 |
| 1.49 | 2.45 | 1.50 | 0.57 | 1.51 | 2.50 | 1.52 | 7.98 |
| 1.53 | 2.87 | 1.54 | 6.48 | 1.55 | 41.9 | 1.56 | 15.2 |
| 1.57 | 12.5 | 1.58 | 13.6 | 1.59 | 6.31 | 1.60 | 6.97 |
| 1.61 | 0.62 | 1.62 | 0.45 | 1.63 | 2.54 | 1.64 | 8.51 |
| 1.65 | 14.1 | 1.66 | 3.76 | 1.67 | 3.08 | 1.68 | 5.09 |
| 1.69 | 6.73 | 1.70 | 12.6 | 1.71 | 5.26 | 1.72 | 5.11 |
| 1.73 | 3.12 | 1.74 | 3.16 | 1.75 | 3.55 | 1.76 | 13.3 |
| 1.77 | 6.82 | 1.78 | 9.64 | 1.79 | 4.24 | 1.80 | 43.8 |
| 1.81 | 14.5 | 1.82 | 28.4 | 1.83 | 8.21 | 1.84 | 3.01 |
| 1.85 | 1.14 | 1.86 | >100 | 1.87 | 1.97 | 1.88 (Ref. Ex.) | 22.2 |
| 1.89 | 4.11 | 1.90 | 1.78 | 1.91 | 11.8 | 1.92 | 4.91 |
| 1.93 | 16.0 | 1.94 | 4.76 | 1.95 | 1.21 | 1.96 | 8.65 |
| 1.97 | 3.25 | 1.98 | 1.84 | 1.99 | 0.471 | 1.100 | 4.90 |
| 1.101 | 4.10 | 1.102 | 2.37 | 1.103 | 9.82 | 1.104 | 0.45 |
| 1.105 | 2.34 | 1.106 | 1.53 | 1.107 | 0.40 | 1.108 | 1.69 |
| 1.109 | 0.21 | 1.110 | 2.24 | 1.111 | 11.5 | 1.112 | 0.77 |
| 1.113 | 0.64 | 1.114 | 1.36 | 1.115 | 0.94 | 1.116 | 1.75 |
| 1.117 | 1.14 | 1.118 | 1.47 | 1.119 | 4.17 | 1.120 | 10.6 |
| 1.121 | 1.09 | 1.122 | 0.72 | 1.123 | 0.14 | 1.124 | 0.80 |
| 1.125 | 1.00 | 1.126 | 0.44 | 1.127 | 9.84 | 1.128 | 15.4 |
| 1.129 | 14.7 | 1.130 | 18.1 | 1.131 | 7.44 | 1.132 | 0.76 |
| 1.133 | 10.7 | 1.134 | 10.8 | 1.135 | 9.00 | 1.136 | 4.77 |
| 1.137 | 1.88 | 1.138 | 15.3 | 1.139 | 1.13 | 1.140 | 0.69 |
| 1.141 | 0.79 | 1.142 | 1.32 | 1.143 | 0.19 | 1.144 | 0.74 |
| 1.145 | 1.56 | 1.146 | 4.66 | 1.147 | 2.96 | 1.148 | 0.63 |
| 1.149 | 0.47 | 1.150 | 0.14 | 1.151 | 1.02 | 1.152 | 1.51 |
| 1.153 | 1.60 | 1.154 | 0.36 | 1.155 | 1.05 | 1.156 | 0.94 |
| 1.157 | 0.094 | 1.158 | 1.52 | 1.159 | 1.53 | 1.160 | 0.73 |
| 1.161 | 1.66 | 1.162 | 0.74 | 1.163 | 0.71 | 1.164 | 1.07 |
| 1.165 | 0.68 | 1.166 | 0.26 | 1.167 | 0.91 | 1.168 | 0.93 |
| 1.169 | 0.47 | 1.170 | >100 | 1.171 | 13.2 | 1.172 | 57 |
| 1.173 | 47.8 | 1.174 | 18.8 | 1.175 | 4.76 | 1.176 | >100 |
| 1.177 | 64.8 | 1.178 | 10.3 | 1.179 | 11.0 | 1.180 | 4.93 |
| 1.181 | 8.04 | 1.182 | 4.73 | 1.183 | 5.29 | 1.184 | 1.18 |
| 1.185 | 1.45 | 1.186 | 6.20 | 1.187 | 5.98 | 1.188 | 7.62 |
| 1.189 | 5.43 | 1.190 | 4.61 | 1.191 | 3.65 | 1.192 | 1.88 |
| 1.193 | 1.25 | 1.194 | 3.51 | 1.195 | 3.33 | 1.196 | 2.43 |
| 1.197 | 2.19 | 1.198 | 3.59 | 1.199 | 5.99 | 1.200 | 1.51 |
| 1.201 | 2.94 | 1.202 | 3.95 | 1.203 | 1.78 | 1.204 | 17.3 |
| 1.205 | 9.01 | 1.206 | 1.34 | 1.207 | 1.16 | 1.208 | 1.64 |
| 1.209 | 3.66 | 1.210 | 2.73 | 1.211 | 0.45 | 1.212 | 1.60 |
| 1.213 | 1.55 | 1.214 | 0.92 | 1.215 | 0.61 | 1.216 | 3.97 |
| 1.217 | 2.03 | 1.218 | 10.6 | 1.219 | 0.43 | 1.220 | 0.57 |
| 1.221 | 0.98 | 1.222 | 8.00 | 1.223 | 16.7 | 1.224 | 14.1 |
| 1.225 | 4.85 | 1.226 | 1.19 | 1.227 | 16.6 | 1.228 | 0.79 |
| 1.229 | >100 | 1.230 | >100 | 1.231 | >100 | 1.232 | 0.97 |
| 1.233 | 1.33 | 1.234 | 1.27 | 1.235 | 1.33 | 1.236 | 0.96 |
| 1.237 | 4.22 | 1.238 | 3.74 | 1.239 | 6.44 | 1.240 | 13.91 |
| 1.241 | 2.58 | 1.242 | 2.90 | 1.243 | 1.33 | 1.244 | 3.29 |
| 1.245 | 1.86 | 1.246 | 1.72 | 1.247 | 2.29 | 1.248 | >100 |
| 1.249 | 1.78 | 1.250 | 0.25 | 1.251 | 0.36 | 1.252 | 0.28 |
| 1.253 | 0.28 | 1.254 | 1.11 | 1.255 | 2.06 | 1.256 | 1.56 |
| 1.257 | 1.78 | 1.258 | 0.98 | 1.259 | 0.62 | 1.260 | 1.41 |
| 1.261 | 1.05 | 1.262 | 0.33 | 1.263 | 1.03 | 1.264 | 1.61 |

TABLE 6-continued

| Ex | Gal-1 IC$_{50}$ | Ex | Gal-1 IC$_{50}$ | Ex | Gal-1 IC$_{50}$ | Ex | Gal-1 IC$_{50}$ |
|---|---|---|---|---|---|---|---|
| 1.265 | 2.58 | 1.266 | 1.56 | 1.267 | 6.10 | 1.268 | 2.49 |
| 1.269 | 0.90 | 1.270 | 3.55 | 1.271 | 1.66 | 1.272 | 3.49 |
| 1.273 | 0.72 | 1.274 | 5.54 | 1.275 | 3.30 | 1.276 | 5.10 |
| 1.277 | 1.47 | 1.278 | 6.70 | 1.279 | 3.21 | 1.280 | 1.82 |
| 1.281 | 2.55 | 1.282 | 1.77 | 1.283 | 0.38 | 1.284 | 5.85 |
| 1.285 | 1.10 | 1.286 | 3.08 | 1.287 | 0.59 | 1.288 | 5.75 |
| 1.289 | 1.77 | 1.290 | 2.12 | 1.291 | 0.94 | 1.292 | 3.54 |
| 1.293 | 2.92 | 1.294 | 14.0 | 1.295 | 17.1 | 1.296 | 52.2 |
|  |  | 1.298 | 0.99 | 1.299 | 3.84 | 1.300 | 2.27 |
| 1.301 | 2.89 | 1.302 | 1.00 | 1.303 | 0.55 | 1.304 | 3.91 |
| 1.305 | 1.18 | 1.306 | 6.19 | 1.307 | 7.22 | 1.308 | 2.37 |
| 1.309 | 2.74 | 1.310 | 0.48 | 1.311 | 0.065 | 1.312 | 4.24 |
| 1.313 | 2.94 | 1.314 | 1.38 | 1.315 | 2.21 | 1.316 | 2.20 |
| 1.317 | 9.69 | 1.318 | 8.87 | 1.319 | 7.16 | 1.320 | 2.62 |
| 1.321 | 9.17 | 1.322 | >100 | 1.323 | 5.08 | 1.324 | 3.57 |
| 1.325 | 0.60 | 1.326 | 2.87 | 1.327 | 4.17 | 1.328 | 0.96 |
| 1.329 | 0.44 | 1.330 | 4.36 | 1.331 | 1.99 | 1.332 | 0.98 |
| 1.333 | 6.99 | 1.334 | 3.31 | 1.335 | 3.78 | 1.336 | 1.88 |
| 1.337 | 0.42 | 1.338 | 1.98 | 1.339 | 10.0 | 1.340 | 10.4 |
| 1.341 | 15.7 | 1.342 | 33.0 | 1.343 | 9.19 | 1.344 | 17.0 |
| 1.345 | 0.72 | 1.346 | 11.7 | 1.347 | 8.21 | 1.348 | 0.25 |
| 1.349 | 7.02 | 1.350 | 6.78 | 1.351 | 1.05 | 1.352 | 1.17 |
| 2.01 | 8.36 | 2.02 | 5.08 | 2.03 | 0.55 | 2.04 | 12.3 |
| 2.05 | 0.39 | 2.06 | 0.26 | 2.07a | 0.31 | 2.07b | 11.7 |
| 2.08 | 4.50 | 2.09 | 8.38 | 2.10 | 4.47 | 2.11 | 13.7 |
| 2.12 | 3.65 | 2.13 | 1.99 | 2.14 | 4.58 | 2.15 | 2.14 |
| 2.16 | 11.6 | 2.17 | 0.78 | 2.18 | 6.30 | 2.19 | 1.05 |
| 2.20 | 2.03 | 2.21 | 0.69 | 2.22 | 27.3 | 2.23 | 2.05 |
| 2.24 | 9.61 | 2.25 | 1.28 | 2.26 | 4.49 | 2.27 | 5.28 |
| 2.28 | 2.18 | 2.29 | 2.33 | 2.30 | 1.98 | 2.31 | 1.29 |
| 2.32 | 2.96 | 2.33 | 2.45 | 2.34 | 1.19 | 2.35 | 2.62 |
| 2.36 | 2.77 | 2.37 | 1.74 | 2.38 | 1.99 | 2.39 | 6.68 |
| 2.40 | 4.58 | 2.41 | 5.84 | 2.42 | 3.27 | 2.43 | 0.55 |
| 2.44 | 0.51 | 2.45 | 2.42 | 2.46 | 0.89 | 2.47 | 4.40 |
| 2.48 | 1.04 | 2.49 | 0.64 | 2.50 | 6.81 | 2.51 | >100 |
| 2.52 | 5.13 | 2.53 | 1.05 | 2.54 | 0.59 | 2.55 | 2.72 |
| 2.56 | 1.77 | 2.57 | 1.45 | 2.58 | 1.46 | 2.59 | 2.30 |
| 2.60 | 7.39 | 2.61 | 0.78 | 2.62 | 2.28 | 2.63 | 1.73 |
| 3.01 | 5.71 | 3.02 | 4.62 | 3.03 | 2.49 | 3.04 | 5.65 |
| 3.05 | 1.86 | 3.06 | 2.09 | 3.07 | 15.1 | 3.08 | 12.5 |
| 3.09 | 13.3 | 3.10 | 5.50 | 3.11 | 1.38 | 3.12 | 0.52 |
| 3.13 | 4.02 | 3.14 | 6.84 | 3.15 | 13.6 | 3.16 | 5.19 |
| 3.17 | 0.96 | 3.18 | 2.22 | 3.19 | 4.72 | 3.20 | 1.85 |
| 3.21 | 0.59 | 3.22 | 1.87 | 3.23 | 3.99 | 3.24 | 9.19 |
| 3.25 | 2.47 | 3.26 | 0.93 | 3.27 | 0.87 | 3.28 | 1.23 |
| 3.29 | 15.8 | 3.30 | 3.62 | 3.31 | 0.85 | 3.32 | 0.61 |
| 3.33 | 1.08 | 3.34 | 1.51 | 3.35 | 0.93 | 3.36 | 8.14 |
| 3.37 | 1.09 | 3.38 | 0.45 | 3.39 | 5.09 | 3.40 | 1.21 |
| 3.41 | 2.96 | 3.42 | 5.90 | 3.43 | 2.83 | 3.44 | 5.32 |
| 3.45 | 0.49 | 3.46 | 0.58 | 3.47 | 0.76 | 3.48 | 0.47 |
| 3.49 | 0.53 | 3.50 | 0.59 | 3.51 | 0.1.32 | 3.52 | 0.23 |
| 3.53 | 2.51 | 3.54 | 1.51 | 3.55 | 2.99 | 3.56 | 0.61 |
| 3.57 | 1.40 | 3.58 | 1.87 | 3.59 | 0.98 | 3.60 | 5.10 |
| 3.61 | 1.12 | 3.62 | 1.35 | 3.63 | 0.56 | 3.64 | 0.76 |
| 3.65 | 1.88 | 3.66 | 3.59 | 3.67 | 0.92 | 3.68 | 2.46 |
| 3.69 | 2.47 | 3.70 | 0.82 |  |  |  |  |
| 4.01 | 13.5 | 4.02 | 20.3 | 4.03 | 1.76 | 4.04 | 0.70 |
| 4.05 | 0.14 | 4.06 | 0.16 | 4.07 | 0.10 | 4.08 | 0.067 |
| 4.09 | 0.10 | 4.10 | 0.27 | 4.11 (Ref. Ex.) | 3.03 | 4.12 (Ref. Ex.) | 3.04 |
| 4.13 | 0.34 | 4.14 | 3.88 | 4.15 | 4.90 | 4.16 | 0.67 |
| 4.17 | 0.17 | 4.18 | 0.24 | 4.19 | 1.00 | 4.20 | 0.52 |
| 4.21 | 0.086 | 4.22 | 0.77 | 4.23 | 1.23 | 4.24 | 0.31 |
| 4.25 | 1.57 | 4.26 | 1.24 | 4.27 | 0.38 | 4.28 | 0.12 |
| 4.29 | 2.74 | 4.30 | 2.92 | 4.31 | 0.32 | 4.32 | 0.884 |
| 4.33 | 0.22 | 4.34 | 0.43 | 4.35 | 0.15 | 4.36 | 0.57 |
| 4.37 | 0.17 | 4.38 | 1.81 | 4.39 | 0.52 | 4.40 | 3.92 |
| 4.41 | 2.49 | 4.42 | 2.62 | 4.43 | 4.43 | 4.44 | 15.0 |
| 4.45 | 1.12 | 4.46 | 0.31 | 4.47 | 3.06 | 4.48 | 2.86 |
| 4.49 | 3.93 | 4.50 | 4.29 | 4.51 | 1.60 | 4.52 | 0.73 |
| 4.53 | 0.75 | 4.54 | 1.50 | 4.55 | 0.95 |  |  |
| 5.01 | 5.28 | 5.02 | 3.55 | 5.03 | 0.65 | 5.04 | 0.79 |
| 5.05 | 0.30 | 5.06 | 0.27 | 5.07 | 7.57 | 5.08 | 0.16 |
| 5.09 | 0.46 | 5.10 | 0.28 | 5.11 | 1.50 | 5.12 | 1.00 |
| 5.13 | 4.73 | 5.14 | 6.41 | 5.15 | 0.21 | 5.16 | 42.1 |
| 5.17 | 9.07 | 5.18 | 0.64 | 5.19 | 1.37 | 5.20 | 2.31 |
| 5.21 | 8.68 | 5.22 | 0.76 | 5.23 | 6.74 | 5.24 | 1.81 |
| 5.25 | 12.7 | 5.26 | 11.8 |  |  |  |  |

TABLE 6-continued

| Ex | Gal-1 IC$_{50}$ | Ex | Gal-1 IC$_{50}$ | Ex | Gal-1 IC$_{50}$ | Ex | Gal-1 IC$_{50}$ |
|---|---|---|---|---|---|---|---|
| 6.01 | 6.38 | 6.02 | 1.97 | 6.03 | 4.16 | 6.04 | 2.38 |
| 6.05 | 8.19 | 6.06 | 1.63 | 6.07 | 0.91 | 6.08 | 0.073 |
| 6.09 | 6.72 | 6.10 | 0.89 | 6.11 | 0.092 | | |

The invention claimed is:
1. A compound of formula (I)

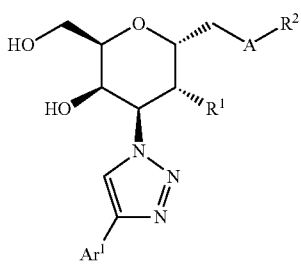

Formula (I)

wherein
Ar$^1$ represents
  aryl which is unsubstituted, or mono-, di-, tri-, tetra-, or penta-substituted, wherein the substituents are independently selected from halogen, methyl, cyano, methoxy, trifluoromethyl, trifluoromethoxy, and ethynyl;
  5- or 6-membered heteroaryl, wherein said 5- or 6-membered heteroaryl independently is unsubstituted, mono- or di-substituted, wherein the substituents are independently selected from halogen, methyl, cyano, and methoxy; or
  9- or 10-membered heteroaryl, wherein said 9- or 10-membered heteroaryl independently is unsubstituted, or mono-substituted with methyl;
R$^1$ represents
  hydroxy; or
  methoxy;
A represents 5-membered heterocycloalkylene or 5-membered heteroarylene; wherein said 5-membered heterocycloalkylene is selected from 4,5-dihydroisoxazole-3,5-diyl, imidazolidin-4-one-1,3-diyl, oxazol-2-one-3,5-diyl and oxazolidine-2-one-3,5-diyl; and said 5-membered heteroarylene is selected from 1,2,3-triazole-1,4-diyl, isoxazole-3,5-diyl, imidazole-1,4-diyl, and isothiazole-3,5-diyl; and
R$^2$ represents
  C$_{1-6}$-alkyl;
  C$_{1-6}$-alkyl wherein said C$_{1-6}$-alkyl is mono-substituted with C$_{1-3}$-alkoxy, —CO—C$_{1-4}$-alkoxy, —NH$_2$ or —NH—CO—C$_{1-4}$-alkoxy;
  C$_{1-4}$-fluoroalkyl;
  C$_{3-6}$-cycloalkyl wherein said C$_{3-6}$-cycloalkyl independently is unsubstituted, mono- or di-substituted wherein the substituents independently are selected from oxo, fluoro, —NH—CO—C$_{1-4}$-alkoxy, C$_{1-3}$-alkyl, C$_{1-3}$-alkoxy, C$_1$-fluoroalkyl, cyano, —CH$_2$—CN, and —NH—CO—C$_{1-4}$-alkyl wherein said C$_{1-4}$-alkyl is mono-substituted with —NH$_2$ or —NH—CO—C$_{1-4}$-alkoxy; or said C$_{3-6}$-cycloalkyl together with 1,3-dioxolan-2,2-diyl forms a spiro-bicyclic moiety;
  4- to 6-membered heterocycloalkyl wherein said heterocycloalkyl contains one ring oxygen atom and wherein said 4- to 6-membered heterocycloalkyl independently is unsubstituted or mono-substituted with C$_{1-4}$-alkyl;
  4- to 6-membered heterocycloalkyl wherein said heterocycloalkyl contains one ring sulfur atom wherein said sulfur atom is unsubstituted or mono-substituted with oxo (=O); or said sulfur atom is disubstituted wherein one substituent is oxo (=O) and the other substituent is selected from oxo (=O), imido (=NH), C$_{1-3}$-alkylimido (=N—C$_{1-3}$-alkyl), 4,4-difluorocyclohexylimido and benzylimido (=N-benzyl);
  4- to 7-membered heterocycloalkyl wherein said heterocycloalkyl contains one ring nitrogen atom, wherein said nitrogen atom is unsubstituted or mono-substituted with
    C$_{1-6}$-alkyl;
    —CO—C$_{1-6}$-alkyl;    —CO—C$_{4-6}$-cycloalkyl;
    —CO—C$_{1-3}$-fluoroalkyl;    —CO—C$_{1-4}$-alkoxy;
    —CO—NH—C$_{1-4}$-alkyl;
    —SO$_2$—C$_{1-4}$-alkyl; —SO$_2$—NH—C$_{1-4}$-alkyl;
    —CH$_2$—C$_{3-6}$-cycloalkyl;
    —CO—C$_{1-6}$-alkyl wherein the C$_{1-6}$-alkyl is mono-substituted with amino;
    —CH$_2$-oxetanyl;
    thiazol-2-yl; oxazol-2-yl; benzo[d]thiazol-2-yl;
    —CO-benzyloxy;
    —CO—NH$_2$; —CO—NH—C$_{3-6}$-cycloalkyl;
    —CO—NR$^{N31}$R$^{N32}$ wherein R$^{N31}$ and R$^{N32}$ both independently represent C$_{1-3}$-alkyl;
    —CO—NR$^{N41}$R$^{N42}$ wherein R$^{N41}$ and R$^{N42}$ together with the nitrogen atom to which they are attached form a 5- or 6-membered heterocycloalkyl wherein said 5- or 6-membered heterocycloalkyl independently is unsubstituted or mono-substituted with C$_{1-3}$-alkyl;
    —SO—C$_{1-6}$-alkyl;
    —SO$_2$—C$_{1-3}$-fluoroalkyl; —SO$_2$—NH$_2$;
    —SO$_2$—NR$^{N51}$R$^{N52}$ wherein R$^{N51}$ and R$^{N52}$ both independently represent C$_{1-3}$-alkyl;
    —SO$_2$—NR$^{N61}$R$^{N62}$ wherein R$^{N61}$ and R$^{N62}$ together with the nitrogen atom to which they are attached form a 5- or 6-membered heterocycloalkyl, wherein said 5- or 6-membered heterocycloalkyl independently is unsubstituted or di-substituted with fluoro;
    —SO$_2$-phenyl wherein said phenyl is unsubstituted or mono-substituted with methyl;
    >—SO(NH)—C$_{1-6}$-alkyl; or —SO(N—C$_{1-3}$-alkyl)-C$_{1-6}$-alkyl;
  and wherein said 4- to 7-membered heterocycloalkyl carries no further substituent in addition to said substituent on the ring nitrogen atom, or carries one further substituent which is C$_{1-4}$-alkyl (wherein it is understood that such C$_{1-4}$-alkyl is attached to a ring carbon atom);

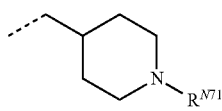

wherein $R^{N71}$ represents hydrogen or —CO—$C_{1-4}$-alkoxy;
cyclopentenyl;
L-OH, wherein L represents
$C_{1-6}$-alkylene;
chloro-$C_{2-6}$-alkylene;
1-phenyl-ethan-1,1-diyl or 1-(2-fluorophenyl)-ethan-1,1-diyl;
(cyclopropyl)-(pyridin-2-yl)-methylene;
$C_{4-6}$-cycloalkylene wherein said $C_{4-6}$-cycloalkylene independently is unsubstituted, mono- or di-substituted wherein the substituents independently are methyl, fluoro, or —CO—$R^{O2}$ wherein $R^{O2}$ represents hydroxy or $C_{1-4}$-alkoxy;
cyclopropylene-$(CH_2)_n$—* wherein n represents the integer 0 or 1, and wherein the asterisk indicates the bond which is connected to the —OH group;
4- to 7-membered heterocycloalkylene wherein said heterocycloalkylene contains one ring oxygen atom; or
4- to 7-membered heterocycloalkylene wherein said heterocycloalkylene contains one ring nitrogen atom, wherein said nitrogen atom is unsubstituted or mono-substituted with —CO—$C_{1-4}$-alkyl, or —CO—$C_{1-4}$-alkoxy;
5- or 6-membered heteroaryl, wherein said 5- or 6-membered heteroaryl independently is unsubstituted or mono-substituted, wherein the substituents independently are $C_{1-4}$-alkyl, $C_{1-3}$-fluoroalkyl, halogen, $C_{1-4}$-alkoxy, or $C_{1-4}$-fluoroalkoxy;
2-oxo-1,2-dihydropyridin-4-yl, 6-oxo-1,6-dihydropyridin-3-yl, or 1-methyl-2-oxo-1,2-dihydropyridin-4-yl;

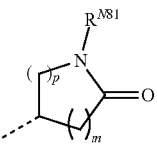

wherein m and p independently represent the integer 1 or 2; and $R^{N81}$ represents hydrogen or $C_{1-4}$-alkyl;
$C_{0-3}$-alkylene-phenyl; wherein the phenyl independently is unsubstituted, mono-, di-, or tri-substituted, wherein the substituents independently are $C_{1-4}$-alkyl, $C_{1-3}$-fluoroalkyl, halogen, hydroxy, $C_{1-4}$-alkoxy, or $C_{1-4}$-fluoroalkoxy;
9-membered heteroaryl;

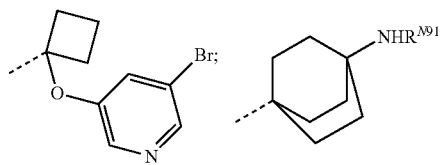

wherein $R^{N91}$ represents hydrogen or —CO—$C_{1-4}$-alkoxy;
or $R^2$ represents a group of the structure ($R^{2-B}$):

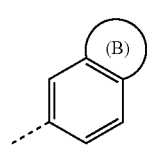

wherein ring (B) represents a non-aromatic 5-membered ring fused to the phenyl group, wherein ring (B) comprises two heteroatoms independently selected from nitrogen and oxygen; wherein said ring (B) independently is mono- or di-substituted, wherein one of said substituents is oxo, and the other substituent, if present, is $C_{1-3}$-alkyl;
or a pharmaceutically acceptable salt thereof.

2. A compound according to claim 1, wherein $Ar^1$ represents phenyl which is mono-, di- or tri-substituted, wherein the substituents are independently selected from halogen, methyl, cyano, methoxy, trifluoromethyl, and ethynyl;
wherein at least one of said substituents is attached in a meta- and/or in para-position of said phenyl;
or a pharmaceutically acceptable salt thereof.

3. A compound according to claim 2, wherein at least one of said substituents is attached in a meta-position of said phenyl and the substituent is halogen;
or a pharmaceutically acceptable salt thereof.

4. A compound according to claim 2, wherein at least one of said substituents is attached in para-position of said phenyl and the substituent is selected from halogen, methyl, cyano, methoxy, trifluoromethyl, and ethynyl;
or a pharmaceutically acceptable salt thereof.

5. A compound according to claim 1, wherein $Ar^1$ represents a phenyl group of the structure

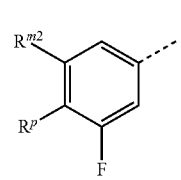

wherein
$R^{m2}$ represents halogen; and
$R^p$ represents hydrogen, halogen, methyl, cyano, or methoxy;
or a pharmaceutically acceptable salt thereof.

6. A compound according to claim 1, wherein $Ar^1$ represents

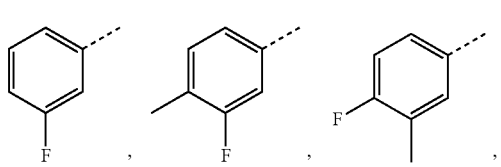

-continued

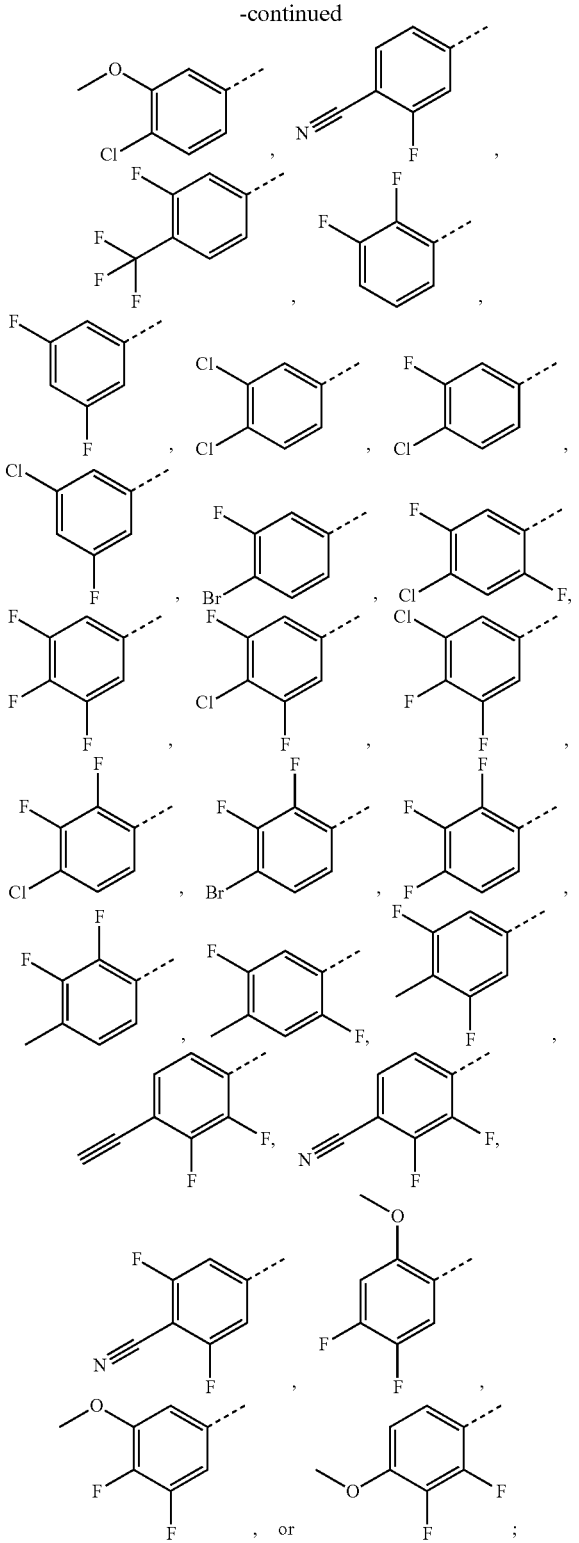

B or a pharmaceutically acceptable salt thereof.

7. A compound according to claim 1, wherein $R^1$ represents methoxy;
or a pharmaceutically acceptable salt thereof.

8. A compound according to claim 1, wherein A represents 1,2,3-triazole-1,4-diyl or isoxazole-3,5-diyl; or a pharmaceutically acceptable salt thereof.

9. A compound according to claim 1, wherein $R^2$ represents
$C_{1-6}$-alkyl;
$C_{1-6}$-alkyl wherein said $C_{1-6}$-alkyl is mono-substituted with $C_{1-3}$-alkoxy, —CO—$C_{1-4}$-alkoxy, —NH$_2$ or —NH—CO—$C_{1-4}$-alkoxy;
$C_{1-4}$-fluoroalkyl;
$C_{3-6}$-cycloalkyl wherein said $C_{3-6}$-cycloalkyl independently is unsubstituted, mono- or di-substituted wherein the substituents independently are selected from oxo, fluoro, —NH—CO—$C_{1-4}$-alkoxy, $C_{1-3}$-alkyl, $C_{1-3}$-alkoxy, $C_1$-fluoroalkyl, cyano, —CH$_2$—CN, and —NH—CO—$C_{1-4}$-alkyl wherein said $C_{1-4}$-alkyl is mono-substituted with —NH$_2$ or —NH—CO—$C_{1-4}$-alkyl;
4- to 6-membered heterocycloalkyl wherein said heterocycloalkyl contains one ring oxygen atom and wherein said 4- to 6-membered heterocycloalkyl independently is unsubstituted or mono-substituted with $C_{1-4}$-alkyl;
4- to 6-membered heterocycloalkyl wherein said heterocycloalkyl contains one ring sulfur atom wherein said sulfur atom is unsubstituted or mono-substituted with oxo (=O); or said sulfur atom is disubstituted wherein one substituent is oxo (=O) and the other substituent is selected from oxo (=O), imido (=NH), $C_{1-3}$-alkylimido (=N—$C_{1-3}$-alkyl), 4,4-difluorocyclohexylimido and benzylimido (=N-benzyl);
4- to 6-membered heterocycloalkyl wherein said heterocycloalkyl contains one ring nitrogen atom, wherein said nitrogen atom is unsubstituted or mono-substituted with
$C_{1-6}$-alkyl;
—CO—$C_{1-6}$-alkyl; —CO—$C_{4-6}$-cycloalkyl; —CO—$C_{1-3}$-fluoroalkyl; —CO—$C_{1-4}$-alkoxy; —CO—NH—$C_{1-4}$-alkyl;
—SO$_2$—$C_{1-4}$-alkyl;
—CH$_2$—$C_{3-6}$-cycloalkyl;
thiazol-2-yl; oxazol-2-yl; benzo[d]thiazol-2-yl;
—CO-benzyloxy;
—CO—NH—$C_{3-6}$-cycloalkyl;
—CO—NR$^{N31}$R$^{N32}$ wherein R$^{N31}$ and R$^{N32}$ both independently represent $C_{1-3}$-alkyl;
—CO—NR$^{N41}$R$^{N42}$ wherein R$^{N41}$ and R$^{N42}$ together with the nitrogen atom to which they are attached form a 5- or 6-membered heterocycloalkyl wherein said 5- or 6-membered heterocycloalkyl independently is unsubstituted or mono-substituted with $C_{1-3}$-alkyl;
—SO—$C_{1-6}$-alkyl;
—SO$_2$—$C_{1-3}$-alkyl;
—SO$_2$—NR$^{N51}$R$^{N52}$ wherein R$^{N51}$ and R$^{N52}$ both independently represent $C_{1-3}$-alkyl;
—SO$_2$—NR$^{N61}$R$^{N62}$ wherein R$^{N61}$ and R$^{N62}$ together with the nitrogen atom to which they are attached form a 5- or 6-membered heterocycloalkyl, wherein said 5- or 6-membered heterocycloalkyl independently is unsubstituted or di-substituted with fluoro;
—SO$_2$-phenyl wherein said phenyl is mono-substituted with methyl;
—SO(NH)—$C_{1-6}$-alkyl; or —SO(N—$C_{1-3}$-alkyl)-$C_{1-6}$-alkyl;
and wherein said 4- to 6-membered heterocycloalkyl carries no further substituent in addition to said substituent on the ring nitrogen atom, or carries one further substituent which is $C_{1-4}$-alkyl (wherein it is understood that such $C_{1-4}$-alkyl is attached to a ring carbon atom);

L-OH, wherein L represents

C$_{1-6}$-alkylene;

chloro-C$_{2-6}$-alkylene;

1-phenyl-ethan-1,1-diyl or 1-(2-fluorophenyl)-ethan-1,1-diyl;

C$_{4-6}$-cycloalkylene wherein said C$_{4-6}$-cycloalkylene independently is unsubstituted, or di-substituted wherein the substituents independently are methyl, or fluoro;

cyclopropylene-(CH$_2$)$_n$—* wherein n represents the integer 0 or 1, and wherein the asterisk indicates the bond which is connected to the —OH group;

4- to 6-membered heterocycloalkylene wherein said heterocycloalkylene contains one ring oxygen atom; or 4- to 6-membered heterocycloalkylene wherein said heterocycloalkylene contains one ring nitrogen atom, wherein said nitrogen atom is unsubstituted or mono-substituted with —CO—C$_{1-4}$-alkyl, or —CO—C$_{1-4}$-alkoxy;

2-oxo-1,2-dihydropyridin-4-yl, 6-oxo-1,6-dihydropyridin-3-yl, or 1-methyl-2-oxo-1,2-dihydropyridin-4-yl;

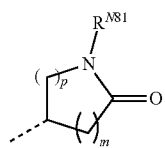

wherein m and p independently represent the integer 1 or 2; and R$^{N81}$ represents hydrogen or C$_{1-4}$-alkyl;

—CH(CH$_3$)-phenyl);

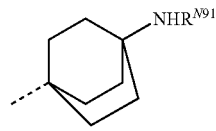

wherein R$^{N91}$ represents hydrogen or —CO—C$_{1-4}$-alkoxy;

or R$^2$ represents a group of the structure (R$^{2-B}$):

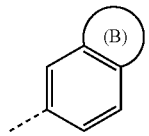

wherein ring (B) represents a non-aromatic 5-membered ring fused to the phenyl group, wherein ring (B) comprises two heteroatoms independently selected from nitrogen and oxygen; wherein said ring (B) independently is mono- or di-substituted, wherein one of said substituents is oxo, and the other substituent, if present, is C$_{1-3}$-alkyl;

or a pharmaceutically acceptable salt thereof.

10. A compound according to claim 1; wherein R$^2$ represents

C$_{1-6}$-alkyl;

C$_{1-6}$-alkyl wherein said C$_{1-6}$-alkyl is mono-substituted with C$_{1-3}$-alkoxy;

C$_{1-4}$-fluoroalkyl; or

L-OH, wherein L represents

C$_{1-6}$-alkylene;

C$_{4-6}$-cycloalkylene wherein said C$_{4-6}$-cycloalkylene independently is unsubstituted; or cyclopropylene-(CH$_2$)$_n$—* wherein n represents the integer 0 or 1, and wherein the asterisk indicates the bond which is connected to the —OH group;

or a pharmaceutically acceptable salt thereof.

11. A compound according to claim 1, wherein R$^2$ represents

C$_{1-6}$-alkyl;

cyclobutyl, or cyclopentyl;

cyclohexyl which is mono- or di-substituted wherein the substituents independently are oxo, fluoro, or —NH—CO—C$_{1-4}$-alkoxy;

4- to 6-membered heterocycloalkyl wherein said heterocycloalkyl contains one ring oxygen atom;

4- to 7-membered heterocycloalkyl wherein said heterocycloalkyl contains one ring nitrogen atom, wherein said nitrogen atom is unsubstituted or mono-substituted with C$_{1-6}$-alkyl, —CO—C$_{1-6}$-alkyl, —CO—C$_{4-6}$-cycloalkyl, —CO—C$_{1-3}$-fluoroalkyl, —CO—C$_{1-4}$-alkoxy, —CO—NH—C$_{1-4}$-alkyl, —SO$_2$—C$_{1-4}$-alkyl, —SO$_2$—NH—C$_{1-4}$-alkyl, —CH$_2$—C$_{3-6}$-cycloalkyl, —CO—C$_{1-6}$-alkyl wherein the C$_{1-6}$-alkyl is mono-substituted with amino, —CH$_2$-oxetanyl, thiazol-2-yl, oxazol-2-yl, or benzo[d]thiazol-2-yl;

L-OH, wherein L represents

C$_{4-6}$-cycloalkylene wherein said C$_{4-6}$-cycloalkylene independently is unsubstituted or mono- or di-substituted wherein the substituents independently are methyl, or fluoro;

4- to 7-membered heterocycloalkylene wherein said heterocycloalkylene contains one ring oxygen atom; or 4- to 7-membered heterocycloalkylene wherein said heterocycloalkylene contains one ring nitrogen atom, wherein said nitrogen atom is unsubstituted or mono-substituted with —CO—C$_{1-4}$-alkyl, or —CO—C$_{1-4}$-alkoxy;

or R$^2$ represents a group of the structure (R$^{2-B}$):

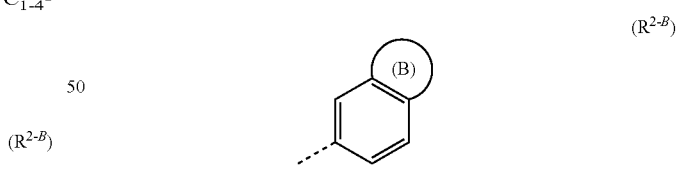

wherein ring (B) represents a non-aromatic 5-membered ring fused to the phenyl group, wherein ring (B) comprises two heteroatoms independently selected from nitrogen and oxygen; wherein said ring (B) independently is mono- or di-substituted, wherein one of said substituents is oxo, and the other substituent, if present, is C$_{1-3}$-alkyl;

or a pharmaceutically acceptable salt thereof.

12. A pharmaceutical composition comprising a compound according to claim 1, or a pharmaceutically acceptable salt thereof, and a pharmaceutically acceptable carrier.

13. A method for the treatment of an indication selected from fibrosis of organs; liver diseases and disorders; cardiovascular diseases and disorders; cell proliferative diseases and cancers; inflammatory and autoimmune diseases and disorders; gastrointestinal tract diseases and disorders; pancreatic diseases and disorders; abnormal angiogenesis-associated diseases and disorders; brain-associated diseases and disorders; neuropathic pain and peripheral neuropathy; ocular diseases and disorders; acute kidney injury and chronic kidney disease; interstitial lung diseases and disorders; and transplant rejection; comprising administering to a subject in a need thereof an effective amount of a compound according to claim 1, or of a pharmaceutically acceptable salt thereof.

14. A compound, wherein said compound is:
- 6-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one;
- 6-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one;
- 6-((S)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)benzo[d]oxazol-2(3H)-one;
- tert-butyl 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate;
- tert-butyl 4-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;
- tert-butyl 4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;
- tert-butyl 4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidine-1-carboxylate;
- tert-butyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;
- (2R,3R,4R,5R,6R)-2-((5-(tert-butyl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol;
- tert-butyl (RS)-3-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate;
- (2R,3R,4R,5R,6R)-2-(hydroxymethyl)-6-((5-(tetrahydro-2H-pyran-4-yl)isoxazol-3-yl)methyl)-4-(4-(3,4,5-trifluorophenyl)-1H-1,2,3-triazol-1-yl)tetrahydro-2H-pyran-3,5-diol;
- tert-butyl 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)-4-hydroxypiperidine-1-carboxylate;
- tert-butyl 4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)piperidine-1-carboxylate;
- (2R,3R,4S,5R,6R)-2-(hydroxymethyl)-5-methoxy-6-((5-(tetrahydro-2H-pyran-4-yl)isoxazol-3-yl)methyl)-4-(4-(3,4,5-trifluorophenyl)-1H-1,2,3-triazol-1-yl)tetrahydro-2H-pyran-3-ol;
- (2R,3R,4S,5R,6R)-6-((5-cyclopentylisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;
- (2R,3R,4S,5R,6R)-6-((5-(1-hydroxycyclohexyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;
- (2R,3R,4S,5R,6R)-6-((5-cyclobutylisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;
- (2R,3R,4S,5R,6R)-6-((5-(4,4-difluorocyclohexyl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;
- tert-butyl ((1R,4R)-4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)cyclohexyl)carbamate;
- tert-butyl ((1S,4S)-4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)cyclohexyl)carbamate;
- (2R,3R,4R,5R,6R)-2-(hydroxymethyl)-6-((5-(1-(oxazol-2-yl)piperidin-4-yl)isoxazol-3-yl)methyl)-4-(4-(3,4,5-trifluorophenyl)-1H-1,2,3-triazol-1-yl)tetrahydro-2H-pyran-3,5-diol;
- (2R,3R,4R,5R,6R)-2-((5-(1-(benzo[d]thiazol-2-yl)piperidin-4-yl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol;
- (2R,3R,4R,5R,6R)-2-(hydroxymethyl)-6-((5-(1-(thiazol-2-yl)piperidin-4-yl)isoxazol-3-yl)methyl)-4-(4-(3,4,5-trifluorophenyl)-1H-1,2,3-triazol-1-yl)tetrahydro-2H-pyran-3,5-diol;
- 5-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one;
- 4-((S)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one;
- 4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one;
- 4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)pyridin-2(1H)-one;
- 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)cyclohexan-1-one;
- (2R,3R,4R,5R,6R)-2-((5-(4-hydroxycyclohexyl)isoxazol-3-yl)methyl)-6-(hydroxymethyl)-4-(4-(3,4,5-trifluorophenyl)-1H-1,2,3-triazol-1-yl)tetrahydro-2H-pyran-3,5-diol;

(2R,3R,4R,5R,6R)-2-((5-((1R,4R)-4-hydroxycyclohexyl) isoxazol-3-yl)methyl)-6-(hydroxymethyl)-4-(4-(3,4,5-trifluorophenyl)-1H-1,2,3-triazol-1-yl)tetrahydro-2H-pyran-3,5-diol;

(2R,3R,4R,5R,6R)-2-(hydroxymethyl)-6-(((RS)-3-(piperidin-4-yl)-4,5-dihydroisoxazol-5-yl)methyl)-4-(4-(3,4,5-trifluorophenyl)-1H-1,2,3-triazol-1-yl)tetrahydro-2H-pyran-3,5-diol;

1-(4-((RS)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one;

1-(4-((RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl) ethan-1-one;

(2R,3R,4S,5R,6R)-2-(hydroxymethyl)-5-methoxy-6-(((S)-3-(piperidin-4-yl)-4,5-dihydroisoxazol-5-yl) methyl)-4-(4-(3,4,5-trifluorophenyl)-1H-1,2,3-triazol-1-yl)tetrahydro-2H-pyran-3-ol;

(2R,3R,4R,5R,6R)-2-(hydroxymethyl)-6-((5-(piperidin-4-yl)isoxazol-3-yl)methyl)-4-(4-(3,4,5-trifluorophenyl)-1H-1,2,3-triazol-1-yl)tetrahydro-2H-pyran-3,5-diol;

1-(4-((S)-5-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl)ethan-1-one;

1-(4-((S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-4,5-dihydroisoxazol-3-yl)piperidin-1-yl) ethan-1-one;

(2R,3R,4S,5R,6R)-2-(hydroxymethyl)-5-methoxy-6-((5-(piperidin-4-yl)isoxazol-3-yl)methyl)-4-(4-(3,4,5-trifluorophenyl)-1H-1,2,3-triazol-1-yl)tetrahydro-2H-pyran-3-ol;

1-(4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidin-1-yl)ethan-1-one;

1-(4-((RS)-3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-5-yl)piperidin-1-yl)ethan-1-one;

1-(4-((S)-3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)-4,5-dihydroisoxazol-5-yl)piperidin-1-yl)ethan-1-one;

1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)ethan-1-one;

ethyl 4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidine-1-carboxylate;

4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)-N-ethylpiperidine-1-carboxamide;

(2R,3R,4R,5R,6R)-2-(hydroxymethyl)-6-((5-(1-(methylsulfonyl)piperidin-4-yl)isoxazol-3-yl)methyl)-4-(4-(3,4,5-trifluorophenyl)-1H-1,2,3-triazol-1-yl)tetrahydro-2H-pyran-3,5-diol;

(2R,3R,4R,5R,6R)-2-(hydroxymethyl)-6-((5-(1-methylpiperidin-4-yl)isoxazol-3-yl)methyl)-4-(4-(3,4,5-trifluorophenyl)-1H-1,2,3-triazol-1-yl)tetrahydro-2H-pyran-3,5-diol;

1-(4-(3-(((2R,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)methyl)isoxazol-5-yl)piperidin-1-yl)-2,2-dimethylpropan-1-one;

ethyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;

methyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;

1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-2-methylpropan-1-one;

1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-2,2-dimethylpropan-1-one;

1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)butan-1-one;

N-ethyl-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxamide;

4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N-isopropylpiperidine-1-carboxamide;

(2R,3R,4S,5R,6R)-2-(hydroxymethyl)-5-methoxy-6-((5-(1-methylpiperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((5-(1-isobutylpiperidin-4-yl)isoxazol-3-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((5-(1-(3,3-dimethylbutyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((5-(1-(cyclopropylmethyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(methylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(propylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((5-(1-(isopropylsulfonyl)piperidin-4-yl)isoxazol-3-yl)methyl)-5-methoxy-4-(4-(3,4,5-trifluorophenyl)-1H-1,2,3-triazol-1-yl)tetrahydro-2H-pyran-3-ol;

1-(4-(3-(((2R,3R,4S,5R,6R)-5-hydroxy-6-(hydroxymethyl)-3-methoxy-4-(4-(3,4,5-trifluorophenyl)-1H-1,2, 3-triazol-1-yl)tetrahydro-2H-pyran-2-yl)methyl)isoxazol-5-yl)piperidin-1-yl)-3-methylbutan-1-one;

cyclopentyl(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)methanone;

cyclobutyl(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)methanone;

3,3,3-trifluoro-1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)propan-1-one;

N-(tert-butyl)-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxamide;

(RS)-1-(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)-2-methylbutan-1-one;

(2R,3R,4S,5R,6R)-2-(hydroxymethyl)-5-methoxy-6-((1-(tetrahydro-2H-pyran-4-yl)-1H-1,2,3-triazol-4-yl)methyl)-4-(4-(3,4,5-trifluorophenyl)-1H-1,2,3-triazol-1-yl)tetrahydro-2H-pyran-3-ol;

1-(4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidin-1-yl)ethan-1-one;

tert-butyl 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxylate;

1-(4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidin-1-yl)ethan-1-one;

(2R,3R,4S,5R,6R)-2-(hydroxymethyl)-5-methoxy-6-((1-(1-(methylsulfonyl)piperidin-4-yl)-1H-1,2,3-triazol-4-yl)methyl)-4-(4-(3,4,5-trifluorophenyl)-1H-1,2,3-triazol-1-yl)tetrahydro-2H-pyran-3-ol;

N-(tert-butyl)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxamide;

(2R,3R,4S,5R,6R)-2-(hydroxymethyl)-5-methoxy-6-((1-(1-(propylsulfonyl)piperidin-4-yl)-1H-1,2,3-triazol-4-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((1-(1-(isopropylsulfonyl)piperidin-4-yl)-1H-1,2,3-triazol-4-yl)methyl)-5-methoxy-4-(4-(3,4,5-trifluorophenyl)-1H-1,2,3-triazol-1-yl)tetrahydro-2H-pyran-3-ol;

tert-butyl 4-((RS)-5-(((2R,3R,4R,5R,6R)-4-(4-(4-chloro-3,5-difluorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(4-chloro-2,3-difluorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(3,4-dichlorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(3,4-difluoro-5-methoxyphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(4-chloro-3-methoxyphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

(RS)-5-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)piperidin-2-one;

tert-butyl 4-((RS)-5-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-1-methylpyridin-2(1H)-one;

(2R,3R,4S,5R,6R)-6-((3-cyclohexylisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

tert-butyl 4-(3-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

tert-butyl 4-(3-(((2R,3R,4S,5R,6R)-4-(4-(3,5-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

tert-butyl 4-(5-(((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate;

tert-butyl 4-(5-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate;

tert-butyl 4-(5-(((2R,3R,4S,5R,6R)-4-(4-(4-bromo-3-fluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate;

tert-butyl 4-(5-(((2R,3R,4S,5R,6R)-4-(4-(3,5-difluorophenyl)-1H-1,2,3-triazol-1-yl)-5-hydroxy-6-(hydroxymethyl)-3-methoxytetrahydro-2H-pyran-2-yl)methyl)isoxazol-3-yl)piperidine-1-carboxylate;

(2R,3R,4S,5R,6R)-6-((5-(4-bromothiazol-2-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-(((S)-5-cyclohexyl-4,5-dihydroisoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

tert-butyl (4-(3-(((2R,3R,4S,5R,6R)-5-hydroxy-6-(hydroxymethyl)-3-methoxy-4-(4-(3,4,5-trifluorophenyl)-

1H-1,2,3-triazol-1-yl)tetrahydro-2H-pyran-2-yl)
methyl)isoxazol-5-yl)bicyclo[2.2.2]octan-1-yl)
carbamate;

(2R,3R,4S,5R,6R)-6-((5-(4-aminobicyclo[2.2.2]octan-1-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol formate;

tert-butyl 4-hydroxy-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxylate;

4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-4-ol formate;

tert-butyl ((1R,4r)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclohexyl)carbamate;

tert-butyl 4-((RS)-5-(((2R,3R,4S,5R,6R)-4-(4-(3,5-difluoro-4-methylphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-4-(4-(3-fluoro-4-methylphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

(2R,3R,4S,5R,6R)-2-(hydroxymethyl)-5-methoxy-6-((5-((S)-1-(N-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-((R)-1-(N-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol;

tert-butyl 4-((RS)-5-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-4-(4-(4-bromo-2,3-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

(2R,3R,4S,5R,6R)-4-(4-(4-bromo-2,3-difluorophenyl)-1H-1,2,3-triazol-1-yl)-2-(hydroxymethyl)-5-methoxy-6-(((RS)-3-(piperidin-4-yl)-4,5-dihydroisoxazol-5-yl)methyl)tetrahydro-2H-pyran-3-ol formate;

tert-butyl 4-((RS)-5-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-4,5-dihydroisoxazol-3-yl)piperidine-1-carboxylate;

(2R,3R,4S,5R,6R)-2-(hydroxymethyl)-5-methoxy-6-(((RS)-3-(piperidin-4-yl)-4,5-dihydroisoxazol-5-yl)methyl)-4-(4-(2,3,4-trifluorophenyl)-1H-1,2,3-triazol-1-yl)tetrahydro-2H-pyran-3-ol formate;

tert-butyl 4-((RS)-5-(((2R,3R,4S,5R,6R)-4-(4-(4-chloro-3,5-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

(2R,3R,4S,5R,6R)-4-(4-(4-chloro-3,5-difluorophenyl)-1H-1,2,3-triazol-1-yl)-2-(hydroxymethyl)-5-methoxy-6-(((RS)-3-(piperidin-4-yl)-4,5-dihydroisoxazol-5-yl)methyl)tetrahydro-2H-pyran-3-ol formate;

(1R,4r)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-1-(isopropylimino)hexahydro-1l6-thiopyran 1-oxide;

(1S,4s)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-1-(isopropylimino)hexahydro-1l6-thiopyran 1-oxide;

ethyl 4-(3-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

ethyl 4-(3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-5-yl)piperidine-1-carboxylate;

ethyl 4-(3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

(2R,3R,4S,5R,6R)-4-(4-(3,5-difluoro-4-methylphenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(3-fluoro-4-methylphenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(4-bromo-2,3-difluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(4-chloro-3-fluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-2-(hydroxymethyl)-5-methoxy-6-((5-(1-(methylsulfonyl)piperidin-4-yl)isoxazol-3-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(4-chloro-3,5-difluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

(2R,3R,4S,5R,6R)-4-(4-(3-chloro-5-fluorophenyl)-1H-1,2,3-triazol-1-yl)-2-(hydroxymethyl)-5-methoxy-6-((5-(1-(methylsulfonyl)piperidin-4-yl)isoxazol-3-yl)methyl)tetrahydro-2H-pyran-3-ol;

1-(4-(3-(((2R,3R,4S,5R,6R)-4-(4-(3,5-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(3-fluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(4-bromo-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(4-chloro-3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-5-yl)piperidin-1-yl)ethan-1-one;

1-(4-(3-(((2R,3R,4S,5R,6R)-4-(4-(4-chloro-3,5-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

1-(4-(3-(((2R,3R,4S,5R,6R)-4-(4-(3-chloro-5-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidin-1-yl)ethan-1-one;

(2R,3R,4S,5R,6R)-4-(4-(4-chloro-2,3-difluorophenyl)-1H-1,2,3-triazol-1-yl)-6-((5-cyclohexylisoxazol-3-yl)methyl)-2-(hydroxymethyl)-5-methoxytetrahydro-2H-pyran-3-ol;

(2R,3R,4S,5R,6R)-6-((5-cyclohexylisoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-4-(4-(3,5-difluoro-4-methylphenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(3-fluoro-4-methylphenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(4-bromo-2,3-difluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(4-chloro-3-fluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-2-(hydroxymethyl)-5-methoxy-6-((5-(tetrahydro-2H-pyran-4-yl)isoxazol-3-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(4-chloro-3,5-difluorophenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(tetrahydro-2H-pyran-4-yl)isoxazol-3-yl)methyl)tetrahydro-2H-pyran-3-ol;

(2R,3R,4S,5R,6R)-6-((5-(tert-butyl)isoxazol-3-yl)methyl)-4-(4-(3,5-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(3-fluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

(2R,3R,4S,5R,6R)-4-(4-(4-bromo-2,3-difluorophenyl)-1H-1,2,3-triazol-1-yl)-6-((5-(tert-butyl)isoxazol-3-yl)methyl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(4-chloro-3-fluorophenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((5-(tert-butyl)isoxazol-3-yl)methyl)-4-(4-(4-chloro-3,5-difluorophenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-2-(hydroxymethyl)-6-((5-(1-(N-isopropylpropan-2-ylsulfonimidoyl)piperidin-4-yl)isoxazol-3-yl)methyl)-5-methoxy-4-(4-(3,4,5-trifluorophenyl)-1H-1,2,3-triazol-1-yl)tetrahydro-2H-pyran-3-ol;

ethyl 4-(3-(((2R,3R,4S,5R,6R)-4-(4-(4-bromo-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

ethyl 4-(3-(((2R,3R,4S,5R,6R)-4-(4-(4-chloro-3,5-difluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

ethyl 4-(3-(((2R,3R,4S,5R,6R)-4-(4-(3-chloro-5-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

ethyl 4-(3-(((2R,3R,4S,5R,6R)-4-(4-(3-fluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

ethyl 4-(3-(((2R,3R,4S,5R,6R)-4-(4-(3,5-difluoro-4-methylphenyl)-1H-1,2,3-triazol-1-yl)-5-hydroxy-6-

(hydroxymethyl)-3-methoxytetrahydro-2H-pyran-2-yl)
methyl)isoxazol-5-yl)piperidine-1-carboxylate;

ethyl 4-(3-(((2R,3R,4S,5R,6R)-4-(4-(4-chloro-2,3-difluo-rophenyl)-1H-1,2,3-triazol-1-yl)-5-hydroxy-6-(hy-droxymethyl)-3-methoxytetrahydro-2H-pyran-2-yl)
methyl)isoxazol-5-yl)piperidine-1-carboxylate;

(2R,3R,4R,5R,6R)-2-((5-(tert-butyl)isoxazol-3-yl)
methyl)-4-(4-(2,3-difluoro-4-methylphenyl)-1H-1,2,3-triazol-1-yl)-6-(hydroxymethyl)tetrahydro-2H-pyran-3,5-diol;

(2R,3R,4S,5R,6R)-6-((3-(tert-butyl)isoxazol-5-yl)
methyl)-2-(hydroxymethyl)-5-methoxy-4-(4-(3,4,5-tri-fluorophenyl)-1H-1,2,3-triazol-1-yl)tetrahydro-2H-pyran-3-ol;

(2R,3R,4S,5R,6R)-6-((3-(1-hydroxy-2-methylpropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

ethyl 3-(5-(((2R,3R,4S,5R,6R)-5-hydroxy-6-(hydroxym-ethyl)-3-methoxy-4-(4-(3,4,5-trifluorophenyl)-1H-1,2,3-triazol-1-yl)tetrahydro-2H-pyran-2-yl)methyl)isoxa-zol-3-yl)-3-methylbutanoate;

(2R,3R,4S,5R,6R)-2-(hydroxymethyl)-5-methoxy-6-((3-(1-methoxycyclopentyl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(1-methoxycyclohexyl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(3-methyloxetan-3-yl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-6-((3-(3-ethyloxetan-3-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((3-(1-fluorocyclopropyl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((3-(1-(difluoromethyl)cyclopropyl)
isoxazol-5-yl)methyl)-2-(hydroxymethyl)-5-methoxy-4-(4-(3,4,5-trifluorophenyl)-1H-1,2,3-triazol-1-yl)tet-rahydro-2H-pyran-3-ol;

(2R,3R,4S,5R,6R)-2-(hydroxymethyl)-5-methoxy-6-((3-(1-methylcyclopropyl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-6-((3-(2-aminopropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

1-(4-(3-(((2R,3R,4S,5R,6R)-4-(4-(3-chloro-4,5-difluoro-phenyl)-1H-1,2,3-triazol-1-yl)-5-hydroxy-6-(hy-droxymethyl)-3-methoxytetrahydro-2H-pyran-2-yl)
methyl)isoxazol-5-yl)piperidin-1-yl)ethan-1-one;

ethyl 4-(3-(((2R,3R,4S,5R,6R)-4-(4-(3-chloro-4,5-difluo-rophenyl)-1H-1,2,3-triazol-1-yl)-5-hydroxy-6-(hy-droxymethyl)-3-methoxytetrahydro-2H-pyran-2-yl)
methyl)isoxazol-5-yl)piperidine-1-carboxylate;

(2R,3R,4S,5R,6R)-6-((5-(tert-butyl)isoxazol-3-yl)
methyl)-4-(4-(3-chloro-4,5-difluorophenyl)-1H-1,2,3-triazol-1-yl)-2-(hydroxymethyl)-5-methoxytetrahydro-2H-pyran-3-ol;

(2R,3R,4S,5R,6R)-6-((3-cyclopentylisoxazol-5-yl)
methyl)-2-(hydroxymethyl)-5-methoxy-4-(4-(3,4,5-tri-fluorophenyl)-1H-1,2,3-triazol-1-yl)tetrahydro-2H-pyran-3-ol;

(2R,3R,4S,5R,6R)-6-((5-cyclobutylisoxazol-3-yl)
methyl)-4-(4-(2,3-difluoro-4-methylphenyl)-1H-1,2,3-triazol-1-yl)-2-(hydroxymethyl)-5-methoxytetra-hydro-2H-pyran-3-ol;

(2R,3R,4S,5R,6R)-6-((5-cyclobutylisoxazol-3-yl)
methyl)-2-(hydroxymethyl)-5-methoxy-4-(4-(2,3,4-tri-fluorophenyl)-1H-1,2,3-triazol-1-yl)tetrahydro-2H-pyran-3-ol;

(2R,3R,4S,5R,6R)-4-(4-(4-chloro-2,3-difluorophenyl)-1H-1,2,3-triazol-1-yl)-6-((5-cyclobutylisoxazol-3-yl)
methyl)-2-(hydroxymethyl)-5-methoxytetrahydro-2H-pyran-3-ol;

tert-butyl 4-(3-(((2R,3R,4S,5R,6R)-4-(4-(3-fluorophe-nyl)-1H-1,2,3-triazol-1-yl)-5-hydroxy-6- (hydroxym-ethyl)-3-methoxytetrahydro-2H-pyran-2-yl)methyl)
isoxazol-5-yl)piperidine-1-carboxylate;

(2R,3R,4S,5R,6R)-2-(hydroxymethyl)-6-((5-(2-hydroxy-propan-2-yl)isoxazol-3-yl)methyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((5-(1-hydroxycyclohexyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((5-(1-hydroxycyclopentyl)isoxa-zol-3-yl)methyl)-2-(hydroxymethyl)-5-methoxy-4-(4-(2,3,4-trifluorophenyl)-1H-1,2,3-triazol-1-yl)tetra-hydro-2H-pyran-3-ol;

(2R,3R,4S,5R,6R)-6-((5-cyclopentylisoxazol-3-yl)
methyl)-2-(hydroxymethyl)-5-methoxy-4-(4-(2,3,4-tri-fluorophenyl)-1H-1,2,3-triazol-1-yl)tetrahydro-2H-pyran-3-ol;

(2R,3R,4S,5R,6R)-6-((5-(1-hydroxycyclobutyl)isoxazol-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-((5-(2-hy-droxypropan-2-yl)isoxazol-3-yl)methyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-(1-hydroxycyclohexyl)
isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-(1-hydroxycyclopentyl)
isoxazol-3-yl)methyl)-2-(hydroxymethyl)-5-methoxytetrahydro-2H-pyran-3-ol;

(2R,3R,4S,5R,6R)-6-((5-cyclopentylisoxazol-3-yl)
methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-(1-hydroxycyclobutyl)
isoxazol-3-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-6-((5-(2-hy-droxypropan-2-yl)isoxazol-3-yl)methyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((5-(1-hydroxycyclohexyl)

isoxazol-3-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((5-(1-hydroxycyclopentyl)isoxazol-3-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((5-cyclopentylisoxazol-3-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((5-(1-hydroxycyclobutyl)isoxazol-3-yl)methyl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(2,5-difluoro-4-methylphenyl)-1H-1,2,3-triazol-1-yl)-2-(hydroxymethyl)-5-methoxytetrahydro-2H-pyran-3-ol;

tert-butyl 4-(3-(((2R,3R,4S,5R,6R)-4-(4-(3-fluorophenyl)-1H-1,2,3-triazol-1-yl)-5-hydroxy-6-(hydroxymethyl)-3-methoxytetrahydro-2H-pyran-2-yl)methyl)isoxazol-5-yl)piperidine-1-carboxylate;

(2R,3R,4S,5R,6R)-6-((3-(tert-butyl)isoxazol-5-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(1-methylcyclopropyl)isoxazol-5-yl)methyl)-4-(4-(2,3,4-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(3-methyloxetan-3-yl)isoxazol-5-yl)methyl)-4-(4-(2,3,4-trifluorophenyl)-1H-1,2,3-triazol-1-yl)tetrahydro-2H-pyran-3-ol;

(2R,3R,4S,5R,6R)-6-((3-(1-hydroxy-2-methylpropan-2-yl)isoxazol-5-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((3-(tert-butyl)isoxazol-5-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((3-(1-methylcyclopropyl)isoxazol-5-yl)methyl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((3-(3-methyloxetan-3-yl)isoxazol-5-yl)methyl)tetrahydro-2H-pyran-3-ol;

(2R,3R,4S,5R,6R)-4-(4-(2,3-difluoro-4-methylphenyl)-1H-1,2,3-triazol-1-yl)-6-((3-(1-hydroxy-2-methylpropan-2-yl)isoxazol-5-yl)methyl)-2-(hydroxymethyl)-5-methoxytetrahydro-2H-pyran-3-ol;

(2R,3R,4S,5R,6R)-6-((3-(tert-butyl)isoxazol-5-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((3-(1-methylcyclopropyl)isoxazol-5-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((3-(3-methyloxetan-3-yl)isoxazol-5-yl)methyl)tetrahydro-2H-pyran-3-ol;

(2R,3R,4S,5R,6R)-4-(4-(4-chloro-2,3-difluorophenyl)-1H-1,2,3-triazol-1-yl)-6-((3-(1-hydroxy-2-methylpropan-2-yl)isoxazol-5-yl)methyl)-2-(hydroxymethyl)-5-methoxytetrahydro-2H-pyran-3-ol;

(2R,3R,4S,5R,6R)-6-((3-(1-chloro-3-hydroxy-2-methylpropan-2-yl)isoxazol-5-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((3-(1-chloro-3-hydroxy-2-methylpropan-2-yl)isoxazol-5-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((3-(1-chloro-3-hydroxy-2-methylpropan-2-yl)isoxazol-5-yl)methyl)-2-(hydroxymethyl)-5-methoxytetrahydro-2H-pyran-3-ol;

(2R,3R,4S,5R,6R)-6-(((RS)-3-(tert-butyl)-4,5-dihydroisoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-(((RS)-3-(tert-butyl)-4,5-dihydroisoxazol-5-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

4-(1-(((2R,3R,4S,5R,6R)-2-((5-(tert-butyl)isoxazol-3-yl)methyl)-5-hydroxy-6-(hydroxymethyl)-3-methoxytetrahydro-2H-pyran-4-yl)-1H-1,2,3-triazol-4-yl)-2,3-difluorobenzonitrile;

(2R,3R,4S,5R,6R)-2-(hydroxymethyl)-5-methoxy-6-((5-(4-methyltetrahydro-2H-pyran-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(4-methyltetrahydro-2H-pyran-4-yl)isoxazol-3-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(4-methyltetrahydro-2H-pyran-4-yl)isoxazol-3-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((5-(4-methyltetrahydro-2H-pyran-4-yl)isoxazol-3-yl)methyl)tetrahydro-2H-pyran-3-ol;

(2R,3R,4S,5R,6R)-2-(hydroxymethyl)-5-methoxy-6-((5-(1-methylcyclopentyl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-methylcyclopentyl)isoxazol-3-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(1-methylcyclopentyl)isoxazol-3-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((5-(1-methylcyclopentyl)isoxazol-3-yl)methyl)tetrahydro-2H-pyran-3-ol;

1-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)cyclopentane-1-carbonitrile;

1-(3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-5-yl)cyclopentane-1-carbonitrile;

1-(3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-5-yl)cyclopentane-1-carbonitrile;

1-(3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-5-yl)cyclopentane-1-carbonitrile;

(2R,3R,4S,5R,6R)-4-(4-(4-chloro-2,3-difluorophenyl)-1H-1,2,3-triazol-1-yl)-6-(((RS)-3-(1-hydroxy-2-methylpropan-2-yl)-4,5-dihydroisoxazol-5-yl)methyl)-2-(hydroxymethyl)-5-methoxytetrahydro-2H-pyran-3-ol;

(2R,3R,4S,5R,6R)-2-(hydroxymethyl)-5-methoxy-6-((3-(4-methyltetrahydro-2H-pyran-4-yl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(4-methyltetrahydro-2H-pyran-4-yl)isoxazol-5-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((3-(4-methyltetrahydro-2H-pyran-4-yl)isoxazol-5-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((3-(4-methyltetrahydro-2H-pyran-4-yl)isoxazol-5-yl)methyl)tetrahydro-2H-pyran-3-ol;

(2R,3R,4S,5R,6R)-2-(hydroxymethyl)-5-methoxy-6-((3-(1-methylcyclopentyl)isoxazol-5-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((3-(1-methylcyclopentyl)isoxazol-5-yl)methyl)-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((3-(1-methylcyclopentyl)isoxazol-5-yl)methyl)tetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-5-methoxy-6-((3-(1-methylcyclopentyl)isoxazol-5-yl)methyl)tetrahydro-2H-pyran-3-ol;

1-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclopentane-1-carbonitrile;

1-(5-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)isoxazol-3-yl)cyclopentane-1-carbonitrile;

1-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)cyclopentane-1-carbonitrile;

1-(5-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)isoxazol-3-yl)cyclopentane-1-carbonitrile;

(2R,3R,4R,5R,6R)-2-((3-(tert-butyl)isoxazol-5-yl)methyl)-4-(4-(4-chloro-2,3-difluorophenyl)-1H-1,2,3-triazol-1-yl)-6-(hydroxymethyl)tetrahydro-2H-pyran-3,5-diol;

(2R,3R,4S,5R,6R)-6-((3-(1,1-difluoro-2-methylpropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((3-isopropylisoxazol-5-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((3-(1-hydroxycyclopentyl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

2-(1-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclopropyl)acetonitrile;

(2R,3R,4S,5R,6R)-2-(hydroxymethyl)-5-methoxy-6-((3-(1-methoxy-2-methylpropan-2-yl)isoxazol-5-yl)methyl)-4-(4-(3,4,5-trifluorophenyl)-1H-1,2,3-triazol-1-yl)tetrahydro-2H-pyran-3-ol;

tert-butyl (2-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-2-methylpropyl)carbamate;

(2R,3R,4S,5R,6R)-6-((3-(1-amino-2-methylpropan-2-yl)isoxazol-5-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-6-((5-((RS)-1-hydroxy-1-phenylethyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-(1-hydroxycyclopropyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-5-methoxy-6-((5-(3-methyloxetan-3-yl)isoxazol-3-yl)methyl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-((5-(1-(hydroxymethyl)cyclopropyl)isoxazol-3-yl)methyl)-5-methoxytetrahydro-2H-pyran-3-ol;

ethyl 4-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)-4-methylpiperidine-1-carboxylate;

(2R,3R,4S,5R,6R)-4-(4-(2,3-difluoro-4-methylphenyl)-1H-1,2,3-triazol-1-yl)-6-((3-(1-hydroxycyclopentyl)isoxazol-5-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((3-(2-ethoxypropan-2-yl)isoxazol-5-yl)methyl)-2-(hydroxymethyl)-5-methoxytetrahydro-2H-pyran-3-ol;

tert-butyl 4-((RS)-5-(((2R,3R,4S,5R,6R)-4-(4-(2,3-difluoro-4-methoxyphenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

tert-butyl 4-((RS)-5-(((2R,3R,4S,5R,6R)-4-(4-(2,3-difluorophenyl)-1H-1,2,3-triazol-1-yl)-5-hydroxy-6-(hydroxymethyl)-3-methoxytetrahydro-2H-pyran-2-yl)methyl)-4,5-dihydroisoxazol-3-yl)piperidine-1-carboxylate;

(2R,3R,4S,5R,6R)-4-(4-(2,3-difluoro-4-methylphenyl)-1H-1,2,3-triazol-1-yl)-2-(hydroxymethyl)-5-methoxy-6-((3-(1-methoxy-2-methylpropan-2-yl)isoxazol-5-yl)methyl)tetrahydro-2H-pyran-3-ol;

tert-butyl (2-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)-2-methylpropyl)carbamate;

2-(1-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)cyclopropyl)acetonitrile;

(2R,3R,4R,5R,6R)-4-(4-(2,3-difluoro-4-methylphenyl)-1H-1,2,3-triazol-1-yl)-2-(hydroxymethyl)-6-((3-(1-methylcyclopropyl)isoxazol-5-yl)methyl)tetrahydro-2H-pyran-3,5-diol;

(2R,3R,4R,5R,6R)-4-(4-(2,3-difluoro-4-methylphenyl)-1H-1,2,3-triazol-1-yl)-2-((3-(1-hydroxy-2-methylpropan-2-yl)isoxazol-5-yl)methyl)-6-(hydroxymethyl)tetrahydro-2H-pyran-3,5-diol;

(2R,3R,4R,5R,6R)-4-(4-(2,3-difluoro-4-methylphenyl)-1H-1,2,3-triazol-1-yl)-2-(hydroxymethyl)-6-((3-(3-methyloxetan-3-yl)isoxazol-5-yl)methyl)tetrahydro-2H-pyran-3,5-diol;

(2R,3R,4S,5R,6R)-6-((3-(1-amino-2-methylpropan-2-yl)isoxazol-5-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(RS)-5-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)azepan-2-one;

4-(1-((2R,3R,4S,5R,6R)-2-((3-(tert-butyl)isoxazol-5-yl)methyl)-5-hydroxy-6-(hydroxymethyl)-3-methoxytetrahydro-2H-pyran-4-yl)-1H-1,2,3-triazol-4-yl)-2,3-difluorobenzonitrile;

(2R,3R,4S,5R,6R)-4-(4-(2,3-difluoro-4-methylphenyl)-1H-1,2,3-triazol-1-yl)-6-((5-((R)-1-hydroxy-1-phenylethyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-((1RS,2RS)-2-hydroxycyclobutyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-5-hydroxy-2-((5-((1RS,2RS)-2-hydroxycyclopentyl)isoxazol-3-yl)methyl)-6-(hydroxymethyl)tetrahydro-2H-pyran-3-yl acetate;

(RS)-5-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)-1-methylazepan-2-one;

(2R,3R,4S,5R,6R)-4-(4-(2,3-difluoro-4-methylphenyl)-1H-1,2,3-triazol-1-yl)-6-((5-((1S,2S)-2-hydroxycyclobutyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-((1R,2R)-2-hydroxycyclobutyl)isoxazol-3-yl)methyl)-2-(hydroxymethyl)-5-methoxytetrahydro-2H-pyran-3-ol;

(RS)-5-(5-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)isoxazol-3-yl)azepan-2-one;

(2R,3R,4S,5R,6R)-4-(4-(2,3-difluoro-4-methylphenyl)-1H-1,2,3-triazol-1-yl)-6-((5-((1S,2R)-2-hydroxycyclopropyl)isoxazol-3-yl)methyl)-2-(hydroxymethyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-6-((5-((1R,2R)-2-hydroxycyclopropyl)isoxazol-3-yl)methyl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(2,3-difluorophenyl)-1H-1,2,3-triazol-1-yl)-2-(hydroxymethyl)-5-methoxytetrahydro-2H-pyran-3-ol;

(2R,3R,4S,5R,6R)-6-((5-(tert-butyl)isoxazol-3-yl)methyl)-4-(4-(2,3-difluoro-4-methoxyphenyl)-1H-1,2,3-triazol-1-yl)-2-(hydroxymethyl)-5-methoxytetrahydro-2H-pyran-3-ol;

(RS)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)-1-methylpiperidin-2-one;

(RS)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)piperidin-2-one;

(RS)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)pyrrolidin-2-one;

tert-butyl 4-((RS)-5-(((2R,3R,4R,5R,6R)-4-(4-(4-chloro-2,5-difluorophenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl 4-((RS)-5-(((2R,3R,4R,5R,6R)-4-(4-(2,3-difluoro-4-methylphenyl)-1H-1,2,3-triazol-1-yl)-3,5-dihydroxy-6-(hydroxymethyl)tetrahydro-2H-pyran-2-yl)methyl)-4,5-dihydroisoxazol-3-yl)piperidine-1-carboxylate;

tert-butyl ((S)-1-(((1R,4S)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclohexyl)amino)-3-methyl-1-oxobutan-2-yl)carbamate;

(S)-2-amino-N-((1R,4S)-4-(5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-3-yl)cyclohexyl)-3-methylbutanamide;

(2R,3R,4S,5R,6R)-6-((5-(tert-butyl)isoxazol-3-yl)methyl)-4-(4-(4-ethynyl-2,3-difluorophenyl)-1H-1,2,3-triazol-1-yl)-2-(hydroxymethyl)-5-methoxytetrahydro-2H-pyran-3-ol;

(2R,3R,4R,5R,6R)-2-((3-(tert-butyl)isoxazol-5-yl)methyl)-6-(hydroxymethyl)-4-(4-(3,4,5-trifluorophenyl)-1H-1,2,3-triazol-1-yl)tetrahydro-2H-pyran-3,5-diol;

(2R,3R,4R,5R,6R)-2-((3-(tert-butyl)isoxazol-5-yl)methyl)-6-(hydroxymethyl)-4-(4-(2,3,4-trifluorophenyl)-1H-1,2,3-triazol-1-yl)tetrahydro-2H-pyran-3,5-diol;

(2R,3R,4R,5R,6R)-2-((3-(tert-butyl)isoxazol-5-yl)methyl)-4-(4-(2,3-difluoro-4-methylphenyl)-1H-1,2,3-triazol-1-yl)-6-(hydroxymethyl)tetrahydro-2H-pyran-3,5-diol;

(2R,3R,4S,5R,6R)-4-(4-(2,3-difluoro-4-methylphenyl)-1H-1,2,3-triazol-1-yl)-6-((3-(1-hydroxycyclobutyl)isoxazol-5-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((3-(1-hydroxycyclobutyl)isoxazol-5-yl)methyl)-2-(hydroxymethyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-6-((3-(1-hydroxycyclobutyl)isoxazol-5-yl)methyl)-2-(hydroxymethyl)-5-methoxytetrahydro-2H-pyran-3-ol;

(2R,3R,4S,5R,6R)-2-(hydroxymethyl)-6-((3-(2-hydroxypropan-2-yl)isoxazol-5-yl)methyl)-5-methoxy-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-((3-(2-hydroxypropan-2-yl)isoxazol-5-yl)methyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-6-((3-(2-hydroxypropan-2-yl)isoxazol-5-yl)methyl)-5-methoxytetrahydro-2H-pyran-3-ol;

(2R,3R,4S,5R,6R)-6-((5-(1-((S)-tert-butylsulfinyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(2-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(N-methylpropan-2-ylsulfonimidoyl)piperidin-4-yl)isoxazol-3-yl)methyl)-4-(4-(3,4,5-trifluorophenyl)-1H-1,2,3-triazol-1-yl)tetrahydro-2H-pyran-3-ol;

4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N,N-dimethylpiperidine-1-sulfonamide;

N-cyclopropyl-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidine-1-carboxamide;

(2R,3R,4S,5R,6R)-2-(hydroxymethyl)-6-(((S)-3-(1-(isopropylsulfonyl)piperidin-4-yl)-4,5-dihydroisoxazol-5-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(morpholinosulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(piperidin-1-ylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((5-(1-(pyrrolidin-1-ylsulfonyl)piperidin-4-yl)isoxazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-6-((5-(1-((4,4-difluoropiperidin-1-yl)sulfonyl)piperidin-4-yl)isoxazol-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)(piperidin-1-yl)methanone;

(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)(pyrrolidin-1-yl)methanone;

N-ethyl-4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N-methylpiperidine-1-carboxamide;

4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)-N,N-dimethylpiperidine-1-carboxamide;

(4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isoxazol-5-yl)piperidin-1-yl)(4-methylpiperazin-1-yl)methanone;

benzyl 4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)piperidine-1-carboxylate;

(2R,3R,4S,5R,6R)-2-(hydroxymethyl)-5-methoxy-6-((1-(tetrahydro-2H-thiopyran-4-yl)-1H-1,2,3-triazol-4-yl)methyl)-4-(4-(3,4,5-trifluorophenyl)-1H-1,2,3-triazol-1-yl)tetrahydro-2H-pyran-3-ol;

4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)tetrahydro-2H-thiopyran 1-oxide;

4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)tetrahydro-2H-thiopyran 1,1-dioxide;

4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)-1-iminohexahydro-1l6-thiopyran 1-oxide;

4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-1-yl)-1-(methylimino)hexahydro-1l6-thiopyran 1-oxide;

(2R,3R,4S,5R,6R)-6-((1-(1-((S)-tert-butylsulfinyl)piperidin-4-yl)-1H-1,2,3-triazol-4-yl)methyl)-2-(hydroxymethyl)-5-methoxy-4-(4-(3,4,5-trifluorophenyl)-1H-1,2,3-triazol-1-yl)tetrahydro-2H-pyran-3-ol;

benzyl 4-(1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1H-1,2,3-triazol-4-yl)piperidine-1-carboxylate;

(2R,3R,4S,5R,6R)-2-(hydroxymethyl)-5-methoxy-6-((1-(1-(2-methylpropan-2-ylsulfonimidoyl)piperidin-4-yl)-1H-1,2,3-triazol-4-yl)methyl)-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-6-((4-(1-(isopropylsulfonyl)piperidin-4-yl)-1H-1,2,3-triazol-1-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((4-(1-tosylpiperidin-4-yl)-1H-1,2,3-triazol-1-yl)methyl)-4-(4-(3,4,5-trifluorophenyl)-1H-1,2,3-triazol-1-yl)tetrahydro-2H-pyran-3-ol;

1-(ethylimino)-4-(4-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)
methyl)-1H-1,2,3-triazol-1-yl)hexahydro-1λ6-
thiopyran 1-oxide;
(2R,3R,4S,5R,6R)-2-(hydroxymethyl)-5-methoxy-6-((4-
(1-(N-methylpropan-2-ylsulfonimidoyl)piperidin-4-
yl)-1H-1,2,3-triazol-1-yl)methyl)-4-(4-(3,4,5-trifluoro-
phenyl)-1H-1,2,3-triazol-1-yl)tetrahydro-2H-pyran-3-
ol;
4-(1-(((2R,3R,4S,5R,6R)-5-hydroxy-6-(hydroxymethyl)-
3-methoxy-4-(4-(3,4,5-trifluorophenyl)-1H-1,2,3-tri-
azol-1-yl)tetrahydro-2H-pyran-2-yl)methyl)-1H-1,2,3-
triazol-4-yl)-N,N-dimethylpiperidine-1-sulfonamide;
N-(tert-butyl)-4-(1-(((2R,3R,4S,5R,6R)-5-hydroxy-6-
(hydroxymethyl)-3-methoxy-4-(4-(3,4,5-trifluorophe-
nyl)-1H-1,2,3-triazol-1-yl)tetrahydro-2H-pyran-2-yl)
methyl)-1H-1,2,3-triazol-4-yl)piperidine-1-
carboxamide;
1-(benzylimino)-4-(4-(((2R,3R,4S,5R,6R)-5-hydroxy-6-
(hydroxymethyl)-3-methoxy-4-(4-(3,4,5-trifluorophe-
nyl)-1H-1,2,3-triazol-1-yl)tetrahydro-2H-pyran-2-yl)
methyl)-1H-1,2,3-triazol-1-yl)hexahydro-1λ6-
thiopyran 1-oxide;
(2R,3R,4S,5R,6R)-6-((1-cyclohexyl-1H-1,2,3-triazol-4-
yl)methyl)-2-(hydroxymethyl)-5-methoxy-4-(4-(3,4,5-
trifluorophenyl)-1H-1,2,3-triazol-1-yl)tetrahydro-2H-
pyran-3-ol;
4-(4-(((2R,3R,4S,5R,6R)-5-hydroxy-6-(hydroxymethyl)-
3-methoxy-4-(4-(3,4,5-trifluorophenyl)-1H-1,2,3-tri-
azol-1-yl)tetrahydro-2H-pyran-2-yl)methyl)-1H-1,2,3-
triazol-1-yl)-1-(isopropylimino)hexahydro-1λ6-
thiopyran 1-oxide;
N-cyclopropyl-4-(1-(((2R,3R,4S,5R,6R)-5-hydroxy-6-
(hydroxymethyl)-3-methoxy-4-(4-(3,4,5-trifluorophe-
nyl)-1H-1,2,3-triazol-1-yl)tetrahydro-2H-pyran-2-yl)
methyl)-1H-1,2,3-triazol-4-yl)piperidine-1-
carboxamide;
1-((4,4-difluorocyclohexyl)imino)-4-(4-(((2R,3R,4S,5R,
6R)-5-hydroxy-6-(hydroxymethyl)-3-methoxy-4-(4-
(3,4,5-trifluorophenyl)-1H-1,2,3-triazol-1-yl)tetra-
hydro-2H-pyran-2-yl)methyl)-1H-1,2,3-triazol-1-yl)
hexahydro-1λ6-thiopyran 1-oxide;
benzyl 4-(4-(((2R,3R,4S,5R,6R)-4-(4-(4-chloro-3-fluoro-
phenyl)-1H-1,2,3-triazol-1-yl)-5-hydroxy-6-(hy-
droxymethyl)-3-methoxytetrahydro-2H-pyran-2-yl)
methyl)-1H-1,2,3-triazol-1-yl)piperidine-1-
carboxylate;
benzyl 4-(4-(((2R,3R,4S,5R,6R)-4-(4-(3-fluorophenyl)-
1H-1,2,3-triazol-1-yl)-5-hydroxy-6- (hydroxymethyl)-
3-methoxytetrahydro-2H-pyran-2-yl)methyl)-1H-1,2,
3-triazol-1-yl)piperidine-1-carboxylate;
benzyl 4-(4-(((2R,3R,4S,5R,6R)-4-(4-(4-bromo-3-fluoro-
phenyl)-1H-1,2,3-triazol-1-yl)-5-hydroxy-6-(hy-
droxymethyl)-3-methoxytetrahydro-2H-pyran-2-yl)
methyl)-1H-1,2,3-triazol-1-yl)piperidine-1-
carboxylate;
benzyl 4-(4-(((2R,3R,4S,5R,6R)-4-(4-(3,5-difluorophe-
nyl)-1H-1,2,3-triazol-1-yl)-5-hydroxy-6-(hydroxym-
ethyl)-3-methoxytetrahydro-2H-pyran-2-yl)methyl)-
1H-1,2,3-triazol-1-yl)piperidine-1-carboxylate;
(2R,3R,4S,5R,6R)-6-((4-(tert-butyl)-1H-1,2,3-triazol-1-
yl)methyl)-2-(hydroxymethyl)-5-methoxy-4-(4-(3,4,5-
trifluorophenyl)-1H-1,2,3-triazol-1-yl)tetrahydro-2H-
pyran-3-ol;
ethyl 4-(1-(((2R,3R,4S,5R,6R)-5-hydroxy-6-(hydroxym-
ethyl)-3-methoxy-4-(4-(3,4,5-trifluorophenyl)-1H-1,2,
3-triazol-1-yl)tetrahydro-2H-pyran-2-yl)methyl)-1H-1,
2,3-triazol-4-yl)piperidine-1-carboxylate;
(2R,3R,4S,5R,6R)-2-(hydroxymethyl)-5-methoxy-6-((4-
(tetrahydro-2H-pyran-4-yl)-1H-1,2,3-triazol-1-yl)
methyl)-4-(4-(3,4,5-trifluorophenyl)-1H-1,2,3-triazol-
1-yl)tetrahydro-2H-pyran-3-ol;
(2R,3R,4S,5R,6R)-2-(hydroxymethyl)-6-((4-(2-hydroxy-
propan-2-yl)-1H-1,2,3-triazol-1-yl)methyl)-5-
methoxy-4-(4-(3,4,5-trifluorophenyl)-1H-1,2,3-triazol-
1-yl)tetrahydro-2H-pyran-3-ol;
(2R,3R,4S,5R,6R)-6-((1-(tert-butyl)-1H-1,2,3-triazol-4-
yl)methyl)-2-(hydroxymethyl)-5-methoxy-4-(4-(3,4,5-
trifluorophenyl)-1H-1,2,3-triazol-1-yl)tetrahydro-2H-
pyran-3-ol;
(2R,3R,4S,5R,6R)-6-((1-(tert-butyl)-1H-1,2,3-triazol-4-
yl)methyl)-2-(hydroxymethyl)-5-methoxy-4-(4-(2,3,4-
trifluorophenyl)-1H-1,2,3-triazol-1-yl)tetrahydro-2H-
pyran-3-ol;
(2R,3R,4S,5R,6R)-6-((4-cyclopentyl-1H-1,2,3-triazol-1-
yl)methyl)-2-(hydroxymethyl)-5-methoxy-4-(4-(3,4,5-
trifluorophenyl)-1H-1,2,3-triazol-1-yl)tetrahydro-2H-
pyran-3-ol;
(2R,3R,4S,5R,6R)-2-(hydroxymethyl)-5-methoxy-6-((4-
(1-methylcyclopentyl)-1H-1,2,3-triazol-1-yl)methyl)-
4-(4-(3,4,5-trifluorophenyl)-1H-1,2,3-triazol-1-yl)tet-
rahydro-2H-pyran-3-ol;
(2R,3R,4S,5R,6R)-2-(hydroxymethyl)-5-methoxy-6-((4-
(4-methyltetrahydro-2H-pyran-4-yl)-1H-1,2,3-triazol-
1-yl)methyl)-4-(4-(3,4,5-trifluorophenyl)-1H-1,2,3-tri-
azol-1-yl)tetrahydro-2H-pyran-3-ol;
(2R,3R,4S,5R,6R)-6-((1-(tert-butyl)-1H-1,2,3-triazol-4-
yl)methyl)-4-(4-(2,3-difluoro-4-methylphenyl)-1H-1,
2,3-triazol-1-yl)-2-(hydroxymethyl)-5-methoxytetra-
hydro-2H-pyran-3-ol;
(2R,3R,4S,5R,6R)-6-((1-(tert-butyl)-1H-1,2,3-triazol-4-
yl)methyl)-4-(4-(4-chloro-2,3-difluorophenyl)-1H-1,2,
3-triazol-1-yl)-2-(hydroxymethyl)-5-methoxytetra-
hydro-2H-pyran-3-ol;
(2R,3R,4S,5R,6R)-6-((4-(tert-butyl)-1H-1,2,3-triazol-1-
yl)methyl)-4-(4-(2,3-difluoro-4-methylphenyl)-1H-1,
2,3-triazol-1-yl)-2-(hydroxymethyl)-5-methoxytetra-
hydro-2H-pyran-3-ol;
(2R,3R,4S,5R,6R)-6-((4-(tert-butyl)-1H-1,2,3-triazol-1-
yl)methyl)-4-(4-(4-chloro-2,3-difluorophenyl)-1H-1,2,
3-triazol-1-yl)-2-(hydroxymethyl)-5-methoxytetra-
hydro-2H-pyran-3-ol;
(RS)-3-(1-acetylpiperidin-4-yl)-5-(((2R,3R,4S,5R,6R)-5-
hydroxy-6-(hydroxymethyl)-3-methoxy-4-(4-(3,4,5-
trifluorophenyl)-1H-1,2,3-triazol-1-yl)tetrahydro-2H-
pyran-2-yl)methyl)oxazolidin-2-one;
(RS)-5-(((2R,3R,4S,5R,6R)-5-hydroxy-6-(hydroxym-
ethyl)-3-methoxy-4-(4-(3,4,5-trifluorophenyl)-1H-1,2,
3-triazol-1-yl)tetrahydro-2H-pyran-2-yl)methyl)-3-(1-
(methylsulfonyl)piperidin-4-yl)oxazolidin-2-one;
(S)-3-(1-acetylpiperidin-4-yl)-5-(((2R,3R,4S,5R,6R)-5-
hydroxy-6-(hydroxymethyl)-3-methoxy-4-(4-(3,4,5-
trifluorophenyl)-1H-1,2,3-triazol-1-yl)tetrahydro-2H-
pyran-2-yl)methyl)oxazolidin-2-one;
(S)-5-(((2R,3R,4S,5R,6R)-5-hydroxy-6-(hydroxym-
ethyl)-3-methoxy-4-(4-(3,4,5-trifluorophenyl)-1H-1,2,
3-triazol-1-yl)tetrahydro-2H-pyran-2-yl)methyl)-3-(1-
(methylsulfonyl)piperidin-4-yl)oxazolidin-2-one;
(R)-5-(((2R,3R,4S,5R,6R)-5-hydroxy-6-(hydroxym-
ethyl)-3-methoxy-4-(4-(3,4,5-trifluorophenyl)-1H-1,2,
3-triazol-1-yl)tetrahydro-2H-pyran-2-yl)methyl)-3-(1-
(methylsulfonyl)piperidin-4-yl)oxazolidin-2-one;
tert-butyl 4-((RS)-5-(((2R,3R,4S,5R,6R)-5-hydroxy-6-
(hydroxymethyl)-3-methoxy-4-(4-(3,4,5-trifluorophenyl)-1H-1,2,3-triazol-1-yl)tetrahydro-2H-pyran-2-yl) methyl)-2-oxooxazolidin-3-yl)piperidine-1-carboxylate;

(RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-isobutyrylpiperidin-4-yl)oxazolidin-2-one;

4-((RS)_5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-3-yl)-N,N-dimethylpiperidine-1-carboxamide;

(S)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-isobutyrylpiperidin-4-yl)oxazolidin-2-one;

tert-butyl 4-((R)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl) methyl)-2-oxooxazolidin-3-yl)piperidine-1-carboxylate;

(RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(tetrahydro-2H-pyran-4-yl)oxazolidin-2-one;

(RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-(isobutylsulfonyl)piperidin-4-yl)oxazolidin-2-one;

(RS)-3-(1-(3,3-dimethylbutanoyl)piperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one;

(RS)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(1-((trifluoromethyl)sulfonyl)piperidin-4-yl)oxazolidin-2-one;

(RS)-3-(1-(tert-butylsulfonyl)piperidin-4-yl)-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one;

(RS)-3-cyclohexyl-5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)oxazolidin-2-one;

tert-butyl 4-((RS)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxooxazolidin-5-yl)piperidine-1-carboxylate;

tert-butyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)isothiazol-5-yl)piperidine-1-carboxylate;

(2R,3R,4S,5R,6R)-2-(hydroxymethyl)-5-methoxy-6-((5-(piperidin-4-yl)isothiazol-3-yl)methyl)-4-(4-(3,4,5-trifluorophenyl)-1H-1,2,3-triazol-1-yl)tetrahydro-2H-pyran-3-ol;

(2R,3R,4S,5R,6R)-6-((4-(tert-butyl)-1H-imidazol-1-yl) methyl)-2-(hydroxymethyl)-5-methoxy-4-(4-(3,4,5-trifluorophenyl)-1H-1,2,3-triazol-1-yl)tetrahydro-2H-pyran-3-ol;

5-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-phenyloxazol-2(3H)-one;

3-cyclohexyl-1-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)imidazolidin-4-one;

1-(1-acetylpiperidin-4-yl)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)imidazolidin-4-one;

3-(1-acetylpiperidin-4-yl)-1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)imidazolidin-4-one;

3-cyclohexyl-1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl) methyl)imidazolidin-4-one;

1-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-3-(tetrahydro-2H-pyran-4-yl)imidazolidin-4-one; or ethyl 4-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-5-oxoimidazolidin-1-yl) piperidine-1-carboxylate;

or a pharmaceutically acceptable salt thereof.

15. A pharmaceutical composition comprising a compound according to claim 14, or a pharmaceutically acceptable salt thereof, and a pharmaceutically acceptable carrier.

16. A method for the treatment of an indication selected from fibrosis of organs; liver diseases and disorders; cardiovascular diseases and disorders; cell proliferative diseases and cancers; inflammatory and autoimmune diseases and disorders; gastrointestinal tract diseases and disorders; pancreatic diseases and disorders; abnormal angiogenesis-associated diseases and disorders; brain-associated diseases and disorders; neuropathic pain and peripheral neuropathy; ocular diseases and disorders; acute kidney injury and chronic kidney disease; interstitial lung diseases and disorders; and transplant rejection; comprising administering to a subject in a need thereof an effective amount of a compound according to claim 14, or of a pharmaceutically acceptable salt thereof.

17. A compound, wherein said compound is (2R,3R,4S,5R,6R)-6-((1-(tert-butyl)-1H-1,2,3-triazol-4-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

or a pharmaceutically acceptable salt thereof.

18. A pharmaceutical composition comprising the compound according to claim 17, or a pharmaceutically acceptable salt thereof, and a pharmaceutically acceptable carrier.

19. A method for the treatment of an indication selected from fibrosis of organs; liver diseases and disorders; cardiovascular diseases and disorders; cell proliferative diseases and cancers; inflammatory and autoimmune diseases and disorders; gastrointestinal tract diseases and disorders; pancreatic diseases and disorders; abnormal angiogenesis-associated diseases and disorders; brain-associated diseases and disorders; neuropathic pain and peripheral neuropathy; ocular diseases and disorders; acute kidney injury and chronic kidney disease; interstitial lung diseases and disorders; and transplant rejection; comprising administering to a subject in a need thereof an effective amount of the compound according to claim 1, or of a pharmaceutically acceptable salt thereof.

20. The compound according to claim 17, wherein said compound is (2R,3R,4S,5R,6R)-6-((1-(tert-butyl)-1H-1,2,3-triazol-4-yl) methyl)-4-(4-(4-chloro-2,3-difluorophenyl)-1H-1,2,3-triazol-1-yl)-2-(hydroxymethyl)-5-methoxytetrahydro-2H-pyran-3-ol.

21. A pharmaceutical composition comprising the compound according to claim 20 and a pharmaceutically acceptable carrier.

22. The compound according to claim 17, wherein said compound is a pharmaceutically acceptable salt of (2R,3R,4S,5R,6R)-6-((1-(tert-butyl)-1H-1,2,3-triazol-4-yl) methyl)-4-(4-(4-chloro-2,3-difluorophenyl)-1H-1,2,3-triazol-1-yl)-2-(hydroxymethyl)-5-methoxytetrahydro-2H-pyran-3-ol.

23. A pharmaceutical composition comprising the compound according to claim 22 and a pharmaceutically acceptable carrier.

* * * * *